(12) United States Patent
Regan et al.

(10) Patent No.: US 9,127,312 B2
(45) Date of Patent: Sep. 8, 2015

(54) ANALYSIS OF NUCLEIC ACIDS

(75) Inventors: John Frederick Regan, San Mateo, CA (US); Serge Saxonov, San Mateo, CA (US); Mike Lucero, South San Francisco, CA (US); Ben Hindson, Livermore, CA (US); Phil Belgrader, Severna Park, MD (US); Simant Dube, Berkeley, CA (US); Austin So, Pleasanton, CA (US); Jeffrey Clark Mellen, San Francisco, CA (US); Nicholas Jack Heredia, Mountain House, CA (US); Kevin Ness, San Mateo, CA (US); Bill Colston, San Ramon, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 482 days.

(21) Appl. No.: 13/385,277

(22) Filed: Feb. 9, 2012

(65) Prior Publication Data

US 2012/0322058 A1    Dec. 20, 2012

Related U.S. Application Data

(60) Provisional application No. 61/441,209, filed on Feb. 9, 2011, provisional application No. 61/444,539, filed on Feb. 18, 2011, provisional application No. 61/454,373, filed on Mar. 18, 2011, provisional application No. 61/476,115, filed on Apr. 15, 2011, provisional application No. 61/478,777, filed on Apr. 25, 2011, provisional application No. 61/484,197, filed on May 9, 2011, provisional application No. 61/490,055, filed on May 25, 2011.

(51) Int. Cl.
C12Q 1/68 (2006.01)
C07H 21/00 (2006.01)

(52) U.S. Cl.
CPC .............. *C12Q 1/683* (2013.01); *C12Q 1/6858* (2013.01)

(58) Field of Classification Search
CPC .................................. C12Q 1/68; C07H 21/00
USPC ................ 435/6.1, 91.2; 536/22.1, 23.1, 24.3
See application file for complete search history.

(56) References Cited

U.S. PATENT DOCUMENTS

| 4,437,975 | A |   | 3/1984  | Gillespie et al. |
|-----------|---|---|---------|------------------|
| 4,683,194 | A | * | 7/1987  | Saiki et al. ................... 435/6.12 |
| 4,683,202 | A |   | 7/1987  | Mullis |
| 4,883,750 | A |   | 11/1989 | Whiteley et al. |
| 4,988,617 | A |   | 1/1991  | Landegren et al. |
| 5,242,794 | A |   | 9/1993  | Whiteley et al. |
| 5,409,818 | A |   | 4/1995  | Davey et al. |
| 5,413,909 | A |   | 5/1995  | Bassam et al. |
| 5,426,180 | A |   | 6/1995  | Kool |
| 5,432,054 | A |   | 7/1995  | Saunders et al. |
| 5,476,930 | A |   | 12/1995 | Letsinger et al. |
| 5,494,810 | A |   | 2/1996  | Barany et al. |
| 5,554,517 | A |   | 9/1996  | Davey et al. |
| 5,593,826 | A |   | 1/1997  | Fung et al. |
| 5,786,146 | A |   | 7/1998  | Herman et al. |
| 5,861,245 | A |   | 1/1999  | Mcclelland et al. |
| 5,866,337 | A |   | 2/1999  | Schon |
| 5,871,921 | A |   | 2/1999  | Landegren et al. |
| 5,952,481 | A | * | 9/1999  | Markham et al. ............ 536/23.2 |
| 6,063,603 | A |   | 5/2000  | Davey et al. |
| 6,143,504 | A |   | 11/2000 | Das et al. |
| 6,180,349 | B1 |  | 1/2001  | Ginzinger et al. |
| 6,200,756 | B1 |  | 3/2001  | Herman et al. |
| 6,203,989 | B1 |  | 3/2001  | Goldberg et al. |
| 6,235,472 | B1 |  | 5/2001  | Landegren et al. |
| 6,251,594 | B1 |  | 6/2001  | Gonzalgo et al. |
| 6,258,540 | B1 |  | 7/2001  | Lo et al. |
| 6,265,171 | B1 |  | 7/2001  | Herman et al. |
| 6,331,393 | B1 |  | 12/2001 | Laird et al. |
| 6,410,276 | B1 |  | 6/2002  | Burg et al. |
| 6,440,706 | B1 |  | 8/2002  | Vogelstein et al. |
| 6,558,928 | B1 |  | 5/2003  | Landegren |
| 6,582,938 | B1 |  | 6/2003  | Su et al. |
| 6,596,493 | B1 |  | 7/2003  | Reeves et al. |
| 6,790,328 | B2 |  | 9/2004  | Jacobson et al. |
| 6,858,412 | B2 |  | 2/2005  | Willis et al. |
| 6,884,586 | B2 |  | 4/2005  | Van Ness et al. |
| 6,927,028 | B2 |  | 8/2005  | Dennis et al. |

(Continued)

FOREIGN PATENT DOCUMENTS

EP       745140 B1    11/2000
EP       0964704 B1    2/2002

(Continued)

OTHER PUBLICATIONS

Alitalo et al.,Homogeneously staining chromosomal regions contain amplified copies of an abundantly expressed cellular oncogene (c-mnc) in malignant neuroendocrine cells from a human colon carcinoma. PNAS 80 :1707 (1983).*
Barber et al.,GAPDH as a housekeeping gene: analysis of GAPDH mRNA expression in a panel of 72 human tissues. Physiological Genetics 21 : 389 (2005).*
Braun et al., Myf-6, a new member of the human gene family of myogenic determination factors : evidence for a gene cluster on chromosome 12. EMBO Journal 9 (3) : 821 (1990).*
Bignell et al., High-Resolution Analysis of DNA Copy Number Using Oligonucleotide Microarrays. Genome Research 14 :287 (2004).*
Capero et al., MET and KRAS Gene Amplification Mediates Acquired Resistance to MET Tyrosine Kinase Inhibitors. Cancer Research 70 (19) : 7580 (2010).*
Dalgleish et al. Copy Number of a Human Type I alpha2 Collagen Gene Journaql of Biological Chemistry 257 (22) : 13816 (1982).*

(Continued)

*Primary Examiner* — Ethan C Whisenant
(74) *Attorney, Agent, or Firm* — Kolisch Hartwell, P.C.

(57) ABSTRACT

Provided herein are improved methods, compositions, and kits for analysis of nucleic acids. The improved methods, compositions, and kits can enable copy number estimation of a nucleic acid in a sample. Also provided herein are methods, compositions, and kits for determining the linkage of two or more copies of a target nucleic acid in a sample (e.g., whether the two or more copies are on the same chromosome or different chromosomes) or for phasing alleles.

28 Claims, 60 Drawing Sheets

(56) References Cited

U.S. PATENT DOCUMENTS

| | | | |
|---|---|---|---|
| 6,953,663 | B1 | 10/2005 | Lipshutz et al. |
| 7,041,481 | B2 | 5/2006 | Anderson et al. |
| 7,074,564 | B2 | 7/2006 | Landegren |
| 7,256,020 | B2 | 8/2007 | Lyamichev et al. |
| 7,320,860 | B2 | 1/2008 | Landegren et al. |
| 7,332,275 | B2 | 2/2008 | Braun et al. |
| 7,351,528 | B2 | 4/2008 | Landegren |
| 7,368,242 | B2 | 5/2008 | Miao et al. |
| 7,424,368 | B2 | 9/2008 | Huang et al. |
| 7,510,829 | B2 | 3/2009 | Faham et al. |
| 7,618,780 | B2 | 11/2009 | Thompson |
| 7,622,280 | B2 | 11/2009 | Holliger et al. |
| 7,674,587 | B2 | 3/2010 | Lipshutz et al. |
| 7,700,323 | B2 | 4/2010 | Willis et al. |
| 7,718,364 | B2 | 5/2010 | Hoon et al. |
| 7,718,370 | B2 | 5/2010 | Dhallan |
| 7,754,428 | B2 | 7/2010 | Lo et al. |
| RE41,780 | E | 9/2010 | Anderson et al. |
| 7,790,388 | B2 | 9/2010 | Landegren et al. |
| 7,790,393 | B2 | 9/2010 | Lyamichev et al. |
| 7,799,531 | B2 | 9/2010 | Mitchell et al. |
| 7,811,757 | B2 | 10/2010 | Shuber |
| 7,822,555 | B2 | 10/2010 | Huang et al. |
| 7,888,017 | B2 | 2/2011 | Quake et al. |
| 8,606,526 | B1 * | 12/2013 | Fernandez et al. ............. 702/19 |
| 2003/0082543 | A1 * | 5/2003 | Su et al. ............................ 435/6 |
| 2004/0005614 | A1 | 1/2004 | Kurn et al. |
| 2004/0101835 | A1 | 5/2004 | Willis et al. |
| 2004/0137470 | A1 | 7/2004 | Dhallan |
| 2004/0157243 | A1 | 8/2004 | Huang et al. |
| 2005/0026180 | A1 | 2/2005 | Willis et al. |
| 2005/0064476 | A1 | 3/2005 | Huang et al. |
| 2005/0112636 | A1 | 5/2005 | Hurt et al. |
| 2005/0130217 | A1 | 6/2005 | Huang et al. |
| 2005/0158739 | A1 | 7/2005 | Jeddeloh et al. |
| 2005/0272070 | A1 | 12/2005 | Ehrich et al. |
| 2006/0073511 | A1 | 4/2006 | Jones et al. |
| 2006/0078893 | A1 | 4/2006 | Griffiths et al. |
| 2006/0094111 | A1 * | 5/2006 | Saito et al. .................... 435/325 |
| 2006/0134674 | A1 | 6/2006 | Huang et al. |
| 2006/0275789 | A1 | 12/2006 | Willis et al. |
| 2006/0281098 | A1 | 12/2006 | Miao et al. |
| 2006/0292585 | A1 | 12/2006 | Nautiyal et al. |
| 2007/0065823 | A1 | 3/2007 | Dressman et al. |
| 2007/0172873 | A1 | 7/2007 | Brenner et al. |
| 2007/0178479 | A1 | 8/2007 | Willis et al. |
| 2007/0225487 | A1 | 9/2007 | Nilsson et al. |
| 2007/0264642 | A1 | 11/2007 | Willis et al. |
| 2008/0014589 | A1 | 1/2008 | Link et al. |
| 2008/0108063 | A1 | 5/2008 | Lucero et al. |
| 2008/0138809 | A1 | 6/2008 | Kapur et al. |
| 2008/0169184 | A1 | 7/2008 | Brown et al. |
| 2008/0254474 | A1 | 10/2008 | Laird et al. |
| 2009/0004646 | A1 | 1/2009 | Schuster et al. |
| 2009/0026082 | A1 | 1/2009 | Rothberg et al. |
| 2009/0035762 | A1 | 2/2009 | Sampas |
| 2009/0068648 | A1 | 3/2009 | Yakhini et al. |
| 2009/0069194 | A1 | 3/2009 | Ramakrishnan |
| 2009/0098547 | A1 | 4/2009 | Ghosh |
| 2009/0155776 | A1 | 6/2009 | Lo et al. |
| 2009/0215633 | A1 | 8/2009 | Van Eijk et al. |
| 2009/0239308 | A1 | 9/2009 | Dube et al. |
| 2010/0070455 | A1 | 3/2010 | Halperin et al. |
| 2010/0092981 | A1 | 4/2010 | Shuber |
| 2010/0105052 | A1 | 4/2010 | Drmanac et al. |
| 2010/0105112 | A1 | 4/2010 | Holtze et al. |
| 2010/0173394 | A1 | 7/2010 | Colston, Jr. et al. |
| 2010/0203538 | A1 | 8/2010 | Dube et al. |
| 2010/0255492 | A1 | 10/2010 | Quake et al. |
| 2010/0256013 | A1 | 10/2010 | Quake et al. |
| 2010/0256015 | A1 | 10/2010 | Lim et al. |
| 2010/0273165 | A1 | 10/2010 | Ehrich et al. |
| 2010/0317542 | A1 | 12/2010 | Lim et al. |
| 2010/0330619 | A1 | 12/2010 | Willis et al. |
| 2011/0015084 | A1 | 1/2011 | Christian et al. |
| 2011/0029251 | A1 | 2/2011 | Huang et al. |
| 2011/0039724 | A1 | 2/2011 | Lo et al. |
| 2011/0105353 | A1 | 5/2011 | Lo et al. |
| 2011/0143949 | A1 | 6/2011 | Heid et al. |
| 2011/0159499 | A1 | 6/2011 | Hindson et al. |
| 2011/0183330 | A1 * | 7/2011 | Lo et al. ....................... 435/6.11 |
| 2011/0217712 | A1 | 9/2011 | Hiddessen et al. |
| 2012/0171683 | A1 | 7/2012 | Ness et al. |
| 2012/0252015 | A1 | 10/2012 | Hindson et al. |
| 2013/0295568 | A1 | 11/2013 | Link |
| 2014/0162266 | A1 * | 6/2014 | Klitgord et al. ............... 435/6.11 |

FOREIGN PATENT DOCUMENTS

| | | |
|---|---|---|
| EP | 951565 B1 | 3/2003 |
| EP | 1366192 B1 | 12/2007 |
| EP | 1644519 B1 | 12/2008 |
| EP | 1066414 B1 | 6/2009 |
| WO | WO 88/10315 A1 | 12/1988 |
| WO | WO 90/06995 A1 | 6/1990 |
| WO | WO 97/09069 A1 | 3/1997 |
| WO | WO 97/41254 A1 | 11/1997 |
| WO | WO 99/49079 A1 | 9/1999 |
| WO | WO 01/77383 A2 | 10/2001 |
| WO | WO 02/057491 A2 | 7/2002 |
| WO | WO 01/77383 A3 | 12/2002 |
| WO | WO 03012119 A2 | 2/2003 |
| WO | WO 03/035671 A2 | 5/2003 |
| WO | WO 02/057491 A3 | 10/2003 |
| WO | WO 03/035671 A3 | 11/2003 |
| WO | WO 03012119 A3 | 11/2003 |
| WO | WO 2004/044225 A2 | 5/2004 |
| WO | WO 2004/096825 A1 | 11/2004 |
| WO | WO 2005/038051 A2 | 4/2005 |
| WO | WO 2005/111242 A2 | 11/2005 |
| WO | WO 2005/111242 A3 | 1/2006 |
| WO | WO 2004/044225 A3 | 4/2006 |
| WO | 2007037678 A2 | 4/2007 |
| WO | WO 2007/044091 A2 | 4/2007 |
| WO | WO 2007/087312 A2 | 8/2007 |
| WO | WO 2007/092473 A2 | 8/2007 |
| WO | WO 2007/100243 A1 | 9/2007 |
| WO | WO 2007/044091 A3 | 11/2007 |
| WO | WO 2007/147076 A2 | 12/2007 |
| WO | WO 2007/147079 A2 | 12/2007 |
| WO | WO 2007/147079 A3 | 3/2008 |
| WO | WO 2007/147076 A3 | 4/2008 |
| WO | WO 2008/063227 A2 | 5/2008 |
| WO | 2008134153 A1 | 11/2008 |
| WO | WO 2008/063227 A3 | 11/2008 |
| WO | WO 2009/014848 A2 | 1/2009 |
| WO | WO 2009/033178 A1 | 3/2009 |
| WO | WO 2009/014848 A3 | 12/2009 |
| WO | WO 2010/009365 A1 | 1/2010 |
| WO | WO 2010/036352 A1 | 4/2010 |
| WO | WO 2011/000604 A2 | 1/2011 |
| WO | WO 2011/034631 A1 | 3/2011 |
| WO | WO 2011/066476 A1 | 6/2011 |
| WO | WO 2011/000604 A3 | 2/2012 |
| WO | WO 2012/116331 A2 | 8/2012 |

OTHER PUBLICATIONS

Dressman et al.,Transforming single DNA molecules into fluorescent magnetic particles for detection and enumeration of genetic variations. PNAS 100 (15) : 8817 (2003).*

Kalinina et al., Nanoliter scale PCR with TaqMan detection. Nucleic Acids Research 25 (10) : 1999 (1997).*

Kallioniemi et al.,ERBB2 amplification in breast cancer analyzed by fluorescence in situ hybridization. PNAS 89 : 5321 (1992).*

Kant et al., Evolution and organization of the fibrinogen locus on chromosome 4: Gene duplication accompanied by transposition and inversion. PNAS 82 : 2344 (1985).*

Kaufhold et al., Identical Genes Confer High-Level Resistance to Gentamicin upon *Enterococcus faecalis, Enterococcus faecium*, and *Streptococcus agalactiae*. Antimicrobial Agents and Chemotherapy 36 (6) : 1215 (1992).*

(56) References Cited

OTHER PUBLICATIONS

Kilpatrick, CW,. Noncryogenic Preservation of Mammalian Tissues for DNA Extraction: An Assessment of Storage Methods. Biochemical Genetics 40(1/2) : 53 (2002).*
Leamon et al.,A massively parallel PicoTiterPlate___based platform for discrete picoliter-scale polymerase chain reactions. Electrophoresis 24 :3769 (2003).*
Manuelidis et al.Genomic representation of the Hind II 1.9 kb repeated DNA. Nucleic Acids Research 10 (10) : 3221(1982).*
Murthy et al.Copy Number Analysis of c-erb-B2 (HER-2/neu) and Topoisomerase IIa Genes in Breast Carcinoma by Quantitative Real-Time Polymerase Chain Reaction Using Hybridization Probes and Fluorescence In Situ Hybridization. Archives of Pathology & Laboratory Medicine 129 : 39 (2005).*
Shumaker et al.Mutation Detection by Solid Phase Primer Extension. Human Mutation 7 : 346 (1996).*
Slamon et al.,Human Breast Cancer: Correlation of Relapse and Survival with Amplification of the HER-2/neu Oncogene. Science 235 : 177 (1987).*
Wilke et al.,Diagnosis of Haploidy and Triploidy Based on Measurement of Gene Copy Number By Real-Time PCR. Human Mutation 16 : 431 (2000).*
Wu et al., Comparative DNA Sequence Analysis of Mouse and Human Protocadherin Gene Clusters. Genome Research 11 :389 (2001).*
International preliminary report on patentability dated May 30, 2012 for PCT/US2010/058124.
International preliminary report on patentability dated Jul. 29, 2008 for PCT/US2007/001796.
International preliminary report on patentability dated Sep. 2, 2008 for PCT/NL2007/000055.
Office action dated Dec. 5, 2012 for U.S. Appl. No. 12/954,634.
European search report dated May 8, 2013 for EP Application No. 10833991.2.
Mazutis, et al. Droplet-based microfluidic systems for high-throughput amplification and analysis. Analytical Chemistry, American Chemical Society. 2009; 81(12):4813-4821.
Boettger, et al. Structural haplotypes and recent evolution of the human 17q21.31 region. Nat Genet. Jul. 1, 2012;44(8):881-5. doi: 10.1038/ng.2334.
Supplementary note for Boettger, et al. Structural haplotypes and recent evolution of the human 17q21.31 region. Nat Genet. Jul. 1, 2012;44(8):881-5. doi: 10.1038/ng.2334.
U.S. Appl. No. 13/400,030, filed Feb. 17, 2012, Hindson et al.
Aitman, et al. Copy number polymorphism in Fcgr3 predisposes to glomerulonephritis in rats and humans. Nature. Feb. 16, 2006;439(7078):851-5.
Alkan, et al. Personalized copy number and segmental duplication maps using next-generation sequencing. Nat Genet. Oct. 2009;41(10):1061-7. Epub Aug. 30, 2009.
Balikova. Autosomal-dominant microtia linked to five tandem of a copy-number-variable region at chromosome 4p16. Am J Hum Genet. Jan. 2008;82(1):181-7.
Barringer, et al. Blunt-end and single-strand ligations by *Escherichia coli* ligase: influence on an in vitro amplification scheme. Gene. Apr. 30, 1990;89(1):117-22.
Bennetzen, et al. Active maize genes are unmodified and flanked by diverse classes of modified, highly repetitive DNA. Genome. Aug. 1994;37(4):565-76.
Bhat, et al. Single molecule detection in nanofluidic digital array enables accurate measurement of DNA copy number. Anal Bioanal Chem. May 2009;394(2):457-67.
Bianchi, et al. Isolation of fetal DNA from nucleated erythrocytes in maternal blood. Proc Natl Acad Sci U S A. May 1990;87(9):3279-83.
Boorsman, et al. Comparison of multiplex ligation-dependent probe amplification and karyotyping in prenatal diagnosis. Obstet Gynecol. Feb. 2010;115(2 Pt 1):297-303.
Brouzes, et al. Droplet microfluidic technology for single-cell high-throughput screening Proc Natl Acad Sci U S A. Aug. 25, 2009;106(34):14195-200.

Bruch, et al. Trophoblast-like cells sorted from peripheral maternal blood using flow cytometry: a multiparametric study involving transmission electron microscopy and fetal DNA amplification. Prenat Diagn. Oct. 1991;11(10):787-98.
Cappuzzo, et al. Increased HER2 gene copy number is associated with response to gefitinib therapy in epidermal growth factor receptor-positive non-small-cell lung cancer patients. J Clin Oncol. Aug. 1, 2005;23(22):5007-18.
Clark, et al. High sensitivity mapping of methylated cytosines. Nucleic Acids Res. Aug. 11, 1994;22(15):2990-7.
Cook, et al. Copy-number variations associated with neuropsychiatric conditions. Nature. Oct. 16, 2008;455(7215):919-23.
Dahl, et al. Circle-to-circle amplification for precise and sensitive DNA analysis. Proc Natl Acad Sci U S A. Mar. 30, 2004;101(13):4548-53. Epub Mar. 15, 2004.
Dahl, et al. DNA methylation analysis techniques. Biogerontology. 2003;4(4):233-50.
Dahl, et al. Multiplex amplification enabled by selective circularization of large sets of genomic DNA fragments. Nucleic Acids Res. Apr. 28, 2005;33(8):e71.
Dube, et al. Mathematical Analysis of Copy Number Variation in a DNA Sample Using Digital PCR on a Nanofluidic Device. PLoS One 2008; 3(8): e2876. doi:10.1371/journal.pone.0002876.
Elmore. Apoptosis: A review of programmed cell death. Toxicol Pathol. Jun. 2007;35(4):495-516.
Elnifro et al., P.E. Multiplex PCR: optimization and application in diagnostic virology. Clin. Microbiol. Rev. 13, 559-570 (2000).
Fan, et al. Analysis of the size distributions of fetal and maternal cell-free DNA by paired-end sequencing. Clin Chem. Aug. 2010;56(8):1279-86. Epub Jun. 17, 2010.
Fan, et al. Microfluidic digital PCR enables rapid prenatal diagnosis of fetal aneuploidy. Am J Obstet Gynecol. May 2009;200(5):543.e1-7.
Fan, et al. Noninvasive diagnosis of fetal aneuploidy by shotgun sequencing DNA from maternal blood. Proc Natl Acad Sci U S A. Oct. 21, 2008;105(42):16266-71. Epub Oct. 6, 2008.
Fire, et al. Rolling replication of short DNA circles. Proc Natl Acad Sci U S A. May 9, 1995;92(10):4641-5.
Fraga, et al. DNA methylation: a profile of methods and applications. Biotechniques. Sep. 2002;33(3):632, 634, 636-49.
Frommer, et al. A genomic sequencing protocol that yields a positive display of 5-methylcytosine residues in individual DNA strands. Proc Natl Acad Sci U S A. Mar. 1, 1992;89(5):1827-31.
Gerdes, et al. Computer-assisted prenatal aneuploidy screening for chromosome 13, 18, 21, X and Y based on multiplex ligation-dependent probe amplification (MLPA). Eur J Hum Genet. Feb. 2005;13(2):171-5.
Gonzalez, et al. Fluidic interconnect for modular assembly of chemical microsystems. Sensors and Actuators. 1998; B49:40-45.
Gonzalez, et al. The influence of CCL3L1 gene-containing segmental duplications on HIV-1/AIDS susceptibility. Science. Mar. 4, 2005;307(5714):1434-40. Epub Jan. 6, 2005.
Guatelli, et al. Isothermal, in vitro amplification of nucleic acids by a multienzyme reaction modeled after retroviral replication. Proc Natl Acad Sci U S A. Mar. 1990;87(5):1874-8.
Guo, et al. Simultaneous detection of trisomies 13, 18, and 21 with multiplex ligation-dependent probe amplification-based real-time PCR. Clin Chem. Sep. 2010;56(9):1451-9.
Hardenbol, et al. Highly multiplexed molecular inversion probe genotyping: over 10,000 targeted SNPs genotyped in a single tube assay. Genome Res. Feb. 2005;15(2):269-75.
Hardenbol, et al. Multiplexed genotyping with sequence-tagged molecular inversion probes. Nat Biotechnol. Jun. 2003;21(6):673-8. Epub May 5, 2003. PMID: 12730666.
Harris, et al. Single-molecule DNA sequencing of a viral genome. Science. Apr. 4, 2008;320(5872):106-9.
Hayatsu, et al. DNA methylation analysis: speedup of bisulfate-mediated deamination of cytosine in the genomic sequencing procedure. Proc. Jpn. Acad. Ser. B. 2004; 80:189-194.
Herzenberg, et al. Fetal cells in the blood of pregnant women: detection and enrichment by fluorescence-activated cell sorting. Proc Natl Acad Sci U S A. Mar. 1979;76(3):1453-5.

(56) References Cited

OTHER PUBLICATIONS

Hindson, et al. High-throughput droplet digital PCR system for absolute quantitation of DNA copy number. Anal Chem. Nov. 15, 2011;83(22):8604-10. Epub Oct. 28, 2011.

Hochstenbach, et al. Rapid detection of chromosomal aneuploidies in uncultured amniocytes by multiplex ligation-dependent probe amplification (MLPA). Prenat Diagn. Nov. 2005;25(11):1032-9.

Huber, et al. High-resolution liquid chromatography of DNA fragments on non-porous poly(styrene-divinylbenzene) particles. Nucleic Acids Res. Mar. 11, 1993;21(5):1061-6.

Hyman, et al. Multiplex identification of microbes. Appl Environ Microbiol. Jun. 2010;76(12):3904-10. Epub Apr. 23, 2010.

International search report and written opinion dated Apr. 7, 2011 for PCT/US2010/058124.

Ji, et al. Molecular inversion probe assay for allelic quantitation. Methods Mol Biol. 2009;556:67-87.

Kass, et al. How does DNA methylation repress transcription? Trends Genet. Nov. 1997;13(11):444-9.

Kato, et al. A new packing for separation of DNA restriction fragments by high performance liquid chromatography. J Biochem. Jan. 1984;95(1):83-6.

Komiyama, et al. Catalysis of diethylenetriamine for bisulfate-induced deamination of cytosine in oligodeoxyribonucleotides. Tetrahedron Letters. 1994; 35(44):8185-8188.

Kwoh, et al. Transcription-based amplification system and detection of amplified human immunodeficiency virus type 1 with a bead-based sandwich hybridization format. Proc Natl Acad Sci U S A. Feb. 1989;86(4):1173-7.

Landegren, et al. A ligase-mediated gene detection technique. Science. Aug. 26, 1988;241(4869):1077-80.

Larijani, et al. Methylation protects cytidines from AID-mediated deamination. Mol Immunol Mar. 2005;42(5):599-604.

Leng, et al. Agarose droplet microfluidics for highly parallel and efficient single molecule emulsion PCR. Lab Chip. Nov. 7, 2010;10(21):2841-3.

Li, et al. Detection of paternally inherited fetal point mutations for beta-thalassemia using size-fractionated cell-free DNA in maternal plasma. JAMA. Feb. 16, 2005;293(7):843-9.

Lieber. The mechanism of double-strand DNA break repair by the nonhomologous DNA end-joining pathway. u Rev Biochem. 2010;79:181-211.

Liu, et al. Rolling Circle DNA Synthesis: Small Circular Oligonucleotides as Efficient Templates for DNA Polymerases. J Am Chem Soc. Feb. 21, 1996;118(7):1587-1594.

Lizardi, et al. Mutation detection and single-molecule counting using isothermal rolling-circle amplification. Nat Genet. Jul. 1998;19(3):225-32.

Lo, et al. Noninvasive prenatal diagnosis of fetal chromosomal aneuploidies by maternal plasma nucleic acid analysis. Clin Chem. Mar. 2008;54(3):461-6.

Lo, et al. Presence of fetal DNA in maternal plasma and serum. Lancet. Aug. 16, 1997;350(9076):485-7.

Lupski. Genomic rearrangements and sporadic disease. Nat Genet. Jul. 2007;39(7 Suppl):S43-7.

Marguiles, et al. Genome sequencing in microfabricated high-density picolitre reactors. Nature. Sep. 15, 2005;437(7057):376-80. Epub Jul. 31, 2005.

Martienssen, et al. DNA methylation in eukaryotes. Curr Opin Genet Dev. Apr. 1995;5(2):234-42.

Martienssen. Transposons, DNA methylation and gene control. Trends Genet. Jul. 1998;14(7):263-4.

Moelans, et al. Absence of chromosome 17 polysomy in breast cancer: analysis by CEP17 chromogenic in situ hybridization and multiplex ligation-dependent probe amplification. Breast Cancer Res Treat. Feb. 2010;120(1):1-7.

Moore, et al. Key features of cereal genome organization as revealed by the use of cytosine methylation-sensitive restriction endonucleases. Genomics. Mar. 1993;15(3):472-82.

Ng, et al. mRNA of placental origin is readily detectable in maternal plasma. Proc Natl Acad Sci U S A. Apr. 15, 2003;100(8):4748-53. Epub Mar. 18, 2003.

Ng, et al. The concentration of circulating corticotropin-releasing hormone mRNA in maternal plasma is increased in preeclampsia. Clin Chem. May 2003;49(5):727-31.

Nolte. Branched DNA signal amplification for direct quantitation of nucleic acid sequences in clinical specimens. Adv Clin Chem. 1998;33:201-35.

Nygren, et al. Quantification of fetal DNA by use of methylation-based DNA discrimination. Clin Chem. Oct. 2010;56(10):1627-35. Epub Aug. 20, 2010.

Olek, et al. A modified and improved method for bisulphite based cytosine methylation analysis. Nucleic Acids Res. Dec. 15, 1996;24(24):5064-6.

Panne, et al. The McrBC endonuclease translocates DNA in a reaction dependent on GTP hydrolysis. J Mol Biol. Jul. 2, 1999;290(1):49-60.

Pathak. Circulating cell-free DNA in plasma/serum of lung cancer patients as a potential screening and prognostic tool. Clin Chem. Oct. 2006;52(10):1833-42.

Perry, et al. Diet and the evolution of human amylase gene copy number variation. Nat Genet. Oct. 2007;39(10):1256-60. Epub Sep. 9, 2007.

Pielberg, et al. A sensitive method for detecting variation in copy numbers of duplicated genes. Genome Res. Sep. 2003;13(9):2171-7.

Pinto, et al. Functional impact of global rare copy number variation in autism spectrum disorders. Nature. Jul. 15, 2010;466(7304):368-72. Epub Jun. 9, 2010.

Putney, et al. A DNA fragment with an alpha-phosphorothioate nucleotide at one end is asymmetrically blocked from digestion by exonuclease III and can be replicated in vivo. Proc Natl Acad Sci U S A. Dec. 1981;78(12):7350-4.

Qin, et al. Studying copy number variations using a nanofluidic platform. Nucleic Acids Res. Oct. 2008;36(18):e116.

Raleigh. Organization and function of the mcrBC genes of *Escherichia coli* K-12.Mol Microbiol. May 1992;6(9):1079-86.

Redon, et al. Global variation in copy number in the human genome. Nature. Nov. 23, 2006;444(7118):444-54.

Rickert, et al. Multiplexed real-time PCR using universal reporters. Clin Chem. Sep. 2004;50(9):1680-3.

Robertson. DNA methylation and human disease. Nat Rev Genet. Aug. 2005;6(8):597-610.

Ropers. New perspectives for the elucidation of genetic disorders. Am J Hum Genet. Aug. 2007;81(2):199-207. Epub Jun. 29, 2007.

San Miguel, et al. Nested retrotransposons in the intergenic regions of the maize genome. Science. 1996; 274:765.

Satoh, et al. Interim safety analysis from TYTAN: a phase III Asian study of lapatinib in combination with paclitaxel as second-line therapy in gastric cancer. J. Clin. Oncol. 2010; 28:15s.

Schouten, et al. MLPA for prenatal diagnosis of commonly occurring aneuploidies. Methods Mol Biol. 2008;444:111-22.

Schouten, et al. Relative quantification of 40 nucleic acid sequences by multiplex ligation-dependent probe amplification. Nucleic Acids. Res. 2002; 30(12):e57.

Sebat, et al. Large-scale copy number polymorphism in the human genome. Science. Jul. 23, 2004;305(5683):525-8.

Sebat, et al. Strong association of de novo copy number mutations with autism. Science. Apr. 20, 2007;316(5823):445-9. Epub Mar. 15, 2007.

Shifman, et al. Quantitative technologies for allele frequency estimation of SNPs in DNA pools. Mol Cell Probes. Dec. 2002;16(6):429-34.

Shlien, et al. Copy number variations and cancer. Genome Med. Jun. 16, 2009;1(6):62.

Shlien, et al. Excessive genomic DNA copy number variation in the Li-Fraumeni cancer predisposition syndrome. Proc Natl Acad Sci U S A. Aug. 12, 2008;105(32):11264-9. Epub Aug. 6, 2008.

Sivaraman, et al. Codon choice in genes depends on flanking sequence information—implications for theoretical reverse translation. Nucleic Acids Res. Feb. 2008;36(3):e16. Epub Jan. 18, 2008.

(56) References Cited

OTHER PUBLICATIONS

Soni, et al. Progress toward ultrafast DNA sequencing using solid-state nanopores. Clin Chem. Nov. 2007;53(11):1996-2001. Epub Sep. 21, 2007.
Stewart, et al. Dependence of McrBC cleavage on distance between recognition elements. Biol Chem. Apr.-May 1998;379(4-5):611-6.
Stewart, et al. Methyl-specific DNA binding by McrBC, a modification-dependent restriction enzyme. J Mol Biol. May 12, 2000;298(4):611-22.
Sudmant, et al. Diversity of human copy number variation and multicopy genes. Science. Oct. 29, 2010;330(6004):641-6.
Sutherland, et al. McrBC a multisubunit GTP-dependent restriction endonuclease. J. Mol. Microbiol. 1992; 225:327-334.
Syvanen. Accessing genetic variation: genotyping single nucleotide polymorphisms. Nat Rev Genet. Dec. 2001;2(12):930-42.
Takai, et al. Comprehensive analysis of CpG islands in human chromosomes 21 and 22. Proc Natl Acad Sci U S A. Mar. 19, 2002;99(6):3740-5. Epub Mar. 12, 2002.
Taylor, et al. Functional copy-number alterations in cancer. PLoS One. Sep. 11, 2008;3(9):e3179.
Timmermans, et al. Characterization of a meiotic crossover in maize identified by a restriction fragment length polymorphism-based method. Genetics. Aug. 1996;143(4):1771-83.
Tong, et al. Noninvasive prenatal detection of trisomy 21 by an epigenetic-genetic chromosome-dosage approach. Clin Chem. Jan. 2010;56(1):90-8. Epub Oct. 22, 2009.
Tosch, et al. Large branched self-assembled DNA complexes. J. of Physics: Conference Series. 2007; 61:1241-1245 doi:10.1088/1742-6596/61/1/245 International Conference on Nanoscience and Technology (ICN&T 2006).
UK combined office action and search report dated Apr. 7, 2011 for GB1100787.9.
Van Opstal, et al. Rapid aneuploidy detection with multiplex ligation-dependent probe amplification: a prospective study of 4000 amniotic fluid samples. Eur J Hum Genet. Jan. 2009;17(1):112-21.
Vogelstein, et al. Digital PCR. Proc Natl Acad Sci U S A. Aug. 3, 1999;96(16):9236-41.
Wang, et al. Allele quantification using molecular inversion probes (MIP). Nucleic Acids Res. Nov. 28, 2005;33(21):e183.
Wang, et al. Analysis of molecular inversion probe performance for allele copy number determination. Genome Biol. 2007; 8(11):R246.
Wang, et al. Digital karyotyping. Proc Natl Acad Sci U S A. Dec. 10, 2002;99(25):16156-61.
Weber, et al. Chromosome-wide and promoter-specific analyses identify sites of differential DNA methylation in normal and transformed human cells. Nat Genet. Aug. 2005;37(8):853-62. Epub Jul. 10, 2005.
White, et al. Digital PCR provides sensitive and absolute calibration for high throughput sequencing BMC Genomics. Mar. 19, 2009;10:116, 12 pages.
White, et al. Retrotransposons in the flanking regions of normal plant genes: a role for copia-like elements in the evolution of gene structure and expression. Proc Natl Acad Sci U S A. Dec. 6, 1994;91(25):11792-6.
Wong, et al. A comprehensive analysis of common copy-number variations in the human genome. Am J Hum Genet. Jan. 2007;80(1):91-104. Epub Dec. 5, 2006.
Wright. The use of cell-free fetal nucleic acids in maternal blood for non-invasive prenatal diagnosis. Hum Reprod Update. Jan.-Feb. 2009;15(1):139-51. Epub Oct. 22, 2008.
Wu, et al. The ligation amplification reaction (LAR)—amplification of specific DNA sequences using sequential rounds of template-dependent ligation. Genomics. May 1989;4(4):560-9.
Yang, et al. A novel universal real-time PCR system using the attached universal duplex probes for quantitative analysis of nucleic acids. BMC Mol Biol. Jun. 4, 2008;9:54 13 pages.
Zejskova, et al. Feasibility of fetal-derived hypermethylated RASSF1A sequence quantification in maternal plasma—next step toward reliable non-invasive prenatal diagnostics. Exp Mol Pathol. Dec. 2010;89(3):241-7.
Kane, et al. Rapid, high-throughput, culture-based PCR methods to analyze samples for viable spores of Bacillus anthracis and its surrogates. J Microbio Methods. 2009; 76:278-284.
Letant, et al. Most-Probable-Number Rapid Viability PCR method to detect viable spores Bacillus anthracis in swab samples. J Microbio Methods. 2010; 81:200-202.
Kiss, et al. High-throughput quantitative polymerase chain reaction in picoliter droplets. Anal Chem. Dec. 1, 2008;80(23):8975-81.
Office action dated Sep. 5, 2014 for U.S. Appl. No. 13/400,030.
Brenner, et al. Gene expression analysis by massively parallel signature sequencing (MPSS) on microbead arrays. Nat Biotechnol. Jun. 2000;18(6):630-4.
Chan, et al. Hypermthylated RASSF1A in maternal plasma: A universal fetal DNA marker that improves the reliability of noninvasive prenatal diagnosis. Clin. Chem. 2006; 52(12):2211-2218.
Conze, et al. Analysis of genes, transcripts, and proteins via DNA ligation. Annu Rev Anal Chem (Palo Alto Calif). 2009;2:215-39.
International search report and written opinion dated Aug. 3, 2012 for PCT/US2012/025760.
International search report and written opinion dated Aug. 3, 2012 for PCT/US2012/024573.
Milbury, et al. PCR-based methods for for the enrichment of minority alleles and mutations. Clin. Chem. 2009; 55(4):632-640.
Shi, et al. Digital quanitification of gene expression emulsion PCR. Electrophoresis. Jan. 2010;31(3):528-34.
Tsui, et al. Epigenetic approaches for the detection of fetal DNA in maternal plasma. Chimerism. Jul. 2010;1(1):30-35.
Yoshimoto, et al. High-resolution analysis of DNA copy number alterations and gene expression in renal clear cell carcinoma. J Pathol. Dec. 2007;213(4):392-401.
Caughey, et al. Chorionic villus sampling compared with amniocentesis and the difference in the rate of pregnancy loss. Obstet Gynecol. Sep. 2006;108(3 Pt 1):612-6.
D'Alton. Prenatal diagnostic procedures. Semin Perinatol. Jun. 1994;18(3):140-62.
Dhallan, et al. Methods to increase the percentage of free fetal DNA recovered from the maternal circulation. JAMA. Mar. 3, 2004;291(9):1114-9.
Nicolaidis, et al. Origin and mechanisms of non-disjunction in human autosomal trisomies. Hum Reprod. Feb. 1998;13(2):313-9.
Office action dated Oct. 3, 2013 for U.S. Appl. No. 12/954,634.
James G. Wetmur et al., "Molecular haplotping by linking emulsion PCR: analysis of paraoxonase 1 haplotypes and phenotypes", Nucleic Acids Research, vol. 33, No. 8, published online May 10, 2005, pp. 2615-2619.
Richard Williams et al., "Amplification of complex gene libraries by emulsion PCR", Nature Methods, published online Jun. 21, 2006, 6 pgs.
Yolanda Schaerli et al., "The potential of microfluidic water-in-oil droplets in experimental biology", Molecular BioSystems, vol. 5, published online Oct. 12, 2009, pp. 1392-1404.
European Patent Office, "European Search Report" in connection with related European Patent Application No. 12744865, dated Dec. 15, 2014, 9 pgs.
James G. Wetmur et al., "Molecular haplotyping by linking emulsion PCR: analysis of paraoxonase 1 haplotypes and phenotypes", Nucleic Acids Research, vol. 33, No. 8, May 10, 2005, pp. 2615-2619.
Stephan Menzel et al., "Experimental Generation of SNP Haplotype Signatures in Patients with Sickle Cell Anaemia", PLoS One, vol. 5, Issue 9, Sep. 24, 2010, 8 pages.
James G. Wetmur et al., "Linking Emulsion PCR Haplotype Analysis", Methods in Molecular Biology, vol. 687, 2011, pp. 165-175.
Wolfgang Barz, Examiner, European Patent Office, "Extended European Search Report" in connection with related European Patent Application No. 12744865.2, dated Apr. 20, 2015, 11 pages.

* cited by examiner

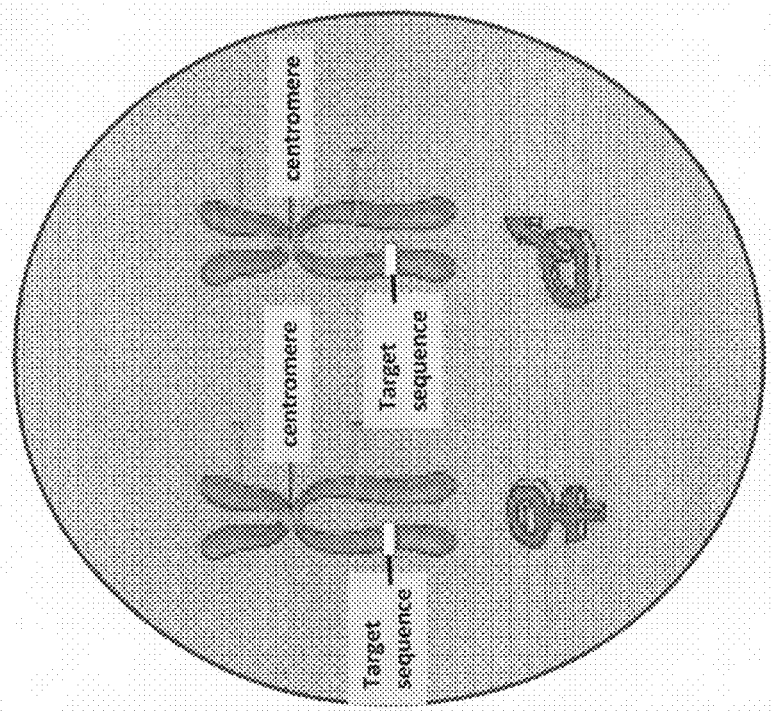
Figure 2
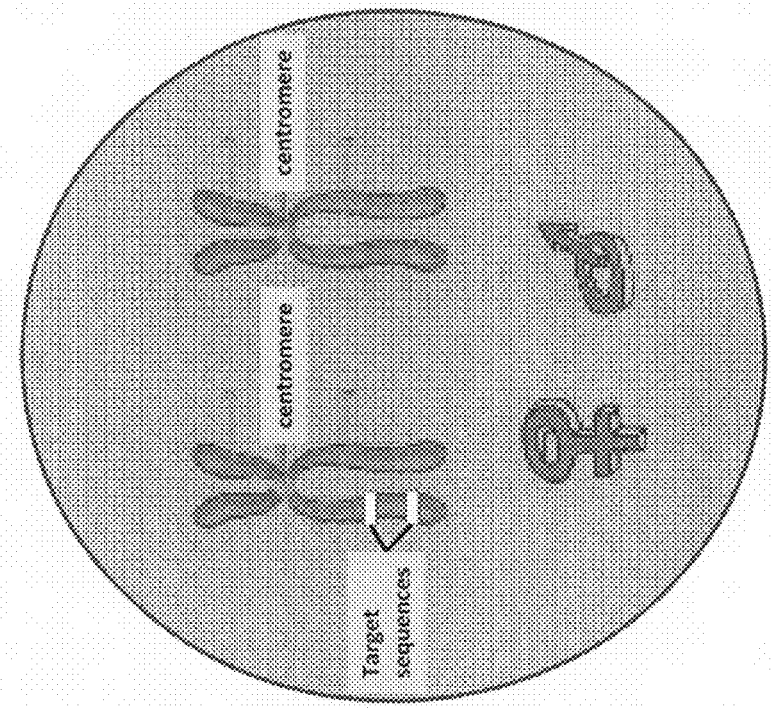

322 Separate a sample into subsamples

324 Physically separate target sequences in a first subsample

326 Separate first subsample into a plurality of partitions

328 Estimate copy number of target sequence in the first subsample

330 Separate second subsample into a plurality of partitions

332 Estimate copy number of target sequence in the second subsample

334 Determine linkage of the target sequence

Figure 13

Enzyme Picker: MRGPRX1 CNV

Assay: MRGPRX1 CNV
Visualize Restriction Sites

Sequence #1:
Amplicon Length: 70bp
Prefix Length: 1000bp
Suffix Length: 1000bp

Single Digests

| Name | # Cuts | Cost/100 units |
|---|---|---|
| NlaIII | 26 | $12.20 |
| DdeI | 24 | $6.10 |
| Fast DdeI | 24 | $12.80 |
| HpyF3I | 24 | $10.00 |
| MboI | 18 | $13.20 |
| DpnII | 18 | $6.30 |
| TseI | 16 | $77.33 |

Figure 14

Cutter Analysis: MRGPRX1 CNV

Select an enzyme and press 'Cut' to determine if an enzyme cuts within the amplicon (green) or surrounding regions (red, blue). You can hover over the color bar with your mouse to see the sequence itself, and whether or not cuts come close to the amplicon. Red color bars indicate a restriction site may be altered by a mutation; green color bars are restriction sites that emerge due to mutations

Assay: MRGPRX1 CNV
Pick Restriction Digests

Amplicon Length: 70bp
Prefix Length: 300bp
Suffix Length: 300bp
Sequence FASTA Codes: chr11 18955710+18956379, chr11 18955710-18956379

Test Cutters
Enzyme: HaeIII
Sequence: GGCC
Fragment Length: 89
Fragment %GC: 39.33%

Results
Cuts both sides
Amplicon Cuts: 0
Prefix Cuts: 6
Suffix Cuts: 4

Figure 15A

Edit Assay: MRGPRX1 CNV

*Name: MRGPRX1 CNV

Gene:

Entered By:

| Enter By Primer | Enter By Location | Enter By SNP |

Forward Primer: TTAAGCTTCATCAGTATCCCCA

Reverse Primer: CAAAGTAGGAAAACATCATCACAGGA

Probe Sequence: ACCATCTCTAAAATCCT

Dye: FAM

Quencher: MGB

Secondary Structure?:

Optimal Anneal Temp:
*In degrees Celsius*

Reference Source: Internal Sites page

Figure 15B

MRGPRX1 CNV

Entered By:  on 2010/10/01
Forward Primer: TTAAGCTTCATCAGTATCCCCCA  43% GC  61.3° tM  ΔG 0.00
Reverse Primer: CAAAGTAGGAAAACATCATCACAGGA  38% GC  61.3° tM  ΔG 0.00
Probe:  5'-FAM-ACCATCTCTAAAATCCT-MGB-3'  35% GC  68.5° tM  ΔG 0.00

Match #1:

Amplicon Region: chr11:18956010-18956079 (70bp)  39% GC  ΔG 0.00

Sequence (hg19 refseq):

```
+: 5'-caaagtaggaaaacatcatcacaggatagaggatttagagatgtatgggatactgatgaagcttaa-3'
-: 5'-TTAAGCTTCATCAGTATCCCCAtaccatctctaaaatcctctatccTGTCATGATGTTTCCTACTTTG-3'
```

Confirmed Sample CNVs

| Sample | Reference | CNV# | Evidence Plate | Other Evidence | Reporter | Actions |
|---|---|---|---|---|---|---|
| NA10851 | | 1 | | Stored | RyanK | Edit |
| NA11994 | | 1 | | Stored | RyanK | Edit |
| NA12155 | | 2 | | Stored | RyanK | Edit |
| NA12872 | | 2 | | Stored | RyanK | Edit |
| NA12873 | | 3 | | Stored | RyanK | Edit |

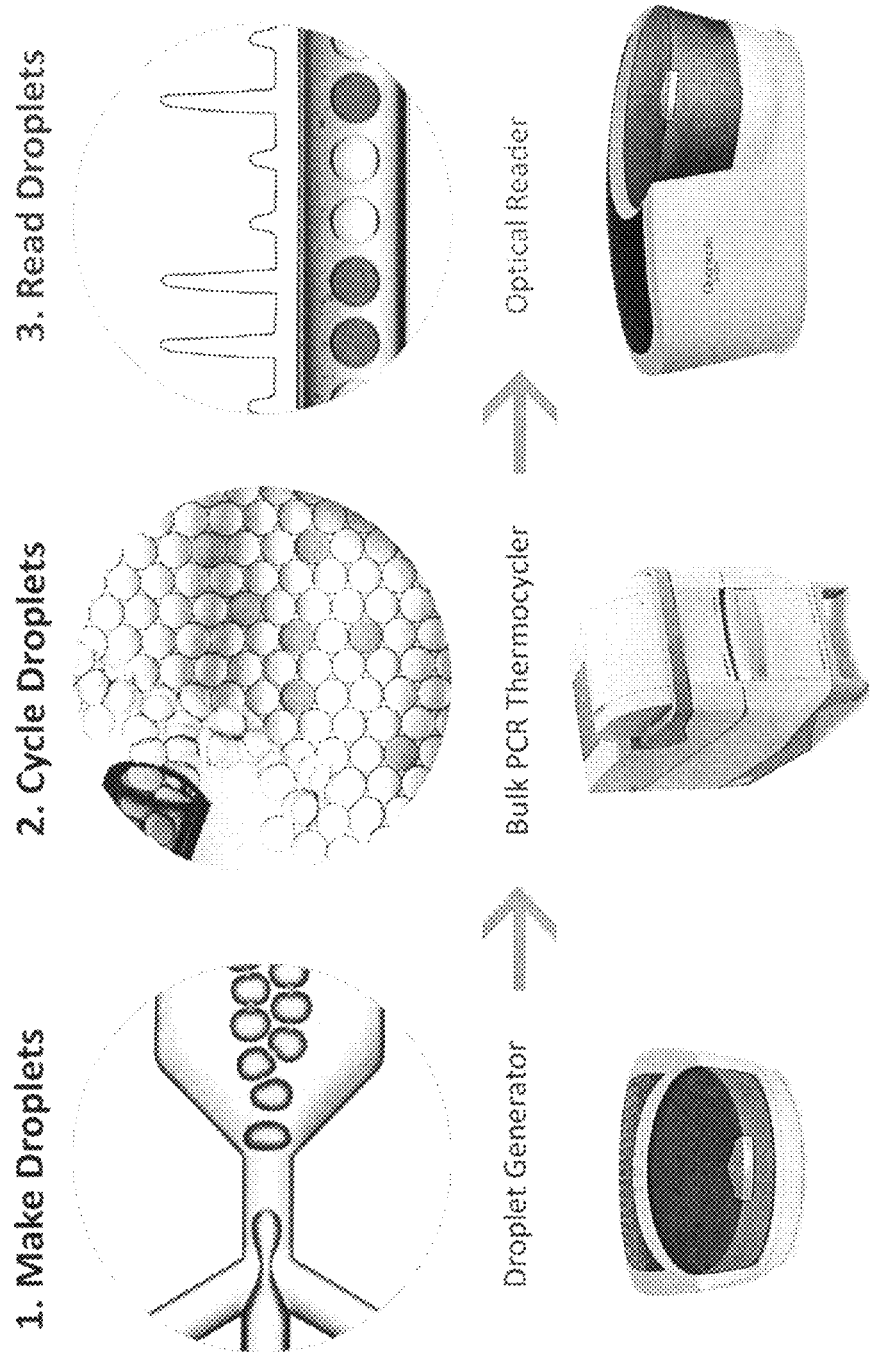

The higher oil/sample ratio shifts the jetting threshold

Figure 19

| sample # | 1 | 2 | 3 | 4 | 5 | 6 | 7 | 8 | Sample Type | Conc (ng/ul) |
| --- | --- | --- | --- | --- | --- | --- | --- | --- | --- | --- |
| nom psi | 0.5 | 1 | 1.5 | 2 | 2.5 | 3 | 3.5 | 4 | | |
| 1 | J | J | J | J | J | J | J | J | Raji undig | 75 |
| 2 | N | N | E | E | J | J | J | J | Raji undig | 37.5 |
| 3 | E | E | E | E | J | J | J | J | Raji undig | 18.75 |
| 4 | N | N | N | N | N | N | N | N | Raji undig | 3.75 |
| 5 | E | E | E | E | E | J | J | J | Raji undig | 0 |
| 6 | E | E | J | J | J | J | J | J | 19205 undig | 75 |
| 7 | J | J | J | J | J | J | J | J | 19205 undig | 37.5 |
| 8 | E | E | E | E | E | E | E | E | 19205 undig | 18.75 |
| 9 | N | N | N | N | E | N | E | air | 19205 undig | 3.75 |
| 10 | E | E | E | E | E | N | J | E | 19205 undig | 0 |
| 11 | N | N | N | N | N | N | N | N | Raji digested | 75 |
| 12 | N | N | N | N | N | N | N | N | Raji digested | 37.5 |
| 13 | N | N | N | N | N | N | N | N | Raji digested | 18.75 |
| 14 | N | N | N | N | N | N | N | N | Raji digested | 3.75 |
| 15 | N | N | N | N | N | J | N | J | Raji digested | 0 |
| 16 | E | E | E | E | E | J | J | N | 19205 digested | 75 |
| 17 | N | N | N | N | N | N | N | N | 19205 digested | 37.5 |
| 18 | N | N | N | N | N | N | N | N | 19205 digested | 18.75 |
| 19 | N | N | N | N | N | N | N | N | 19205 digested | 3.75 |
| 20 | N | N | N | N | N | N | N | N | 19205 digested | 0 |

J = jetting
E = extension
N = normal (no jetting or extension)

Copy Number Variation

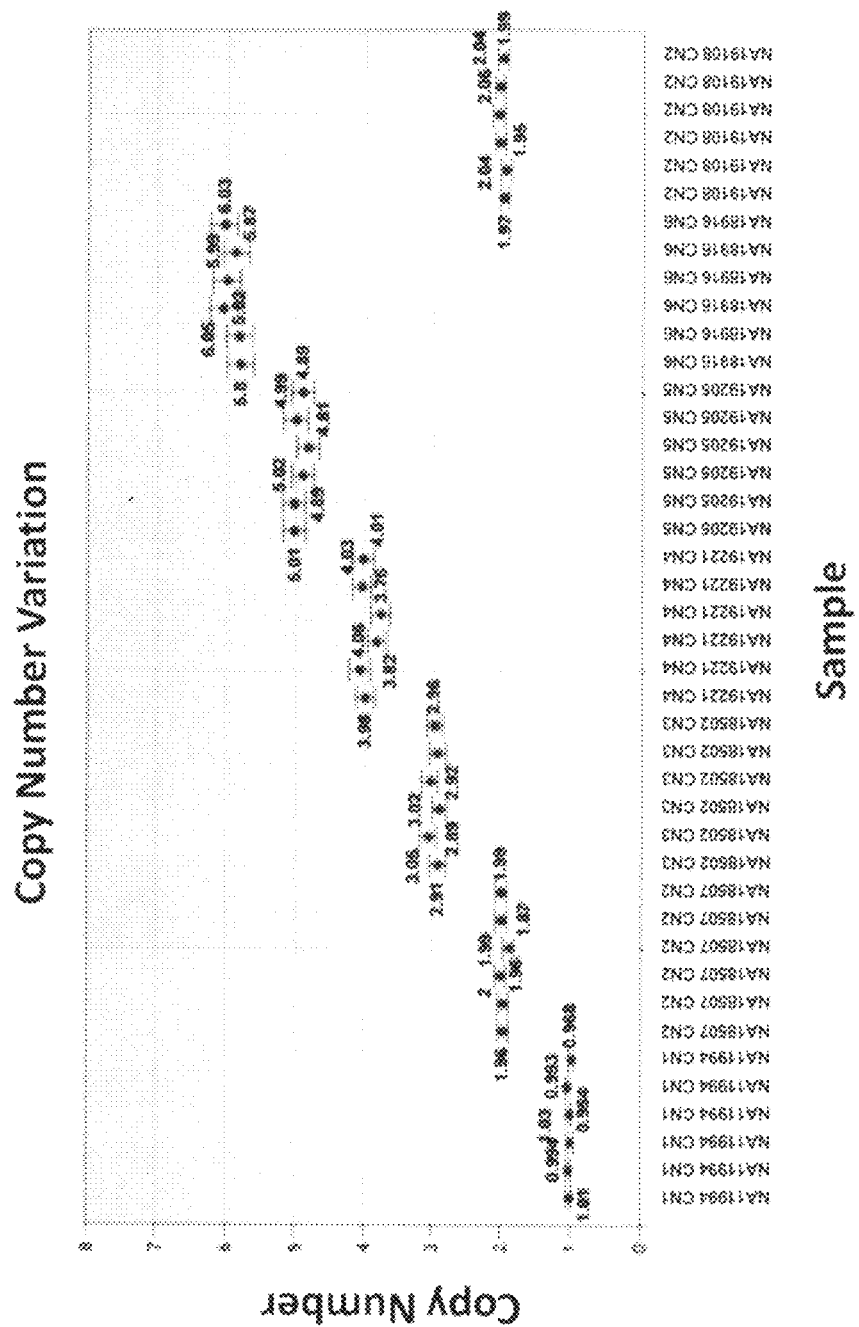

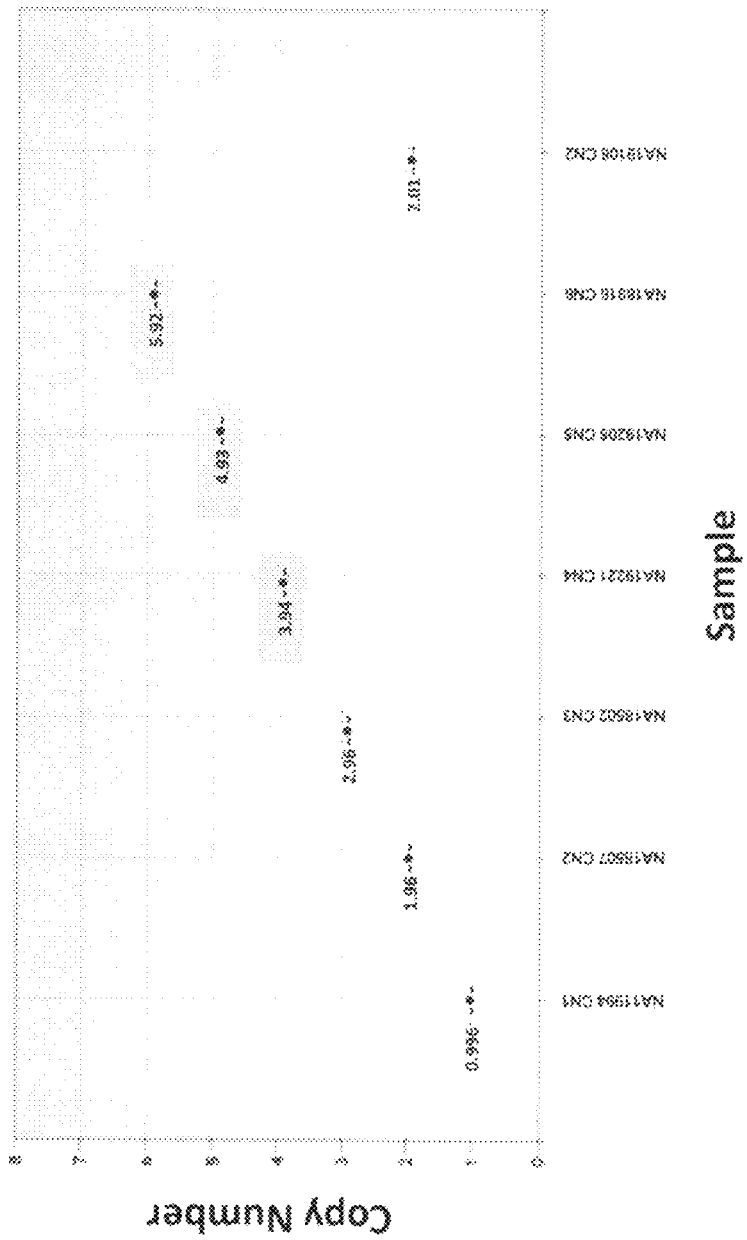

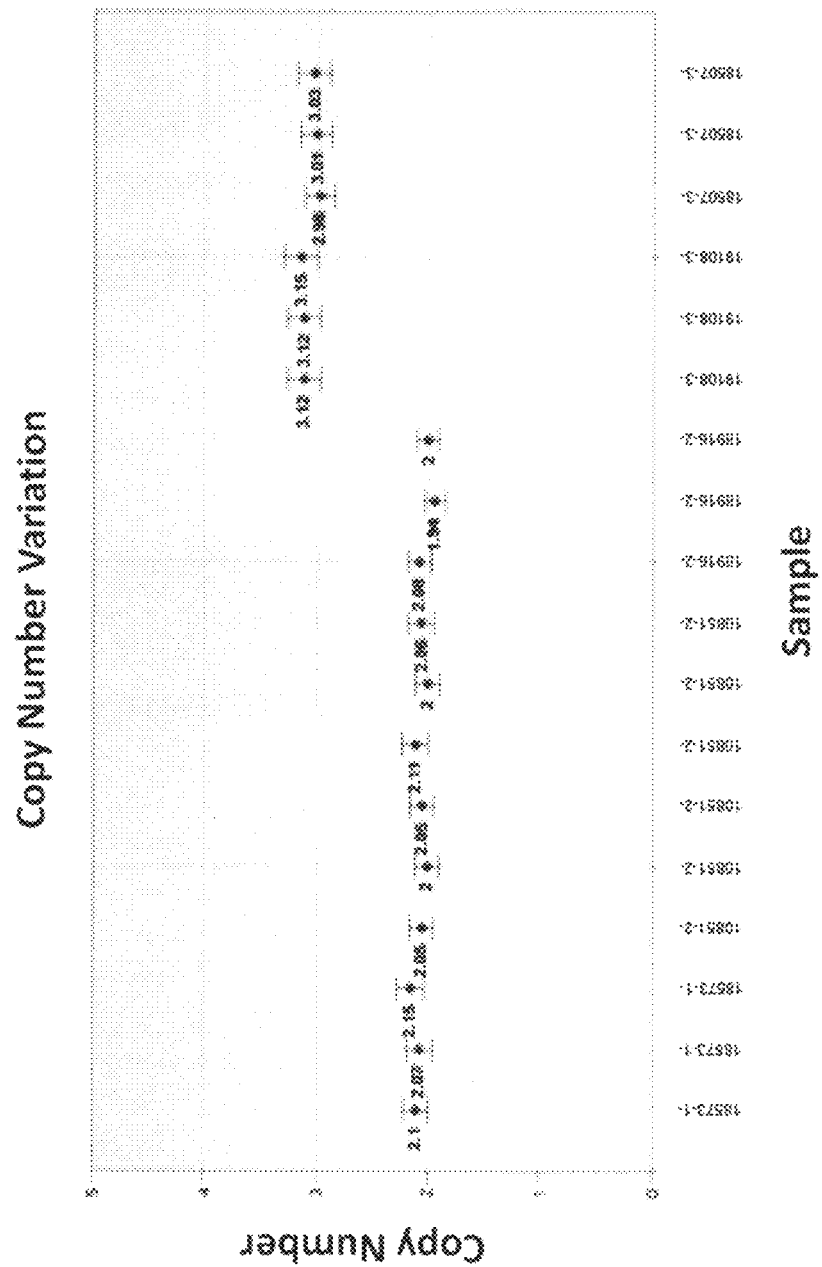

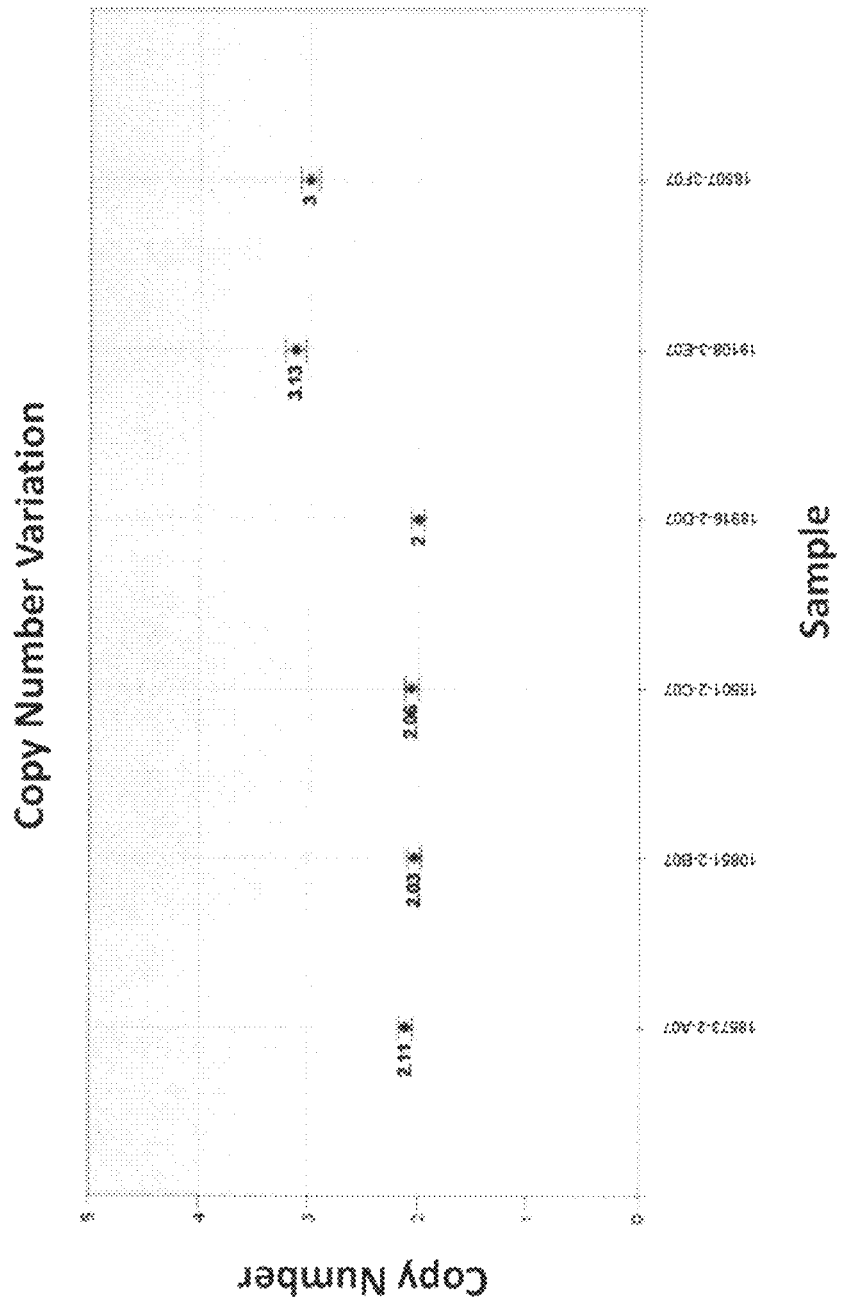

Fluorescence Intensity at 28 cycles

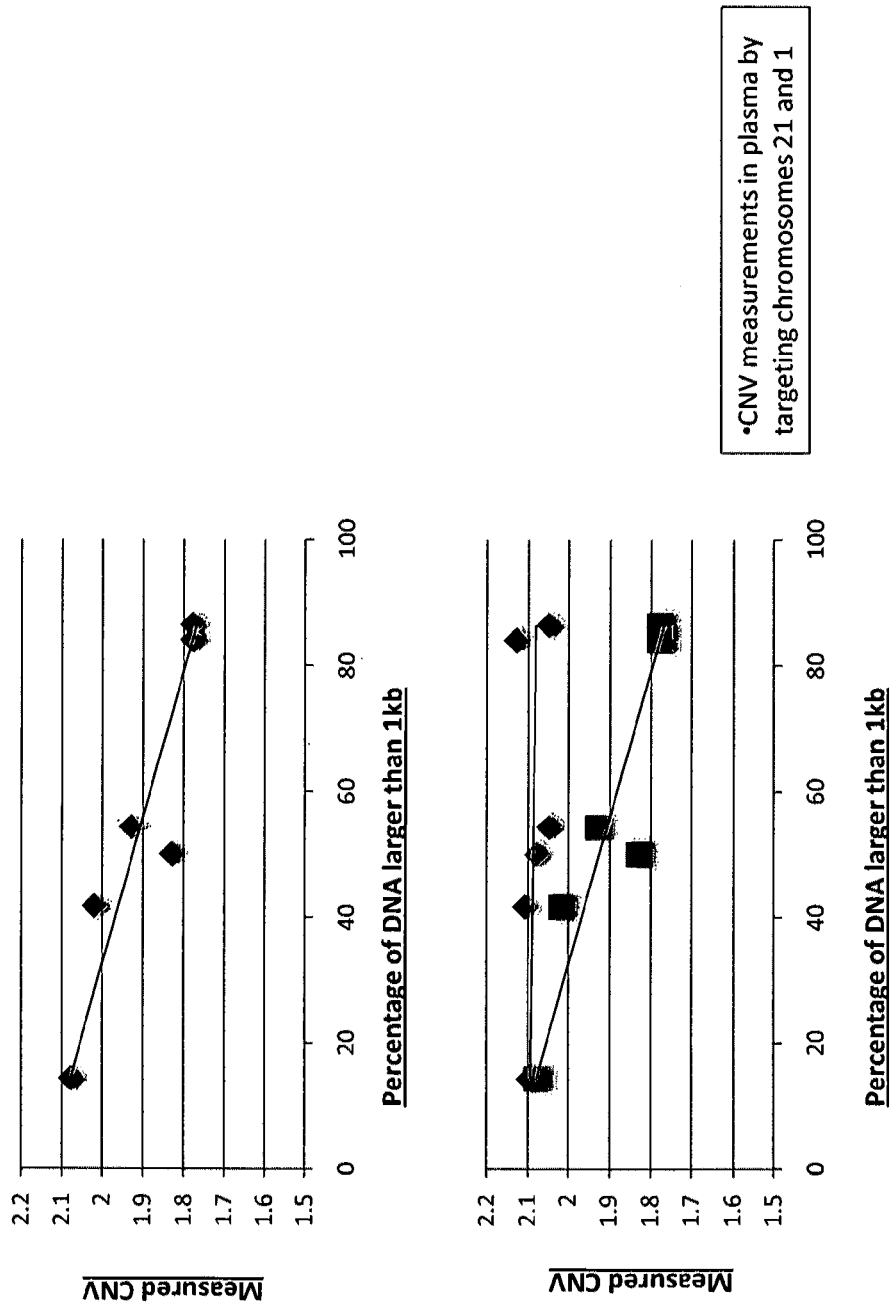

Figure 45

| Restriction Enzyme | Methylation Sensitivity | Digestion Buffer | Inc. Temp | Test Assays | | |
|---|---|---|---|---|---|---|
| EcoRI | OL CpG | EcoRI Buffer | 37 | MRGPRX1 | CYP2D6 | CCL3L1 |
| | | | | QL_RPP30 | QL_RPP30 | QL_RPP30 |
| RsaI | CQL Dam | NEB 4 | 37 | MRGPRX1 | CYP2D6 | CCL3L1 |
| | | | | QL_RPP30 | Chrm 16 | QL_RPP30 |
| MseI | ok | NEB 4, BSA | 37 | MRGPRX1 | CYP2D6 | CCL3L1 |
| | | | | QL_RPP30 | QL_RPP30 | QL_RPP30 |
| MboI | OL Dam, CpG Imp | NEB 4 | 37 | MRGPRX1 | Chrm X | CCL3L1 |
| | | | | QL_RPP30 | QL_RPP30 | QL_RPP30 |
| AluI | ok | NEB 4 | 37 | MRGPRX1? | SRY | CCL3L1 |
| | | | | QL_RPP30 | QL_RPP30 | QL_RPP30 |
| TaqaI | OL Dam | NEB 4, BSA | 37 | MRGPRX1 | CYP2D6 | CCL3L1 |
| | | | | QL_RPP30 | QL_RPP30 | QL_RPP30 |
| BsmI | ok | NEB 4 | 65 | MRGPRX1 | CYP2D6 | CCL3L1 |
| | | | | QL_RPP30 | QL_RPP30 | QL_RPP30 |
| BstYI | ok | NEB 2 | 60 | MRGPRX1 | CYP2D6 | CCL3L1 |
| | | | | QL_RPP30 | QL_RPP30 | QL_RPP30 |
| XhoI | CpG Imp | NEB 4, BSA | 37 | MRGPRX1 | CYP2D6 | CCL3L1 |
| | | | | QL_RPP30 | QL_RPP30 | QL_RPP30 |
| DpnII | Dam | DpnII Buffer | 37 | MRGPRX1 | CYP2D6 | CCL3L1 |
| | | | | QL_RPP30 | QL_RPP30 | QL_RPP30 |
| HaeIII | ok | NEB 4 | 37 | MRGPRX1 | Chrm X | CCL3L1 |
| | | | | QL_RPP30 | QL_RPP30 | QL_RPP30 |
| HpaII | CpG | NEB 1 | 37 | MRGPRX1 | CYP2D6 | CCL3L1 |
| | | | | QL_RPP30 | QL_RPP30 | QL_RPP30 |
| HhaI | CpG | NEB 4, BSA | 37 | MRGPRX1 | CYP2D6 | CCL3L1 |
| | | | | Chrm 14 | QL_RPP30 | Chrm 14 |
| MspI | ok | NEB 4 | 37 | MRGPRX1 | CYP2D6 | CCL3L1 |
| | | | | QL_RPP30 | QL_RPP30 | QL_RPP30 |
| TseI | CQL CpG | NEB 4 | 65 | MRGPRX1 | CYP2D6 | CCL3L1 |
| | | | | QL_RPP30 | QL_RPP30 | QL_RPP30 |
| BstUI | CpG | NEB 4 | 60 | MRGPRX1 | CYP2D6 | CCL3L1 |
| | | | | Chrm 14 | QL_RPP30 | Chrm 14 |
| NlaIII | ok | NEB 4, BSA | 37 | MRGPRX1 | CYP2D6 | CCL3L1 |
| | | | | QL_RPP30 | QL_RPP30 | QL_RPP30 |

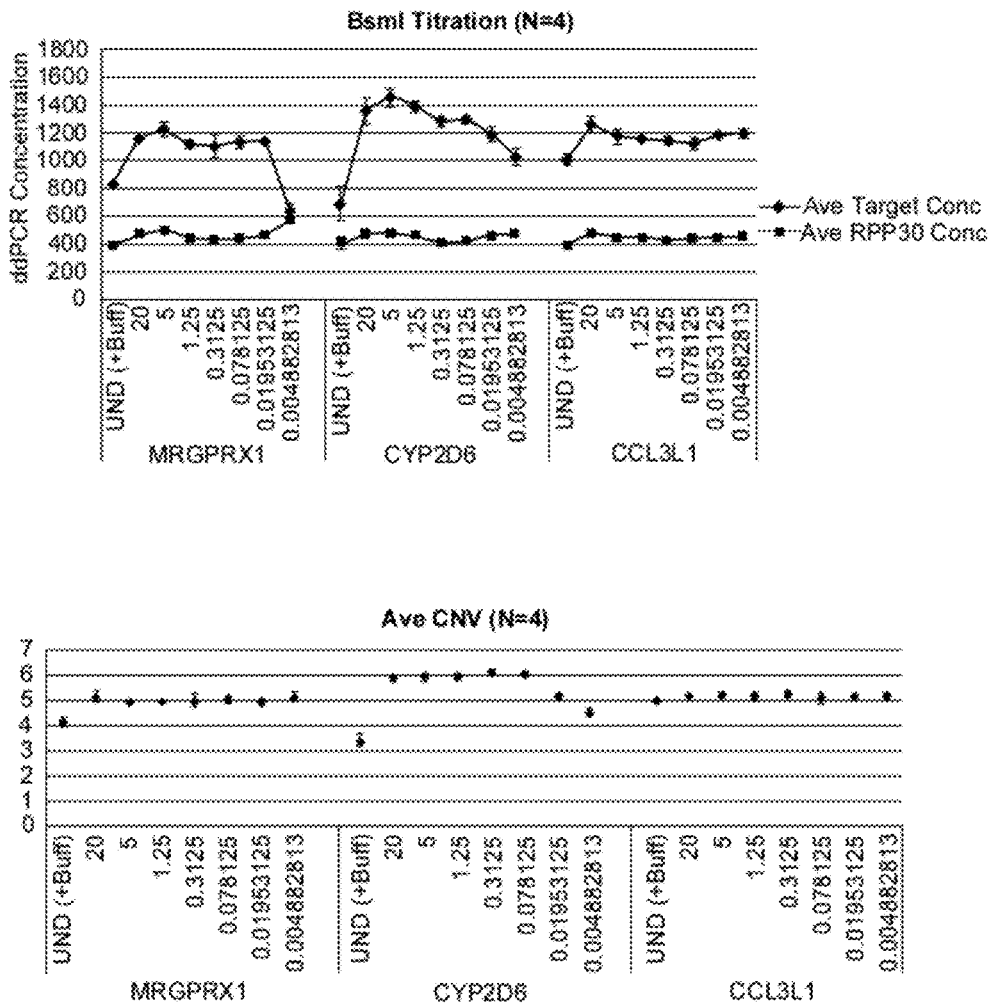

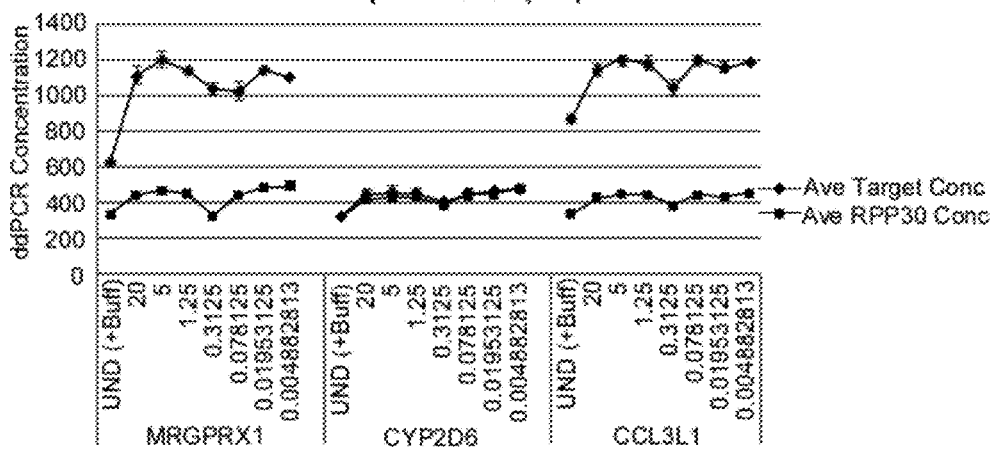
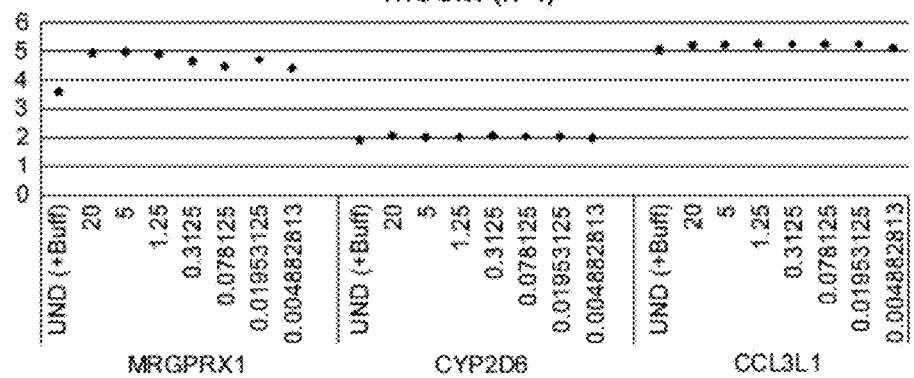
Figure 46
(Continued)

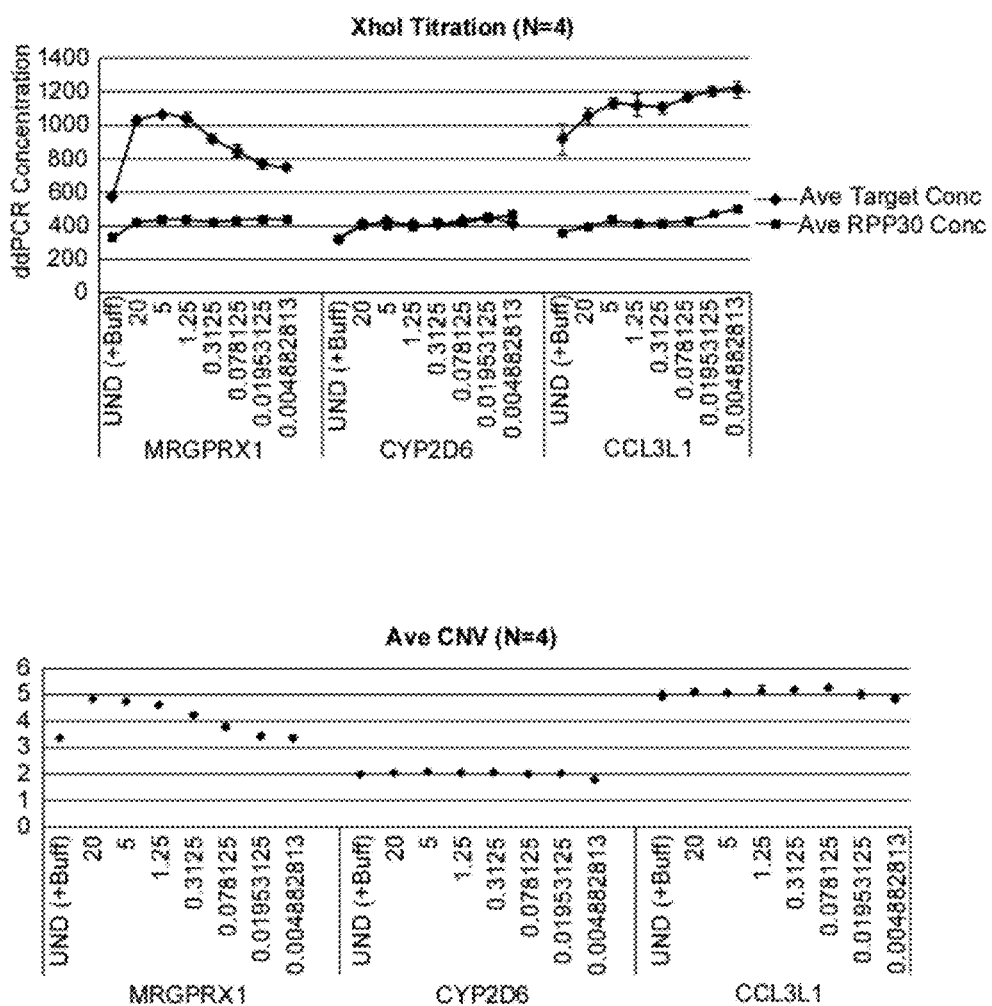

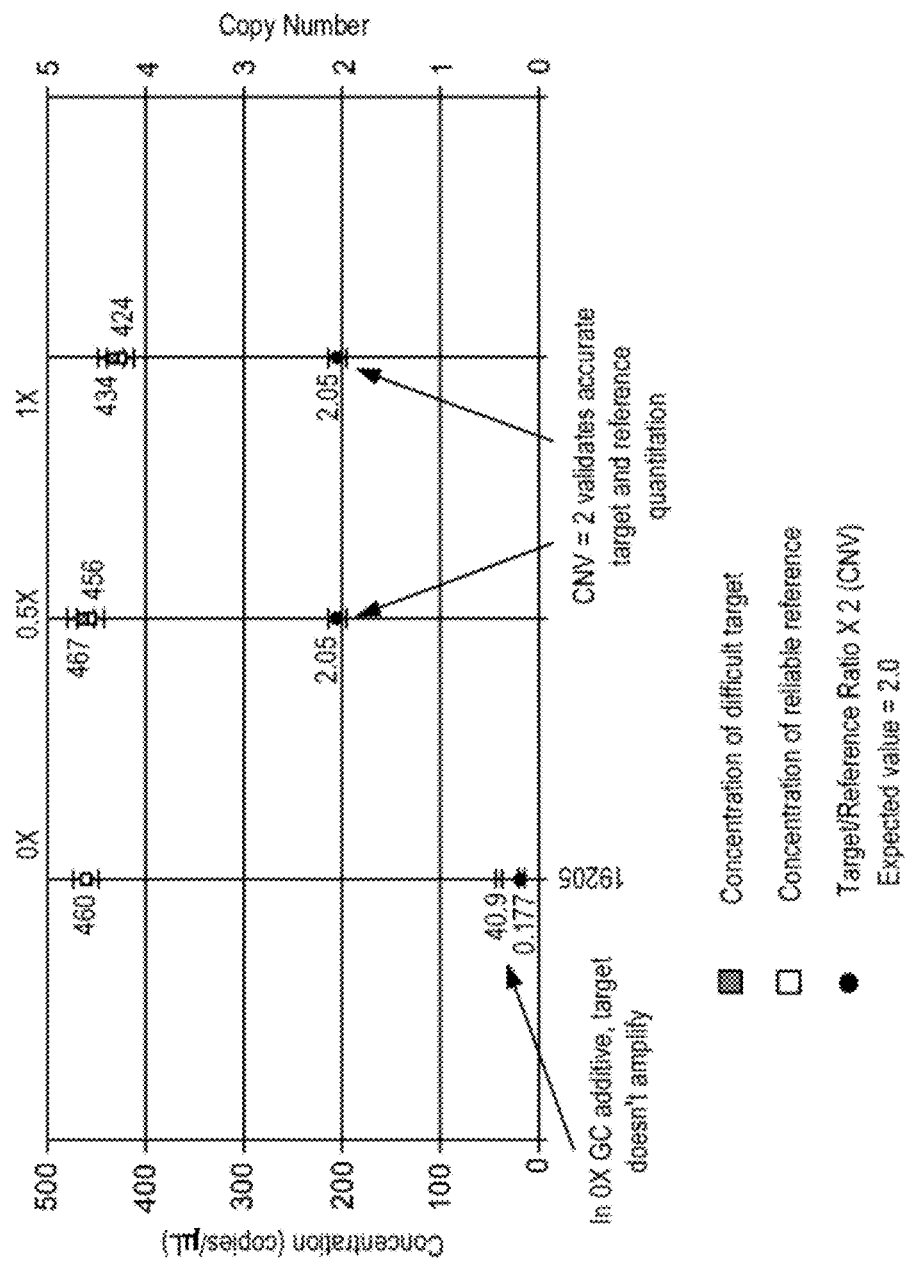

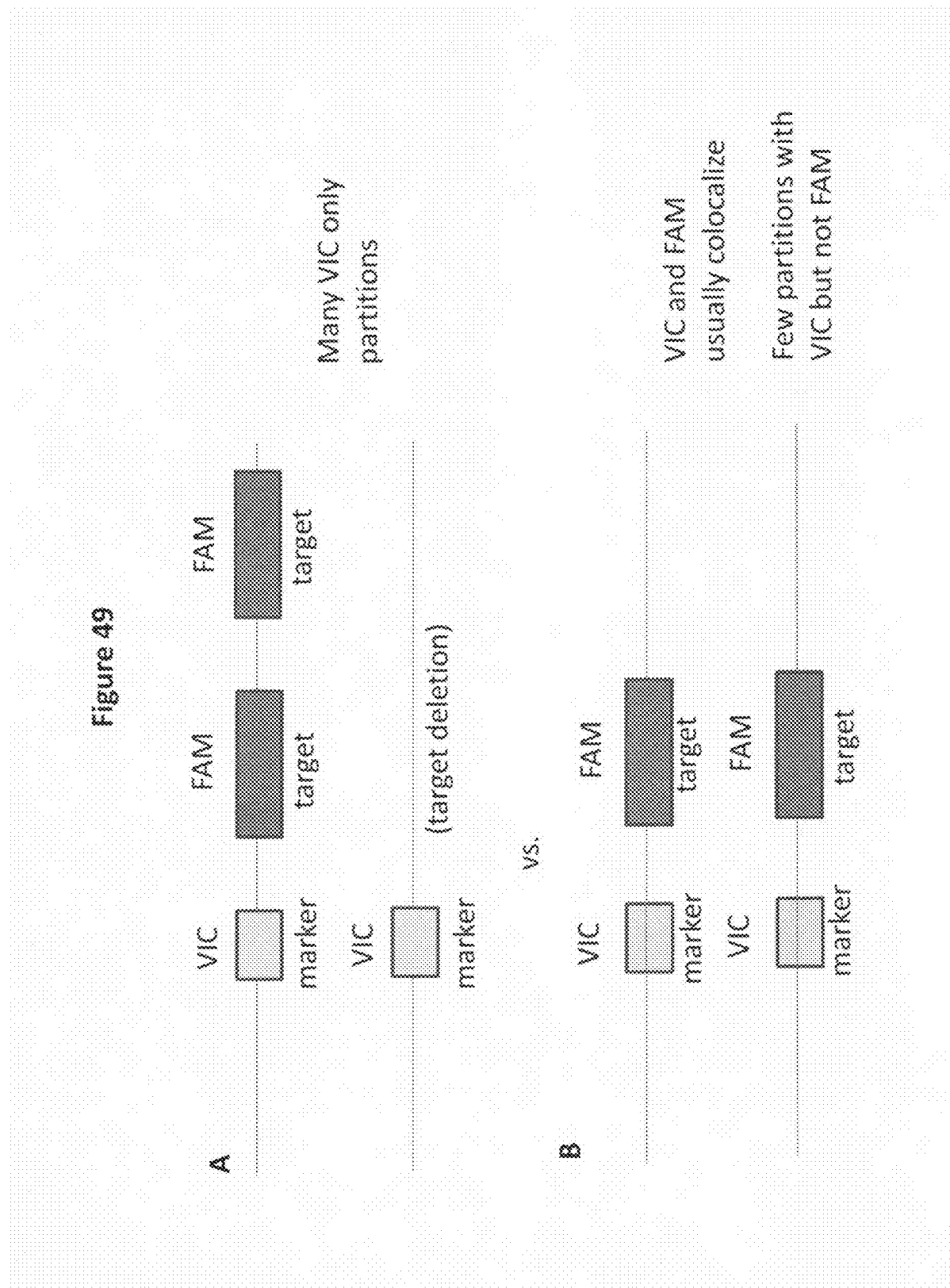

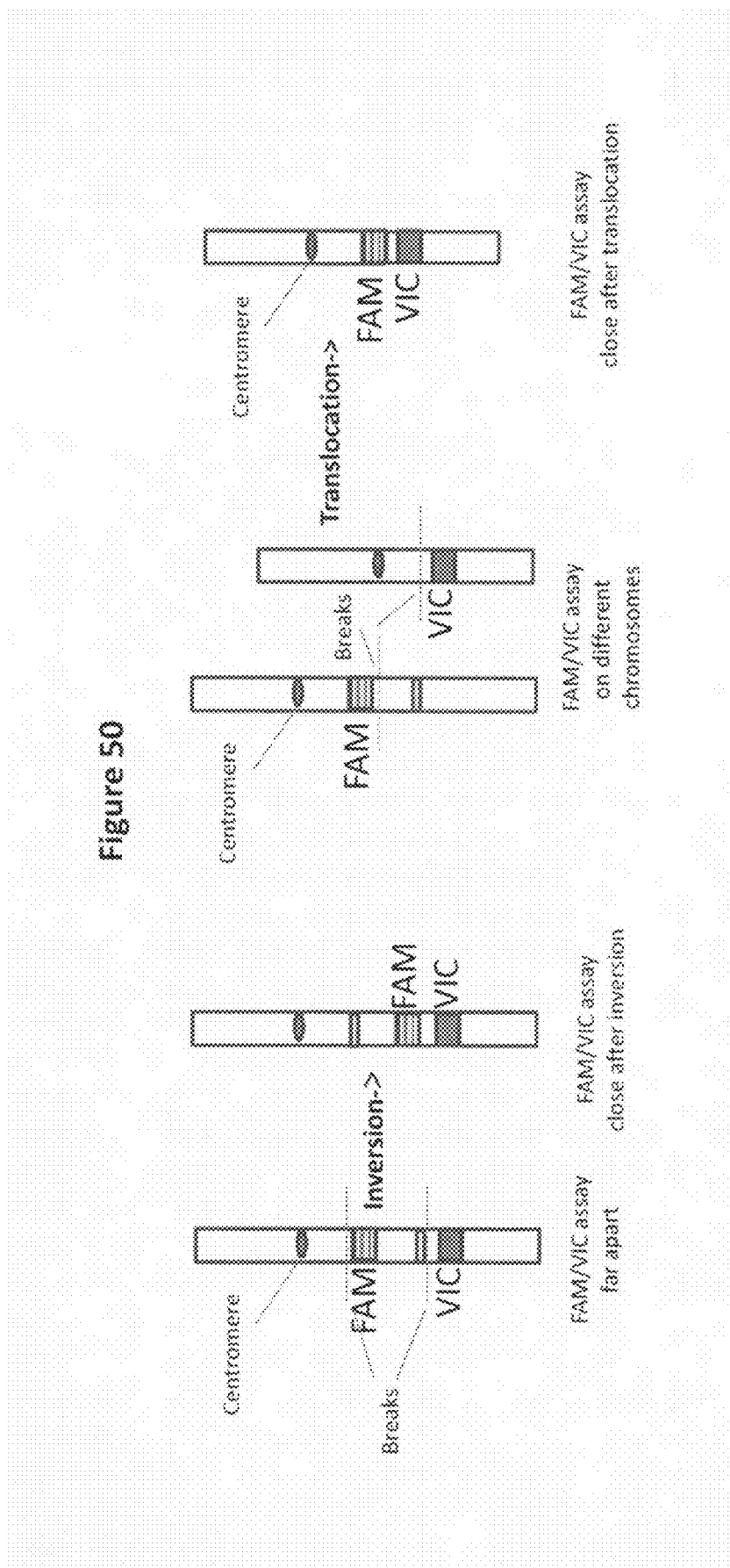

SEQUENCE LISTING

<160> NUMBER OF SEQ ID NOS: 48

<210> SEQ ID NO 1
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(8)
<223> OTHER INFORMATION: a, c, t, g, unknown or other

<400> SEQUENCE: 1
gacnnnnngt c                                                          11

<210> SEQ ID NO 2
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base -continued

```
<222> LOCATION: (4)..(7)
<223> OTHER INFORMATION: a, c, t, g, unknown or other

<400> SEQUENCE: 2 cacnnnngtg                                                          10

<210> SEQ ID NO 3
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(6)
<223> OTHER INFORMATION: a, c, t, g, unknown or other

<400> SEQUENCE: 3
acnnnngtay c                                                        11

<210> SEQ ID NO 4
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(9)
<223> OTHER INFORMATION: a, c, t, g, unknown or other

<400> SEQUENCE: 4
cgannnnnnt gc                                                       12

<210> SEQ ID NO 5
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(8)
<223> OTHER INFORMATION: a, c, t, g, unknown or other

<400> SEQUENCE: 5
gccnnnnngg c                                                        11

<210> SEQ ID NO 6
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(7)
<223> OTHER INFORMATION: a, c, t, g, unknown or other

<400> SEQUENCE: 6 gatnnnnatc                                                          10

<210> SEQ ID NO 7
<211> LENGTH: 11
<212> TYPE: DNA
```

```
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(9)
<223> OTHER INFORMATION: a, c, t, g, unknown or other

<400> SEQUENCE: 7 ccnnnnnng g                                                                 11

<210> SEQ ID NO 8
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(8)
<223> OTHER INFORMATION: a, c, t, g, unknown or other

<400> SEQUENCE: 8
gcannnnntg c                                                                11

<210> SEQ ID NO 9
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(9)
<223> OTHER INFORMATION: a, c, t, g, unknown or other

<400> SEQUENCE: 9
gacnnnnnng tc                                                               12

<210> SEQ ID NO 10
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
cgtaactata acggtcctaa ggtagcgaa                                             29

<210> SEQ ID NO 11
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
tagggataac agggtaat                                                         18

<210> SEQ ID NO 12
<211> LENGTH: 11
<212> TYPE: DNA
<213> ORGANISM: Artificial Sequence
<220> FEATURE:
```

```
<223> OTHER INFORMATION: Description of Artificial Sequence: Synthetic
      oligonucleotide
<220> FEATURE:
<221> NAME/KEY: modified_base
<222> LOCATION: (3)..(9)
<223> OTHER INFORMATION: a, c, t, g, unknown or other

<400> SEQUENCE: 12
gcnnnnnnng c                                                           11

<210> SEQ ID NO 13
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
tggcaaacag ctattatggg tattatgggt                                       30

<210> SEQ ID NO 14
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
atctatgtcg ggtgcggaga aagaggtaat                                       30

<210> SEQ ID NO 15
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(7)
<223> OTHER INFORMATION: a, c, t, g, unknown or other

<400> SEQUENCE: 15 gacnnnngtc                                                             10

<210> SEQ ID NO 16
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(9)
<223> OTHER INFORMATION: a, c, t, g, unknown or other

<400> SEQUENCE: 16
ggccnnnnng gcc                                                         13

<210> SEQ ID NO 17
<211> LENGTH: 26
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 17
ttctgagatt tatctagagg ctggga                                        26

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
ccctgacaga ccgacaagac                                               20

<210> SEQ ID NO 19
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 19
ctggttcagg agccct                                                   16

<210> SEQ ID NO 20
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
gatttggacc tgcgagcg                                                 18

<210> SEQ ID NO 21
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
gcggctgtct ccacaagt                                                 18

<210> SEQ ID NO 22
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 22
ctgacctgaa ggctct                                                   16

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 23
gggtccagaa atacgtcagt                                               20

<210> SEQ ID NO 24
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
catgttccca aggctcag                                                 18

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 25
ttcgaggccc agcgacctca                                               20

<210> SEQ ID NO 26
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
ttaagcttca tcagtatccc cca                                           23

<210> SEQ ID NO 27
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
caaagtagga aaacatcatc acagga                                        26

<210> SEQ ID NO 28
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 28
accatctcta aaatcct                                                  17

<210> SEQ ID NO 29
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
```
atagctattt tttttaactt cctttatttt cc                           32

<210> SEQ ID NO 30
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
tgagcacctt ccttcttttt ga                                      22

<210> SEQ ID NO 31
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 31
ttgtctgaaa ccctg                                              15

<210> SEQ ID NO 32
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 32
ttttgtctaa aaccc                                              15

<210> SEQ ID NO 33
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
ggcacacgtg gcttttcg                                           18

<210> SEQ ID NO 34
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
ggtgaacctc gtaagtttat gcaa                                    24

<210> SEQ ID NO 35
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 35

```
tcaggacgtc gagtggacac ggtg                                          24
```

<210> SEQ ID NO 36
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36

```
ccctgagcaa agagtcacag ataaa                                         25
```

<210> SEQ ID NO 37
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37

```
tgccagggtc tgagtctct                                                19
```

<210> SEQ ID NO 38
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 38

```
actgcgtttg tcctgg                                                   16
```

<210> SEQ ID NO 39
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39

```
gatctagcta agagacagag atagacacat g                                  31
```

<210> SEQ ID NO 40
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40

```
ggccctcatc caccataaca c                                             21
```

<210> SEQ ID NO 41
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41

```
gtgtggagca gagcttggt                                                19
```

<210> SEQ ID NO 42
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 42
tccgaaagag ctggtc                                                    16

<210> SEQ ID NO 43
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
ctccctctcc atagctactt aagga                                          25

<210> SEQ ID NO 44
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
caaggagccc taaccaatgg a                                              21

<210> SEQ ID NO 45
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 45
aaggcagaga ttaaag                                                    16

<210> SEQ ID NO 46
<211> LENGTH: 70
<212> TYPE: DNA
<213> ORGANISM: Homo sapiens

<400> SEQUENCE: 46
caaagtagga aaacatcatc acaggataga ggattttaga gatggtatgg gggatactga    60
tgaagcttaa                                                           70

<210> SEQ ID NO 47
<211> LENGTH: 70
<212> TYPE: DNA
<213> ORGANISM: Homo sapiens

<400> SEQUENCE: 47
ttaagcttca tcagtatccc ccataccatc tctaaaatcc tctatcctgt gatgatgttt    60
tcctactttg                                                           70

<210> SEQ ID NO 48

```
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
cagtattttt gcactgcttt cctcat                                            26
```

ANALYSIS OF NUCLEIC ACIDS

CROSS-REFERENCE

This application claims the benefit of U.S. Provisional Patent Application Nos. 61/441,209, filed Feb. 9, 2011; 61/444,539, filed Feb. 18, 2011; 61/454,373, filed Mar. 18, 2011; 61/476,115, filed Apr. 15, 2011; 61/478,777, filed Apr. 25, 2011; 61/484,197, filed May 9, 2011; and 61/490,055, filed May, 25, 2011, all of which applications are incorporated herein by reference in their entireties.

SEQUENCE LISTING

The instant application contains a Sequence Listing which has been submitted in ASCII format via EFS-Web and is hereby incorporated by reference in its entirety. Said ASCII copy, created on Apr. 27, 2012, is named 38938721.txt and is 12,681 bytes in size.

BACKGROUND OF THE INVENTION

Determining the copy number of a target nucleic acid in a sample from a subject can provide useful information for a variety of clinical applications. However, some assays for determining copy number of a target nucleic acid can underestimate the copy number of the target nucleic acid if multiple copies of the target nucleic acid are on the same polynucleotide in the sample. For instance, in a digital polymerase chain reaction (dPCR), a spatially isolated polynucleotide comprising two copies of a target sequence can be counted as only having one copy of the target nucleic acid. There is a need for improved methods, compositions, and kits for copy number estimation of nucleic acid target sequences in assays, such as dPCR assays, that take into account the linkage of target nucleic acid sequences (e.g., whether multiple copies of a target nucleic acid sequence are on the same polynucleotide in a sample).

Knowledge of haplotypes or phasing of neighboring polymorphisms can be useful in a variety of settings. Humans are diploid organisms, because each chromosome type is represented twice as a pair of individual chromosomes in each of a person's somatic cells. One copy of the pair is inherited from the person's father and the other copy from the person's mother. Therefore, most genes exist as two copies in each diploid cell. However, the copies generally have many loci where sequence variation occurs between the copies to form distinct sequences known as alleles.

It can often be useful to know the pattern of alleles, the haplotype, for each individual chromosome of a chromosome pair. For example, if a person has inactivating mutations at two different loci within a gene, the mutations may be of limited consequence if present together on the same individual chromosome, but could exert a major effect if distributed between both individual chromosomes of a chromosome pair. In the first case, one copy of the gene is inactivated at two different loci, but the other copy is available to supply active gene product. In the second case, each copy of the gene has one of the inactivating mutations, so neither gene copy supplies active gene product. Depending on the gene in question, mutation of both copies of the gene could lead to a variety of physiological consequences including non-viable phenotypes, increased risk of disease, or inability to metabolize a class of medications, among others.

Information on haplotype can be useful information for life sciences applications, the medical field, and in applied markets, such as forensics. The issue of haplotype determination, arises in many contexts of human (and non-human) genetics. For example, many genetic associations are tied to and thus predicted by haplotypes. The HLA (human leukocyte antigen) region is one prominent instance where particular genetic diseases have been associated with various haplotypes of the major histocompatibility complex.

Conventional genotyping technologies interrogate different loci of sequence variation, such as SNPs (single nucleotide polymorphisms), in isolation from one another. Thus, the technologies can confidently determine that a pair of distinct alleles is present at each of two linked loci in a sample of genetic material. However, the technologies cannot tell which combination of alleles from the two loci is located on the same chromosome copy. A new approach to determining haplotypes is needed to overcome this obstacle.

Similarly, new methods are needed for determining the probability of fragmentation between two target nucleic acid sequences in a sample, determining levels of degradation in a sample of nucleic acids (e.g., DNA, RNA), assessing alternative splicing, or detecting inversions, translocations, or deletions.

SUMMARY OF THE INVENTION

In some aspects, this disclosure provides a method of detecting variations in copy number of a target nucleic acid comprising: a. contacting a sample comprising a plurality of polynucleotides with at least one agent, wherein the polynucleotides comprise a first and second target nucleic acid; b. subjecting the sample to conditions that enable the agent to cleave a specifically-selected target site between the two target nucleic acids when the two target nucleic acids are located on the same polynucleotide, thereby separating the two target nucleic acids; c. separating the sample contacted with the agent into a plurality of spatially isolated partitions; d. enumerating the number of spatially isolated partitions comprising the target nucleic acid; and e. determining a copy number of the target nucleic acid based on said enumerating. In some embociments, the spatially isolated partitions are droplets within an emulsion. In some embodiments, the target nucleic acids are present at an average concentration of less than about five copies per droplet, less than about four copies per droplet, less than about three copies per droplet, less than about two copies per droplet, or less than about one copy per droplet. In some embodiments, the specifically-selected target site is located between the first and second target nucleic acids. In some embodiments, the method further comprises subjecting the first and second target nucleic acids to an amplification reaction.

In some embodiments of this aspect, the sequences of the first and second target nucleic acids are identical or near-identical. In some embodiments, the first and second target nucleic acids have different sequences. In some embodiments, the specifically-selected target site is a site capable of digestion with a restriction enzyme. In some embodiments, the agent is one or more restriction enzymes. In some embodiments, the specifically-selected site and the first target nucleic acid are located within the same gene. In some embodiments, the target nucleic acid is correlated with a disease or disorder. In some embodiments, the method further comprises enumerating (or counting) the number of spatially isolated partitions comprising a reference nucleic acid. In some embodiments, the reference nucleic acid is present at a fixed number of copies in a genome from which the sample is derived. In some embodiments, the reference nucleic acid is a housekeeping gene. In some embodiments, the reference nucleic acid is present at two copies per diploid genome from which the sample is derived. In some embodiments, the determining the copy number of the target nucleic acid comprises dividing the number of enumerated target nucleic acids by the number of enumerated reference nucleic acids.

In some embodiments of this aspect, the agent does not cut the sequence of the target nucleic acid. In some embodiments, the agent does not cut the sequence of the reference nucleic acid. In some embodiments, the target nucleic acid is present in multiple copies on a single polynucleotide. In some embodiments, the one or more restriction enzymes have more than one recognition sequence between the two target sequences. In some embodiments, the one or more restriction enzymes do not exhibit significant star activity. In some embodiments, the one or more restriction enzymes comprise two or more restriction enzymes. In some embodiments, the software is used to select the one or more restriction enzymes. In some embodiments, the one or more restriction enzymes are heat-inactivated after digesting the polynucleotides. In some embodiments, the temperature of the heat inactivation is below the melting point of the restricted target fragments in order to maintain the double-stranded nature of the target fragments. In some embodiments, a control restriction enzyme digest is performed to measure the efficiency of digestion of nucleic acid by the one or more restriction enzymes. In some embodiments, the percentage of linked target sequences that are fragmented in the sample is determined.

In another aspect, this disclosure provides a method of detecting variations in copy number of a nucleic acid comprising: a. providing a sample comprising a plurality of polynucleotides, the plurality comprising a first and second target nucleic acid located within at least one of the plurality of polynucleotides; b. cleaving the at least one polynucleotide between the first and a second target nucleic acids, when the first and second target nucleic acids are present within the same polynucleotide to form a cleaved sample; c. separating the cleaved sample into a plurality of spatially isolated regions; d. enumerating the number of spatially isolated regions comprising the target nucleic acids; and e. determining a copy number of the target nucleic acid based on said enumerating; wherein two of the at least two target nucleic acids are located within a same region of the same polynucleotide.

In some embodiments, less than 1 megabase separates the two target nucleic acids. In some embodiments, less than 1 kilobase separates the two target nucleic acids. In some embodiments, the cleaving is accomplished with a restriction enzyme. In some embodiments, the plurality of spatially-isolated regions are droplets within an emulsion. In some embodiments, the method further comprises conducting a PCR reaction prior to the enumerating of step d. In some embodiments, the method does not comprise a sequencing reaction.

In another aspect, the method comprises a method of detecting variations in copy number of a target nucleic acid comprising: a. obtaining a sample comprising (i) a plurality of polynucleotides, wherein at least one of the polynucleotides comprises a first target nucleic acid and a copy of the first target nucleic acid; (ii) a probe with a fluorescent label to detect the target nucleic acid; and (iii) reagents to enable a PCR reaction; b. separating the sample into a plurality of spatially-isolated partitions, wherein the spatially-isolated partitions comprise on average less than five target nucleic acids; c. subjecting the samples to a PCR amplification reaction in order to detect the target nucleic acids; d. detecting the fluorescence intensity of the fluorescent labels before any of the reagents for the PCR reaction become limiting, wherein a higher fluorescence intensity within a partition is indicative of the presence of more than one target nucleic acid on a polynucleotide; e. enumerating the number of partitions that have a fluorescence intensity above a threshold value indicative of one copy of the target nucleic acid; f. enumerating the number of partitions that have a fluorescence intensity above a threshold value indicative of multiple copies of the target nucleic acid; and g. either: (i) calculating the copy number of the target nucleic acid based on the numbers obtained in step e and step for (ii) determining whether two target nucleic acids are present on the same polynucleotide.

In some embodiments, an increased copy number of the target nucleic acid is correlated with a disease or disorder.

In yet another aspect, this disclosure provides a method of identifying a plurality of target nucleic acids as being present on the same polynucleotide comprising, a. separating a sample comprising a plurality of polynucleotides into at least two subsamples, wherein the polynucleotides comprise a first and second target nucleic acid; b. contacting the first subsample with an agent capable of physically separating the first target nucleic acid from the second target nucleic acid if they are present on the same polynucleotide; c. following step b, separating the first subsample into a first set of partitions; d. determining the number of partitions in the first set of partitions that comprise the target nucleic acid; e. separating a second subsample into a second set of partitions; f. determining the number of partitions in the second set of partitions that comprise a target nucleic acid; and g. comparing the value obtained in step d with the value obtained in step f to determine the whether the first and second target nucleic acid are present within the same polynucleotide.

In some embodiments, the first and second target nucleic acids comprise the same sequence. In some embodiments, the agent is a restriction enzyme. In some embodiments, linkage of the first and second target nucleic acid is indicated when the number obtained in step d is significantly higher than the number obtained in step f. In some embodiments, the restriction enzyme recognizes a site between the first and second target nucleic acid. In some embodiments, the first and second target sequences are located within less than 1 megabase of each other. In some embodiments, after contacting the sample with one or more restriction enzymes, the sample is stored for less than 24 hrs before the subsample is separated. In some embodiments, the target sequences are not physically separated in the second subsample. In some embodiments, the method further comprises determining whether the first and second target nucleic acids are on the same chromosome or different chromosomes. In some embodiments, the sequence of the first target nucleic acid is different from the sequence of the second target nucleic acid. In some embodiments, the sequence of the first target nucleic acid is a genetic variation of the second target nucleic acid. In some embodiments, the genetic variation is a single nucleotide polymorphism. In some embodiments, wherein the first and second target nucleic acids are within the same gene. In some embodiments, at least two of the polynucleotides are chromosomes. In some embodiments, the first and second target nucleic acid are located on separate chromosomes. In some embodiments, the first and second target nucleic acid are located on the same chromosome. In some embodiments, at least one of the chromosomes comprises two copies of the first target nucleic acid. In some embodiments, at least one of the chromosomes comprises at least three copies of the first target nucleic acid. In other embodiments, a chromosome comprises at least 1, 2, 3, 4, 5, 6, 7, 8, 9, or 10 copies of the first target nucleic acid. In some embodiments, one or more of the restriction enzymes is a methyl-sensitive restriction enzyme.

In yet another aspect, this disclosure provides a method of determining the probability of fragmentation of polynucleotides in a sample comprising: a. obtaining a sample comprising (i) a plurality of polynucleotides, wherein at least one of the polynucleotides comprises a first target nucleic acid and a second target nucleic acid; (ii) a first labeled probe to detect the first target nucleic acid; (iii) a second labeled probe to detect the second target nucleic acid; and (iii) reagents to enable a PCR reaction; b. separating the sample into a plurality of spatially-isolated partitions, wherein the spatially-isolated partitions comprise on average less than five target polynucleotides; c. subjecting the samples to a PCR amplification reaction in order to detect the first and second target nucleic acids; d. detecting the labeled probe in the partitions; e. based on step d, enumerating the number of partitions that comprise both the first and second target nucleic acids; and f. correlating the number of partitions that comprise both the first and second target nucleic acids with the degree of fragmentation of the sample. In some embodiments, the first and second target nucleic acid are within one megabase apart. In some embodiments, in a normal subject, the first and second target nucleic acids are separated by greater than one kilobase. In some embodiments, the method further comprises calculating the expected number of partitions containing both first and second, target nucleic acids if the target nucleic acids are physically linked. In some embodiments, the probability of fragmentation is positively correlated with a decreased number of partitions that contain both the first and second target nucleic acid.

In yet another different but related aspect, this disclosure provides a method for determining the probability of fragmentation of two genetically linked loci in a sample of polynucleotides comprising: a. performing digital PCR (dPCR) on said sample, wherein the dPCR comprises separating the polynucleotides into separated units; b. determining a first sum of the number of units with signal indicating the presence of a first locus and the number of units with signal indicating the presence of the first locus and a second locus; c. determining a second sum of the number of units with signal indicating the presence of the second locus and the number of units with signal indicating the presence of the first locus and the second locus; and inputting the first and second sums into an algorithm to determine the percentage of the two genetically linked loci in the sample that are fragmented.

In some embodiments, the polynucleotides in the sample are partially degraded. In some embodiments, the polynucleotides are DNA. In some embodiments, the polynucleotides are RNA. In some embodiments, the polynucleotides comprise a mixture of DNA and RNA.

The present disclosure also provides a method for determining the probability that a first target nucleic acid is present on the same polynucleotide as a second target nucleic acid comprising:
a) dividing a sample of polynucleotides into at least two subsamples; b) in a first subsample, pre-amplifying the first and second target nucleic acid with short cycle PCR; c) separating the first subsample into a first set of partitions; d) enumerating the number of partitions from the first subsample that contain the first and second target nucleic acids together; e) separating the second subsample into a second set of partitions; f) enumerating the number of partitions from the second subsample that contain the first and second target nucleic acids together; and g) comparing the value of step f with that of step d in order to determine the probability that the first and second target nucleic acids are linked on the same polynucleotide.

In some embodiments, the short cycle PCR comprises less than 24 cycles of PCR reaction. In some embodiments, the method further comprises use of an algorithm to determine the probability that the first and second target nucleic acids are phased or present on the same polynucleotide.

In another aspect, this disclosure provides a method of identifying the probability of a deletion of a target nucleic acid from a chromosome comprising: (a) subdividing a sample into multiple partitions wherein the sample comprises: (i) a pair of chromosomes such that at least one of the chromosomes contains a first target nucleic acid and wherein both chromosomes contain the same marker nucleic acid; (ii) a first labeled probe to detect the first target nucleic acid; (iii) a second labeled probe to detect the marker nucleic acid; and (iii) reagents to enable a PCR reaction; (b) performing an amplification reaction to detect the first target nucleic acid and the marker nucleic acid within the partitions; (c) enumerating the number of partitions containing the marker nucleic acid and no target nucleic acid; and (d) determining the probability of a deletion of the target nucleic acid from at least one of the chromosomes based on the value of step c, where a higher value in step c is correlated with an increased probability that the target nucleic acid is absent from one of the chromosomes within the pair of chromosomes.

In some embodiments, the target nucleic acid is suspected to be present in multiple copies on at least one of the chromosomes. In some embodiments, the marker and the target nucleic acid are located in close proximity to each other on at least one of the chromosomes. In some embodiments, the marker and the target nucleic acid are within 5000 base pairs apart. In some embodiments, the marker nucleic acid comprises a single nucleotide polymorphism. In some embodiments, the method further comprises performing a separate assay to determine fragmentation of a different polynucleotide. In some embodiments, the method further comprises using the results of the separate assay to aid the determining of step d, wherein a determination of a high probability of a deletion is strengthened by a determination that the different polynucleotide is fragmented. In some embodiments, the method further comprises performing a separate assay to determine the presence of high molecule weight DNA in the sample.

In yet another aspect, this disclosure provides a method of identifying the probability of a deletion or translocation of a target region from a polynucleotide comprising: (a) subdividing a sample into multiple partitions wherein the sample comprises: (i) a polynucleotide suspected of comprising a first marker nucleic acid and a second marker nucleic acid, wherein the first and second marker nucleic acids are separated by at least one megabase and wherein the target region is suspected to be positioned between the first and second marker nucleic acids; (ii) a first labeled probe to detect the first marker nucleic acid; (iii) a second labeled probe to detect the second marker nucleic acid; and (iii) reagents to enable a PCR reaction; (b) performing an amplification reaction to detect the first and second marker nucleic acids within the partitions; (c) enumerating the number of partitions containing both the first and second marker nucleic acids within the partitions; and (d) determining the probability of a deletion or translocation of the target region based on the value of step c, where a higher value in step c is correlated with an increased probability that the target nucleic acid is absent from the polynucleotide. In some embodiments, the polynucleotide is a chromosome. In some embodiments, the target region is a specific region of a chromosome known to be present in a wild-type subject. In some embodiments, the method further comprises performing a separate assay to determine fragmentation of a different polynucleotide. In some embodiments, the method further comprises using the results of the separate assay to aid the determining of step d, wherein a determination of a high probability of a deletion or translocation is strengthened by a determination that the different polynucleotide is not fragmented.

In one aspect, this disclosure provides methods for haplotype analysis comprising: (a) partitioning an aqueous phase containing nucleic acid into a plurality of discrete volumes; (b) amplifying in the volumes at least one allele sequence from each of a first polymorphic locus and a second polymorphic locus that exhibit sequence variation in the nucleic acid; (c) determining at least one measure of co-amplification of allele sequences from both loci in the same volumes; and (d) selecting a haplotype of the first and second loci based on the at least one measure of co-amplification.

In some embodiments of this aspect, the first and second loci are contained in a target region of the nucleic acid, wherein the step of partitioning results in an average concentration of less than several copies of the target region per volume. In some embodiments, the step of partitioning results in an average concentration of less than about one copy of the target region per volume.

In some embodiments of this aspect, the step of determining at least one measure includes a step of determining at least one correlation coefficient for allele-specific amplification data of the first locus correlated with allele-specific amplification data of the second locus from the same volumes. In, some cases, the step of determining at least one measure includes a step of determining a first correlation coefficient and a second correlation coefficient for allele-specific amplification data of a first allele sequence and a second allele sequence of the first locus correlated respectively with allele-specific amplification data of the second locus from the same volumes, and wherein the step of selecting a haplotype is based on a step of comparing the first and second correlation coefficients with each other. In some cases, the step of determining at least one measure includes a step of determining a number of volumes that exhibit co-amplification of a particular allele sequence of the first locus and a particular allele sequence of the second locus, and wherein the step of selecting a haplotype is based on the number of volumes exhibiting co-amplification. The step of determining a number of volumes may further comprise a step of determining a first number of volumes and a second number of volumes that exhibit respective co-amplification of a first allele sequence or a second allele sequence of the first locus with a particular allele sequence of the second locus, and wherein the step of selecting a haplotype is based on first and second numbers of volumes.

In some embodiments, the step of determining at least one measure comprises collecting allele-specific amplification data for each of the loci from individual volumes, and correlating allele-specific amplification data for the first locus with allele-specific amplification data for the second locus from the same volumes.

In some embodiments of this aspect, the step of partitioning includes a step of forming an emulsion, in which the volumes are droplets. In some embodiments, the step of collecting may include collecting allele-specific amplification data from individual droplets of the emulsion.

In some embodiments, the step of forming an emulsion includes a step of passing the aqueous phase through an orifice such that monodisperse droplets of the aqueous phase are generated. In some embodiments, the step of partitioning includes a step of forming droplets that are about 10 to 1000 micrometers in diameter. In some embodiments, the step of partitioning includes a step of forming at least about 1000 volumes. In some cases, the step of partitioning includes a step of partitioning an aqueous phase including optically distinguishable fluorescent probes capable of hybridizing specifically to each allele sequence amplified.

In some embodiments, the nucleic acid is obtained or derived from a diploid subject. In some cases, the nucleic acid is genetic material obtained from a subject. In some cases, the nucleic acid includes cDNA obtained by reverse transcription of RNA obtained from a subject. In some cases, the subject is a multicellular organism. In some cases, the subject is a person.

In some embodiments, the step of amplifying includes a step of amplifying a pair of different allele sequences from the first locus, and the step of collecting data includes a step of collecting data that distinguishes amplification of each allele sequence of the pair in individual droplets.

In some embodiments, the step of correlating includes a step of separately correlating allele-specific amplification data for each allele sequence of the first locus with allele-specific amplification data for the allele sequence of the second locus.

In some cases, the step of correlating includes applying a threshold to the allele-specific amplification data to convert it to binary form, and the step of correlating is performed with the binary form of the data. In some cases, the step of correlating further comprises a step of determining a number of volumes exhibiting co-amplification of a particular allele sequence from both loci. In some cases, the step of correlating further comprises a first step of determining a first number of volumes exhibiting co-amplification of the second locus allele sequence and a first allele sequence from the first locus and a second number of droplets exhibiting co-amplification of the second locus allele sequence and a second allele sequence from the first locus, and a second step of comparing the first and second numbers of volumes.

In some embodiments, the step of selecting a haplotype is based on which allele-specific amplification data for the first locus exhibits a higher correlation with such allele-specific amplification data for the second locus. In some embodiments, the step of selecting a haplotype is based on correlation coefficients corresponding to respective distinct allele sequences amplified from the first locus. In some embodiments, the step of selecting a haplotype is based on whether the step of correlating indicates a negative or a positive correlation for co-amplification of particular allele sequences of the first and second loci in the same volumes.

In another aspect, this disclosure provides a system for haplotype analysis comprising: (a) a droplet generator configured to form droplets of an aqueous phase including nucleic acid; (b) a detector configured to collect allele-specific amplification data for each of the loci from individual droplets; and (c) a processor configured to correlate allele-specific amplification data for the first locus with allele-specific amplification data for the second locus from the same volumes and to select a haplotype of the nucleic acid for the first and second loci based on correlation of the allele-specific amplification data.

In some aspects, this disclosure provides a method of determining the degree of methylation of CpG islands within a sample of genomic DNA comprising: a. obtaining a sample of genomic DNA, wherein the genomic DNA comprises a first target nucleic acid that is separated from a second target nucleic acid by a CpG island; b. contacting the sample of genomic DNA with a methyl-sensitive restriction enzyme under conditions suitable for enabling digestion of unmethylated nucleic acids within the genomic DNA; c. contacting the sample with a probe that detects the presence of the first target nucleic acid; d. contacting the sample with a probe that detects the presence of the second target nucleic acid; e. separating the sample into a plurality of spatially isolated partitions; f. within the partitions, conducting an amplification reaction suitable for detecting the first and second target nucleic acids; g. determining the number of partitions that comprise both the first and second target nucleic acids; h. comparing the number obtained in step g with a number of partitions comprising first or second target nucleic acids; and i. from the comparison in step h, determining the degree of methylation of CpG islands within the genomic DNA sample. In some embodiments, the genomic DNA is human genomic DNA. In some embodiments, the genomic DNA comprises maternal and fetal DNA. In some embodiments, the genomic DNA comprises fetal DNA.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 2 illustrates an example where two target sequences are on a maternal chromosome and an example where one target sequence is on a maternal chromosome and one is on a paternal chromosome.

FIG. 3a illustrates a flowchart for determining the linkage of a target sequence.

FIG. 10A illustrates unlinked targets T1 and T2.

FIG. 10B illustrates a mixture of linked T1 and T2 and unlinked T1 and T2. FIG. 10C illustrates different spacings between T1 and T2.

FIGS. 13 and 14 illustrate information that can be considered when selecting a restriction enzyme.

FIGS. 15A and 15B illustrate assay information that can be entered into a database. FIG. 15A discloses SEQ ID NOS 26-28, respectively, in order of appearance. FIG. 15B discloses SEQ ID NOS 26-28 and 46-47, respectively, in order of appearance.

FIG. 16 illustrates an example of a workflow for a ddPCR experiment.

FIG. 19 depicts droplet properties of undigested samples 1-10 and digested samples 11-20.

FIGS. 23A and 23B illustrate copy number variation for the MRGPRX1.

FIGS. 24A and 24B illustrate copy number variation for CYP2D6.

FIG. 42A illustrates a scenario in which T1 and T2 are always on separate nucleic acids (total fragmentation). FIG. 42B illustrates a scenario in which T1 and T2 are always linked on a nucleic acid (no fragmentation). FIG. 42C illustrates a scenario in which T1 and T2 are linked on some nucleic acids and are also on separate nucleic acids (partial fragmentation).

FIG. 44 illustrates contamination by large DNA in plasma affects CNV values.

FIG. 45 illustrates restriction enzymes for titration for CNV analysis.

FIGS. 49A and 49B illustrate haplotyping through collocation.

FIG. 50 illustrates examples of genetic rearrangements that can be analyzed with a collocation assay.

DETAILED DESCRIPTION OF THE INVENTION

Overview

In general, provided herein are methods, compositions, and kits for analyzing nucleic acid sequence, e.g., digital partitioning. For example, provided herein are methods, compositions, and kits for estimating the number of copies of a target nucleic acid sequence in a sample, e.g., a genome. Also provided herein are methods, compositions, and kits for determining linkage or haplotype information of one or more target sequences in a sample, e.g., a genome. The haplotyping information can be information regarding whether or not multiple copies of one target sequence are on a single or multiple chromosomes. Using the concept of collocation of different targets within the same partition, it can be practical to infer phase, i.e., whether a particular allele of one mutation or a SNP is physically linked to an allele of another mutation or a SNP. In another aspect, methods, compositions, and kits are provided herein for determining the extent of fragmentation or degradation in a nucleic acid sample (e.g., a genomic DNA sample, RNA sample, mRNA sample, DNA sample, cRNA sample, cDNA sample, miRNA sample, siRNA sample), by, e.g., digitally analyzing collocation signal. In another aspect, methods are provided herein for analyzing nucleic acid methylation status, alternative splicing, finding inversions, translocations, and deletions.

Copy Number Variation Estimation

Copy number variation of one or more target sequences can play a role in a number of diseases and disorders. One method to analyze copy number variation of a target sequence is through a digital analysis, such as digital PCR, or droplet digital PCR. However, digital analysis of copy number of a target sequence can underestimate the number of copies of a target nucleic acid sequence in a sample if multiple copies of the target nucleic acid sequence are on the same polynucleotide in a sample. For example, in a digital PCR assay that has multiple compartments (e.g., partitions, spatially isolated regions), nucleic acids in a sample can be partitioned such that each compartment receives on average about 0, 1, 2, or several target polynucleotides. Each partition can have, on average, less than 5, 4, 3, 2, or 1 copies of a target nucleic acid per partition (e.g., droplet). In some cases, at least 0, 1, 2, 3, 4, 5, 6, 7, 8, 9, 10, 20, 30, 40, 50, 60, 70, 80, 90, 100, 125, 150, 175, or 200 partitions (e.g., droplets) have zero copies of a target nucleic acid. The number of compartments that contain a polynucleotide can be enumerated. However, if two copies of a target nucleic acid sequence are on a single polynucleotide a compartment containing that polynucleotide can be counted as having only one target sequence.

Figure 1:
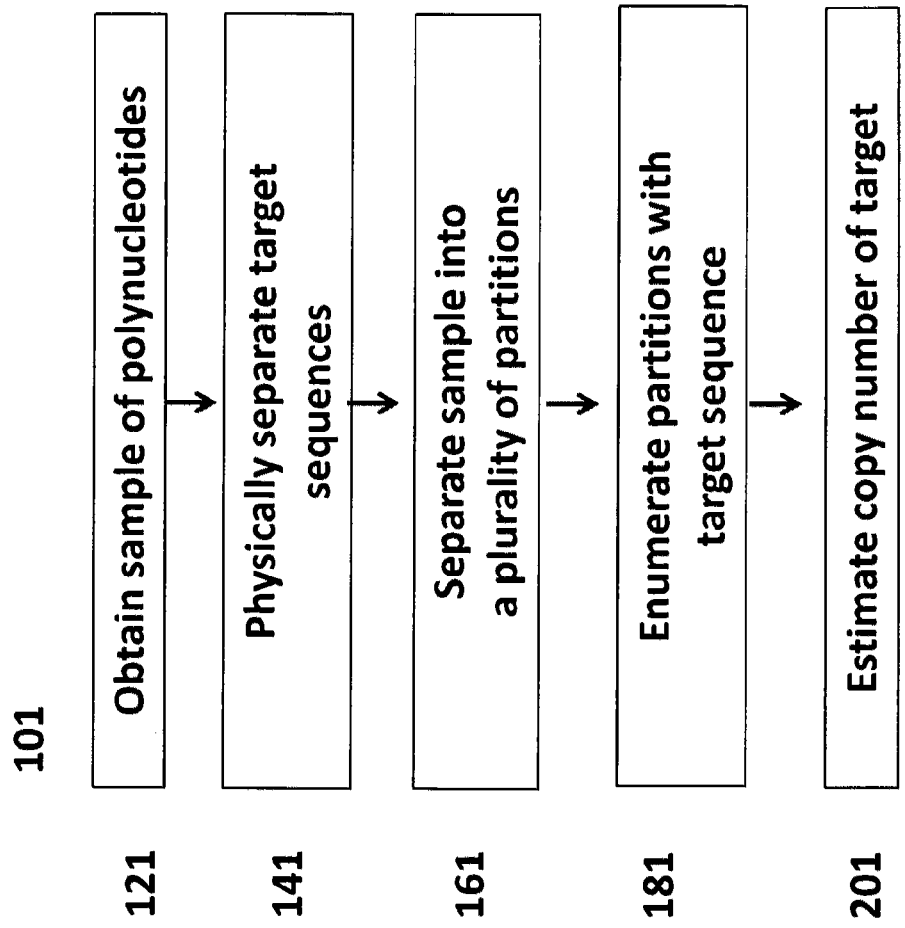
FIG. 1 illustrates a flowchart for estimating the copy number of a target sequence.

Provided herein are methods for physically separating target nucleic acids sequences. Often, the methods provided herein avoid underestimating copy numbers of a target sequence due to the presence of multiple copies of the target sequence on a single polynucleotide. FIG. 1 illustrates an overview of an embodiment of a method of copy number estimation (101); this figure and the remaining figures provided in this disclosure are for illustrative purposes only and are not intended to limit the invention. The steps in FIG. 1 can be performed in any suitable order and combination and can be united with any other steps of the present disclosure. A first sample of polynucleotides is obtained (121); the first sample can be, e.g., a genomic DNA sample. The target nucleic acid sequences in the first sample can be physically separated (e.g., by contacting the first sample with one or more restriction enzymes) (141). The first sample can be separated into a plurality of partitions (161). The number of partitions with the target sequence can be enumerated (181). The copy number of the target can then be estimated (201).

The target nucleic acids can be identical; or, in other cases, the target nucleic acids can be different. In some cases, the target nucleic acids are located within the same gene. In some cases, the target nucleic acids are each located in a different copy (identical or near identical copy) of a gene. In still other cases, the target sequences are located within introns, or in a region between genes. Sometimes, one target sequence is located in a gene; and the second target sequence is located outside of the gene. In some cases, a target sequence is located within an exon.

In some cases, a genome comprises one target sequence. In some cases, a genome comprises two or more target sequences. When a genome comprises two or more target sequences, the target sequences can be about, or more than about 50%, 55%, 60%, 65%, 70%, 75%, 80%, 85%, 90%, 95%, or 100% identical.

Physically separating two target sequences can comprise physically separating the target sequences by cleaving a specific site on the nucleic acid sequence. In some cases, the physically separating target nucleic acid sequences can comprise contacting the first sample with one or more restriction enzymes. Physically separating the target nucleic acid sequences can comprise digesting a polynucleotide at a site located between the target nucleic acid sequences. In some cases, the target nucleic acid sequences are each located within a gene. In some cases, the site that is targeted for digestion is located between the two genes. In some cases, the site selected for digestion is located in a gene; and, in some cases, the gene is the same gene as the gene which contains the target sequences. In other cases, the site selected for digestion is located in a different gene from that of the target sequence. In some cases, a target sequence and the site targeted for digestion are located in the same gene; and the target sequence is located upstream of the site targeted for digestion. In other cases, a target sequence and the site targeted for digestion are located in the same gene; but the target sequence is located downstream of the site targeted for digestion. In some cases, target nucleic acids can be separated by treatment of a nucleic acid sample with one or more restriction enzymes. In some cases, target nucleic acids can be separated by shearing. In some cases, target nucleic acids can be separated by sonication.

Following the physical separation step (e.g., digesting with one or more restriction enzymes), the sample can be partitioned into multiple partitions. Each of the plurality of partitions can comprise about 0, 1, 2 or several target polynucleotides. Each partition can have, on average, less than 5, 4, 3, 2, or 1 copies of a target nucleic acid per partition (e.g., droplet). In some cases, at least 0, 1, 2, 3, 4, 5, 6, 7, 8, 9, 10, 20, 30, 40, 50, 60, 70, 80, 90, 100, 125, 150, 175, or 200 droplets have zero copies of a target nucleic acid.

Often, target nucleic acid is amplified in the partitions. In some cases, the amplification comprises use of one or more TaqMan probes.

In another embodiment, the method further comprises the step of enumerating the number of partitions comprising a reference nucleic acid sequence. A reference nucleic acid sequence can be known to be present in a certain number of copies per genome and can be used to estimate the number of genome copies of a target nucleic acid sequence in a sample. In another embodiment, estimating the copy number can comprise comparing the number of partitions comprising the target sequence to the number of partitions comprising the reference nucleic acid sequence. In another embodiment, a CNV estimate is determined by a ratio of the concentration of target nucleic acid sequence to a reference sequence.

In another embodiment, the method further comprises the step of analyzing a second sample, wherein the second sample and the first sample are derived from the same sample (e.g., a nucleic acid sample is split to the first sample and the second sample). The method can further comprise not contacting the second sample with one or more restriction enzymes. In some cases, the method further comprises separating the second sample into a plurality of partitions. The method can further comprise enumerating the number of partitions of the second sample that comprise the target sequence. In another embodiment, the method further comprises enumerating the number of partitions of the second sample that comprise a reference sequence. In another embodiment, the method comprises estimating the copy number of the target sequence in the second sample. In another embodiment, estimating the copy number of the target sequence in the second sample comprises comparing the number of partitions from the second sample with the target sequence and the number of partitions from the second sample with the reference sequence.

The copy number of the target sequence from the first sample and the copy number of the target sequence in the second sample can be compared to determine whether the copy number of the target sequence in the second sample was underestimated. The degree to which the copy number was underestimated may be indicative of whether interrogated copies were all on one chromosome or if at least one copy was on one homologous chromosome and at least one copy was on the other homologous chromosome. Values closer to one per diploid genome may indicate the first case, while values closer to two may indicate the second case.

Additional methods of determining copy number differences by amplification are described, e.g., in U.S. Patent Application Publication No. 20100203538. Methods for determining copy number variation are described in U.S. Pat. No. 6,180,349 and Taylor et al. (2008) *PLoS One* 3(9): e3179.

When employing methods described herein, a variety of features can be considered:

Sample preparation: Properties of nucleic acids to be considered can include secondary structure, amplicon length, and degree of fragmentation. An assay can be performed to determine the degree of fragmentation of a nucleic acid sample. If the degree of fragmentation of a nucleic acid sample is too high, the sample can be discarded from an analysis. Steps can be taken to eliminate secondary structure of nucleic acids in a sample. Secondary structure of a nucleic acid can be modulated, for example, by regulating the temperature of a sample or by adding an additive to a sample. It can be determined whether a potential amplicon is too large to be efficiently amplified. In one embodiment, a Bioanalyzer is used to assess nucleic acid (e.g., DNA) fragmentation. In another embodiment, size exclusion chromatography is used to assess nucleic acid (e.g., DNA) fragmentation.

Dynamic range: Increasing the number of partitions or spatially isolated regions can increase the dynamic range of a method. Template nucleic acid can be diluted into a dynamic range.

Accuracy: If a homogenous sample is used, CNV values can be expected to fall on integer values (self-referencing). Drop-out amplification can cause inaccurate concentration measurements and, therefore, inaccurate CNV determinations. Additives (e.g., DMSO) can be added in GC-rich assays.

Multiplexing: An experiment can be multiplexed. For example, two colors can be used in the methods provided herein: FAM: BHQ and NFQ-MGB assays; VIC: NFQ-MGB, TAMRA. HEX: BHQ. 5' and 3' labeling can be used, and an internal labeled dye can be used. In some cases, the number of colors used in the methods provided herein is greater than two, e.g., greater than 3, 4, 5, 6, 7, 8, 9, or 10 colors.

Precision: Increased precision can be accomplished in several ways. In some cases, increasing the number of droplets in a dPCR experiment can increase the ability to resolve small differences in concentration between target and reference nucleic acids. Software can enable "metawell" analysis by pooling replicates from individual wells. In some cases, the methods provided herein enable detection of a difference in copy number that is less than 30%, 20%, 15%, 14%, 13%, 12%, 11%, 10%, 9%, 8%, 7%, 6%, 5%, 4%, 3%, 2%, or 1%.

Assay landscape: Target gene assays described herein can be combined with commercially available or custom designed target gene assays.

Copy number variations described herein can involve the loss or gain of nucleic acid sequence. Copy number variations can be inherited or can be caused by a de novo mutation. A CNV can be in one or more different classes. See, e.g. Redon et al. (2006) Global variation in copy number in the human genome. *Nature* 444 pp. 444-454. A CNV can result from a simple de novo deletion, from a simple de novo duplication, or from both a deletion and duplication. A CNV can result from combinations of multi-allelic variants. A CNV can be a complex CNV with de novo gain. A CNV can include about, or more than about 0, 1, 2, 3, 4, 5, 6, 7, 8, 9, or 10 contiguous genes. A CNV can include about 1 to about 10, about 1 to about 5, about 1 to about 4, about 1 to about 3, about 1 to about 2, about 0 to about 10, about 0 to about 5, or about 0 to about 2 contiguous genes. A copy number variation can involve a gain or a loss of about, or more than about, 100, 500, 1000, 2000, 3000, 4000, 5000, 6000, 7000, 8000, 9000, 10,000, 20,000, 30,000, 40,000, 50,000, 60,000, 70,000, 80,000, 90,000, 100,000, 200,000, 500,000, 750,000, 1 million, 5 million, or 10 million base pairs. In some cases, a copy number variation can involve the gain or loss of about 1,000 to about 10,000,000, about 10,000 to about 10,000,000, about 100,000 to about 10,000,000, about 1,000 to about 100,000, or about 1,000 to about 10,000 base-pairs of nucleic acid sequence. A copy number variation can be a deletion, insertion, or duplication of nucleic acid sequence. In some cases, a copy number variation can be a tandem duplication.

In another embodiment, CNV haplotypes can be estimated from fluorescent signals generated by real-time PCR or ddPCR of partitioned samples. Before the late stages of a real-time PCR or ddPCR experiment, when reagents can become limiting, a partition with a higher copy number of a target sequence can have a higher signal than a partition with a lower copy number of the target sequence. In one embodiment, a sample (e.g., a subsample of a sample used in a linkage experiment) can be partitioned, and PCR can be performed on the partitions (e.g., droplets). The mean fluorescence intensity of partitions can be determined as they undergo exponential amplification for a target and/or reference nucleic acid sequence. The mean intensity can correspond to the number of starting copies of the target. If multiple targets are linked along a single polynucleotide strand, the intensity in the partition (e.g., droplet) that captures this strand may be higher than that of a partition (e.g., droplet) that captures a strand with only a single copy of the target. Excess presence of positive droplets with higher mean amplitudes can suggest the presence of a haplotype with multiple CNV copies. Conversely, presence of positive droplets with only low mean amplitudes can suggest that only haplotypes with single CNV copies are present in the sample. In another embodiment, the number of cycles used to estimate CNV can be optimized based on the size of the partitions and the amount of reagent in the partitions. For example, smaller partitions with lower amounts of reagent may require fewer amplification cycles than larger partitions that would be expected to have higher amounts of reagent.

The method can be useful because it can be used to analyze even target copies that are near each other on the polynucleotide, e.g., less than about 10, 9, 8, 7, 6, 5, 4, 5, 2, 1, 0.7, 0.5, 0.3, 0.2, 0.1, 0.05, or 0.01 megabases apart; or that are very near each other on the polynucleotide, e.g., less than about 10, 9, 8, 7, 6, 5, 4, 3, 2, or 1 kilobase apart. In some cases, the method is useful for analyzing target copies that are very close to each other on the polynucleotide, e.g., within about 1, 10, 20, 30, 40, 50, 60, 70, 80, 90, 100, 200, 300, 400, 500, 600, 700, 800, 900, or 950 base pairs (bp's) apart. In some cases, the method is useful for analyzing target copies that are separated by zero (0) base pairs. In some cases, the method can be applied to identical, near identical, and completely different targets.

Additional embodiments of methods for estimating the copy number of one or more target sequences are described herein.

Determining Linkage of Target Sequences

Methods described herein can indicate whether two or more target sequences are linked on a polynucleotide (e.g., the methods can be used to determine the linkage of target sequences). In one embodiment, a method is provided comprising physically separating target sequence copies (e.g., by using one or more restriction enzymes) so that the copies can be assorted independently into partitions for a digital readout, and using a readout of undigested DNA together with a readout from digested DNA to estimate how the target copies are linked. For example, methods described herein can be used to determine if the target sequences are present on the same chromosome or if they are on different chromosomes (see e.g., FIG. 2). FIG. 2 illustrates a nucleus (left) in which a maternal chromosome comprises two copies of a target sequence, but the corresponding paternal chromosome comprises no copies; in the nucleus on the right, a maternal chromosome and the corresponding paternal chromosome each comprise one copy of the target.

FIG. 3a illustrates a workflow of an embodiment of a method, without being restricted to any order of the steps. In one aspect, a method (320) is provided comprising a) separating a sample comprising a plurality of polynucleotides into at least two subsamples (322); b) physically separating physically linked target sequences in a first subsample (324); c) separating the first subsample into a first set of a plurality of partitions (326); d) estimating the copy number of a target sequence in the first subsample (328); e) separating a second subsample into a second set of a plurality of partitions (330); f) estimating the copy number of the target sequence in the second subsample (332); g) comparing the estimated copy number of the target sequence in the first subsample to the estimated copy number of the target sequence in the second subsample to determine the haplotypes of the target sequence in the sample (334).

In one embodiment, physically separating physically linked target sequences in the first subsample comprises contacting the first subsample with one or more restriction enzymes. In another embodiment, contacting the sample comprising polynucleotides with one or more restriction enzymes comprises digesting nucleic acid sequence between at least two target nucleic acid sequences. In some cases, physically linked target nucleic acids can be separated by contacting a nucleic acid sample with one or more restriction enzymes. In some cases, physically linked target nucleic acids can be separated by shearing. In some cases, physically linked target nucleic acids can be separated by sonication.

In another embodiment, each of the plurality of partitions of the first and second subsample comprise about 0, 1, 2 or several target polynucleotides. Each partition can have, on average, less than 5, 4, 3, 2, or 1 copies of a target nucleic acid per partition (e.g., droplet). In some cases, at least 0, 1, 2, 3, 4, 5, 6, 7, 8, 9, 10, 20, 30, 40, 50, 60, 70, 80, 90, 100, 125, 150, 175, or 200 partitions (e.g., droplets) have zero copies of a target nucleic acid.

In another embodiment, target sequences are amplified in the partitions.

In another embodiment, estimating the copy number of the target sequence in the first subsample comprises enumerating the number of partitions of the first subsample comprising the target sequence. In another embodiment, estimating the copy number of the target sequence in the first subsample comprises enumerating the number of partitions of the first subsample comprising a reference nucleic acid sequence. In another embodiment, estimating the copy number of the target sequence in the first subsample comprises comparing the number of partitions of the first subsample comprising the target sequence to the number of partitions comprising the reference nucleic acid sequence in the first subsample.

In another embodiment, the method further comprises not contacting the second subsample with one or more restriction enzymes. In another embodiment, estimating the copy number of the target sequence in the second subsample comprises enumerating the number of partitions of the second subsample that comprise the target sequence. In another embodiment, estimating the copy number of the target sequence in the second subsample comprises enumerating the number of partitions of the second subsample that comprise a reference sequence. In another embodiment, estimating the copy number of the target sequence in the second subsample comprises comparing the number of partitions from the second subsample with the target sequence and the number of partitions from the second subsample with the reference sequence. In another embodiment, the reference sequence for the first and second subsample is the same sequence or a different sequence.

In another embodiment, determining haplotypes of the target sequence comprises comparing the estimated copy number of the target sequence in the first subsample to the estimated copy number of the target sequence in the second subsample. In another embodiment, the haplotypes comprises two copies of the target sequence on a single polynucleotide and no copies on the homologous polynucleotide. In another embodiment, the haplotyping comprises one copy of a target sequence on a first polynucleotide and a second copy of the target sequence on a second (possibly homologous) polynucleotide.

Often, the greater the difference between copy numbers in the first subsample and the second subsample, the more likely it is that one of the chromosomes does not carry a copy of the target.

Figure 3B:
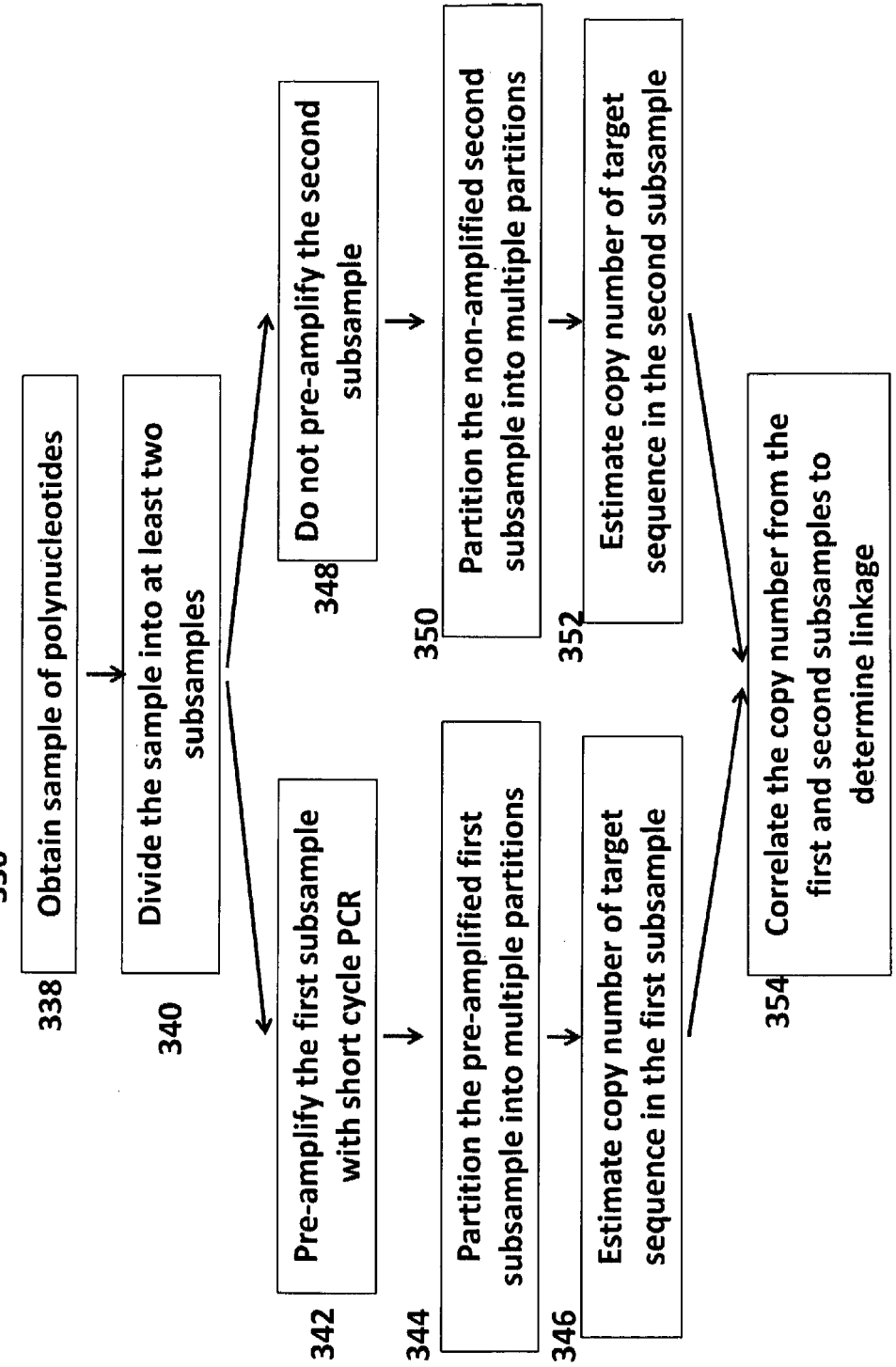
FIG. 3b illustrates an alternative workflow for determining the linkage of a target sequence.

FIG. 3b illustrates a workflow of another embodiment of a method, without being restricted to any order of the steps. In one aspect, a method (336) is provided comprising, a) obtaining a sample of polynucleotides (338) comprising a plurality of polynucleotides into at least two subsamples (340); b) pre-amplifying target sequence in the first subsample with short cycle PCR (342); c) separating the first subsample into a first set of a plurality of partitions (344); d) estimating the copy number of a target sequence in the first subsample (346); e) taking a second subsample that has not been pre-amplified (348) into a second set of a plurality of partitions (350); f) estimating the copy number of the target sequence in the second subsample (352); g) comparing the estimated copy number of the target sequence in the first subsample to the estimated copy number of the target sequence in the second subsample to determine the linkage of the target sequence in the sample (354).

In some cases, the preamplification used to separate targets is Specific Target Amplification (STA) (Qin et al. (2008) Nucleic Acids Research 36 e16), which entails performing a short pre-amplification step to generate separate unlinked amplicons for the target nucleic acids.

In one embodiment, pre-amplifying target sequence in the first subsample comprises contacting the first subsample with a reaction mixture comprising DNA polymerase, nucleotides, and primers specific to the target sequence and amplifying the target sequence for a limited number of cycles. Optionally, the method also comprises using primers for a reference sequence and, optionally, amplifying the reference sequence for a limited number of cycles. In some embodiments, the number for the number of cycles can range from 4-25 cycles. In some cases, the number of cycles is less than 25, 24, 23, 22, 21, 20, 19, 18, 17, 16, 15, 14, 13, 12, 11, 10, 9, 8, 7, 6, 5, or 4 cycles. The number of cycles may vary depending on the droplet size and the quantity of available reagents. For example, few cycles may be necessary for partitions (e.g., droplets) that are of smaller size.

The pre-amplified first subsample may be partitioned into multiple partitions, each partition comprising on average less than one target polynucleotide. Each partition can have, on average, less than 5, 4, 3, 2, or 1 copies of a target nucleic acid per partition (e.g., droplet). In some cases, at least 0, 1, 2, 3, 4, 5, 6, 7, 8, 9, 10, 20, 30, 40, 50, 60, 70, 80, 90, 100, 125, 150, 175, or 200 partitions (e.g., droplets) have zero copies of a target nucleic acid.

In another embodiment, estimating the copy number of the target sequence in the first subsample comprises enumerating the number of partitions of the first subsample comprising a reference nucleic acid sequence. In another embodiment, estimating the copy number of the target sequence in the first subsample comprises comparing the number of partitions of the first subsample comprising the target sequence to the number of partitions comprising the reference nucleic acid sequence in the first subsample.

In another embodiment, the method further comprises not subjecting the second to a pre-amplification step. In another embodiment, the second subsample is partitioned into multiple partitions, each partition containing on average about 0, 1, 2, or several target polynucleotides. Each partition can have, on average, less than 5, 4, 3, 2, or 1 copies of a target nucleic acid per partition (e.g., droplet). In some cases, at least 0, 1, 2, 3, 4, 5, 6, 7, 8, 9, 10, 20, 30, 40, 50, 60, 70, 80, 90, 100, 125, 150, 175, or 200 partitions (e.g., droplets) have zero copies of a target nucleic acid. In another embodiment, estimating the copy number of the target sequence in the second subsample comprises enumerating the number of partitions of the second subsample that comprise the target sequence. In another embodiment, estimating the copy number of the target sequence in the second subsample comprises enumerating the number of partitions of the second subsample that comprise a reference sequence. In another embodiment, estimating the copy number of the target sequence in the second subsample comprises comparing the number of partitions from the second subsample with the target sequence and the number of partitions from the second subsample with the reference sequence. In another embodiment, the reference sequence for the first and second subsample is the same sequence or a different sequence.

In another embodiment, determining haplotypes of the target sequence comprises comparing the estimated copy number of the target sequence in the first subsample to the estimated copy number of the target sequence in the second subsample. In another embodiment, the haplotypes comprise two copies of the target sequence on a single polynucleotide and no copies on the homologous polynucleotide. In another embodiment, the haplotypes comprise one copy of a target sequence on a first polynucleotide and a second copy of the target sequence on a second (possibly homologous) polynucleotide.

The greater the difference between copy numbers in the first subsample and the second subsample, the more likely it is that one of the chromosomes does not carry a copy of the target.

In yet another aspect, this disclosure provides a method of identifying a plurality of target nucleic acids as being present on the same polynucleotide comprising, a. separating a sample comprising a plurality of polynucleotides into at least two subsamples, wherein the polynucleotides comprise a first and second target nucleic acid; b. contacting the first subsample with an agent capable of physically separating the first target nucleic acid from the second target nucleic acid if they are present on the same polynucleotide; c. following step b, separating the first subsample into a first set of partitions; d. determining the number of partitions in the first set of partitions that comprise the target nucleic acid; e. separating a second subsample into a second set of partitions; f. determining the number of partitions in the second set of partitions that comprise a target nucleic acid; and g. comparing the value obtained in step d with the value obtained in step f to determine the whether the first and second target nucleic acid are present within the same polynucleotide.

The sample can be of sufficiently high molecular weight so that if a pair of targets is on the same chromosome, they can be mostly linked in solution as well. If the nucleic acid (e.g., DNA) in a sample is completely unfragmented, the readout can be 0, 1, or 2 copies of the target (integers). However, because nucleic acid (e.g., DNA) can be partially degraded, copy numbers can span non-integer values, as well as numbers greater than 2. Another step can be taken to assess nucleic acid fragmentation of a sample, e.g., by using gels, a Bioanalyzer, size exclusion chromatography, or a digital PCR co-location method (milepost assay). If a nucleic acid sample is found to be overly fragmented, this decreases the likelihood information can be gleaned about linkage.

This approach can used to determine smaller copy number states, e.g., 2, 3, 4.

In another embodiment, a method of linkage determination of a target nucleic acid sequence is provided making use of probes with two different labels (e.g., VIC and FAM) to detect the same target sequence. For example, a nucleic acid sequence can be separated into a plurality of spatially-isolated partitions, the target sequence can be amplified in the partitions, and the two different probes can be used to detect the target sequence. The nucleic acid sample can be partitioned such that on average about 0, 1, 2, or several target polynucleotides are in each partition. Each partition can have, on average, less than 5, 4, 3, 2, or 1 copies of a target nucleic acid per partition (e.g., droplet). In some cases, at least 0, 1, 2, 3, 4, 5, 6, 7, 8, 9, 10, 20, 30, 40, 50, 60, 70, 80, 90, 100, 125, 150, 175, or 200 partitions (e.g., droplets) have zero copies of a target nucleic acid.

If a partition comprises two targets linked on a polynucleotide, the partition can have signal for VIC only (VIC/VIC), FAM only (FAM/FAM), or VIC and FAM. Overabundance of partitions with VIC and FAM signal in a partition compared to what is expected from random dispersion of FAM and VIC targets can indicate that the sample contained polynucleotides that have at least two targets linked on a polynucleotide. Lack of overabundance of partitions with both VIC and FAM signal can indicate that two target nucleic acid sequences are not linked in a sample.

Collocalization

Sample partitioning and the ability to analyze multiple targets in a partition can allows one to detect when targets are spatially clustered together in the sample. This can be done by assessing whether the number of partitions with a particular combination of targets is in statistical excess compared to what would be expected if the targets were randomly distributed in the partitions. The extent of overabundance of such partitions can be used to estimate the concentration of the combination of targets.

For example, one can measure two targets: A and B using a digital PCR (e.g., ddPCR). For example, there would be four types of droplets: droplets negative for both targets, droplets positive for A, droplets positive for B and droplets positive for both. Under random distribution the number of double positive droplets should be close to (total number of droplets)* (fraction of droplets with at least B)*(fraction of droplets with at least A). If the number of double positive droplets significantly exceeds the expectation, an inference can be made that the two targets are in proximity to each other in the sample. This result can mean that target A and B are physically linked by virtue of, e.g., being on the same polynucleotide, that they are part of the same protein/nucleic acid complex, that they are part of the same exosome, or that they are part of the same cell.

The presence of a particular target in a partition may be assessed by using a fluorophore specific to that target as part of a probe-based TaqMan assay scheme. For example, when measuring two targets A and B, one can use FAM for A and VIC for B. In some embodiments different targets can be assessed with the same fluorophore or intercalating dye using endpoint fluorescence to distinguish partitions containing A from those containing B from those containing A and B.

Alternative Splicing

Alternative splicing is a pervasive feature of eukaryotic biology. This phenomenon occurs when different transcripts are constructed from the same genomic region, by employing exons in different configurations often depending on cell-type, cell state, or external signals. For example, a particular gene may have two exons: exon A and exon B and three possible transcripts: Transcript 1 containing A only, Transcript 2 containing B only, Transcript 3 containing A and B. Being able to specify which transcripts are actually expressed and their levels can have multiple implications for our understanding of basic biology, disease, diagnostics, and therapy.

Collocalization can be used to detect and quantify alternative splicing by measuring concentrations of RNA molecules that possess two or more exons of interest. For example, one assay may target one exon, while another assay may target another exon. Statistically significant collocalization of the two assays may suggest the presence of RNA molecules containing both exons. Additional exons and locations on potential transcript molecules can be targeted and assessed in this fashion.

Rearrangements

In another embodiment, two assays (amplicons) can be constructed that are normally far apart from each other on a polynucleotide (e.g., two genes separated by millions of by on a chromosome). One assay is on one channel (e.g., FAM), the other on another channel (e.g., VIC). In a digital amplification method, e.g., dPCR or ddPCR, normally, co-localization in the same partition (e.g., droplet) should not be observed above the baseline statistical expectation. If collocalization of FAM and VIC occurs (e.g., as measured a linkage analysis described herein), that can be an indication that the two loci were brought in the vicinity of each other on the genome. This result can indicate an inversion or a translocation depending on where the loci are normally. The assays can also be multiplexed on the same channel if their endpoint fluorescences are distinct enough. More than two assays can be multiplexed to catch multiple inversion/translocation events or to account for the fact that a given translocation may present with different breakpoints.

Detection of rearrangements can be used for diagnosing and prognosing a variety of conditions, including cancer and fetal defects. Detection of rearrangements can be used to select one or more therapeutic treatments for a subject. For example, detection of translocation t(9;22)(q34.1;q11.2) can lead to generation of a BCR-ABL fusion protein, associated with chronic myelogenous leukemia (CML). CML patients that express BCR-ABL can be treated with imatinib (Gleevec).

Rearrangements that can be detected with methods described here include, e.g., inversions, translocations, duplications, or deletions (see e.g., FIG. 50).

Confirming Linkage (Haplotype) Information Generated by Digital Experiment

In another embodiment, linkage information determined using digital analysis and restriction enzyme digest of samples can be confirmed by one or more other assays. In one embodiment, signal generation during a real-time PCR or ddPCR experiment of a partitioned sample as described herein can be used to confirm linkage information. In one embodiment, a sample (e.g., a subsample of a sample used in a linkage experiment) can be partitioned, and PCR can be performed on the partitions (e.g., droplets). The mean fluorescence intensity of partitions can be determined as they undergo exponential amplification for a target and/or reference nucleic acid sequence. Partitions with a polynucleotide with multiple (e.g., 2) linked copies of a target nucleic acid sequence can have higher fluorescence intensity than droplets with only one copy of a target nucleic acid sequence.

In another embodiment, long range PCR can be used to confirm linkage information. For example, PCR can be used to detect the presence of two tandemly arranged copies of a target nucleic acid sequence on the same chromosome (cis-configuration), and it can be used to detect deletion of the target nucleic acid sequence on another chromosome. In one embodiment, primers outside of the amplified region (region suspected of having tandem copies of the target) can be used. In another embodiment, DNA polynucleotides can be partitioned into droplets. Partitioning DNA polynucleotides into droplets can be beneficial, as it can permit detection of two types of DNA species: a) the DNA segment with tandemly arranged targets and b) a DNA segment with the deletion of the target. If a similar reaction is performed in bulk (e.g., without partitioning polynucleotides), the smaller PCR product representing the DNA with the deleted target can outcompete the PCR product representing the DNA segment with tandemly arranged target sequences. As a result, only one PCR product can be generated. The size difference of these PCR products can be estimated using, e.g., gel electrophoresis or a Bioanalyzer.

In some cases, DNA with tandemly arranged copies of a target nucleic acid sequence can be too large to be successfully PCR amplified (e.g., >20 KB in size). In these cases, often only the smaller PCR product is amplified, representing the DNA segment with the deleted target nucleic acid sequence. If the target nucleic acid sequence is too long to permit generation of a PCR product, PCR can be performed on a chromosome that contains a deletion for the target nucleic acid sequence. In this case, a product can be generated if the PCR is over a region deleted for the sequence, but a product may not be generated if the target sequence is present because the distance between the primers can be too great.

In some embodiments, long range PCR can be used to resolve linkage or determine copy number estimation. In some cases, long range PCR is used in conjunction with the methods provided herein. In some cases, genotypes of parents or other relatives can be used (alone or in combination with the methods provided herein) to infer the copy number state of the target individual.

In some cases, the method may comprise cloning a chromosomal region using recombinant DNA technology and sequencing individual copies of the chromosomal region. In some embodiments, the method comprises (a) using next-generation sequencing, to identify information related to polymorphisms that are closely spaced (e.g., less than about 2000 nucleotides, less than about 1000 nucleotides, less than about 500 nucleotides, less than about 200 nucleotides, or less than about 100 nucleotides apart) and are present together in the same sequencing read and (b) using a method provided herein to identify information related to polymorphisms that are further apart (e.g., greater than about 5, 10, 50, 100, 150, 200, 250, 300, 400, 450, 500, 550, 600, 650, 700, 750, 800, 850, 900, 950, 1000, 1250, 1500, 1750, 2000, 2500, 3000, 3500, 4000, 4500, or 5000 nucleotides apart). In some embodiments, the method comprises using a method provided herein to identify information related to polymorphisms that are further apart (e.g., greater than about 5, 10, 50, 100, 150, 200, 250, 300, 400, 450, 500, 550, 600, 650, 700, 750, 800, 850, 900, 950, 1000, 1250, 1500, 1750, 2000, 2500, 3000, 3500, 4000, 4500, or 5000 nucleotides apart). In some cases, the method comprises using a method provided herein in conjunction with using the genotype information for the parents or other close relatives of a subject to infer phase information using Mendelian rules of inheritance. However, this approach cannot phase every polymorphism. Some embodiments comprise a method provided herein used in conjunction with statistical approaches to linkage determination.

Haplotypes

A haplotype can refer to two or more alleles that are present together or linked on a single chromosome (e.g., on the same chromosome copy) and/or on the same piece of nucleic acid and/or genetic material. Phasing can be the process of determining whether or not alleles exist together on the same chromosome. Determination of which alleles in a genome are linked can be useful for considering how genes are inherited. The present disclosure provides a system, including method and apparatus, for haplotype analysis by amplification of a partitioned sample.

Figure 4:
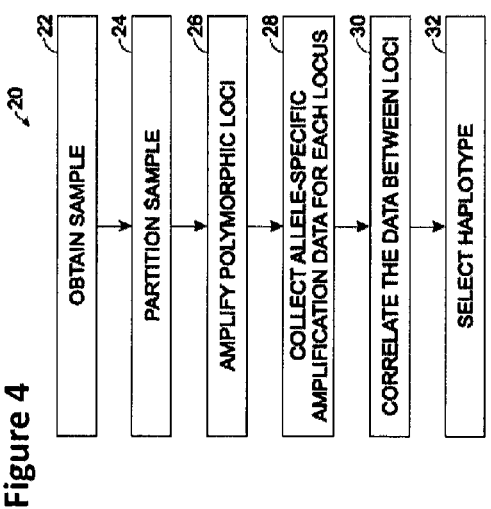
FIG. 4 is a flowchart listing steps that may be performed in an exemplary method of haplotype analysis using amplification performed in sample partitions, in accordance with aspects of the present disclosure.

FIG. 4 shows a flowchart listing steps that can be performed in an exemplary method (20) of haplotype analysis. The steps can be performed in any suitable order and combination and can be united with any other steps of the present disclosure. A sample can be obtained (22), generally from a subject with a diploid or higher complement of chromosomes. The sample can be partitioned (24). Partitioning the sample may include partitioning or dividing an aqueous phase that includes nucleic acid of the sample. A pair (or more) of polymorphic loci may be amplified (26). Allele-specific amplification data may be collected for each polymorphic locus (28). Amplification data for the polymorphic loci and from the same volumes may be correlated (30). A haplotype for the polymorphic loci can be selected (32).

A method of haplotype analysis may be performed with a sample obtained from a subject, such as a person. An aqueous phase containing nucleic acid of the sample may be partitioned into a plurality of discrete volumes, such as droplets. Each volume may contain on average less than about one genome equivalent of the nucleic acid, such that each volume contains on average less that about one copy of an allele of a first polymorphic locus and an allele of a linked second polymorphic locus. At least one allele sequence from each of the first polymorphic locus and the second polymorphic locus in the nucleic acid may be amplified. Distinguishable allele-specific amplification data for each of the loci may be collected from individual volumes. Allele-specific amplification data for the first locus may be correlated with allele-specific amplification data for the second locus from the same volumes. A haplotype of the nucleic acid for each of the first and second loci may be selected based on correlation of the allele-specific amplification data. In general, the method can rely on co-amplification, in the same volumes, of allele sequences from distinct loci, if the allele sequences constitute a haplotype of the subject, and, conversely, lack of co-amplification if they do not.

A system for haplotype analysis may be capable of performing the method disclosed herein. The system may comprise a droplet generator configured to form droplets of an aqueous phase including nucleic acid. The system also may comprise a detector configured to collect allele-specific amplification data for each of the loci from individual droplets. The system further may comprise a processor. The processor may be configured to correlate allele-specific amplification data for the first locus with allele-specific amplification data for the second locus from the same volumes and to select a haplotype of the nucleic acid based on correlation of the allele-specific amplification data.

Optionally, the sample may be divided into subsamples. Optionally, the first subsample may be contacted with a restriction enzyme that cleaves a site between the polymorphic loci; and the second subsample may optionally be exposed to a restriction enzyme. Optionally, allele-specific amplification data from the first subsample may be correlated with allele-specific amplification data from the second subsample.

Further aspects of the present disclosure are presented in the following sections: (I) definitions, (II) system overview, (III) exemplary potential haplotypes created by linked SNPs, (IV) exemplary haplotype analysis with amplification in droplets, and (V) selected embodiments.

I. Definitions

Technical terms used in this disclosure have the meanings that are commonly recognized by those skilled in the art. However, the following terms may have additional meanings, as described below.

Sequence variation can be any divergence in genome sequence found among members of a population or between/among copies of a chromosome type of a subject and/or a sample. Sequence variation also may be termed polymorphism.

Locus can be a specific region of a genome, generally a relatively short region of less than about one kilobase or less than about one-hundred nucleotides.

Polymorphic locus can be a locus at which sequence variation exists in the population and/or exists in a subject and/or a sample. A polymorphic locus can be generated by two or more distinct sequences coexisting at the same location of the genome. The distinct sequences may differ from one another by one or more nucleotide substitutions, a deletion/insertion, and/or a duplication of any number of nucleotides, generally a relatively small number of nucleotides, such as less than about 50, 10, or 5 nucleotides, among others. In exemplary embodiments, a polymorphic locus is created by a single nucleotide polymorphism (a "SNP"), namely, a single nucleotide position that varies within the population.

Allele can be one of the two or more forms that coexist at a polymorphic locus. An allele also may be termed a variant. An allele may be the major or predominant form or a minor or even very rare form that exits at a polymorphic locus. Accordingly, a pair of alleles from the same polymorphic locus may be present at any suitable ratio in a population, such as about 1:1, 2:1, 5:1, 10:1, 100:1, 1000:1, etc.

Allele sequence can be a string of nucleotides that characterizes, encompasses, and/or overlaps an allele. Amplification of an allele sequence can be utilized to determine whether the corresponding allele is present at a polymorphic locus in a sample partition.

Haplotype can be two or more alleles that are present together or linked on a single chromosome (e.g., on the same chromosome copy) and/or on the same piece of nucleic acid and/or genetic material; haplotype can also refer to two or more target nucleic acids that are present together or linked on a single chromosome. The target nucleic acids can be the same or different.

Linkage can be a connection between or among alleles from distinct polymorphic loci and can also be a connection between or among target nucleic acids that are identical or nearly identical. Polymorphic loci that show linkage (and/or are linked) generally include respective alleles that are present together on the same copy of a chromosome, and may be relatively close to one another on the same copy, such as within about 10, 1, or 0.1 megabases, among others.

II. System Overview for Haplotype Analysis

FIG. 4 shows a flowchart listing steps that may be performed in an exemplary method 20 of haplotype analysis. The steps may be performed in any suitable order and combination and may be united with any other steps of the present disclosure.

A sample may be obtained, indicated at 22. The sample may be obtained from a subject, generally a subject with a diploid or higher complement of chromosomes. In other words, the subject typically has at least two sets of chromosomes, and at least a pair of each type of chromosome in the subject's cells. For example, somatic cells of humans each contain two copies of chromosome 1, 2, 3, etc., to give 23 chromosome pairs (two sets of chromosomes) and a total of 46 chromosomes.

The sample may be partitioned, indicated at 24. Partitioning the sample may include partitioning or dividing an aqueous phase that includes nucleic acid of the sample. Partitioning divides the aqueous phase into a plurality of discrete and separate volumes, which also may be called partitions. The volumes may be separated from one another by fluid, such as a continuous phase (e.g., an oil). Alternatively, the volumes may be separated from one another by walls, such as the walls of a sample holder. The volumes may be formed serially or in parallel. In some embodiments, the volumes are droplets forming a dispersed phase of an emulsion.

A pair (or more) of polymorphic loci may be amplified, indicated at 26. More particularly, at least one allele sequence from each of the polymorphic loci may be amplified. Each allele sequence is characteristic of a corresponding allele of the locus. In some embodiments, only one allele sequence may be amplified from each locus, or a pair of allele sequences may be amplified from at least one of the loci. The particular allele sequences and number of distinct allele sequences that are amplified may be determined by the particular primer sets included in the aqueous phase before the aqueous phase is partitioned.

Allele-specific amplification data may be collected for each polymorphic locus, indicated at 28. The data may relate to distinguishable amplification (or lack thereof) of each of the allele sequences in individual volumes. The data may be detected from distinguishable probes corresponding to and capable of hybridizing specifically to each of the allele sequences amplified. The data may be collected in parallel or serially from the volumes. In exemplary embodiments, the data may be collected by optical detection of amplification signals. For example, optical detection may include detecting fluorescence signals representing distinguishable amplification of each allele sequence.

Amplification data for the polymorphic loci and from the same volumes may be correlated, indicated at 30. Correlation generally determines which allele sequences are most likely to be present together in individual volumes, and thus originally linked to one another on the same chromosome copy in genetic material of the subject. Correlation may include determining at least one correlation coefficient corresponding to co-amplification of distinct allele sequences in the same volumes. In some cases, correlation may include determining a pair of correlation coefficients corresponding to co-amplification of each of a pair of allele sequences of the same locus with an allele sequence of another locus. Correlation also may include comparing correlation coefficients with each other and/or with a threshold, or may include determining whether a correlation coefficient is negative or positive. In some embodiments, correlation may be performed with amplification data that has been converted to a binary form by applying a threshold that distinguishes amplification-positive and amplification-negative signals. Correlation also or alternatively may include comparing the numbers of volumes that exhibit co-amplification of different sets of allele sequences and/or comparing the number of volumes that exhibits co-amplification of a set of allele sequences versus the number that exhibits amplification of only one of the allele sequences.

In some embodiments, one or both of the steps indicated at 28 and 30 may be substituted by a step of determining at least one measure of co-amplification of allele sequences from both loci in the same volumes. Any suitable measure(s) of co-amplification may be used, such as at least one correlation coefficient obtained by correlation of allele-specific amplification data for the polymorphic loci from the same volumes. In other examples, the measure of co-amplification may be at least one value representing at least one number or frequency of co-amplification of an allele sequence from each locus. Further aspects of correlating amplification data and determining measures of co-amplification are described elsewhere in the present disclosure, such as in Section IV.

In some embodiments, the sample containing polynucleotides may be divided into two or more subsamples. The first subsample may be exposed to a restriction enzyme which cleaves at a site between the two polymorphic loci. The first subsample may then be partitioned into multiple partitions. Allele-specific amplification data may then be collected for each polymorphic locus, as described herein. The second subsample, having not been exposed to a restriction enzyme which cleaves at a site between the two polymorphic loci, may be partitioned into multiple partitions. Allele-specific amplification may then be collected for each polymorphic locus. Amplification data from the first and second subsamples may be correlated to determine the haplotype for the polymorphic loci.

A haplotype for the polymorphic loci may be selected, indicated at 32. Selection may be based on correlation of amplification data and/or based on the at least one measure of co-amplification. The haplotype may be selected from among a set of potential haplotypes for the polymorphic loci being investigated. The selected haplotype generally includes designation of at least a pair of particular alleles that are likely to be linked to one another on the same chromosome copy of the subject.

Figure 5:
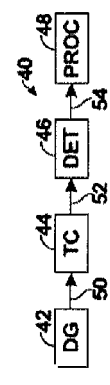
FIG. 5 is a schematic view of selected aspects of an exemplary system for performing the method of FIG. 4, in accordance with aspects of present disclosure.

FIG. 5 shows a schematic view of selected aspects of an exemplary system 40 for performing method 20 of FIG. 4. The system may include a droplet generator (DG) 42, a thermocycler (TC) 44, a detector (DET) 46, and a processor (PROC) 48. Arrows 50-54 extend between system components to indicate movement of droplets (50 and 52) and data (54), respectively.

Droplet generator 42 can form droplets of an aqueous phase including nucleic acid. The droplets may be formed serially or in parallel.

Thermocycler 44 can expose the droplets to multiple cycles of heating and cooling to drive amplification, such as PCR amplification, of allele sequences. The thermocycler may be a batch thermocycler, which amplifies all of the droplets in parallel, or may be a flow-based thermocycler, which amplifies droplets serially, among others.

Detector 46 collects amplification data, such as allele-specific amplification data from the droplets. The detector may, for example, be a fluorescence detector, and may detect droplets serially or in parallel.

Processor 48, which also may be termed a controller, can be in communication with detector 46 and can be programmed to process amplification data from the detector. The processor, which may be a digital processor, may be programmed to process raw data from the detector, such as to subtract background and/or normalize droplet data based on droplet size. The processor also or alternatively may be programmed to apply a threshold to convert the data to binary form, to perform a correlation of amplification data, to calculate and/or compare one or more measures of co-amplification, to select a haplotype based on the correlation and/or measures, or any combination thereof.

Further aspects of droplet generators, thermocyclers, detectors, and controllers are described in U.S. Patent Application Publication No. 2010/0173394 A1, published Jul. 8, 2010, which is incorporated herein by reference.

III. Exemplary Potential Haplotypes Created by Linked SNPs

Figure 6:
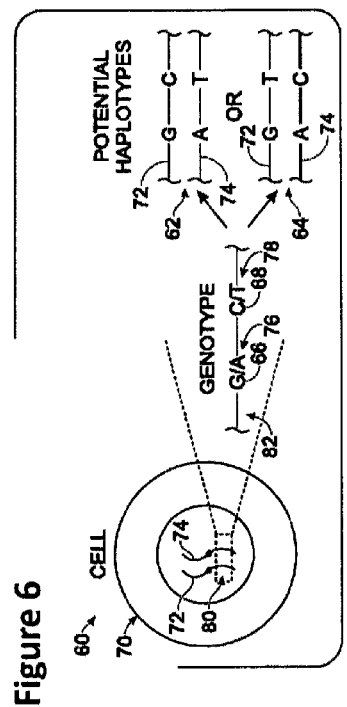
FIG. 6 is a schematic view of exemplary haplotypes that may be created by a pair of SNPs located on the same chromosome type in the genetic material of a subject, in accordance with aspects of the present disclosure.

FIG. 6 schematically illustrates a haplotyping situation created by linked SNPs in which the genetic material of a diploid subject 60 has two different nucleotides at each of two different loci. The goal of haplotyping is to determine which nucleotide at the first locus is combined with which nucleotide at the second locus on each chromosome copy.

Subject 60 can have either of two alternative haplotype configurations 62, 64 created by a pair of single nucleotide polymorphisms 66, 68. Each configuration represents two haplotypes: configuration 62 has haplotypes (G, C) and (A, T), and configuration 64 has haplotypes (G, T) and (A, C). A cell 70 of the subject includes a pair of chromosome copies 72, 74 of the same type. (Other types of chromosomes that may be present in the cell are not shown.) Chromosome copies 72, 74 may be mostly identical in sequence to each other, but the copies also typically have many loci of sequence variation, such as polymorphic loci 76, 78, where the two chromosome copies differ in sequence. Loci 76, 78 are contained in a genome region or target region 80, which is outlined by a dashed box in the nucleus of cell 70 and which is shown enlarged adjacent the cell as a composite sequence that represents a genotype 82 for loci 76, 78. (Only one strand of each chromosome copy and target region is shown in FIG. 6 (and FIG. 7) to simplify the presentation.)

Genotype 82 may be determined by any suitable genotyping technology, either before haplotype analysis or as a part of a haplotype analysis. Genotype 82 shows that the single polymorphic nucleotide of locus 76 is a "G" and an "A" on chromosome copies 72 and 74 (or vice versa), and for locus 78 is a "C" and a "T." However, the genotype does not indicate how the individual nucleotides of the two loci are combined on chromosome copies 72, 74. Accordingly, the genotype can be produced by alternative, potential haplotype configurations 62, 64. Haplotype analysis, as disclosed herein, permits determination of which of the potential haplotypes are present in the subject's genetic material.

V. Exemplary Haplotype Analysis with Amplification in Droplets

Figure 7:
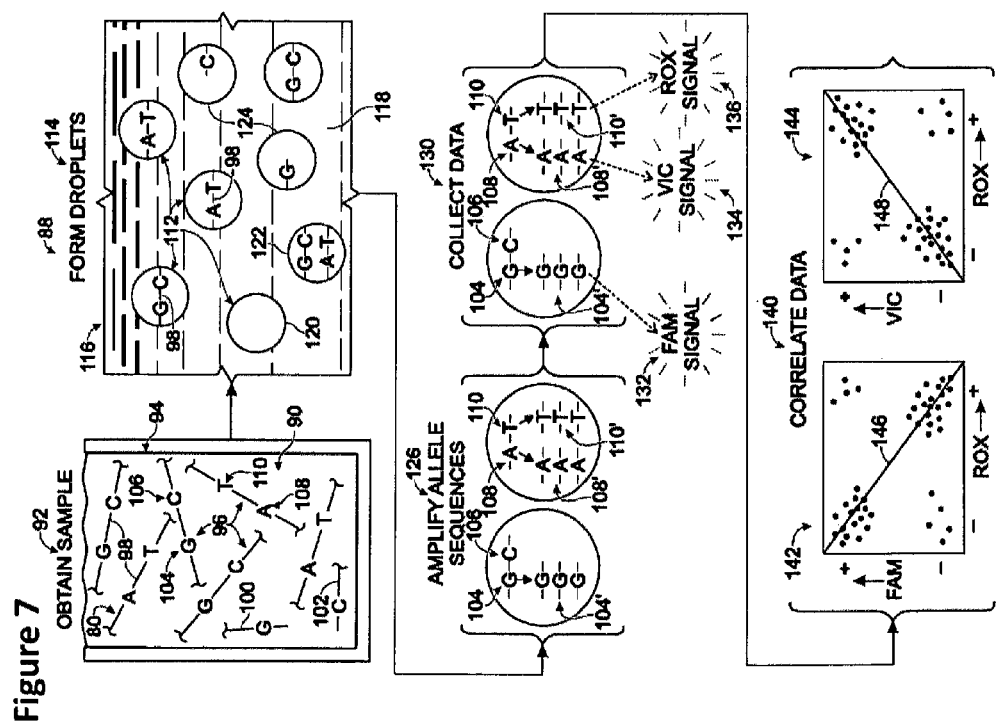
FIG. 7 is a schematic view of a flowchart illustrating performance of an exemplary version of the method of FIG. 4, with droplets as partitions and with the genetic material from the subject of FIG. 6 being analyzed to distinguish the potential haplotypes presented in FIG. 6, in accordance with aspects of the present disclosure.

FIG. 7 schematically illustrates performance of an exemplary version 88 of the method of FIG. 4. Here, genetic material from the subject of FIG. 6 is analyzed to distinguish the alternative, potential haplotype configurations described in the preceding section.

A sample 90 is obtained, indicated at 92. The sample is disposed in an aqueous phase 94 including nucleic acid 96 of the subject. In this view, for simplification, only fragments 98 containing genome region 80 are depicted. Fragments 98 are long enough that only a minority (e.g., incomplete fragments 100, 102) fail to include an allele sequence 104-110 from both loci 76, 78 (also see FIG. 6). The aqueous phase may be configured for PCR amplification of allele sequences 104-110.

Droplets 112 are formed, indicated at 114. The droplets may be part of an emulsion 116 that includes a continuous phase 118 separating the droplets from one another. The droplets may be monodisperse, that is, of substantially the same size. Exemplary degrees of monodispersity that may be suitable are described in U.S. Patent Application Publication No. 2010/0173394 A1, published Jul. 8, 2010, which is incorporated herein by reference.

Fragments 98 may distribute randomly into the droplets as they are formed. At a proper dilution of fragments 98 in the aqueous phase that is partitioned, and with a proper selection of droplet size, an average of less than about one copy or molecule of target region 80 is contained in each droplet. Accordingly, some droplets, such as the empty droplet indicated at 120, contain no copies of the target, many contain only one copy of the target region, some contain two or more copies of the target (e.g., the droplet indicated at 122), and some contain only one of the allele sequences of the target region (e.g., the droplets indicated at 124).

Allele sequences can be amplified, indicated at 126. Here, two allele sequences, 104 and 108, are amplified from locus 76 and only allele sequence 110 is amplified from locus 78 (also see FIG. 6). Amplified copies of each allele sequence are indicated at 104', 108', and 110'. In other embodiments, only one allele sequence may be amplified from each locus, or at least two allele sequences may be amplified from each locus, among others. (For example, allele sequence 106 may be amplified with the same primers that amplify allele sequence 110, but amplification of allele sequence 106 is not shown here to simplify the presentation.)

Allele-specific amplification data can be collected from the droplets, indicated at 130. In this example, fluorescence data is collected, with a different, distinguishable fluorescent dye, each included in a different allele-specific probe, providing amplification signals for each allele sequence 104', 108', 110'.

In particular, the dyes FAM, VIC, and ROX emit FAM-, VIC-, and ROX signals 132-136 that relate to amplification of allele sequences 104, 108, and 110, respectively. In other embodiments, allele-specific amplification of all four allele sequences 104-110 or of only two allele sequences (one from each locus) may be detected.

The amplification data is correlated, indicated at 140, and/or at least one measure of co-amplification of allele sequences in the same droplets is determined. Graphs 142, 144 schematically illustrate an approach to correlation and/or determination of measures of co-amplification. Graph 142 plots FAM and ROX signal intensities for individual droplets (represented by dots in the plot), while graph 144 plots VIC and ROX signal intensities for individual droplets. Signal values that represent amplification-negative ("−") and amplification-positive ("+") droplets for a given signal type (and thus a given allele sequence) are indicated adjacent each axis of the graphs.

Lines 146, 148 represent a best-fit of the amplification data of each graph to a linear relationship. However, the two fits have associated correlation coefficients of opposite polarity. The amplification data in graph 142 provides a negative correlation coefficient, because there is a negative correlation for co-amplification of allele sequence 104 (as reported by FAM signals) and allele sequence 110 (as reported by ROX signals) in the same droplets. In contrast, the amplification data in graph 144 provides a positive correlation coefficient, because there is a positive correlation for co-amplification of allele sequence 108 (as reported by VIC signals) and allele sequence 110 (as reported by ROX signals) in the same droplets. The correlation coefficients may be compared to one another to select a haplotype. For example, the haplotype may be selected based on which correlation coefficient is larger (e.g., closer to 1.0) and/or which is positive (if only one is positive). Here, a first haplotype including allele sequences 104 and 106 and a second haplotype including allele sequences 108 and 110 may be selected based on the positive correlation of VIC and ROX signals. In some embodiments, a haplotype may be selected based on only one correlation, such as based on whether a correlation coefficient is negative or positive or based on comparison of the correlation coefficient to a predefined value.

Figure 8:
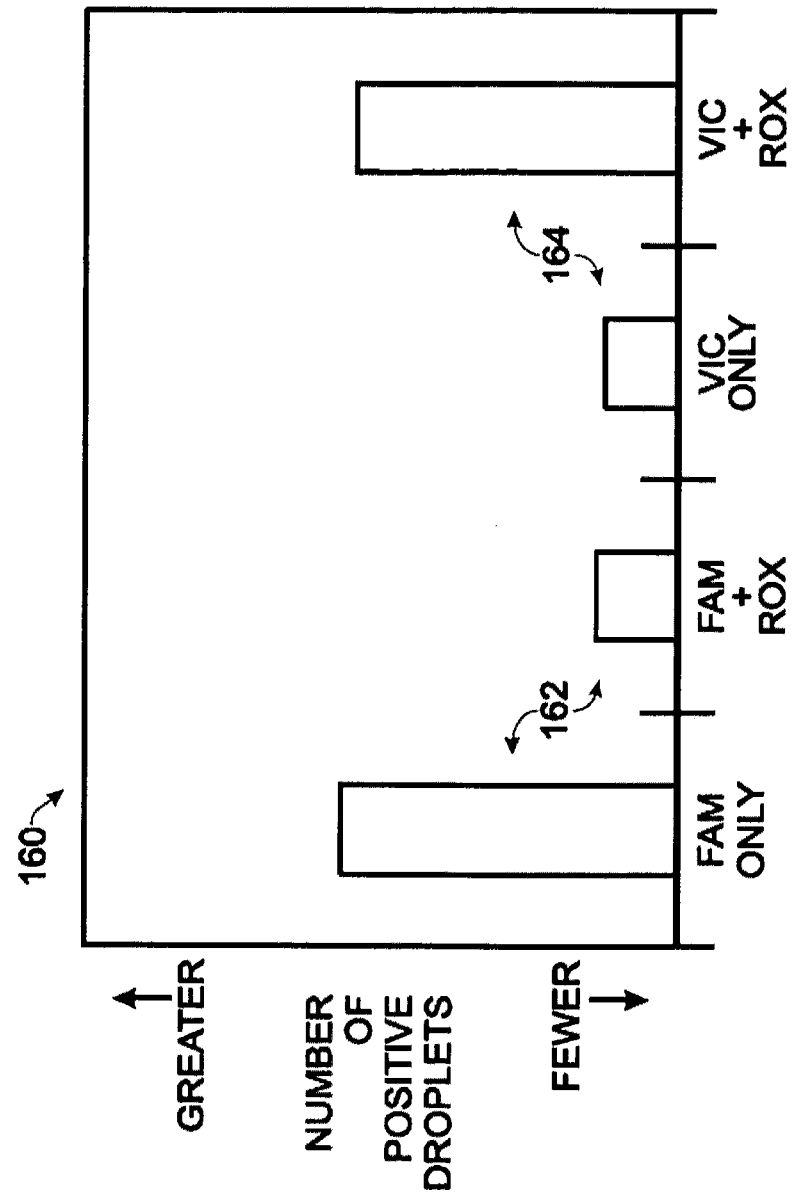
FIG. 8 is a graph illustrating an alternative approach to correlating the amplification data of FIG. 7, in accordance with aspects of the present disclosure.

FIG. 8 shows a bar graph 160 illustrating an alternative approach to correlating the amplification data of FIG. 7. The amplification data of FIG. 7 has been converted to binary form by comparing each type of droplet signal (FAM, VIC, and ROX) with a threshold that distinguishes amplification-positive droplets (assigned a "1") from amplification-negative droplets (assigned a "0") for each allele sequence. Graph 160 tabulates the binary form of the data to present the number of amplification-positive droplets for various allele sequences alone or in combination. The leftward two bars, indicated at 162, allow a comparison of the number of droplets that contain only allele sequence 104 (FAM) with the number that contain both allele sequences 104 (FAM) and 110 (ROX). The leftward data shows that amplification of allele sequence 104 does not correlate well with amplification of allele sequence 110. In other words, allele sequences 104 and 110 tend not to be co-amplified in the same droplets. The rightward two bars, indicated at 164, allow a comparison of the number of droplets that contain only allele sequence 108 (VIC) with the number that contain both allele sequences 108 (VIC) and 110 (ROX). The rightward data shows that amplification of allele sequence 108 correlates well with amplification of allele sequence 110. In other words, allele sequences 108 and 110 tend to be co-amplified in the same droplets. The leftward pair of bars and the rightward pair of bars considered separately or collectively indicate a haplotype in which allele sequence 108 is associated with allele sequence 110.

A sample comprising genetically linked loci can be subjected to fragmentation before being analyzed by the methods, compositions, or kits described herein. A sample comprising genetically linked loci can be fragmented by, e.g., mechanical shearing, passing the sample through a syringe, sonication, heat treatment (e.g., 30 mins at 90° C.), and/or nuclease treatment (e.g., with DNase, RNase, endonuclease, exonuclease, restriction enzyme). A sample comprising genetically linked loci can be subjected to no or limited processing before being analyzed.

In another embodiment, using droplet digital PCR (ddPCR), a duplex reaction can be performed targeting two genomic loci, e.g., two genes on a common chromosome. The droplets can be categorized into four populations according to their fluorescence. For example, if a FAM-labeled probe is used to detect to one loci, and a VIC-labeled probe is used to detect another loci, the four populations can be FAM+/VIC+, FAM+/VIC−, FAM−/VIC+, and FAM−/VIC−. By comparing the number of droplets with each of these populations, it is possible to determine the frequency at which loci co-segregate to the same droplet. Using Poisson statistics, the percentage of species that are actually linked to one another can be estimated versus instances where two separated loci are in the same droplet by chance.

The number of genetically linked loci that can be examined to determine if they are still linked in a sample or are separated in the sample using the methods, compositions, and kits described herein can be about, at least about, or more than about 2, 3, 4, 5, 6, 7, 8, 9, or 10. The number of genetically linked loci that can be examined to determine if they are still linked in a sample or are separated in the sample using the methods, compositions, and kits described herein can be about 2 to about 10, about 2 to about 8, about 2 to about 6, about 2 to about 4, about 3 to about 10, about 3 to about 8, about 3 to about 6, about 4 to about 10, or about 4 to about 6.

The number of base pairs between each of the genetically linked loci can be about, at least about, or less than about 10 bp, 25 bp, 50 bp, 75 bp, 100 bp, 250 bp, 500 bp, 750 bp, 1000 bp, 2000 bp, 3000 bp, 4000 bp, 5000 bp, 6000 bp, 7000 bp, 8000 bp, 9000 bp, 10,000 bp, 15,000 bp, 20,000 bp, 33,000 bp, 50,000 bp, 75,000 bp, 100,000 bp, 250,000 bp, 500,000 bp, 750,000 bp, 1,000,000 bp, 1,250,000 bp, 1,500,000 bp, 2,000,000 bp, 5,000,000 bp, or 10,000,000 bp. The number of base pairs between each of the genetically linked loci can be about 10 to about 10,000,000 bp, about 100 to about 10,000,000 bp, about 1,000 to about 10,000,000 bp, about 1,000 to about 1,000,000 bp, about 1,000 to about 500,000 bp, about 1,000 to about 100,000 bp, about 3000 to about 100,000 bp, about 1000 to about 33,000 bp, about 1,000 to about 10,000 bp, or about 3,000 to about 33,000 bp. The number of base pairs between each genetically linked alleles can be 0 bp.

In some embodiments, a method of haplotying comprises examining if two alleles at two different loci co-localize to the same spatially-isolated partition. In one embodiment, additional alleles at the two loci can be analyzed. For example, if two alleles at two different loci do not co-localize in a digital experiment, one or more other alleles at the two loci can be analyzed to provide a positive control for colocalization. For example, assume a maternally-inherited chromosome has allele A is at locus 1 and allele Y is at locus 2, 100 bp away from locus 1. On the corresponding paternally-inherited chromosome, assume allele B is at locus 1 and allele Z is at locus 2. If a nucleic acid sample comprising these nucleic acids is separated into spatially isolated partitions, and amplification for allele A and allele Z is performed, the amplification signal for allele A and allele Z should rarely or never colocalize to a single partition because allele A and allele Z are not linked. A digital analysis can be performed to confirm that allele A and allele Y are linked on the maternally-inherited chromosome or that allele B and allele Z are linked on the paternally-inherited chromosome.

Haplotyping with Two Colors

While embodiments shown herein demonstrate the use of a three-color system to measure phasing, phasing may also be measured using a two color system. For example, if two heterozygous SNPs (Aa and Bb) need to be phased, one may design a FAM assay targeting A and a VIC assay targeting B. Excess of partitions containing both A and B would be indicative of linkage between A and B, suggesting that the two haplotypes are A-B and a-b. Absence of such excess may be suggestive of the alternative combination of haplotypes: A-b and a-B. One can determine that the DNA is of high enough molecular weight to make this later inference. In order to confirm the alternative combination of haplotypes, it can be necessary to run another duplex assay in a separate well, where a different combination of alleles is targeted. For example, one may run a FAM assay targeting A and a VIC assay targeting b. Excess of partitions containing both A and b would be indicative of linkage between A and b, suggesting that the two haplotypes are A-b and a-B.

Reference Sequences

In methods involving the analysis of copy number (or other applications described herein), it is useful to count the number of times a particular sequence (e.g., target) is found, e.g., in a given genome. In some embodiments, this analysis is done by assessing (or comparing) the concentrations of a target nucleic acid sequence and of a reference nucleic acid sequence known to be present at some fixed number of copies in every genome. For the reference, a housekeeping gene (e.g., a gene that is required for the maintenance of basic cellular function) can be used that is present at two copies per diploid genome. Dividing the concentration or amount of the target by the concentration or amount of the reference can yield an estimate of the number of target copies per genome. One or more references can also be used to determine target linkage.

A housekeeping gene that can be used as reference in the methods described herein can include a gene that encodes a transcription factor, a transcription repressor, an RNA splicing gene, a translation factor, tRNA synthetase, RNA binding protein, ribosomal protein, RNA polymerase, protein processing protein, heat shock protein, histone, cell cycle regulator, apoptosis regulator, oncogene, DNA repair/replication gene, carbohydrate metabolism regulator, citric acid cycle regulator, lipid metabolism regulator, amino acid metabolism regulator, nucleotide synthesis regulator, NADH dehydrogenase, cytochrome C oxidase, ATPase, mitochondrial protein, lysosomal protein, proteosomal protein, ribonuclease, oxidase/reductase, cytoskeletal protein, cell adhesion protein, channel or transporter, receptor, kinase, growth factor, tissue necrosis factor, etc. Specific examples of housekeeping genes that can be used in the methods described include, e.g., HSP90, Beta-actin, tRNA, rRNA, ATF4, RPP30, and RPL3.

For determining the linkage of a target, one of the loci genetically linked to another locus can be a common reference, e.g., RPP30. Any genetically linked loci can be used in the methods described herein.

A single copy reference nucleic acid (e.g., gene) can be used to determine copy number variation. Multi-copy reference nucleic acids (e.g., genes) can be used to determine copy number to expand the dynamic range. For example, the multi-copy reference gene can comprise about, or more than about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 500, 1000, 2000, 3000, 4000, 5000, 6000, 7000, 8000, 9000, 10,000, 20,000, 30,000, 40,000, 50,000, 60,000, 70,000, 80,000, 90,000, or 100,000 copies in a genome. Multiple different nucleic acids (e.g., multiple different genes) can be used as a reference.

Determining Probability of Nucleic Acid Fragmentation

Figure 9:
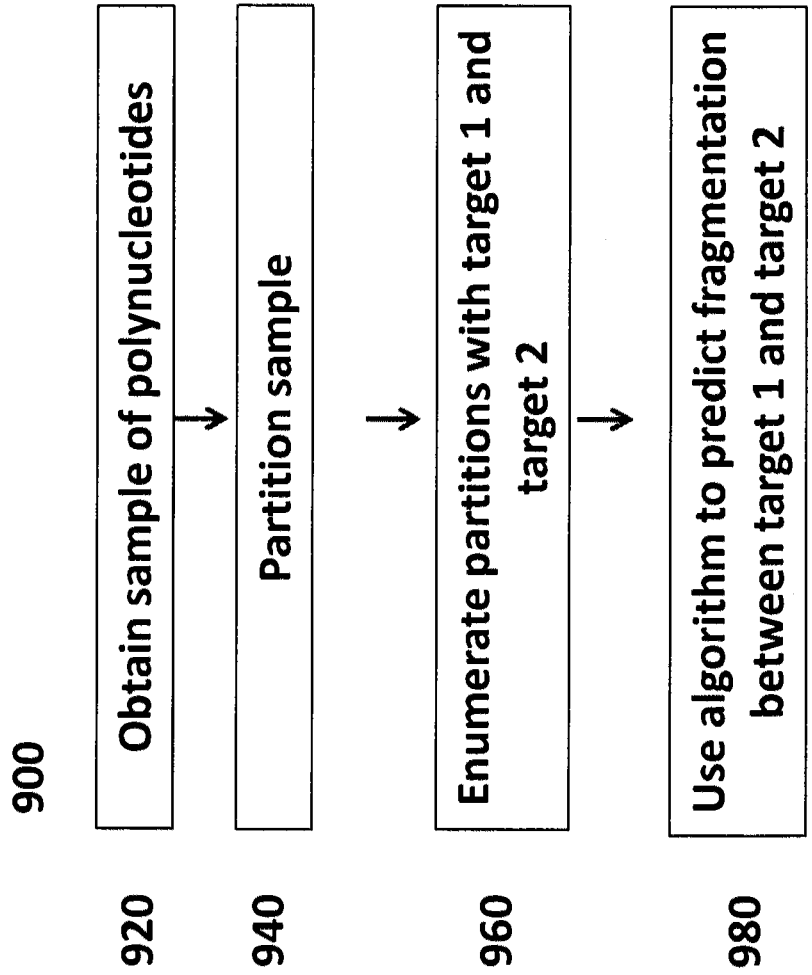
FIG. 9 illustrates a flowchart for predicting fragmentation between two targets.

Digital analysis can be performed to determine the extent of fragmentation between two markers in a nucleic acid sample. FIG. 9 illustrates a workflow (900). The steps in FIG. 9 can be performed in any suitable order and combination and can be united with any other steps of the present disclosure. A sample of polynucleotides can be obtained (920). The sample can be partitioned into a plurality of partitions (940) such that each partition contains on average only about 0, 1, 2, or several target polynucleotides. Each partition can have, on average, less than 5, 4, 3, 2, or 1 copies of a target nucleic acid per partition (e.g., droplet). In some cases, at least 0, 1, 2, 3, 4, 5, 6, 7, 8, 9, 10, 20, 30, 40, 50, 60, 70, 80, 90, 100, 125, 150, 175, or 200 partitions (e.g., droplets) have zero copies of a target nucleic acid.

The partitions can be assayed to enumerate partitions with a first target and a second target sequence (960) and an algorithm can be used to predict fragmentation between the first and second target sequence (980).

Figure 10:
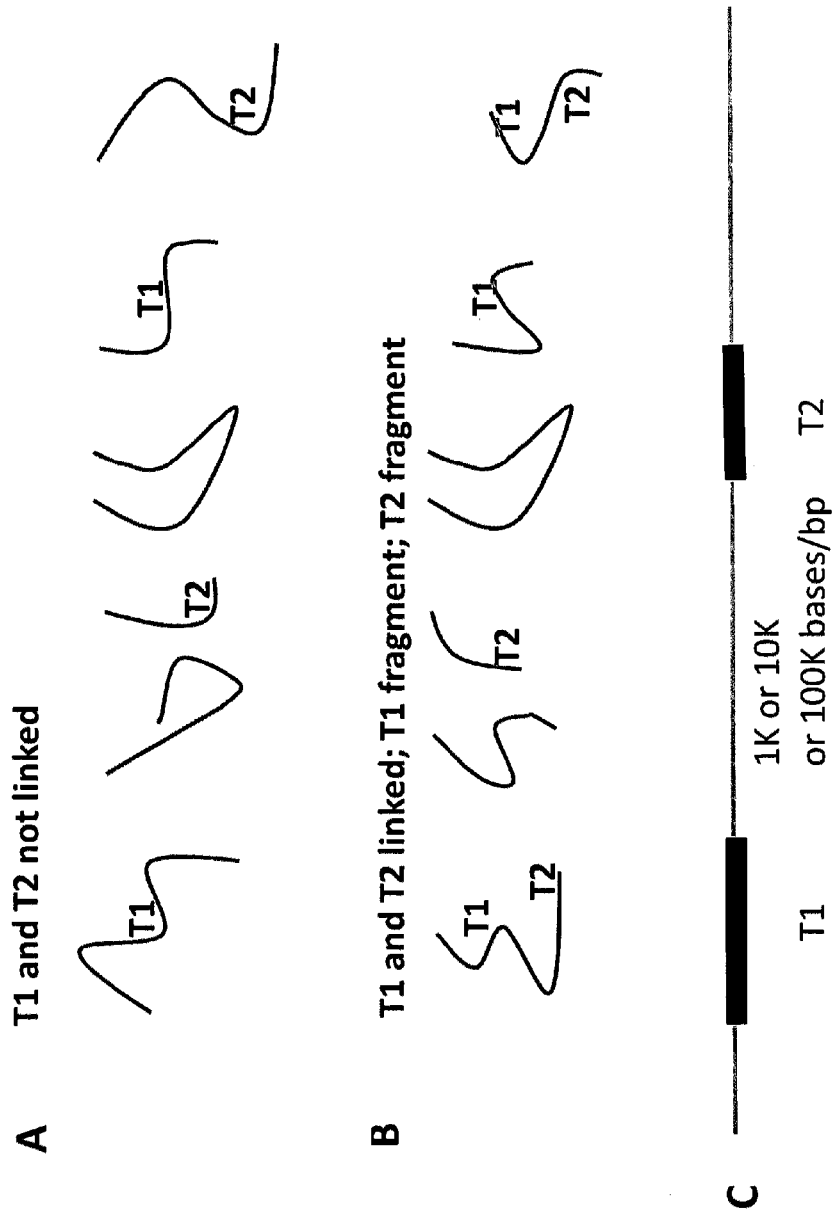
FIG. 10 illustrates linked and unlinked targets.

If two different loci (T1 and T2) are on different polynucleotides, a sample with the polynucleotides (920) will contain polynucleotides with T1 only and T2 only (see FIG. 10A). However, if T1 and T2 are on the same polynucleotide, a sample containing polynucleotides with T1 and T2 can have three species: fragmented polynucleotides with T1, fragmented polynucleotides with T2, and fragmented polynucleotides with T1 and T2 (FIG. 10B). The longer the distance between T1 and T2, the higher the probability of fragmentation between T1 and T2. The sample can be partitioned (FIG. 9: 940). A digital analysis can be performed, such as digital PCR or droplet digital PCR, and partitions with signal for T1, T2, and T1 and T2 can be enumerated (960). An algorithm can be developed and used to determine the probability of fragmentation between T1 and T2 (980). The algorithm can make use of the number of bases or base pairs between T1 and T2 if known. This method can be used to determine the extent of fragmentation of a DNA sample. If there are a number of partitions containing signal for T1 and T2 is greater than the number of partitions one would expect T1 and T2 to be in the same partition, this observation can indicate that T1 and T2 are linked.

It can be advantageous to use the above methods on a nucleic acid (e.g., DNA) sample to ensure that DNA is of high enough molecular weight that linkage information is preserved in the sample.

In any of the methods described herein making use of DNA, an assay can be performed to estimate the fragmentation of the DNA in the sample, and the methods can incorporate the information on fragmentation of the DNA. In another embodiment, results of an assay can be normalized based on the extent of fragmentation of DNA in a sample.

Nucleic acid fragmentation can also be measured by, e.g., gels, a Bioanalyzer, or size exclusion chromatography.

Measurement of Methylation Burden

A milepost assay can be used to determine methylation status of a CpG island. In one embodiment, a method is provided herein comprising using linkage of amplicons that can be measured through ddPCR (Milepost assay). The distance between amplicons can span greater than 10 kb, fully covering the range of sizes observed for CpG islands.

CpG islands can be common in the 5' region of human genes, including in promoter sequences. Methylation of CpG islands can play a role in gene silencing during X-chromosome inactivation and imprinting. Aberrant methylation of promoter region CpG islands can be associated with transcriptional inactivation of tumor suppressor genes in neoplasia. For example, abnormal methylation of tumor suppression genes p16, hMLH1, and THBS1 has been observed. There is an association between microsatellite instability and promoter-associated CpG island methylation. Determination of methylation status can play a role in determining fetal DNA load in maternal plasma. Methylation of CpG sequences can be a marker for cancer.

Figure 11:
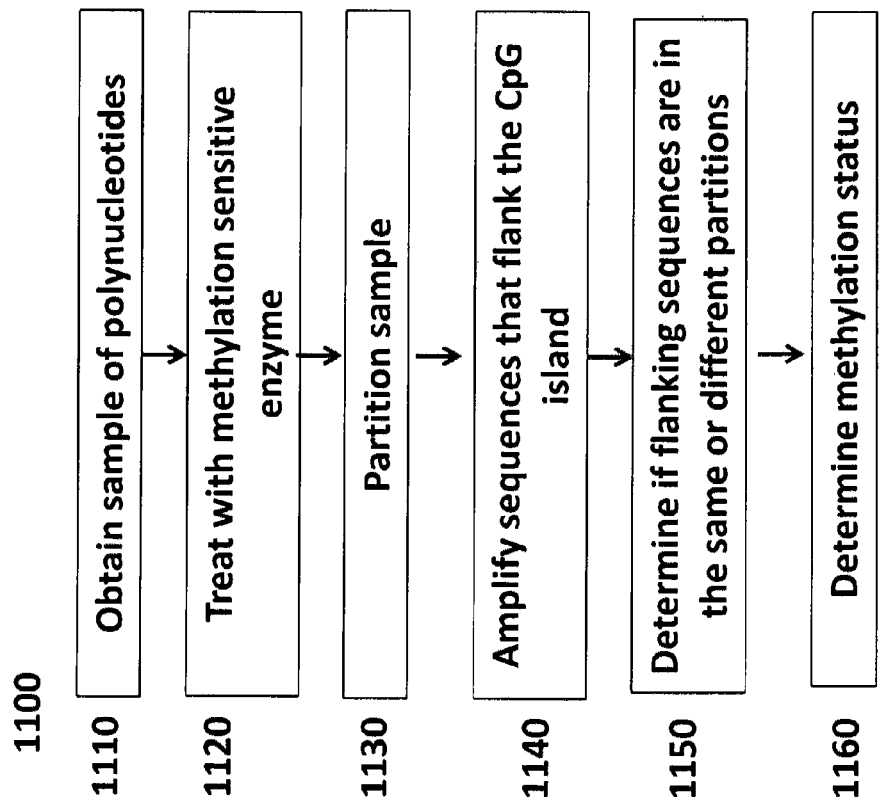
FIG. 11 illustrates a flowchart for analyzing methylation burden.

FIG. 11 illustrates a workflow of a method of determining the methylation status of a CpG island (1100). The steps in FIG. 11 can be performed in any suitable order and combination and can be united with any other steps of the present disclosure. A sample of polynucleotides can be obtained (1110). The polynucleotide sample can be treated with a methylation sensitive enzyme (1120). The sample can be partitioned into a plurality of partitions (1130) such that each partition contains on average only about 0, 1, 2, or several target polynucleotides. Each partition can have, on average, less than 5, 4, 3, 2, or 1 copies of a target nucleic acid per partition (e.g., droplet). In some cases, at least 0, 1, 2, 3, 4, 5, 6, 7, 8, 9, 10, 20, 30, 40, 50, 60, 70, 80, 90, 100, 125, 150, 175, or 200 partitions (e.g., droplets) have zero copies of a target nucleic acid. Nucleic acid sequences that flank the 5' and 3' end of the CpG island can be amplified (1140). The partitions can be assayed to determine if the sequences that flank the CpG island are in the same or different partitions (1150) to determine methylation status (1160). If the CpG is methylated, it will not be cleaved by a methylation sensitive enzyme, and the flanking sequences (mileposts) can be in the same partition. If the CpG is not methylated, the CpG island can be cleaved by the methylation sensitive enzyme, and the flanking sequences (mileposts) can be in different partitions. In another embodiment, a methylated CpG island can be cleaved by a methylation sensitive enzyme that can cleave methylated but not unmethylated sequence. In another embodiment, a methylated CpG island can be cleaved by a methylation sensitive enzyme that can recognize (e.g., bind) methylated sequence by not unmethylated sequence.

In another embodiment, the mileposts (markers) can be within a CpG island. In another embodiment, the mileposts (markers) can flank a single CpG sequence. In another embodiment, the mileposts (markers) can flank about, or at least about 2, 3, 4, 5, 6, 7, 8, 9, 10, 20, 30, 40, 50, 60, 70, 80, 90, 100, 150, 200, 250, 300, 350, 400, or 500 CpGs (e.g., one marker is 5' of the CpGs and the other marker is 3' of the CpGs).

In another embodiment, demethylation of a CpG island can be determined. The methylation status of a CpG island can be measured over a period of time (e.g., in samples taken at different time points, e.g., days, months, years). The methylation status of a CpG island among samples from different individuals can be compared.

A CpG can be a cytosine linked to a guanine through a phosphodiester bond, and a CpG island can be a cluster of such dinucleotide sequences. A CpG island, or CG island, can be a region of a genome that contains a high frequency of CpG sites. A CpG island can be about, less than about, or more than about, 100, 150, 200, 250, 300, 350, 400, 450, 500, 550, 600, 650, 700, 750, 800, 850, 900, 950, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 5100, 5200, 5300, 5400, 5500, 5600, 5700, 5800, 5900, or 6000 base pairs in length. A CpG island can be about 100 to about 6000 bp, about 100 to about 5000 bp, about 100 to about 4000 bp, about 100 to about 3000 bp, about 100 to about 2000 bp, about 100 to about 1000 bp, about 300 to about 6000 bp, about 300 to about 5000 bp, about 300 to about 4000 bp, about 300 to about 3000 bp, about 300 to about 2000 bp, or about 300 to about 1000 bp. In one embodiment, a CpG island can be a stretch of DNA at least 200 bp in length with a C+G content of at least 50% and an observed CpG/expected CpG ratio of at least 0.6 (Gardiner-Garden, M. and Frommer M. (1987) *J. Mol. Biol.* 196: 261-282). In another embodiment, a CpG island can be stretch of DNA of greater than 500 bp with a G+C content equal to or greater than 55% and an observed CpG/expected CpG ratio of at least 0.65 (Takai D. and Jones P. (2001) *PNAS* 99: 3740-3745).

In one method to identify methylated cytosines, bisulfite treatment is used to convert cytosines to uracils; methylated cytosines, however, are protected. Subsequent PCR converts uracil to a thymidine, resulting in a different sequence output for the same region of interest. Alternatively, conversion of C→T through bisulfite treatment can change the melting temperature of the amplicon, which can be measured through melting curve analysis post amplification. The limit of sensitivity is about 1-5% with this method, however. Furthermore, complete conversion requires extensive bisulfite treatment, which can lead to degradation of DNA.

Figure 12:
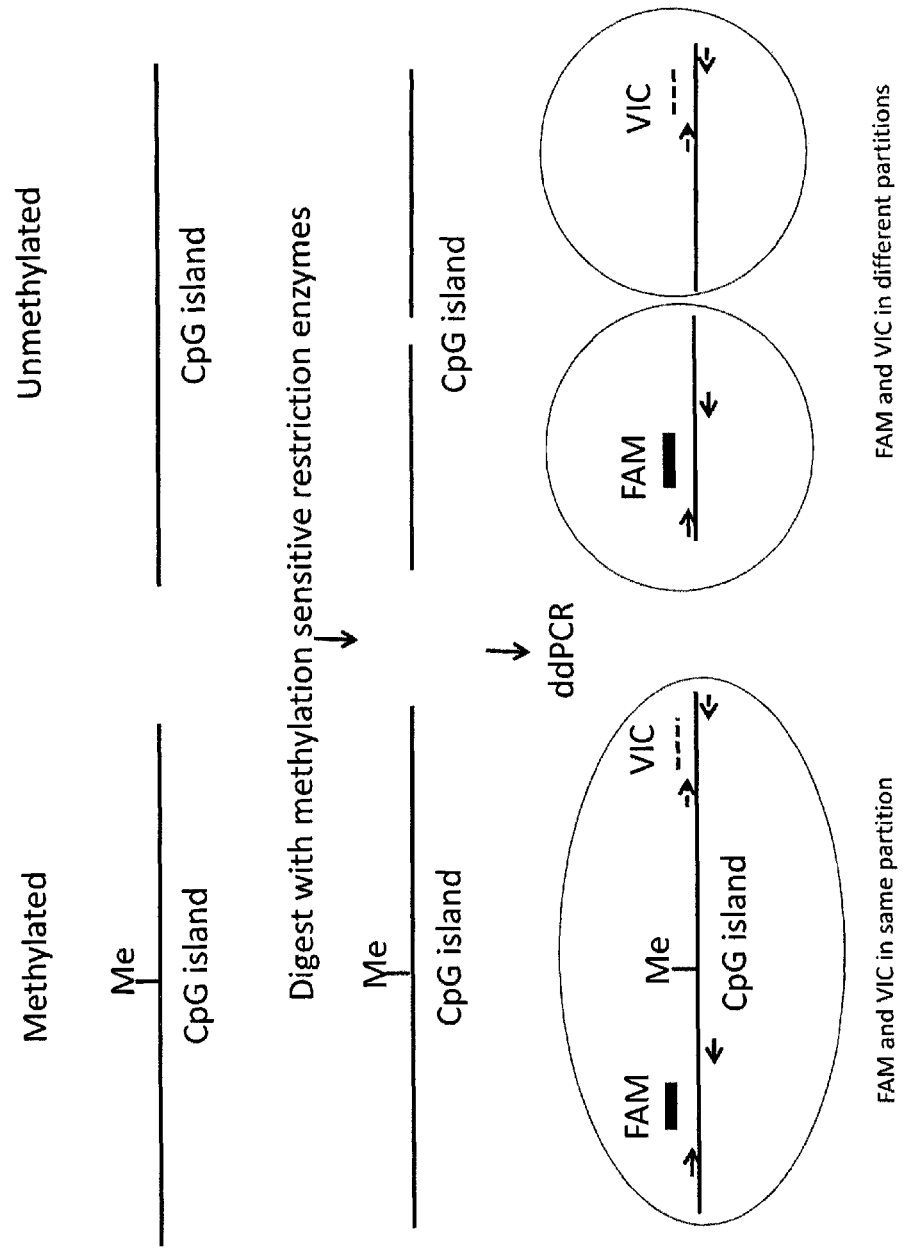
FIG. 12 illustrates an embodiment of a methylation burden assay.

In one embodiment of the method, two amplicons (e.g., FAM & VIC labeled) are designed flanking the CpG island of interest. DNA samples are digested with one or more methylation sensitive restriction enzymes, and digested and undigested samples can be analyzed via digital PCR, e.g., ddPCR. Undigested samples should exhibit 100% linkage of the FAM and VIC amplicons, and digested samples will exhibit 0% linkage of the FAM and VIC amplicons, indicating a difference in methylation status. The extended precision of this system can detect at least about 1/10, 1/50, 1/100, 1/200, 1/300, 1/400, 1/500, 1/600, 1/700, 1/800, 1/900, 1/1000, 1/2000, 1/3000, 1/4000, 1/5000, 1/6000, 1/7000, 1/8000, 1/9000, 1/10,000 differences in methylation status between two samples. FIG. 12 illustrates an embodiment of the method.

The regions to be amplified can be within about, or at least about, 1, 10, 20, 30, 40, 50, 60, 70, 80, 90, 100, 110, 120, 130, 140, 150, 160, 170, 180, 190, 200, 250, 300, 350, 400, 450, or 500 bp of the 5' or 3' end of the CpG island.

One or more methylation sensitive restriction enzymes can be used in the methods, compositions, and kits provided herein. The one or more methylation sensitive enzyme can include, e.g., DpnI, Ace65I, KpnI, ApaI, Bsp120I, Bsp143I, MboI, BspOI, NheI, Cfr9I, SmaI, Csp6I, RsaI, Ecl136II, SacI, EcoRII, MvaI, HpaII, MSpJI, LpnPI, FsnEI, DpnII, McrBc, or MspI. In one embodiment, a methylation sensitive restriction enzyme can cleave nucleic acid that is not methylated, but cannot cleave nucleic acid this is methylated. The one or more methylation sensitive enzymes can be about 1, 2, 3, 4, 5, 6, 7, 8, 9, 10, 11, 12, 13, 14, 15, 16, 17, 18, 19, 20, 21, 22, 23, 24, or 25 methylation-sensitive enzymes.

In some embodiments, nucleic is subject to Dam methylation and or Dcm methylation.

Table 1 includes a list of restriction enzymes for which the ability of the restriction enzyme to cleave DNA can be blocked or impaired by CpG methylation.

TABLE 1

List of restriction enzymes whose ability to cleave can be blocked or impeded by CpG methylation.

| Enzyme | Sequence |
|---|---|
| AatII | GACGT/C |
| Acc65I | G/GTACC |
| AccI | GT/MKAC |
| AciI | CCGC(-3/-1) |
| AclI | AA/CGTT |
| AfeI | AGC/GCT |
| AgeI | A/CCGGT |
| AgeI-HF ™ | A/CCGGT |
| AhdI | GACNNN/NNGTC (SEQ ID NO: 1) |
| AleI | CACNN/NNGTG (SEQ ID NO: 2) |
| ApaI | GGGCC/C |
| ApaLI | G/TGCAC |
| AscI | GG/CGCGCC |
| AsiSI | GCGAT/CGC |
| AvaI | C/YCGRG |
| AvaII | G/GWCC |
| BaeI | (10/15)ACNNNNGTAYC(12/7) (SEQ ID NO: 3) |
| BanI | G/GYRCC |
| BbvCI | CCTCAGC(-5/-2) |
| BceAI | ACGGC(12/14) |
| BcgI | (10/12)CGANNNNNNTGC(12/10) (SEQ ID NO: 4) |
| BcoDI | GTCTC(1/5) |
| BfuAI | ACCTGC(4/8) |
| BfuCI | /GATC |
| BglI | GCCNNNN/NGGC (SEQ ID NO: 5) |
| BmgBI | CACGTC(-3/-3) |
| BsaAI | YAC/GTR |
| BsaBI | GATNN/NNATC (SEQ ID NO: 6) |
| BsaHI | GR/CGYC |
| BsaI | GGTCTC(1/5) |
| BsaI-HF ™ | GGTCTC(1/5) |
| BseYI | CCCAGC(-5/-1) |
| BsiEI | CGRY/CG |
| BsiWI | C/GTACG |

TABLE 1-continued

List of restriction enzymes whose ability to cleave can be blocked or impeded by CpG methylation.

| Enzyme | Sequence |
|---|---|
| BslI | CCNNNNN/NNGG (SEQ ID NO: 7) |
| BsmBI | GTCTC(1/5) |
| BsmBI | CGTCTC(1/5) |
| BsmFI | GGGAC(10/14) |
| BspDI | AT/CGAT |
| BspEI | T/CCGGA |
| BsrBI | CCGCTC(-3/-3) |
| BsrFI | R/CCGGY |
| BssHII | G/CGCGC |
| BssKI | /CCNGG |
| BstAPI | GCANNNN/NTGC (SEQ ID NO: 8) |
| BstBI | TT/CGAA |
| BstUI | CG/CG |
| BstZ17I | GTA/TAC |
| BtgZI | GCGATG(10/14) |
| BtsIMutI | CAGTG(2/0) |
| Cac8I | GCN/NGC |
| ClaI | AT/CGAT |
| DpnI | GA/TC |
| DraIII | CACNNN/GTG |
| DraIII-HF™ | CACNNN/GTG |
| DrdI | GACNNNN/NNGTC (SEQ ID NO: 9) |
| EaeI | Y/GGCCR |
| EagI | C/GGCCG |
| EagI-HF™ | C/GGCCG |
| EarI | CTCTTC(1/4) |
| EciI | GGCGGA(11/9) |
| Eco53kI | GAG/CTC |
| EcoRI | G/AATTC |
| EcoRI-HF™ | G/AATTC |
| EcoRV | GAT/ATC |
| EcoRV-HF™ | GAT/ATC |
| FauI | CCCGC(4/6) |
| Fnu4HI | GC/NGC |
| FokI | GGATG(9/13) |
| FseI | GGCCGG/CC |
| FspI | TGC/GCA |
| HaeII | RGCGC/Y |
| HgaI | GACGC(5/10) |
| HhaI | GCG/C |
| HincII | GTY/RAC |
| HinfI | G/ANTC |
| HinP1I | G/CGC |
| HpaI | GTT/AAC |
| HpaII | C/CGG |
| Hpy166II | GTN/NAC |
| Hpy188III | TC/NNGA |
| Hpy99I | CGWCG/ |
| HpyAV | CCTTC(6/5) |
| HpyCH4IV | A/CGT |
| I-CeuI | CGTAACTATAACGGTCCTAAGGTAGCGAA(-9/-13) (SEQ ID NO: 10) |
| I-SceI | TAGGGATAACAGGGTAAT(-9/-13) (SEQ ID NO: 11) |
| KasI | G/GCGCC |
| MboI | /GATC |
| MluI | A/CGCGT |
| MmeI | TCCRAC(20/18) |
| MspA1I | CMG/CKG |
| MwoI | GCNNNNN/NNGC (SEQ ID NO: 12) |
| NaeI | GCC/GGC |
| NarI | GG/CGCC |
| Nb.BtsI | GCAGTG |
| NciI | CC/SGG |
| NgoMIV | G/CCGGC |
| NheI | G/CTAGC |
| NheI-HF™ | G/CTAGC |
| NlaIV | GGN/NCC |
| NotI | GC/GGCCGC |
| NotI-HF™ | GC/GGCCGC |
| NruI | TCG/CGA |
| Nt.BbvCI | CCTCAGC(-5/-7) |
| Nt.BsmAI | GTCTC(1/-5) |

TABLE 1-continued

List of restriction enzymes whose ability to cleave can be blocked or impeded by CpG methylation.

| Enzyme | Sequence |
| --- | --- |
| Nt.CviPII | (0/−1)CCD |
| PaeR7I | C/TCGAG |
| PhoI | GG/CC |
| PI-PspI | TGGCAAACAGCTATTATGGGTATTATGGGT (−13/−17) (SEQ ID NO: 13) |
| PI-SceI | ATCTATGTCGGGTGCGGAGAAAGAGGTAAT (−15/−19) (SEQ ID NO: 14) |
| PleI | GAGTC(4/5) |
| PmeI | GTTT/AAAC |
| PmlI | CAC/GTG |
| PshAI | GACNN/NNGTC (SEQ ID NO: 15) |
| PspOMI | G/GGCCC |
| PspXI | VC/TCGAGB |
| PvuI | CGAT/CG |
| PvuI-HF ™ | CGAT/CG |
| RsaI | GT/AC |
| RsrII | CG/GWCCG |
| SacII | CCGC/GG |
| SalI | G/TCGAC |
| SalI-HF ™ | G/TCGAC |
| Sau3AI | /GATC |
| Sau96I | G/GNCC |
| ScrFI | CC/NGG |
| SfaNI | GCATC(5/9) |
| SfiI | GGCCNNNN/NGGCC (SEQ ID NO: 16) |
| SfoI | GGC/GCC |
| SgrAI | CR/CCGGYG |
| SmaI | CCC/GGG |
| SnaBI | TAC/GTA |
| StyD4I | /CCNGG |
| TfiI | G/AWTC |
| TliI | C/TCGAG |
| TseI | G/CWGC |
| TspMI | C/CCGGG |
| XhoI | C/TCGAG |
| XmaI | C/CCGGG |
| ZraI | GAC/GTC |

In another embodiment, a nucleic acid comprising a CpG sequence or CpG island is contacted with one or more DNA methyltransferase (MTases), and a method of analyzing methylation of the CpG sequence described herein is performed. A DNA methyltransferase can transfer a methyl group from S-adenosylmethionine to a cytosine or adenine residue. The methyltransferase can be, e.g., a CpG MTase. The DNA MTase can be an m6a MTase (an MTase that can generate N6-methyladenine); an m4C MTase (an MTase that can generate N4-methylcytosine); or an m5C MTase (an MTase that can generate C5-methylcytosine. The MTase can be, e.g., DNMT1, DNMT3A, and DNMT3B.

Separation

Physical separation of target sequences can occur in a sequence-specific or non-sequences specific manner. Nonsequence specific means for separating target sequences include use of a syringe, sonication, heat treatment (e.g., 30 mins at 90° C.), and some types of nuclease treatment (e.g., with DNase, RNase, endonuclease, exonuclease).

Restriction Enzymes

A sequence specific method of separation of nucleic acid sequences can involve use of one or more restriction enzymes. One or more restriction enzymes can be used in any of the methods described herein. For example, restriction enzymes can be used to separate target copies in order to estimate copy number states accurately, to assess phasing, to generate haplotypes, or determine linkage, among other methods. One or more enzymes can be chosen so that the nucleic acid (e.g., DNA or RNA) between the target nucleic acids sequences is restricted, but the regions to be amplified or analyzed are not. In some embodiments, restriction enzymes can be chosen so that the restriction enzyme does cleave within the target sequence, e.g., within the 5' or 3' end of a target sequence. For example, if target sequences are tandemly arranged without spacer sequence, physical separation of the targets can involve cleavage of sequence within the target sequence. The digested sample can be used in the digital analysis (e.g., ddPCR) reaction for copy number estimation, linkage determination, haplotyping, examining RNA or DNA degradation, or determining methylation burden, e.g., of a CpG island.

Restriction enzymes can be selected and optimal conditions can be identified and validated across numerous sample and assay types for broad applications, e.g., digital PCR (e.g., ddPCR) for CNV determinations and any of the other methods described herein.

Computer software can be used to select one or more restriction enzymes for the methods, compositions, and/or kits described herein. For example, the software can be Qtools software.

One or more restriction enzyme used in the methods, compositions, and/or kits described herein can be any restriction enzyme, including a restriction enzyme available from New England BioLabs®, Inc. (see www.neb.com). A restriction enzyme can be, e.g., a restriction endonuclease, homing endonuclease, nicking endonuclease, or high fidelity (HF) restriction enzyme. A restriction enzyme can be a Type I, Type II, Type III, or Type IV enzyme or a homing endonuclease. In some cases, the restriction digest occurs under conditions of high star activity. In some cases, the restriction digest occurs under conditions of low star activity.

A Type I enzyme can cleave at sites remote from the recognition site; can require both ATP and S-adenosyl-L-methionine to function; and can be a multifunctional protein with both restriction and methylase activities. The recognition sequence for a Type I restriction endonuclease can be bipartite or interrupted. The subunit configuration of a restriction endonuclease can be a penatmeric complex. Coactivators and activators of Type I restriction endonucleases include, e.g., magnesium, AdoMet (S-Adenosyl methionine; SAM, SAMe, SAM-e), and ATP. Type I restriction endonucleases can cleave at a cleavage site distant and variable form the recognition site. Examples of Type I restriction endonucleases can include, e.g., EcoKI, EcoAI, EcoBI, CfrAI, StyLTII, StyLTIII, and StySPI.

A Type II enzyme can cleave within or at short specific distances from a recognition site; can require magnesium; and can function independent of methylase. The recognition sequence for a Type II restriction endonuclease can be palindromic or an interrupted palindrome. The subunit structure of a Type II restriction endonuclease can be a homodimer. Cleavage of a cleavage site with a Type II restriction endonuclease can result in fragments with a 3' overhang, 5' overhang, or a blunt end. Examples of Type II restriction endonucleases include, e.g., EcoRI, BamHI, KpnI, NotI, PstI, SmaI, and XhoI.

There are several subtypes of Type II restriction enzymes, including Type IIb, Type IIs, and Type IIe.

A Type IIb restriction endonuclease can have a recognition sequence with is bipartite or interrupted. The subunit structure of a Type IIb restriction endonuclease can be a heterotrimer. Cofactors and activators of Type IIb restriction endonucleases can include magnesium and AdoMet (for methylation). A Type IIb restriction endonuclease can cleave at a cleavage site on both strands on both sides of a recognition site a defined, symmetric, short distance away and leave a 3' overhang. Examples of Type IIb restriction endonucleases include, e.g., BcgI, Bsp24I, CjeI, and CjePI.

A Type IIe restriction endonuclease can have a recognition site that is palindromic, palindromic with ambiguities, or non-palindromic. The subunit structure of a Type IIe restriction endonuclease can be a homodimer or monomer. Cofactors and activators of Type IIe restriction endonuclease can include magnesium, and a second recognition site that can act in cis or trans to the endonuclease can act as an allosteric affector. A Type IIe restriction enzyme can cleave a cleavage site in a defined manner with the recognition sequence or a short distance away. Activator DNA can be used to complete cleavage. Examples of Type IIe restriction enzymes include, e.g., NaeI, NarI, BspMI, HpaII, Sa II, EcoRII, Eco57I, AtuBI, Cfr9I, SauBMKI, and Ksp632I.

A Type IIs restriction enzyme can have a recognition sequence that is non-palindromic. The recognition sequence can be contiguous and without ambiguities. The subunit structure of a Type IIs restriction endonuclease can be monomeric. A cofactor that can be used with a Type IIs restriction enzyme can be magnesium. A Type IIs restriction enzyme can cleave at a cleavage site in a defined manner with at least one cleavage site outside the recognition sequence. Examples of Type IIs restriction enzymes include, e.g., FokI, Alw26I, BbvI, BsrI, EarI, HphI, MboII, SfaNI, and Tth111I.

A Type III enzyme can cleave at a short distance from a recognition site and can require ATP. S-adenosyl-L-methionine can stimulate a reaction with a Type III enzyme but is not required. A Type III enzyme can exist as part of a complex with a modification methylase. The recognition sequence of a Type III restriction endonuclease can be non-palindromic. Cofactors and activators that can be used with Type III restriction endonucleases include, e.g., magnesium, ATP (not hydrolyzed), and a second unmodified site in the opposite orientation, a variable distance away. Examples of Type III restriction endonucleases include, e.g., EcoP15I, EcoPI, HinfIII, and StyLTI.

A Type IV enzyme can target methylated DNA. Examples of Type IV restriction enzymes include, e.g., McrBC and Mrr systems of *E. coli*.

The restriction enzyme can be a homing endonuclease. A homing endonuclease can be a double stranded DNase. A homing endonuclease can have large, asymmetric recognition sites (e.g., 12-40 base pairs). Coding sequences for homing endonucleases can be embedded in introns or inteins. An intein can be a "protein intron" that can excise itself and rejoin the remaining portions (the exteins) with a peptide bond. A homing endonuclease can tolerate some sequence degeneracy within its recognition sequence. The specificity of a homing endonuclease can be 10-12 base pairs. Examples of homing endonucleases include I-CeuI, I-SceI, I-PpoI, PI-SceI, PI-PspI, and PI-SceI.

A restriction enzyme used in the methods, compositions, and/or kits herein can be a dimer, trimer, tetramer, pentamer, hexamer, etc.

The one or more restriction enzymes used in the methods, compositions and/or kits described herein can be a component of a hybrid or chimeric protein. For example, a domain of a restriction enzyme comprising an enzymatic activity (e.g., endonuclease activity) can be fused to another protein, e.g., a DNA binding protein. The DNA binding protein can target the hybrid to a specific sequence on a DNA. The nucleic acid cleavage activity of the domain with enzymatic activity can be sequence specific or sequence non-specific. For example, the non-specific cleavage domain from the type IIs restriction endonuclease FoId can be used as the enzymatic (cleavage) domain of the hybrid nuclease. The sequence the domain with the enzymatic activity can cleave can be limited by the physical tethering of the hybrid to DNA by the DNA binding domain. The DNA binding domain can be from a eukaryotic or prokaryotic transcription factor. The DNA binding domain can recognize about, or at least about, 2, 3, 4, 5, 6, 7, 8, 9, 10, 11, 12, 13, 14, 15, 16, 17, 18, 19, 20, 21, 22, 23, 24, or 25 base pairs of continuous nucleic acid sequence. In some cases, the restriction enzyme is a 4-base cutter, 6-base cutter, or 8-base cutter. The DNA binding domain can recognize about 9 to about 18 base pairs of sequence. The DNA binding domain can be, e.g., a zinc finger DNA binding domain. The hybrid can be a zinc finger nuclease (e.g., zinc finger nuclease). The hybrid protein can function as a multimer (e.g., dimer, trimer, tetramer, pentamer, hexamer, etc.).

Examples of specific restriction enzymes that can be used in the methods, compositions, and/or kits described herein include AaaI, AagI, AarI, AasI, AatI, AatII, AauI, AbaI, AbeI, AbrI, AccI, AccII, AccIII, Acc16I, Acc36I, Acc65I, Acc113I, AccB1I, AccB2I, AccB7I, AccBSI, AccEBI, AceI, AceII, AceIII, AciI, AcII, AcINI, AcIWI, AcpI, AcpII, AcrII, AcsI, AcuI, AcvI, AcyI, AdeI, AeuI, AfaI, Afa22MI, Afa16RI, AfeI, AfII, AflII, AflIII, AgeI, AgeI-HF, AglI, AhaI, AhaII, AhaIII, AhaB8I, AhdI, AhlI, AhyI, AitI, AjnI, AjoI, AleI, AlfI, AliI, AliAJI, AloI, AluI, AIwI, Alw21I, Alw26I, Alw44I, AlwNI, AlwXI, Ama87I, AcoI, AocII, AorI, Aor13HI, Aor51HI, AosI, AocII, ApaI, ApaBI, ApaCI, ApaLI, ApaORI, ApeKI, ApiI, ApoI, ApyI, AquI, AscI, AseI, AselII, AsiSI, AvaI, AvaII, AvrII, BaeGI, BaeI, BamHI, BamHI-HF, BanI, BanII, BbsI, BbvCI, BbvI, BccI, BceAi, BcgI, BciVI, BcoDI, BfaI, BfuCI, BfuCI, BglI, BglII, BlpI, BmgBI, BmrI, BmtI, BpmI, Bpu10I, BpuEI, BsaAI, BsaBI, BsaHI, BsaI, BsaI-HF, BsaJI, BsaWI, BsaXI, BseRI, BseYI, BsgI, BsiEI, BsiHKAI, BsiWI, BslI, BsmAI, BSmBI, BsmFI, BsmI, BsoBI, Bsp1286I, BspCNI, BspDI, BspEI, BspHI, BspMI, BspQI, BsrBI, BsrDI, BsrFI, BsrGI, BsrI, BssHII, BssKI, BssSI, BstAPI, BstBI, BsteII, BstNI, BstUI, BstXI, BstYI, BstZ17I, Bsu36I, BtgI, BtgZI, BtsCI, BtsI, BtsIMutI, Cac8I, ClaI, CspCI, CviAII, CviKI-1, CviQI, DdeI, DpnI, DpnII, DraI, DraIII, DraIII-HF™, DrdI, EaeI, EagI, EagI-HF™, EarI, EciI, Eco53kI, EcoNI, EcoO109I, EcoP15I, EcoRI, EcoRI-HF™, EcoRV, EcoRV-HF™, FatI, FauI, Fnu4HI, FokI, FseI, FspEI, FspI, HaeII, HaeIII, HgaI, HhaI, HincII, HindIII, HindIII-HF™, HinfI, HinPlI, HpaI, HpaII, HphI, Hpy166II, Hpy188I, Hpy188III, Hpy99I, HpyAV, HpyCH4III, HpyCH4IV, HpyCH4IV, I-CeuI, I-SceI, KasI, KpnI, KpnI-HF™, LpnPI, MboI, MboII, MfeI, MfeI-HF™, MluCI, MluI, MlyI, MmeI, MnlI, MscI, MseI, MslI, MspA1I, MspI, MspJI, MwoI, NaeI, NarI, Nb.BbvCI, Nb.BsmI, Nb.BsrDI, Nb.BtsI, NciI, NcoI, NcoI-HF™, NdeI, NgoMIV, NheI, NheI-HF™, NlaIII, NlaIV, NmeAIII, NotI, NotI-HF™, NruI, NsiI, NspI, Nt.AlwI, Nt.BbvCI, Nt.BsmAI, Nt.BspQI, Nt.BstNBI, Nt.CviPII, PacI, PaeR7I, PciI, PflFI, PflMI, PhoI, PI-PspI, PI-SceI, PleI, PmeI, PmlI, PpuMI, PshAI, PsiI, PspGI, PspOMI, PspXI, PstI, PstI-HF™, PvuI, PvuI-HF™, PvuII, PvuII-HF™, RsaI, RsrII, SacI, SacII, SalI, SalI-HF™, SapI, Sau3AI, Sau96I, SbfI, SbfI-HF™, ScaI, ScaI-HF™, ScrFI, SexAI, SfaNI, SfcI, SfiI, SfoI, SgrAI, SmaI, SmlI, SnaBI, SpeI, SphI, SphI-HF™, SspI, SspI-HF™, StuI, StyD4I, StyI, StyI-HF™, SwaI, TaqαI, TfiI, TliI, TseI, Tsp45I, Tsp509I, TspMI, TspRI, Tth111I, XbaI, XcmI, XhoI, XmaI, XmnI, and ZraI.

The one or more restriction enzymes used in the methods, compositions, and/or kits described herein can be derived from a variety of sources. For example, the one or more restriction enzymes can be produced from recombinant nucleic acid. The one or more restriction enzymes can be produced from recombinant nucleic acid in a heterologous host (e.g., in a bacteria, yeast, insect, or mammalian cell). The one or more restriction enzymes can be produced from recombinant nucleic acid in a heterologous host and purified from the heterologous host. The one or more restriction enzymes can be purified from a native source, e.g., a bacterium or archaea. If more than one restriction enzyme is used, at least one of the restriction enzymes can be from a recombinant source and at least one of the more than one restriction enzymes can be from a native source.

A recognition site for the one or more restriction enzymes can be any of a variety of sequences. For example, a recognition site for the one or more restriction enzymes can be a palindromic sequence. A recognition site for the one or more restriction enzymes can be a partially palindromic sequence. In some embodiments, a recognition site for the one or more restriction enzymes is not a palindromic sequence. A recognition site for the one or more restriction enzymes can be about, or more than about, 1, 2, 3, 4, 5, 6, 7, 8, 9, 10, 11, 12, 13, 14, 15, 16, 17, 18, 19 or 20 bases or base pairs. A recognition site for a restriction enzyme can be about 2 to about 20, about 5 to about 20, about 5 to about 15, about 5 to about 10, about 7 to about 20, about 7 to about 15, or about 7 to about 10 bases or base pairs.

Two or more restriction enzymes can be used to digest a polynucleotide. The two or more restriction enzymes can recognize the same or different recognition sites. There can be one or more recognition sites for a single restriction enzyme between two target nucleic acid sequences on a single polynucleotide. There can be about, or at least about, 1, 2, 3, 4, 5, 6, 7, 8, 9, 10 or more recognition sites for a single restriction enzyme between two target nucleic acid sequences on a single polynucleotide. There can be two or more different restriction enzyme recognition sites between two target nucleic acid sequences on a single polynucleotide. There can be about, or at least about, 1, 2, 3, 4, 5, 6, 7, 8, 9, 10 or more different restriction enzyme recognition sites between two target nucleic acid sequences on a single polynucleotide. There can be one or more different restriction enzyme restriction sites between two target nucleic acid sequences on a single polynucleotide. There can be about, or at least about, 1, 2, 3, 4, 5, 6, 7, 8, 9, 10 or more restriction enzyme restriction sites between two target nucleic acid sequences on a single polynucleotide.

A restriction enzyme digest can comprise one or more isoschizomer. Isoschizomers are restriction endonucleases that recognize the same sequence. The isoschizomers can have different cleavage sites; these enzymes are referred to as neoschizomers.

In some embodiments, cleavage by a restriction enzyme results in a blunt end. In some embodiments, cleavage by a restriction enzyme does not result in a blunt end. In some embodiments, cleavage by a restriction enzyme results in two fragments, each with a 5' overhang. In some embodiments, cleavage by a restriction enzyme results in two fragments each with a 3' overhang.

Primers for one or more amplification reactions can be designed to amplify sequences upstream and downstream of restriction enzyme cleavage site.

In one embodiment, a restriction enzyme does not cut the target nucleic acid sequence or a reference amplicon. One can use a reference sequence, e.g., a genome sequence, to predict whether a restriction enzyme will cut a nucleic acid sequence. In another embodiment, a restriction enzyme does cut the target nucleic acid sequence. The cleavage can occur near (within about 5, 10, 15, 25, 50, or 100 bp) of the 5' or 3' end of the target sequence, within the target sequence.

In another embodiment, a restriction enzyme does not cut the target or the reference nucleic acid sequence or amplicon even if the sequence or amplicon contains one or more SNPs. SNP information can be obtained from several databases, most readily from dbSNP (www.ncbi.nlm.nih.gov/projects/SNP/).

One or more methylation sensitive restriction enzymes can be used in the methods, compositions, and kits provided herein. The one or more methylation sensitive enzyme can include, e.g., DpnI, Acc65I, KpnI, Apt Bsp120I, Bsp143I, MboI, BspOI, NheI, Cfr9I, SmaI, Csp6I, RsaI, Ecl136II, SacI, EcoRII, MvaI, HpaII, or MspI. In one embodiment, a methylation sensitive restriction enzyme can cleave nucleic acid that is not methylated, but cannot cleave nucleic acid this is methylated.

The restriction enzymes used in the present disclosure can be selected to specifically digest a selected region of nucleic acid sequence. In one embodiment, the one or more restriction enzymes cut between target nucleic acid sequences or target amplicons. One or more enzymes can be chosen whose recognition sequences occur e.g., once or multiple times—near the target nucleic acid sequences or target amplicons. In one embodiment, care is taken to ensure that these recognition sequences are not affected by the presence of SNPs.

In one embodiment, a restriction enzyme is an efficient but specific (no star activity) cutter. This property, along with digestion time and enzyme concentration, can be determined in advance by performing appropriate enzyme titration experiments. In one embodiment, a restriction enzyme can have star activity. Star activity can be the cleavage of sequences that are similar but not identical to a defined recognition sequence.

The ratio of the number of "units" of a restriction enzyme to an amount of nucleic acid (e.g., DNA or RNA) can be, e.g., about, or at least about, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 155, 160, 165, 170, 175, 180, 185, 190, 195, 200, 205, 210, 215, 220, 225, 230, 235, 240, 245, 250, 300, 350, 400, 500, 600, 700, 800, 900, 1000, 2000, 3000, 4000, 5000, 6000, 7000, 8000, 9000, 10,000, 12,000, 14,000, 15,000, 16,000, 18,000, or 20,000 units/µg of nucleic acid. The ratio of the number of units of restriction enzyme to an amount of nucleic acid can be about 1 to about 20,000, about 1 to about 10,000, about 1 to about 5,000, about 100 to about 10,000, about 100 to about 1,000, about 50 to about 500, or about 50 to about 250 units/µg.

One or more restriction enzymes can be incubated with a sample comprising polynucleotides for about, or more than about, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 minutes. One or more restriction enzymes can be incubated with a sample comprising polynucleotides for about, or more than about, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, or 48 hours. One or more restriction enzymes can be incubated with a sample comprising polynucleotides for about 1 to about 60 min., about 1 min. to about 48 hrs, about 1 min. to about 24 hrs, about 1 min. to about 20 hrs, about 1 min to about 16 hrs, about 0.5 hr to about 6 hrs, about 0.5 hr to about 3 hrs, about 1 hr to about 10 hrs, about 1 hr to about 5 hr, or about 1 hr to about 3 hr.

A restriction enzyme digest can be performed at a temperature of about, or more than about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, or 65° C. A restriction enzyme digest can be performed at a temperature of about 10 to about 65° C., about 20 to about 65° C., about 30 to about 65° C., about 37 to about 65° C., about 40 to about 65° C., about 50 to about 65° C., about 25 to about 37° C., or about 30 to about 37° C.

The pH of a restriction enzyme digest using one or more restriction enzymes can be about 2, 2.5, 3, 3.5, 4, 4.5, 5, 5.5, 6, 6.5, 6.6, 6.7, 6.8, 6.9, 7, 7.1, 7.2, 7.3, 7.4, 7.5, 7.5, 7.6, 7.7, 7.8, 7.9, 8, 8.1, 8.2, 8.3, 8.4, 8.5, 8.6, 8.7, 8.8, 8.9, 9, 9.5, 10, 10.5, 11, 11.5, 12, or 12.5. The pH of a restriction enzyme digest can be about 5 to about 9, about 5 to about 8, about 5 to about 7, about 6 to about 9, or about 6 to about 8.

A restriction enzyme digest can contain one or more buffers. The one or more buffers can be, e.g., tris-HCl, bis-tris-propane-HCl, TAPs, bicine, tris, tris-acetate, tris-HCl, tricine, TAPSO, HEPES, TES, MOPS, PIPES, cacodylate, SSC, phosphate buffer, collidine, veronal acetate, MES., ADA, ACES, cholamine chloride, acetamidoglycine, glycinamide, maleate, CABS, piperidine, glycine, citrate, glycylglycine, malate, formate, succinate, acetate, propionate, pyridine, piperazine, histidine, bis-tris, ethanolamine, carbonate, MOPSO, imidazole, BIS-TRIS propane, BES, MOBS, triethanolamine (TEA), HEPPSO, POPSO, hydrazine, Trizma (tris), EPPS, HEPPS, bicine, HEPBS, AMPSO, taurine (AES), borate, CHES, 2-amino-2-methyl-1-propanol (AMP), ammonium hydroxide, or methylamine. The concentration of a buffer in a solution can be, e.g., about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 mM. The concentration of buffer in a solution can be about 10 to about 100 mM, about 10 to about 75 mM, about 25 to about 75 mM, or about 10 to about 50 mM.

A restriction enzyme digest using one or more restriction enzymes can comprise bovine serum albumin (BSA). The concentration of BSA in a restriction digest can be about, or more than about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 1.5, 2, 3, 4, 5, 6, 7, 8, 9, or 10 mg/ml. The concentration of BSA in a restriction digest can be about 0.01 to about 10 mg/ml, about 0.01 to about 1 mg/ml, about 0.05 to about 1 mg/ml, or about 0.05 to about 0.5 mg/ml.

A restriction enzyme digest using one or more restriction enzymes can comprise glycerol. Glycerol can be at a concentration (volume to volume) of about, or at least about, 1, 2, 3, 4, 5, 6, 7, 8, 9, 10, 11, 12, 13, 14, 15, 16, 17, 18, 19, 20, 21, 22, 23, 24, or 25 percent. The concentration of glycerol in a restriction enzyme digest can be about 1 to about 25%, about 1 to about 20%, about 1 to about 15%, about 1 to about 10%, or about 1 to about 5%.

A restriction enzyme digest can comprise one or more organic solvents, e.g., DMSO, ethanol, ethylene glycol, dimethylacetamide, dimethylformamide, or suphalane. A restriction enzyme digest can be free of one or more organic solvents.

A restriction enzyme digest can comprise one or more divalent cations. The one or more divalent cations can be, e.g., $Mg^{2+}$, $Mn^{2+}$, $Cu^{2+}$, $Co^{2+}$, or $Zn^{2+}$.

A restriction digest can comprise one or more salts. The one or more salts can include, for example, potassium acetate, potassium chloride, magnesium acetate, magnesium chloride, sodium acetate, or sodium chloride. The concentration of each of the one or more salts can be, e.g., about, or more than about, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 155, 160, 165, 170, 175, 180, 185, 190, 195, 200, 205, 210, 215, 220, 225, 230, 235, 240, 245, or 250 mM. The concentration of each of the one or more salts can be about 5 to about 250, about 5 to about 200, about 5 to about 150, about 5 to about 100, about 10 to about 100, about 10 to about 90, about 10 to about 80, about 10 to about 70, about 10 to about 60, or about 10 to about 50 mM.

A restriction digest can comprise one or more reducing agents. The one or more reducing agents can inhibit the formation of disulfide bonds in a protein. A reducing agent can be, for example, dithiothreitol (DTT), 2-mercaptoethanol (BME), 2-mercaptoethylamine-HCl, tris(2-carboxythyl) phosphine (TCEP), or cysteine-HCl. The concentration of the one or more reducing agents in a restriction enzyme digest can be about, or more than about, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 3, 4, 5, 6, 7, 8, 9, 10, 11, 12, 13, 14, 15, 16, 17, 18, 19, 20, or 25 mM. The concentration of the one or more reducing agents in a restriction enzyme digest can be about 0.01 to about 25 mM, about 0.01 to about 15 mM, about 0.01 to about 10 mM, about 0.01 to about 5 mM, about 0.1 to about 5 mM, or about 0.5 to about 2.5 mM.

More than one restriction enzyme can be used in a restriction enzyme digest of nucleic acid. For example, multiple-digests can be employed if one or more of the restriction enzymes do not efficiently cut a nucleic acid, or if they do not all work universally well across all samples (e.g., because of SNPs). The number of different restriction enzymes that can be used in a restriction digest can be about, or at least about, 1, 2, 3, 4, 5, 6, 7, 8, 9, 10, 11, 12, 13, 14, 15, 16, 17, 18, 19, or 20. The number of different restriction enzymes that can be used in a restriction enzyme digest can be, e.g., about 1 to about 20, about 1 to about 15, about 1 to about 10, about 1 to about 7, about 1 to about 6, about 1 to about 5, about 1 to about 4, about 1 to about 3, or about 1 to about 2.

There is some evidence that a PCR works better when the size of the fragment containing the amplicon or targets is relatively small. Therefore, selecting restriction enzymes with cutting sites near the amplicons or target can be desirable. For example, a restriction enzyme recognition site or cleavage site can be within about, or less than about, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79; 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 155, 160, 165, 170, 175, 180, 185, 190, 195, 200, 205, 210, 215, 220, 225, 230, 235, 240, 245, 250, 300, 350, 400, 500, 600, 700, 800, 900, 1000, 2000, 3000, 4000, 5000, 6000, 7000, 8000, 9000, 10,000, 12,000, 14,000, 15,000, 16,000, 18,000, or 20,000 base pairs from the 5' end or 3' end of one of the targets on a polynucleotide. A restriction enzyme recognition site or cleavage site can be within about 1 to about 10,000, about 1 to about 5,000, about 1 to about 2,500, about 1 to about 1,000, about 1 to about 100, about 100 to about 1000, about 100 to about 500, or about 100 to about 250 bp from the 5' or 3' end of a target nucleic acid sequence.

A single sample can be analyzed for multiple CNVs. In this case, it can be desirable to select the smallest number of digests that would work well for the entire set of CNVs. In one embodiment, a single restriction enzyme cocktail can be found that does not cut within any of the amplicons or target nucleic acid sequences but has recognition sites or cleavage sites near each one of them. A restriction enzyme recognition site or cleavage site can be within about, or less than about, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 155, 160, 165, 170, 175, 180, 185, 190, 195, 200, 205, 210, 215, 220, 225, 230, 235, 240, 245, 250, 300, 350, 400, 500, 600, 700, 800, 900, 1000, 2000, 3000, 4000, 5000, 6000, 7000, 8000, 9000, 10,000, 12,000, 14,000, 15,000, 16,000, 18,000, or 20,000 base pairs from the 5' end or 3' end of one of the targets on a polynucleotide. A restriction enzyme recognition site or cleavage site can be within about 1 to about 20,000, about 10 to about 20,000, about 100 to about 20,000, about 1000 to about 20,000, about 10 to about 10,000, about 10 to about 1000, about 10 to about 100, about 50 to about 20,000, about 50 to about 1000, about 50 to about 500, about 50 to about 250, about 50 to about 150, or about 50 to 100 base pairs from the 5' end or 3' end of one or the targets on a polynucleotide.

Appropriate software can be written and/or used to automate the process of restriction enzyme choice and present an interface for a user, e.g., an experimental biologist, to choose the most appropriate enzymes given the criteria above. Additional considerations can be employed by the software, such as enzyme cost, enzyme efficiency, buffer compatibility of restriction enzymes, methylation sensitivity, number of cleavage sites in a segment of nucleic acid, or availability. The software can be used on a computer. An algorithm can be generated on a computer readable medium and be used to select one or more restriction enzymes for digesting nucleic acid. A computer can be connected to the internet and can be used to access a website that can permit selection of restriction endonucleases. A web tool can be used to select restriction enzymes that will cut around an amplicon in order to separate linked gene copies for CNV estimation. For example, enzymes and assays can be stored in a database and selection of a restriction enzyme can be automatic. Additional statistics that can be considered include, e.g., length of shortest fragment, % GC content, frequency of cuts around (or in) an amplicon, and cost of enzymes. QTools can be used to assist in the selection of one or more restriction enzymes. FIGS. 13 and 14 illustrate information that can be considered when selecting a restriction enzyme.

For assay storage for data analysis, a researcher can enter assays by location or primer sequence. QTools can automatically retrieve and stores amplicon sequences and known SNPs and compute thermodynamic parameters. As researchers use the assay more, they can enter additional data, including confirmed sample CNVs and annealing temperatures.

Digestion with more than one enzyme, performed serially or together in a single tube, can help to ensure complete cutting of difficult targets. A series of restriction enzyme digests of one sample can be performed with different enzymes, e.g., about 1, 2, 3, 4, 5, 6, 7, 8, 9, or 10.

One or more restriction enzymes in a digest can be inactivated following the restriction enzyme digest. In some embodiments, the one or more restriction enzymes cannot be inactivated by exposure to heat. Most restriction enzymes can be heat-inactivated after restriction by raising the temperature of the restriction reaction. The temperature for heat-inactivation can be, e.g., about, or more than about, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 degrees Celsius. The temperature for heat inactivation can be about 50 to about 100, about 50 to about 90, about 60 to about 90, about 65 to about 90, about 65 to about 85, or about 65 to about 80 degrees Celsius. The duration of heat-inactivation can be, e.g., about, or more than about, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 65, 70, 80, 90, 100, 110, 120, 180, 240, or 300 minutes. The duration of heat-inactivation can be about 5 to about 300, about 5 to about 200, about 5 to about 150, about 5 to about 100, about 5 to about 75, about 5 to about 50, about 5 to about 40, about 5 to about 30, about 5 to about 35, about 5 to about 25, about 5 to about 20, or about 10 to about 20 minutes. The temperature of heat-inactivation can be below the melt point of the restricted target fragments, so as to maintain double-stranded template copies.

A restriction enzyme digest can be stopped by addition of one or more chelating agents to the restriction enzyme digest. The one or more chelating agents can be, e.g., EDTA, EGTA, citric acid, or a phosphonate. The concentration of the one or more chelating agents in a restriction enzyme digest can be, e.g., about, or at least about, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 mM. The concentration of the one or more chelating agents can be about 1 to about 100 mM, about 1 to about 75 mM, or about 25 to about 75 mM.

A control assay and template can be used to measure the efficiency of a restriction enzyme digestion step.

Samples

Samples to be analyzed using the methods, compositions, and kits provided herein can be derived from a non-cellular entity comprising nucleic acid (e.g., a virus) or from a cell-based organism (e.g., member of archaea, bacteria, or eukarya domains). A sample can be obtained in some cases from a hospital, laboratory, clinical or medical laboratory. The sample can comprise nucleic acid, e.g., RNA or DNA. The sample can comprise cell-free nucleic acid. In some cases, the sample is obtained from a swab of a surface, such as a door or bench top.

The sample can from a subject, e.g., a plant, fungi, eubacteria, archeabacteria, protest, or animal. The subject may be an organism, either a single-celled or multi-cellular organism. The subject may be cultured cells, which may be primary cells or cells from an established cell line, among others. The sample may be isolated initially from a multi-cellular organism in any suitable form. The animal can be a fish, e.g., a zebrafish. The animal can be a mammal. The mammal can be, e.g., a dog, cat, horse, cow, mouse, rat, or pig. The mammal can be a primate, e.g., a human, chimpanzee, orangutan, or gorilla. The human can be a male or female. The sample can be from a human embryo or human fetus. The human can be an infant, child, teenager, adult, or elderly person. The female can be pregnant, can be suspected of being pregnant, or planning to become pregnant.

The sample can be from a subject (e.g., human subject) who is healthy. In some embodiments, the sample is taken from a subject (e.g., an expectant mother) at at least 4, 5, 6, 7, 8, 9, 10, 11, 12, 13, 14, 15, 16, 17, 18, 19, 20, 21, 22, 23, 24, 25, or 26 weeks of gestation. In some embodiments, the subject is affected by a genetic disease, a carrier for a genetic disease or at risk for developing or passing down a genetic disease, where a genetic disease is any disease that can be linked to a genetic variation such as mutations, insertions, additions, deletions, translocation, point mutation, trinucleotide repeat disorders and/or single nucleotide polymorphisms (SNPs). In other embodiments, the sample is taken from a female patient of child-bearing age and, in some cases, the female patient is not pregnant or of unknown pregnancy status. In still other cases, the subject is a male patient, a male expectant father, or a male patient at risk of, diagnosed with, or having a specific genetic abnormality. In some cases, the female patient is known to be affected by, or is a carrier of, a genetic disease or genetic variation, or is at risk of, diagnosed with, or has a specific genetic abnormality. In some cases, the status of the female patient with respect to a genetic disease or genetic variation may not be known. In further embodiments, the sample is taken from any child or adult patient of known or unknown status with respect to copy number variation of a genetic sequence. In some cases, the child or adult patient is known to be affected by, or is a carrier of, a genetic disease or genetic variation.

The sample can be from a subject who has a specific disease, disorder, or condition, or is suspected of having (or at risk of having) a specific disease, disorder or condition. For example, the sample can be from a cancer patient, a patient suspected of having cancer, or a patient at risk of having cancer. The cancer can be, e.g., acute lymphoblastic leukemia (ALL), acute myeloid leukemia (AML), adrenocortical carcinoma, Kaposi Sarcoma, anal cancer, basal cell carcinoma, bile duct cancer, bladder cancer, bone cancer, osteosarcoma, malignant fibrous histiocytoma, brain stem glioma, brain cancer, craniopharyngioma, ependymoblastoma, ependymoma, medulloblastoma, medulloeptithelioma, pineal parenchymal tumor, breast cancer, bronchial tumor, Burkitt lymphoma, Non-Hodgkin lymphoma, carcinoid tumor, cervical cancer, chordoma, chronic lymphocytic leukemia (CLL), chromic myelogenous leukemia (CML), colon cancer, colorectal cancer, cutaneous T-cell lymphoma, ductal carcinoma in situ, endometrial cancer, esophageal cancer, Ewing Sarcoma, eye cancer, intraocular melanoma, retinoblastoma, fibrous histiocytoma, gallbladder cancer, gastric cancer, glioma, hairy cell leukemia, head and neck cancer, heart cancer, hepatocellular (liver) cancer, Hodgkin lymphoma, hypopharyngeal cancer, kidney cancer, laryngeal cancer, lip cancer, oral cavity cancer, lung cancer, non-small cell carcinoma, small cell carcinoma, melanoma, mouth cancer, myelodysplastic syndromes, multiple myeloma, medulloblastoma, nasal cavity cancer, paranasal sinus cancer, neuroblastoma, nasopharyngeal cancer, oral cancer, oropharyngeal cancer, osteosarcoma, ovarian cancer, pancreatic cancer, papillomatosis, paraganglioma, parathyroid cancer, penile cancer, pharyngeal cancer, pituitary tumor, plasma cell neoplasm, prostate cancer, rectal cancer, renal cell cancer, rhabdomyosarcoma, salivary gland cancer, Sezary syndrome, skin cancer, nonmelanoma, small intestine cancer, soft tissue sarcoma, squamous cell carcinoma, testicular cancer, throat cancer, thymoma, thyroid cancer, urethral cancer, uterine cancer, uterine sarcoma, vaginal cancer, vulvar cancer, Waldenstrom Macroglobulinemia, or Wilms Tumor. The sample can be from the cancer and/or normal tissue from the cancer patient.

The sample can be from a subject who is known to have a genetic disease, disorder or condition. In some cases, the subject is known to be wild-type or mutant for a gene, or portion of a gene, e.g., CFTR, Factor VIII (F8 gene), beta globin, hemachromatosis, G6PD, neurofibromatosis, GAPDH, beta amyloid, or pyruvate kinase gene. In some cases, the status of the subject is either known or not known, and the subject is tested for the presence of a mutation or genetic variation of a gene, e.g., CFTR, Factor VIII (F8 gene), beta globin, hemachromatosis, G6PD, neurofibromatosis, GAPDH, beta amyloid, or pyruvate kinase gene.

The sample can be aqueous humour, vitreous humour, bile, whole blood, blood serum, blood plasma, breast milk, cerebrospinal fluid, cerumen, enolymph, perilymph, gastric juice, mucus, peritoneal fluid, saliva, sebum, semen, sweat, tears, vaginal secretion, vomit, feces, or urine. The sample can be obtained from a hospital, laboratory, clinical or medical laboratory. The sample can taken from a subject. The sample can comprise nucleic acid. The nucleic acid can be, e.g., mitochondrial DNA, genomic DNA, mRNA, siRNA, miRNA, cRNA, single-stranded DNA, double-stranded DNA, single-stranded RNA, double-stranded RNA, tRNA, rRNA, or cDNA. The sample can comprise cell-free nucleic acid. The sample can be a cell line, genomic DNA, cell-free plasma, formalin fixed paraffin embedded (FFPE) sample, or flash frozen sample. A formalin fixed paraffin embedded sample can be deparaffinized before nucleic acid is extracted. The sample can be from an organ, e.g., heart, skin, liver, lung, breast, stomach, pancreas, bladder, colon, gall bladder, brain, etc.

When the nucleic acid is RNA, the source of the RNA can be any source described herein. For example, the RNA can a cell-free mRNA, can be from a tissue biopsy, core biopsy, fine needle aspirate, flash frozen, or formalin-fixed paraffin embedded (FFPE) sample. The FFPE sample can be deparaffinized before the RNA is extracted. The extracted RNA can be heated to about 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99° C. before analysis. The extracted RNA can be heated to any these temperatures for about, or at least about, 15 min, 30 min, 45 min, 60 min, 1.5 hr, 2 hr, 2.5 hr, 3 hr, 3.5 hr, 4 hr, 4.5 hr, 5 hr, 5.5 hr, 6 hr, 6.5 hr, 7 hr, 7.5 hr, 8 hr, 8.5 hr, 9 hr, 9.5 hr, or 10 hr.

RNA can be used for a variety of downstream applications. For example, the RNA can be converted to cDNA with a reverse transcriptase and the cDNA can optionally be subject to PCR, e.g., real-time PCR. The RNA or cDNA can be used in an isothermal amplification reaction, e.g., an isothermal linear amplification reaction. The RNA, resulting cDNA, or molecules amplified therefrom can be used in a microarray experiment, gene expression experiment, Northern analysis, Southern analysis, sequencing reaction, next generation sequencing reaction, etc. Specific RNA sequences can be analyzed, or RNA sequences can be globally analyzed.

Nucleic acids can be extracted from a sample by means available to one of ordinary skill in the art.

The sample may be processed to render it competent for amplification. Exemplary sample processing may include lysing cells of the sample to release nucleic acid, purifying the sample (e.g., to isolate nucleic acid from other sample components, which may inhibit amplification), diluting/concentrating the sample, and/or combining the sample with reagents for amplification, such as a DNA/RNA polymerase (e.g., a heat-stable DNA polymerase for PCR amplification), dNTPs (e.g., dATP, dCTP, dGTP, and dTTP (and/or dUTP)), a primer set for each allele sequence or polymorphic locus to be amplified, probes (e.g., fluorescent probes, such as TAQ-MAN probes or molecular beacon probes, among others) capable of hybridizing specifically to each allele sequence to be amplified, $Mg^{2+}$, DMSO, BSA, a buffer, or any combination thereof, among others. In some examples, the sample may be combined with a restriction enzyme, uracil-DNA glycosylase (UNG), reverse transcriptase, or any other enzyme of nucleic acid processing.

Target Polynucleotide

The methods described herein can be used for analyzing or detecting one or more target nucleic acid molecules. The term polynucleotide, or grammatical equivalents, can refer to at least two nucleotides covalently linked together. A nucleic acid described herein can contain phosphodiester bonds, although in some cases, as outlined below (for example in the construction of primers and probes such as label probes), nucleic acid analogs are included that can have alternate backbones, comprising, for example, phosphoramide (Beaucage et al., Tetrahedron 49(10):1925 (1993) and references therein; Letsinger, J. Org. Chem. 35:3800 (1970); Sprinzl et al., Eur. J. Biochem. 81:579 (1977); Letsinger et al., Nucl. Acids Res. 14:3487 (1986); Sawai et al, Chem. Lett. 805 (1984), Letsinger et al., J. Am. Chem. Soc. 110:4470 (1988); and Pauwels et al., Chemica Scripta 26:141 91986)), phosphorothioate (Mag et al., Nucleic Acids Res. 19:1437 (1991); and U.S. Pat. No. 5,644,048), phosphorodithioate (Briu et al., J. Am. Chem. Soc. 111:2321 (1989), O-methylphosphoroamidite linkages (see Eckstein, Oligonucleotides and Analogues: A Practical Approach, Oxford University Press), and peptide nucleic acid (also referred to herein as "PNA") backbones and linkages (see Egholm, J. Am. Chem. Soc. 114:1895 (1992); Meier et al., Chem. Int. Ed. Engl. 31:1008 (1992); Nielsen, Nature, 365:566 (1993); Carlsson et al., Nature 380: 207 (1996), all of which are incorporated by reference). Other analog nucleic acids include those with bicyclic structures including locked nucleic acids (also referred to herein as "LNA"), Koshkin et al., J. Am. Chem. Soc. 120.13252 3 (1998); positive backbones (Denpcy et al., Proc. Natl. Acad. Sci. USA 92:6097 (1995); non-ionic backbones (U.S. Pat. Nos. 5,386,023, 5,637,684, 5,602,240, 5,216,141 and 4,469, 863; Kiedrowshi et al., Angew. Chem. Intl. Ed. English 30:423 (1991); Letsinger et al., J. Am. Chem. Soc. 110:4470 (1988); Letsinger et al., Nucleoside & Nucleotide 13:1597 (1994); Chapters 2 and 3, ASC Symposium Series 580, "Carbohydrate Modifications in Antisense Research", Ed. Y. S. Sanghui and P. Dan Cook; Mesmaeker et al., Bioorganic & Medicinal Chem. Lett. 4:395 (1994); Jeffs et al., J. Biomolecular NMR 34:17 (1994); Tetrahedron Lett. 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within the definition of nucleic acids (see Jenkins et al., Chem. Soc. Rev. (1995) pp 169 176). Several nucleic acid analogs are described in Rawls, C & E News Jun. 2, 1997 page 35. "Locked nucleic acids" are also included within the definition of nucleic acid analogs. LNAs are a class of nucleic acid analogues in which the ribose ring is "locked" by a methylene bridge connecting the 2'-O atom with the 4'-C atom. All of these references are hereby expressly incorporated by reference. These modifications of the ribose-phosphate backbone can be done to increase the stability and half-life of such molecules in physiological environments. For example, PNA:DNA and LNA-DNA hybrids can exhibit higher stability and thus can be used in some embodiments. The target nucleic acids can be single stranded or double stranded, as specified, or contain portions of both double stranded or single stranded sequence. Depending on the application, the nucleic acids can be DNA (including, e.g., genomic DNA, mitochondrial DNA, and cDNA), RNA (including, e.g., mRNA and rRNA) or a hybrid, where the nucleic acid contains any combination of deoxyribo- and ribo-nucleotides, and any combination of bases, including uracil, adenine, thymine, cytosine, guanine, inosine, xathanine hypoxathanine, isocytosine, isoguanine, etc.

The methods and compositions provided herein can be used to evaluate a quantity of polynucleotides (e.g., DNA, RNA, mitochondrial DNA, genomic DNA, mRNA, siRNA, miRNA, cRNA, single-stranded DNA, double-stranded DNA, single-stranded RNA, double-stranded RNA, tRNA, rRNA, cDNA, etc.). The methods and compositions can be used to evaluate a quantity of a first polynucleotide compared to the quantity of a second polynucleotide. The methods can be used to analyze the quantity of synthetic plasmids in a solution; to detect a pathogenic organism (e.g., microbe, bacteria, virus, parasite, retrovirus, lentivirus, HIV-1, HIV-2, influenza virus, etc.) within a sample obtained from a subject or obtained from an environment. The methods also can be used in other applications wherein a rare population of polynucleotides exists within a larger population of polynucleotides.

The number of copies of a target nucleic acid sequence in a sample (e.g., a genome) of a subject whose sample is analyzed using the methods, compositions, and kits provided herein can be 0, or about, or at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 150, 200, 250, 300, 350, 400, 450, 500, 550, 600, 650, 700, 750, 800, 850, 900, 950, 1000, 5000, 10,000, 20,000, 50,000, or 100,000. The number of copies of a target nucleic acid sequence in a genome of a subject whose sample is analyzed using the methods, compositions, and kits provided herein can be about 1 to about 20, about 1 to about 15, about 1 to about 10, about 1 to about 7, about 1 to about 5, about 1 to about 3, about 1 to about 1000, about 1 to about 500, about 1 to about 250, about 1 to about 100, about 10 to about 1000, about 10 to about 500, about 10 to about 250, about 10 to about 100, about 10 to about 50, about 10 to about 20, about 0 to about 100, about 0 to about 50, about 0 to about 25 or about 0 to about 10.

The target nucleic acid sequence can be on one chromosome. If the target nucleic acid is in a sample derived from a human subject, the target nucleic acid sequence can be on one or more of chromosome 1, 2, 3, 4, 5, 6, 7, 8, 9, 10, 11, 12, 13, 14, 15, 16, 17, 18, 19, 20, 21, 22, X, or Y. The target nucleic acid can be on about, or more than about, 1, 2, 3, 4, 5, 6, 7, 8, 9, 10, 11, 12, 13, 14, 15, 16, 17, 18, 19, 20, 21, 22, or 23 chromosomes. Two or more copies of the target nucleic acid sequence can be on the same or different chromosomes. In a human subject, two or more copies of the target nucleic acid sequence can be on chromosome 1, 2, 3, 4, 5, 6, 7, 8, 9, 10, 11, 12, 13, 14, 15, 16, 17, 18, 19, 20, 21, 22, X, or Y. Two or more copies of the target nucleic acid sequence can be on one polynucleotide (e.g., chromosome) in a subject, but the target nucleic acids can be separated in a sample taken from the subject due to handling of the sample (e.g., by fragmentation).

When two copies of a target nucleic acid are on the same polynucleotide, e.g., same chromosome, the two copies can be spaced apart on the polynucleotide by about, more than about, or less than about 1, 2, 3, 4, 5, 6, 7, 8, 9, 10, 25, 50, 75, 100, 200, 300, 400, 500, 600, 700, 800, 900, 1000, 2000, 3000, 4000, 5000, 6000, 7000, 8000, 9000, 10,000, 20,000, 30,000, 40,000, 50,000, 60,000, 70,000, 80,000, 90,000, 100,000, 200,000, 300,000, 400,000, 500,000, 600,000, 700,000, 800,000, 900,000, 1 million, 2 million, 3 million, 4 million, 5 million, 6 million, 7 million, 8 million, 9 million, 10 million, 20 million, 30 million, 40 million, 50 million, 60 million, 70 million, 80 million, 90 million, or 100 million bases or base pairs. Two target nucleic acids can be spaced apart by about 100 to about 100,000, about 100 to about 10,000, about 100 to about 1,000, about 10 to about 10,000, or about 10 to about 1,000 bases or base pairs.

The target sequence can be a gene. For example, the gene can be ERBB2, EGFR, BRCA1, BRCA2, APC, MSH2, MSH6, MLH1, CYP2D6, a low-copy repeat (LCR)-rich sequence (see e.g., Balikova et al. (2008) *Am J. Hum Genet.* 82: 181-187), TAS1R1, GNAT1, IMPDH1, OPN1SW, OR2A12, OR2A14, OR2A2, OR2A25, OR2A5, OR2A1, OR2A42, OR2A7, OR4F21, OR4F29, OR4C6, OR4P4, OR4S2, OR5D13, ROM1, TAS@R14, TAS2R44, TAS2R48, TAS2R49, TAS2R50, OR6C2, OR6C4, OR6C68, OR6C70, OR4M1, OR4Q3, OR4K1, OR4K2, OR4K5, OR4N2, OR4K13, OR4K14, OR4K15, OR4M2, OR4N4, OR1F1, ACTG1, FSCN2, OR2Z1, OR11H1, MYH9, SKI, TP73, TNFRSF25, RAB3B, VAV3, RALB, BOK, NAT6, TUSC2, TUSC4, TAB33B, C6orf210, ESR1, MAFK, MAD1L1, MYC, VAV2, MAP3K8, CDKN1C, WT1, WIT-1, C1QTNF4, MEN1, CCND1, ORAOV1, MLL2, C13orf10, TNFAIP2, AXIN1, BCAR1, TAXIBP3, NF1, PHB, MAFG, C1QTNF1, YES1, DCC, SH3GL1, TNFSF9, TNFSF7, TNFSF14, VAV1, RAB3A, PTOV1, BAX, RRAS, BCAS4, HIC2, NROB2, TTN, SGCB, SMA3, SMA4, SMN1, LPA, PARK2, GCK, GPR51, BSCL2, A2M, TBXA2R, FKRP, or COMT.

The target sequence can encode a microRNA, e.g., hsa-let-7g, hsa-mir-135a-1, hsa-mir-95, hsa-mir-218-1, hsa-mir-320, has-let-7a-1, has-let-7d, has-let-7f-1, has-mir-202, has-mir-130a, has-mir-130a, has-mir-338, has-mir-199a-1, has-mir-181c, has-mir-181d, has-mir-23a, has-mir-24-2, has-mir-27a, has-mir-150, has-mir-499, has-mir-124a-3, or has-mir-185.

The target sequence can be any sequence listed in Wong et al. (2007) *Am J of Hum Genetics* 80: 91-104.

Amplification and Detection

The methods described herein can make use of nucleic acid amplification. Amplification of target nucleic acids can be performed by any means known in the art. Amplification can be performed by thermal cycling or isothermally. In exemplary embodiments, amplification may be achieved by the polymerase chain reaction (PCR).

Examples of PCR techniques that can be used include, but are not limited to, quantitative PCR, quantitative fluorescent PCR (QF-PCR), multiplex fluorescent PCR (MF-PCR), real time PCR(RT-PCR), single cell PCR, restriction fragment length polymorphism PCR (PCR-RFLP), PCR-RFLP/RT-PCR-RFLP, hot start PCR, nested PCR, in situ polony PCR, in situ rolling circle amplification (RCA), bridge PCR, picotiter PCR, digital PCR, droplet digital PCR, and emulsion PCR. Other suitable amplification methods include the ligase chain reaction (LCR), transcription amplification, molecular inversion probe (MIP) PCR, self-sustained sequence replication, selective amplification of target polynucleotide sequences, consensus sequence primed polymerase chain reaction (CP-PCR), arbitrarily primed polymerase chain reaction (AP-PCR), degenerate oligonucleotide-primed PCR (DOP-PCR) and nucleic acid based sequence amplification (NABSA). Other amplification methods that can be used herein include those described in U.S. Pat. Nos. 5,242,794; 5,494,810; 4,988,617; and 6,582,938. Amplification of target nucleic acids can occur on a bead. In other embodiments, amplification does not occur on a bead. Amplification can be by isothermal amplification, e.g., isothermal linear amplification. A hot start PCR can be performed wherein the reaction is heated to 95° C. for two minutes prior to addition of the polymerase or the polymerase can be kept inactive until the first heating step in cycle 1. Hot start PCR can be used to minimize nonspecific amplification. Other strategies for and aspects of amplification are described in U.S. Patent Application Publication No. 2010/0173394 A1, published Jul. 8, 2010, which is incorporated herein by reference.

Techniques for amplification of target and reference sequences are known in the art and include the methods described in U.S. Pat. No. 7,048,481. Briefly, the techniques can include methods and compositions that separate samples into small droplets, in some instances with each containing on average less than about 5, 4, 3, 2, or one target nucleic acid molecule (polynucleotide) per droplet, amplifying the nucleic acid sequence in each droplet and detecting the presence of a target nucleic acid sequence. In some cases, the sequence that is amplified is present on a probe to the genomic DNA, rather than the genomic DNA itself. In some cases, at least 200, 175, 150, 125, 100, 90, 80, 70, 60, 50, 40, 30, 20, 10, or 0 droplets have zero copies of a target nucleic acid.

Information about an amplification reaction can be entered into a database. For example, FIGS. 15A and 15B illustrate assay information that can be entered into a database.

Primers

Primers can be designed according to known parameters for avoiding secondary structures and self-hybridization. Different primer pairs can anneal and melt at about the same temperatures, for example, within about 1, 2, 3, 4, 5, 6, 7, 8, 9 or 10° C. of another primer pair. In some cases, greater than about 1, 2, 3, 4, 5, 6, 7, 8, 9, 10, 15, 20, 25, 30, 35, 40, 45, 50, 100, 200, 500, 1000, 5000, 10,000 or more primers are initially used. Such primers may be able to hybridize to the genetic targets described herein. In some embodiments, about 2 to about 10,000, about 2 to about 5,000, about 2 to about 2,500, about 2 to about 1,000, about 2 to about 500, about 2 to about 100, about 2 to about 50, about 2 to about 20, about 2 to about 10, or about 2 to about 6 primers are used.

Primers can be prepared by a variety of methods including but not limited to cloning of appropriate sequences and direct chemical synthesis using methods well known in the art (Narang et al., Methods Enzymol. 68:90 (1979); Brown et al., Methods Enzymol. 68:109 (1979)). Primers can also be obtained from commercial sources such as Integrated DNA Technologies, Operon Technologies, Amersham Pharmacia Biotech, Sigma, and Life Technologies. The primers can have an identical melting temperature. The melting temperature of a primer can be about 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 81, 82, 83, 84, or 85° C. In some embodiments, the melting temperature of the primer is about 30 to about 85° C., about 30 to about 80° C., about 30 to about 75° C., about 30 to about 70° C., about 30 to about 65° C., about 30 to about 60° C., about 30 to about 55° C., about 30 to about 50° C., about 40 to about 85° C., about 40 to about 80° C., about 40 to about 75° C., about 40 to about 70° C., about 40 to about 65° C., about 40 to about 60° C., about 40 to about 55° C., about 40 to about 50° C., about 50 to about 85° C., about 50 to about 80° C., about 50 to about 75° C., about 50 to about 70° C., about 50 to about 65° C., about 50 to about 60° C., about 50 to about 55° C., about 52 to about 60° C., about 52 to about 58° C., about 52 to about 56° C., or about 52 to about 54° C.

The lengths of the primers can be extended or shortened at the 5' end or the 3' end to produce primers with desired melting temperatures. One of the primers of a primer pair can be longer than the other primer. The 3' annealing lengths of the primers, within a primer pair, can differ. Also, the annealing position of each primer pair can be designed such that the sequence and length of the primer pairs yield the desired melting temperature. An equation for determining the melting temperature of primers smaller than 25 base pairs is the Wallace Rule (Td=2(A+T)+4(G+C)). Computer programs can also be used to design primers, including but not limited to Array Designer Software (Arrayit Inc.), Oligonucleotide Probe Sequence Design Software for Genetic Analysis (Olympus Optical Co.), NetPrimer, and DNAsis from Hitachi Software Engineering. The TM (melting or annealing temperature) of each primer can be calculated using software programs such as Net Primer (free web based program at http://www.premierbiosoft.com/netprimer/index.html). The annealing temperature of the primers can be recalculated and increased after any cycle of amplification, including but not limited to about cycle 1, 2, 3, 4, 5, about cycle 6 to about cycle 10, about cycle 10 to about cycle 15, about cycle 15 to about cycle 20, about cycle 20 to about cycle 25, about cycle 25 to about cycle 30, about cycle 30 to about cycle 35, or about cycle 35 to about cycle 40. After the initial cycles of amplification, the 5' half of the primers can be incorporated into the products from each loci of interest; thus the TM can be recalculated based on both the sequences of the 5' half and the 3' half of each primer.

The annealing temperature of the primers can be recalculated and increased after any cycle of amplification, including but not limited to about cycle 1, 2, 3, 4, 5, about cycle 6 to about cycle 10, about cycle 10 to about cycle 15, about cycle 15 to about cycle 20, about cycle 20 to about cycle 25, about cycle 25 to about cycle 30, about cycle 30 to about cycle 35, or about cycle 35 to about cycle 40. After the initial cycles of amplification, the 5' half of the primers can be incorporated into the products from each loci of interest, thus the TM can be recalculated based on both the sequences of the 5' half and the 3' half of each primer.

DNA Polymerase

Any DNA polymerase that catalyzes primer extension can be used including but not limited to E. coli DNA polymerase, Klenow fragment of E. coli DNA polymerase 1, T7 DNA polymerase, T4 DNA polymerase, Taq polymerase, Pfu DNA polymerase, Pfx DNA polymerase, Tth DNA polymerase, Vent DNA polymerase, bacteriophage 29, REDTaq™. Genomic DNA polymerase, or sequenase. A thermostable DNA polymerase can be used. The DNA polymerase can have 3' to 5' exonuclease activity. The DNA polymerase can possess 5' to 3' exonuclease activity. The DNA polymerase can possess both 3' to 5' exonuclease activity and 5' to 3' exonuclease activity.

Thermocycling

Any number of PCR cycles can be used to amplify the DNA, e.g., about, more than about, or less than about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44 or 45 cycles. The number of amplification cycles can be about 1 to about 45, about 10 to about 45, about 20 to about 45, about 30 to about 45, about 35 to about 45, about 10 to about 40, about 10 to about 30, about 10 to about 25, about 10 to about 20, about 10 to about 15, about 20 to about 35, about 25 to about 35, about 30 to about 35, or about 35 to about 40.

Thermocycling reactions can be performed on samples contained in droplets. The droplets can remain intact during thermocycling. Droplets can remain intact during thermocycling at densities of greater than about 10,000 droplets/mL, 100,000 droplets/mL, 200,000 droplets/mL, 300,000 droplets/mL, 400,000 droplets/mL, 500,000 droplets/mL, 600,000 droplets/mL, 700,000 (droplets/mL, 800,000 droplets/mL, 900,000 droplets/mL or 1,000,000 droplets/mL. In other cases, two or more droplets may coalesce during thermocycling. In other cases, greater than 100 or greater than 1,000 droplets may coalesce during thermocycling.

Probes

Universal probes can be designed by methods known in the art. In some embodiments, the probe is a random sequence. The universal probe can be selected to ensure that it does not bind the target polynucleotide in an assay, or to other non-target polynucleotides likely to be in a sample (e.g., genomic DNA outside the region occupied by the target polynucleotide).

A label (fluorophore, dye) used on a probe (e.g., a Taqman probe) to detect a target nucleic acid sequence or reference nucleic acid sequence in the methods described herein can be, e.g., 6-carboxyfluorescein (FAM), tetrachlorofluorescin (TET), 4,7,2'-trichloro-7'-phenyl-6-carboxyfluorescein (VIC), HEX, Cy3, Cy 3.5, Cy 5, Cy 5.5, Cy 7, tetramethylrhodamine, ROX, and JOE. The label can be an Alexa Fluor dye, e.g., Alexa Fluor 350, 405, 430, 488, 532, 546, 555, 568, 594, 633, 647, 660, 680, 700, and 750. The label can be Cascade Blue, Marina Blue, Oregon Green 500, Oregon Green 514, Oregon Green 488, Oregon Green 488-X, Pacific Blue, Rhodamine Green, Rhodol Green, Rhodamine Green-X, Rhodamine Red-X, and Texas Red-X. The label can be at the 5' end of a probe, 3' end of the probe, at both the 5' and 3' end of a probe, or internal to the probe. A unique label can be used to detect each different locus in an experiment.

A probe, e.g., a Taqman probe, can comprise a quencher, e.g., a 3' quencher. The 3' quencher can be, e.g., TAMARA, DABCYL, BHQ-1, BHQ-2, or BHQ-3. In some cases, a quencher used in the methods provided herein is a black hole quencher (BHQ). In some cases, the quencher is a minor groove binder (MGB). In some cases, the quencher is a fluorescent quencher. In other cases, the quencher is a non-fluorescent quencher (NFQ).

A probe can be about, or at least about, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 bases long. A probe can be about 8 to about 40, about 10 to about 40, about 10 to about 35, about 10 to about 30, about 10 to about 25, about 10 to about 20, about 15 to about 40, about 15 to about 35, about 15 to about 30, about 15 to about 25, about 15 to about 20, about 18 to about 40, about 18 to about 35, about 18 to about 30, about 18 to about 25, or about 18 to 22 bases.

Reagents and Additives

Solution and reagents for performing a PCR reaction can include buffers. The buffered solution can comprise about, more than about, or less than about 1, 5, 10, 15, 20, 30, 50, 100, or 200 mM Tris. In some cases, the concentration of potassium chloride can be about, more than about, or less than about 10, 20, 30, 40, 50, 60, 80, 100, 200 mM. The buffered solution can comprise about 15 mM Tris and 50 mM KCl. The nucleotides can comprise deoxyribonucleotide triphosphate molecules, including dATP, dCTP, dGTP, dTTP, in concentrations of about, more than about, or less than about 50, 100, 200, 300, 400, 500, 600, or 700 µM each. In some cases, a non-canonical nucleotide, e.g., dUTP is added to amplification reaction to a concentration of about, more than about, or less than about 50, 100, 200, 300, 400, 500, 600, or 700, 800, 900, or 1000 µM. In some cases, magnesium chloride ($MgCl_2$) is added to an amplification reaction at a concentration of about, more than about, or less than about 1.0, 2.0, 3.0, 4.0, or 5.0 mM. The concentration of $MgCl_2$ can be about 3.2 mM.

A non-specific blocking agent such as BSA or gelatin from bovine skin can be used, wherein the gelatin or BSA is present in a concentration range of approximately 0.1 to about 0.9% w/v. Other possible blocking agents can include betalactoglobulin, casein, dry milk, or other common blocking agents. In some cases, preferred concentrations of BSA and gelatin are about 0.1% w/v.

In some embodiments, an amplification reaction can also comprise one or more additives including, but not limited to, non-specific background/blocking nucleic acids (e.g., salmon sperm DNA), biopreservatives (e.g. sodium azide), PCR enhancers (e.g. Betaine, Trehalose, etc.), and inhibitors (e.g. RNAse inhibitors). The one or more additives can include, e.g., 2-pyrrolidone, acetamide, N-methylpyrolidone (NMP), B-hydroxyethylpyrrolidone (HEP), propionamide, NN-dimethylacetamide (DMA), N-methylformamide (MMP), NN-dimethylformamide (DMF), formamide, N-methylacetamide (MMA), dimethyl sulfoxide (DMSO), polyethylene glycol, betaine, tetramethylammonium chloride (TMAC), 7-deaza-2'-deoxyguanosine, bovine serum albumin (BSA), T4 gene 32 protein, glycerol, or nonionic detergent (Triton X-100, Tween 20, Nonidet P-40 (NP-40), Tween 40, SDS (e.g., about 0.1% SDS)), salmon sperm DNA, sodium azide, betaine (N,N,N-trimethylglycine; [carboxymethyl]trimethylammonium), formamide, trehalose, dithiothreitol (DTT), betamercaptoethanol (BME), a plant polysaccharide, or an RNase inhibitor.

In some embodiments, an amplification reaction comprises one or more buffers. The one or more buffers can comprise, e.g., TAPS, bicine, Tris, Tricine, TAPSO, HEPES, TES, MOPS, PIPES, cacodylate, SSC, ADA, ACES, cholamine chloride, acetamidoglycine, glycinamide, maleate, phosphate, CABS, piperidine, glycine, citrate, glycylglycine, malate, formate, succinate, acetate, propionate, pyridine, piperazine, histidine, bis-tris, ethanolamine, carbonate, MOPSO, imidazole, BIS-TRIS propane, BES, MOBS, triethanolamine (TEA), HEPPSO, POPSO, hydrazine, Trizma (tris), EPPS, HEPPS, bicine, HEPBS, AMPSO, taurine (AES), borate, CHES, 2-amino-2-methyl-1-propanol (AMP), ammonium hydroxide, methylamine, or MES.

In some cases, a non-ionic Ethylene Oxide/Propylene Oxide block copolymer is added to an amplification reaction in a concentration of about 0.1%, 0.2%, 0.3%, 0.4%, 0.5%, 0.6%, 0.7%, 0.8%, 0.9%, or 1.0%. Common biosurfactants include non-ionic surfactants such as Pluronic F-68, Tetronics, Zonyl FSN. Pluronic F-68 can be present at a concentration of about 0.5% w/v.

In some cases magnesium sulfate can be substituted for magnesium chloride, at similar concentrations. A wide range of common, commercial PCR buffers from varied vendors can be substituted for the buffered solution.

Detection

Fluorescence detection can be achieved using a variety of detector devices equipped with a module to generate excitation light that can be absorbed by a fluorescer, as well as a module to detect light emitted by the fluorescer. In some cases, samples (such as droplets) may be detected in bulk. For example, samples can be allocated in plastic tubes that are placed in a detector that measures bulk fluorescence from plastic tubes. In some cases, one or more samples (such as droplets) can be partitioned into one or more wells of a plate, such as a 96-well or 384-well plate, and fluorescence of individual wells may be detected using a fluorescence plate reader.

In some cases, the detector further comprises handling capabilities for droplet samples, with individual droplets entering the detector, undergoing detection, and then exiting the detector. For example, a flow cytometry device can be adapted for use in detecting fluorescence from droplet samples. In some cases, a microfluidic device equipped with pumps to control droplet movement is used to detect fluorescence from droplets in single file. In some cases, droplets are arrayed on a two-dimensional surface and a detector moves relative to the surface, detecting fluorescence at each position containing a single droplet.

Computers

Following acquisition of fluorescence detection data, a computer can be used to store and process the data. A computer-executable logic can be employed to perform such functions as subtraction of background fluorescence, assignment of target and/or reference sequences, and quantification of the data. A computer can be useful for displaying, storing, retrieving, or calculating diagnostic results from the molecular profiling; displaying, storing, retrieving, or calculating raw data from genomic or nucleic acid expression analysis; or displaying, storing, retrieving, or calculating any sample or patient information useful in the methods of the present invention.

Digital Analysis

A digital readout assay, e.g., digital PCR, can be used to count targets (e.g., target nucleic acid sequences) by partitioning the targets in a sample and identifying partitions containing the target. A digital readout is an all or nothing analysis in that it specifies whether a given partition contains the target of interest, but does not necessarily indicate how many copies of the target are in the partition. For example, a single polynucleotide containing two targets can be in a partition, but under normal analysis conditions, the partition will only be considered to contain one target. If the targets on the same polynucleotide are separated by a large number of base pairs, some of the target nucleic acid sequences may be separated by fragmentation during purification of a sample—some linked target nucleic acid sequences may not remain physically linked after sample preparation. Digital PCR is described generally, e.g., at Vogelstein and Kinzler (1999) *PNAS* 96:9236-9241. Applications of this technology include, e.g., high-resolution CNV measurements, follow-up to genome-wide association studies, cytogenetic analysis, CNV alterations in cancerous tissue, and CNV linkage analysis.

In general, dPCR can involve spatially isolating (or partitioning) individual polynucleotides from a sample and carrying out a polymerase chain reaction on each partition. The partition can be, e.g., a well (e.g., wells of a microwell plate), capillary, dispersed phase of an emulsion, a chamber (e.g., a chamber in an array of miniaturized chambers), a droplet, or a nucleic acid binding surface. The sample can be distributed so that each partition has about 0, 1, or 2 target polynucleotides. Each partition can have, on average, less than 5, 4, 3, 2, or 1 copies of a target nucleic acid per partition (e.g., droplet). In some cases, at least 0, 1, 2, 3, 4, 5, 6, 7, 8, 9, 10, 20, 30, 40, 50, 60, 70, 80, 90, 100, 125, 150, 175, or 200 partitions (e.g., droplets) have zero copies of a target nucleic acid. After PCR amplification, the number of partitions with or without a PCR product can be enumerated. The total number of partitions can be about, or more than about, 500, 1000, 2000, 3000, 4000, 5000, 6000, 7000, 8000, 9000, 10,000, 11,000, 12,000, 13,000, 14,000, 15,000, 16,000, 17,000, 18,000, 19,000, 20,000, 30,000, 40,000, 50,000, 60,000, 70,000, 80,000, 90,000, 100,000, 150,000, 200,000, 500,000, 750,000, or 1,000,000. The total number of partitions can be about 500 to about 1,000,000, about 500 to about 500,000, about 500 to about 250,000, about 500 to about 100,000, about 1000 to about 1,000,000, about 1000 to about 500,000, about 1000 to about 250,000, about 1000 to about 100,000, about 10,000 to about 1,000,000, about 10,000 to about 100,000, or about 10,000 to about 50,000.

In one embodiment, the digital PCR is droplet digital PCR. In some embodiments of a droplet digital PCR experiment, less than about 0.00001, 0.00005, 0.00010, 0.00050, 0.001, 0.005, 0.01, 0.05, 0.1, 0.5, 1, 2, 2.5, 3, 3.5, 4, 4.5, 5, 6, 7, 8, 9, or 10 copies of target polynucleotide can detected. In some cases, less than about 1, 2, 3, 4, 5, 6, 7, 8, 9, 10, 11, 12, 13, 14, 15, 20, 25, 30, 35, 40, 45, 50, 55, 60, 65, 70, 75, 80, 85, 90, 95, 100, 150, 200, 250, 300, 350, 400, 450, or 500 copies of a target polynucleotide are detected. In some cases, the droplets described herein are generated at a rate of greater than 1, 2, 3, 4, 5, 10, 50, 100, 200, 300, 400, 500, 600, 700, 800, 900, or 1000 droplets/second.

Droplet digital PCR (ddPCR™) can offer a practical solution for validating copy number variations identified by next generation sequencers and microarrays. Methods using ddPCR™ can empower one person to screen many samples, e.g., hundreds of samples, for CNV analysis in a single work shift. In one embodiment, a ddPCR™ workflow is provided that involves using one or more restriction enzymes to separate tandem copies of a target nucleic acid sequence prior to assembling a duplex TaqMan® assay that includes reagents to detect both the target nucleic acid sequence (e.g., a first gene) and a single-copy reference nucleic acid sequence (e.g., a second gene). When ddPCR is used, the reaction mixture can then be partitioned into about, less than about, or more than about, 500, 1000, 2000, 3000, 4000, 5000, 6000, 7000, 8000, 9000, 10,000, 11,000, 12,000, 13,000, 14,000, 15,000, 16,000, 17,000, 18,000, 19,000, 20,000, 30,000, 40,000, 50,000, 60,000, 70,000, 80,000, 90,000, 100,000, 150,000, 200,000, 500,000, 750,000, 1,000,000, 2,000,000, 3,000,000, 4,000,000, 5,000,000, 6,000,000, 7,000,000, 8,000,000, 9,000,000, or 10,000,000 nanoliter droplets that can be thermo-cycled to end-point before being analyzed. In some cases, the droplets are greater than one nanoliter; in other cases, the droplets are less than one nanoliter (e.g., picoliter). The number of droplets per reaction can be about 1000 to about 1,000,000, about 1000 to about 750,000, about 1000 to about 500,000, about 1000 to about 250,000, about 1000 to about 100,000, about 1000 to about 50,000, about 1000 to about 30,000, about 1000 to about 10,000, about 10,000 to about 1,000,000, about 10,000 to about 750,000, about 10,000 to about 500,000, about 10,000 to about 250,000, about 10,000 to about 100,000, about 10,000 to about 50,000, or about 10,000 to about 30,000. The number of droplets per reaction can be about 20,000 to about 1,000,000, about 20,000 to about 750,000, about 20,000 to about 500,000, about 20,000 to about 250,000, about 20,000 to about 200,000, about 20,000 to about 50,000, about 50,000 to about 100,000, about 50,000 to about 200,000; or about 50,000 to about 300,000.

An analysis can occur in a two-color reader. The fraction of positive-counted droplets can enable the absolute concentrations for the target and reference nucleic acid sequences (e.g., genes) to be measured. This information can be used to determine a relative copy number. For example, at least 20,000 PCR replicates per well can provide the statistical power to resolve higher-order copy number differences. This low-cost method can reliably generate copy number measurements with 95% confidence intervals that span integer without overlap of adjacent copy number states. This technology is capable of determining the linkage of copy number variants, and it can be used to determine whether gene copies are on the same or different chromosomes.

The volumes may have any suitable size. In some embodiments, the volumes may have a diameter or characteristic cross-sectional dimension of about 10 to 1000 micrometers.

The nucleic acid that is partitioned may have any suitable characteristics. The nucleic acid may include genetic material of the subject (e.g., the subject's genomic DNA and/or RNA), messenger RNA of the subject, and/or cDNA derived from RNA of the subject, among others. The nucleic acid may have any suitable average length. Generally, the average length is substantially greater than the distance on a chromosome between the polymorphic loci to be analyzed. With this average length, alleles linked in the subject are also linked frequently in the isolated nucleic acid and thus tend to distribute together to the same volumes when the aqueous phase is partitioned. In some embodiments, each primer set may be capable of amplifying at least a pair of distinct alleles from a polymorphic locus.

Each volume may be partitioned to contain any suitable average concentration of nucleic acid. Generally, the process of partitioning, in combination with a suitable starting concentration of the nucleic acid in the aqueous phase, produces volumes that have an average of less than about several genome equivalents of the nucleic acid per volume. Although the method may be performed with an average of more than one genome equivalent per volume (e.g., about two genome equivalents per volume), the analysis generally becomes more efficient and reliable, with less background, by limiting the concentration to an average of less than about one genome equivalent per volume. Accordingly, each volume may contain on average less than about one copy or molecule of a target region that includes each polymorphic locus and/or an average of less than about one copy of any allele sequence of each polymorphic locus.

An integrated, rapid, flow-through thermal cycler device can be used in the methods described herein. See, e.g., International Application No. PCT/US2009/005317, filed Sep. 23, 2009. In such an integrated device, a capillary is wound around a cylinder that maintains 2, 3, or 4 temperature zones. As droplets flow through the capillary, they are subjected to different temperature zones to achieve thermal cycling. The small volume of each droplet results in an extremely fast temperature transition as the droplet enters each temperature zone.

A digital PCR device (e.g., droplet digital PCR device) for use with the methods, compositions, and kits described herein can detect multiple signals (see e.g. U.S. Provisional Patent Application No. 61/454,373, filed Mar. 18, 2011, herein incorporated by reference in its entirety).

Droplet digital PCR can involve the generation of thousands of discrete, robust microdroplet reactors per second. ddPCR can involve standard thermal cycling with installed-base instruments, which can make digital data accessible immediately to researchers. Rapid interrogation of each droplet can yield counts of target molecules present in the initial sample.

FIG. 16 illustrates an example of a general workflow for a ddPCR experiment. As shown in FIG. 16, the process can start by partitioning a sample into multiple partitions (e.g., droplets), followed by thermal cycling the sample in a thermal cycler. The fluorescence of the droplets can then be detected using a reader (e.g., an optical reader).

Droplet Generation

The present disclosure includes compositions and methods using droplet digital PCR. The droplets described herein include emulsion compositions (or mixtures of two or more immiscible fluids) described in U.S. Pat. No. 7,622,280, and droplets generated by devices described in International Application No. PCT/US2009/005317, filed Sep. 23, 2009. The term emulsion, as used herein, can refer to a mixture of immiscible liquids (such as oil and water). Oil-phase and/or water-in-oil emulsions allow for the compartmentalization of reaction mixtures within aqueous droplets. The emulsions can comprise aqueous droplets within a continuous oil phase. The emulsions provided herein can be oil-in-water emulsions, wherein the droplets are oil droplets within a continuous aqueous phase. The droplets provided herein are designed to prevent mixing between compartments, with each compartment protecting its contents from evaporation and coalescing with the contents of other compartments.

The mixtures or emulsions described herein can be stable or unstable. The emulsions can be relatively stable and have minimal coalescence. Coalescence occurs when small droplets combine to form progressively larger ones. In some cases, less than about 0.00001%, 0.00005%, 0.00010%, 0.00050%, 0.001%, 0.005%, 0.01%, 0.05%, 0.1%, 0.5%, 1%, 2%, 2.5%, 3%, 3.5%, 4%, 4.5%, 5%, 6%, 7%, 8%, 9%, or 10% of droplets generated from a droplet generator coalesce with other droplets. The emulsions can also have limited flocculation, a process by which the dispersed phase comes out of suspension in flakes.

Splitting a sample into small reaction volumes as described herein can enable the use of reduced amounts of reagents, thereby lowering the material cost of the analysis. Reducing sample complexity by partitioning also improves the dynamic range of detection because higher-abundance molecules are separated from low-abundance molecules in different compartments, thereby allowing lower-abundance molecules greater proportional access to reaction reagents, which in turn enhances the detection of lower-abundance molecules.

Droplets can be generated having an average diameter of about, less than about, or more than about 0.001, 0.01, 0.05, 0.1, 1, 5, 10, 20, 30, 40, 50, 60, 70, 80, 100, 120, 130, 140, 150, 160, 180, 200, 300, 400, or 500 microns. Droplets can have an average diameter of about 0.001 to about 500, about 0.01 to about 500, about 0.1 to about 500, about 0.1 to about 100, about 0.01 to about 100, or about 1 to about 100 microns. Microfluidic methods of producing emulsion droplets using microchannel cross-flow focusing or physical agitation are known to produce either monodisperse or polydisperse emulsions. The droplets can be monodisperse droplets. The droplets can be generated such that the size of said droplets does not vary by more than plus or minus 5% of the average size of said droplets. In some cases, the droplets are generated such that the size of said droplets does not vary by more than plus or minus 2% of the average size of said droplets. A droplet generator can generate a population of droplets from a single sample, wherein none of the droplets vary in size by more than plus or minus about 0.1%, 0.5%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, or 10% of the average size of the total population of droplets.

Higher mechanical stability can be useful for microfluidic manipulations and higher-shear fluidic processing (e.g., in microfluidic capillaries or through 90 degree turns, such as valves, in a fluidic path). Pre- and post-thermally treated droplets or capsules can be mechanically stable to standard pipet manipulations and centrifugation.

A droplet can be formed by flowing an oil phase through an aqueous sample. The aqueous phase can comprise a buffered solution and reagents for performing a PCR reaction, including nucleotides, primers, probe(s) for fluorescent detection, template nucleic acids, DNA polymerase enzyme, and optionally, reverse transcriptase enzyme.

The aqueous phase can comprise one or more buffers and/or additives described herein.

Primers for amplification within the aqueous phase can have a concentration of about, more than about, or less than about 0.05, 0.1, 0.2, 0.3, 0.4, 0.5, 0.6, 0.7, 0.8, 0.9, 1.0, 1.2, 1.5, 1.7, or 2.0 µM. Primer concentration within the aqueous phase can be about 0.05 to about 2, about 0.1 to about 1.0, about 0.2 to about 1.0, about 0.3 to about 1.0, about 0.4 to about 1.0, or about 0.5 to about 1.0 µM. The concentration of primers can be about 0.5 µM. The aqueous phase can comprise one or more probes for fluorescent detection, at a concentration of about, more than about, or less than about 0.05, 0.1, 0.2, 0.3, 0.4, 0.5, 0.6, 0.7, 0.8, 0.9, 1.0, 1.2, 1.4, 1.6, 1.8, or 2.0 µM. The aqueous phase can comprise one or more probes for fluorescent detection, at a concentration of about 0.05 to about 2.0, about 0.1 to about 2.0, about 0.25 to about 2.0, about 0.5 to about 2.0, about 0.05 to about 1, about 0.1 to about 1, or about 0.1 to about 0.5 µM. The concentration of probes for fluorescent detection can be about 0.25 µM. Amenable ranges for target nucleic acid concentrations in PCR are between about 1 pg and about 500 ng.

The oil phase can comprise a fluorinated base oil which can be additionally stabilized by combination with a fluorinated surfactant such as a perfluorinated polyether. In some cases, the base oil can be one or more of HFE 7500, FC-40, FC-43, FC-70, or another common fluorinated oil. In some cases, the anionic surfactant is Ammonium Krytox (Krytox-AM), the ammonium salt of Krytox FSH, or morpholino derivative of Krytox-FSH. Krytox-AS can be present at a concentration of about, more than about, or less than about 0.1%, 0.2%, 0.3%, 0.4%, 0.5%, 0.6%, 0.7%, 0.8%, 0.9%, 1.0%, 2.0%, 3.0%, or 4.0% w/w. In some preferred embodiments, the concentration of Krytox-AS is 1.8%. In other preferred embodiments, the concentration of Krytox-AS is 1.62%. Morpholino derivative of Krytox-FSH can be present at a concentration of about 0.1%, 0.2%, 0.3%, 0.4%, 0.5%, 0.6%, 0.7%, 0.8%, 0.9%, 1.0%, 2.0%, 3.0%, or 4.0% w/w. The concentration of morpholino derivative of Krytox-FSH can be about 1.8%. The concentration of morpholino derivative of Krytox-FSH can be about 1.62%.

The oil phase can further comprise an additive for tuning the oil properties, such as vapor pressure or viscosity or surface tension. Nonlimiting examples include perfluoro-octanol and 1H,1H,2H,2H-Perfluorodecanol. 1H,1H,2H,2H-Perfluorodecanol can be added to a concentration of about, more than about, or less than about 0.05%, 0.06%, 0.07%, 0.08%, 0.09%, 1.00%, 1.25%, 1.50%, 1.75%, 2.00%, 2.25%, 2.50%, 2.75%, or 3.00% w/w. 1H,1H,2H,2H-Perfluorodecanol can be added to a concentration of about 0.18% w/w.

The emulsion can be formulated to produce highly monodisperse droplets having a liquid-like interfacial film that can be converted by heating into microcapsules having a solid-like interfacial film; such microcapsules can behave as bioreactors able to retain their contents through a reaction process such as PCR amplification. The conversion to microcapsule form can occur upon heating. For example, such conversion can occur at a temperature of greater than about 50, 60; 70, 80, 90, or 95 degrees Celsius. In some cases this heating occurs using a thermocycler. During the heating process, a fluid or mineral oil overlay can be used to prevent evaporation. Excess continuous phase oil may or may not be removed prior to heating. The biocompatible capsules can be resistant to coalescence and/or flocculation across a wide range of thermal and mechanical processing.

Following conversion, the capsules can be stored at about, more than about, or less than about 3, 4, 5, 6, 7, 8, 9, 10, 15, 20, 25, 30, 35, or 40 degrees Celsius. These capsules can be useful in biomedical applications, such as stable, digitized encapsulation of macromolecules, particularly aqueous biological fluids containing a mix of nucleic acids or protein, or both together; drug and vaccine delivery; biomolecular libraries; clinical imaging applications, and others.

The microcapsules can contain one or more polynucleotides and may resist coalescence, particularly at high temperatures. Accordingly, PCR amplification reactions can occur at a very high density (e.g., number of reactions per unit volume). In some cases, greater than about 100,000, 500,000, 1,000,000, 1,500,000, 2,000,000, 2,500,000, 5,000,000, or 10,000,000 separate reactions can occur per ml. In some cases, the reactions occur in a single well, e.g., a well of a microtiter plate, without inter-mixing between reaction volumes. The microcapsules can also contain other components necessary to enable a PCR reaction to occur, e.g., primers, probes, dNTPs, DNA or RNA polymerases, etc. These capsules exhibit resistance to coalescence and flocculation across a wide range of thermal and mechanical processing.

In one embodiment, droplet generation can be improved after the size of DNA is reduced by, e.g., digestion, heat treatment, or shearing.

Figure 17:
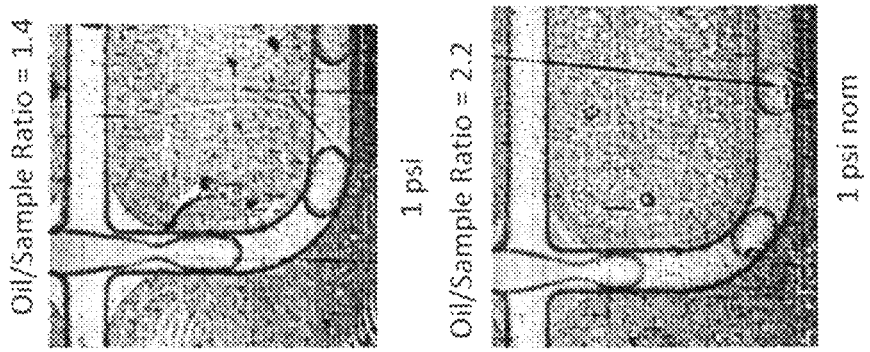
FIG. 17 illustrates maximum extension in droplet generation.
Figure 18:
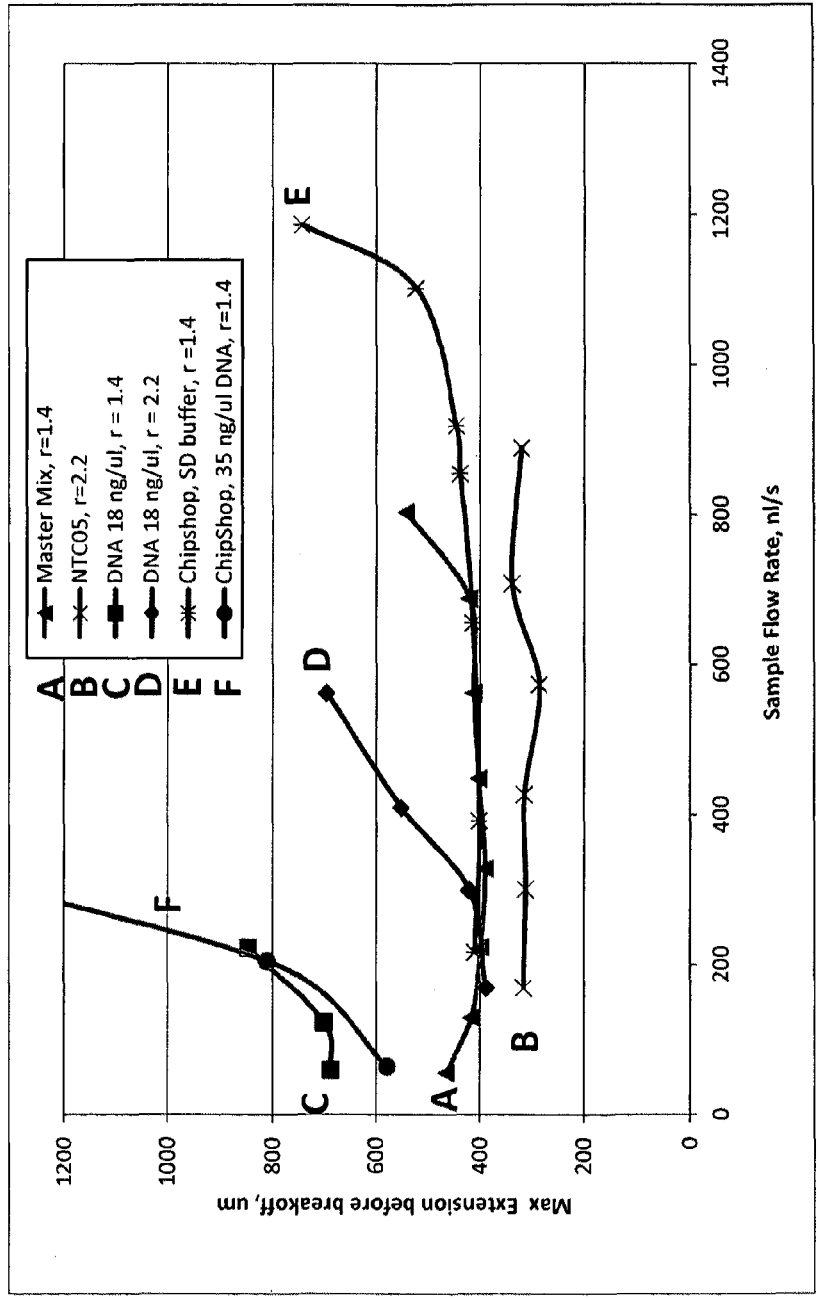
FIG. 18 illustrates maximum extension as a function of sample flow rate.

FIG. 17 displays several images of droplets showing a) droplet formation as a droplet is pinched by inflow of oil from the sides and b) stretching/necking down as the droplet pulls away from the bulk fluid FIG. 18 shows the effect of increasing DNA load. FIG. 18 plots maximum extension versus flow rate. Extension is measured from the center of the cross to the farthest extent of the droplet just as it breaks off. Some droplet extension is tolerable, but if it becomes excessive, a long "thread" is drawn that connects the droplet to the bulk fluid. As the droplet breaks off, this thread may collapse to microdroplets, leading to undesirable polydispersity. In extreme cases, the droplet does not break off; instead the aqueous phase flows as a continuous phase down the center of the channel, while the oil flows along the channel walls, and no droplets are formed.

One way to decrease extension is to decrease flow rate. Decreasing flow rate can have the undesirable side effects of lower throughput and also increased droplet size. The purple (B), teal (E) and green (A) curves have zero DNA. These samples can tolerate high flow rates without substantially increasing their extension into the channel.

The blue (D), orange (F) and red (C) curves have higher DNA loads. For these conditions, higher flow rates cause droplet extension into the channel. Low flow rates can be used to avoid excessive droplet extension.

FIG. 19 shows undigested samples 1-10 and digested samples 11-20 in an experiment to investigate droplet properties. DNA load is shown in the right-most column; pressure (roughly proportional to flow rate) is shown in the 2nd row. The table is color and letter coded: J (RED) indicates jetting, E (YELLOW) indicates extension, and N (GREEN) indicates normal (no jetting or extension) droplet generation. As can be seen, digestion (with restriction enzymes) resulted in improved droplet generation, even at high DNA loads and high flow rates.

Applications

The methods described herein can be used for diagnosing or prognosing a disorder or disease.

The methods and compositions provided herein can be useful for both human and non-human subjects. The applications of the methods and compositions provided herein are numerous, e.g., high-resolution CNV measurements, follow-up to genome-wide association studies, cytogenetic analysis, CNV alterations in cancerous tissue, CNV linkage analysis, as well as haplotype analysis.

The applications provided herein include applications for diagnosing, predicting, determining or assessing the genetic characteristics of a fetus or embryo. In some cases, the applications can be used to diagnose, predict, determine, or assess the nucleic acids in an embryo produced by in vitro fertilization or other assisted reproductive technology. Furthermore, the methods provided herein can be used to provide information to an expectant parent (e.g., a pregnant woman) in order to assess CNV or genetic phasing within the genome of a developing fetus. In other cases, the methods provided herein can be used to help counsel patients as to possible genetic attributes of future offspring. In some cases, the methods can be used in connection with an Assisted Reproductive Technology. For example, the information can be used to assess CNV or genetic phasing in a sample taken from an embryo produced by in vitro fertilization.

One or more CNVs can be found in a cancer cell. For example, EGFR copy number can be increased in non-small cell lung cancer. CNVs can be associated with efficacy of a therapy. For example, increased HER2 gene copy number can enhance the response to gefitinib therapy in advanced non-small cell lung cancer. See Cappuzzo F. et al. (2005) *J. Clin. Oncol.* 23: 5007-5018. High EGFR gene copy number can predict for increased sensitivity to lapatinib and capecitabine. See Fabi et al. (2010) *J. Clin. Oncol.* 28:15s (2010 ASCO Annual Meeting). High EGFR gene copy number is associated with increased sensitivity to cetuximab and panitumumab.

In one embodiment, a method is provided comprising determining number of copies of a target sequence using a method described herein, and designing a therapy based on said determination. In one embodiment, the target is EGFR, and the therapy comprises administration of cetuximab, panitumumab, lapatinib, and/or capecitabine. In another embodiment, the target is ERBB2, and the therapy comprises trastuzumab (Herceptin).

Copy number variation can contribute to genetic variation among humans. See e.g. Shebat J. et al. (2004) *Science* 305: 525-528.

Diseases associated with copy number variations can include, for example, DiGeorge/velocardiofacial syndrome (22q11.2 deletion), Prader-Willi syndrome (15q11-q13 deletion), Williams-Beuren syndrome (7q11.23 deletion), Miller-Dieker syndrome (MDLS) (17p13.3 microdeletion), Smith-Magenis syndrome (SMS) (17p11.2 microdeletion), Neurofibromatosis Type 1 (NF1) (17q11.2 microdeletion), Phelan-McErmid Syndrome (22q13 deletion), Rett syndrome (loss-of-function mutations in MECp2 on chromosome Xq28), Merzbacher disease (CNV of PLP1), spinal muscular atrophy (SMA) (homozygous absence of telomerec SMN1 on chromosome 5q13), Potocki-Lupski Syndrome (PTLS, duplication of chromosome 17p. 11.2). Additional copies of the PMP22 gene can be associated with Charcot-Marie-Tooth neuropathy type IA (CMT1A) and hereditary neuropathy with liability to pressure palsies (HNPP). The methods of detecting CNVs described herein can be used to diagnose CNV disorders described herein and in publications incorporated by reference. The disease can be a disease described in Lupski J. (2007) *Nature Genetics* 39: S43-S47.

Aneuploides, e.g., fetal aneuploidies, can include, e.g., trisomy 13, trisomy 18, trisomy 21 (Down Syndrome), Klinefelter Syndrome (XXY), monosomy of one or more chromosomes (X chromosome monosomy, Turner's syndrome), trisomy X, trisomy of one or more chromosomes, tetrasomy or pentasomy of one or more chromosomes (e.g., XXXX, XXYY, XXXY, XYYY, XXXXX, XXXXY, XXXYY, XYYYY and XXYYY), triploidy (three of every chromosome, e.g. 69 chromosomes in humans), tetraploidy (four of every chromosome, e.g. 92 chromosomes in humans), and multiploidy. In some embodiments, an aneuploidy can be a segmental aneuploidy. Segmental aneuploidies can include, e.g., 1p36 duplication, dup(17)(p11.2p11.2) syndrome, Down syndrome, Pelizaeus-Merzbacher disease, dup (22)(q11.2q11.2) syndrome, and cat-eye syndrome. In some cases, an abnormal genotype, e.g., fetal genotype, is due to one or more deletions of sex or autosomal chromosomes, which can result in a condition such as Cri-du-chat syndrome, Wolf-Hirschhorn, Williams-Beuren syndrome, Charcot-Marie-Tooth disease, Hereditary neuropathy with liability to pressure palsies, Smith-Magenis syndrome, Neurofibromatosis, Alagille syndrome, Velocardiofacial syndrome, DiGeorge syndrome, Steroid sulfatase deficiency, Kallmann syndrome, Microphthalmia with linear skin defects, Adrenal hypoplasia, Glycerol kinase deficiency, Pelizaeus-Merzbacher disease, Testis-determining factor on Y, Azospermia (factor a), Azospermia (factor b), Azospermia (factor c), or 1p36 deletion. In some embodiments, a decrease in chromosomal number results in an XO syndrome.

Excessive genomic DNA copy number variation was found in Li-Fraumeni cancer predisposition syndrome (Shlien et al. (2008) *PNAS* 105:11264-9). CNV is associated with malformation syndromes, including CHARGE (coloboma, heart anomaly, choanal atresia, retardation, gential, and ear anomalies), Peters-Plus, Pitt-Hopkins, and thrombocytopenia-absent radius syndrome (see e.g., Ropers H H (2007) *Am J of Hum Genetics* 81: 199-207). The relationship between copy number variations and cancer is described, e.g., in Shlien A. and Malkin D. (2009) *Genome Med.* 1(6): 62. Copy number variations are associated with, e.g., autism, schizophrenia, and idiopathic learning disability. See e.g., Sebat J., et al. (2007) *Science* 316: 445-9; Pinto J. et al. (2010) *Nature* 466: 368-72; Cook E. H. and Scherer S. W. (2008) *Nature* 455: 919-923.

Copy number variations can be associated with resistance of cancer patients to certain therapeutics. For example, amplification of thymidylate synthase can result in resistance to 5-fluorouracil treatment in metastatic colorectal cancer patients. See Wang et al. (2002) *PNAS USA vol.* 99, pp. 16156-61.

High copy number of CCL3L1 is associated with lower susceptibility to HIV infection (Gonzalez E. et al. (2005) *Science* 307: 1434-1440). Low copy number of FCGR3B (CD16 cell surface immunoglobulin receptor) can increase susceptibility to systemic lupus erythematosus (Aitman T. J. et al. (2006) *Nature* 439: 851-855). Autosomal-dominant microtia was found to be linked to five tandem copies of a copy-number-variable region at chromosome 4p16 (Balikova I. (2008) *Am J. Hum Genet.* 82: 181-187). The methods, compositions, and kits described herein can be used to investigate any of these conditions.

Individuals from populations with high-starch diets generally have more amylase gene (AMY1) copies than individuals from populations with low-starch diets (Perry H. et al. (2007) *Nature Genetics* 39:1256-1260). Thus, copy number can be subject to positive selection during evolution. The methods, compositions, and kits described herein can be used to study evolution.

Other examples of copy number variations associated with disease include, e.g., trisomy 21 (Down Syndrome), trisomy 18 (Edwards syndrome), and trisomy 13 (Patau syndrome).

Determining whether nucleic acids are linked or separated (fragmented) can provide useful information for a variety of applications. For example, the methods described herein can be used to diagnose or prognose a disorder or disease, for example, a genetic disorder. The methods described herein can be used to diagnose and prognose fetal disorders, e.g., fetal aneuploidy.

The methods described herein can be useful for evaluating an infection, e.g., a viral or bacterial infection. For example, the methods can be used to determine whether two or more mutations lie within a single virus or bacterium or whether two or more mutations are in different individual viruses or bacteria.

The methods described herein can be useful monitoring the generation of transgenic mice. For example, the methods can be used to determine whether a transgene has been introduced once or multiple times into the genome of a transgenic organism.

Apoptosis

Determining whether nucleic acids are linked or separated (fragmented) can be used to study apoptosis or diagnose or prognosis disease related to apoptosis. Apoptosis is a process of programmed cell death. Signs of apoptosis can include, e.g., blebbing, loss of cell membrane asymmetry and attachment, cell shrinkage, nuclear fragmentation, chromatin condensation, and chromosomal DNA fragmentation. During apoptosis, endogenenous endonucleases (e.g., $Ca^{2+}$ and $Mg^{2+}$ dependent endonucleases) can cleave chromatin DNA into internucleosomal fragments of about 180-200 base pairs or multiples of about 180-200 base pairs. Using the methods, compositions, and/or kits described herein, the fragmentation status of different forms of genetic material at different stages of the apoptosis can be determined. The methods described herein can be used with one or more other methods to analyze apopotosis, including, e.g., flow cytometry, fluorescent assays, or (TUNEL) (terminal deoxynucleotidyl transferase dUTP nick end labeling).

Apoptosis can involve an extrinsic, or death receptor pathway, or an intrinsic, or mitochondrial pathway, and/or a pathway that involves T-cell mediated cytotoxicity and perforin-granzyme-dependent death of a cell. The death receptor pathway can involve binding of a death ligand to a death receptor (e.g., FasL (fatty acid synthetase ligand, TNFSF6, Apo1, apoptosis antigen ligand 1, CD95L, CD178, APTILG1)/FasR (fatty acid synthetase receptor, TNFRSF6, ATP1, CD95); TNF-α (tumor necrosis factor alpha, TNF ligand, TNFA, cachectin)/TNFR1 (tumor necrosis factor receptor 1, TNF receptor, TNFRSF1A, p55 TNFR, CD120a); Apo3L (Apo3 ligand, TNFSF12, Apo3 ligand, TWEAK, DR3LG)/DR3 (Death receptor 3, TNFRSF12, Apo3, WSL-1, TRAMP, LARD, DDR3); Apo2L (Apo2 ligand, TNFSF10, TRAIL, TNF-related apoptosis inducing ligand)/DR4 (death receptor 4, TNFRSF10A, TRAILR1, APO2); and Apo2L/DR5 (death receptor 5, TNFRS10B, TRAIL-R2, TRICK2, KILLER, ZTNFR9). A TNF receptor can comprise a cysteine-rich extracellular domain and a cytoplasmic "death domain." Fas binding to Fas receptor can result in the binding of the FADD adapter protein. Binding of the TNF ligand to the TNF receptor can result in the binding of the TRADD (TNF receptor-associated death domain) adapter protein and recruitment of FADD (Fas-associated death domain, MORT1) and RIP (receptor-interacting protein, RIPK1). FADD can then associate with procaspase-8 by dimerization with a death effector domain to form a death-inducing signaling complex (DISC). This action can result in the autocatalytic activation of procaspase-8. Activation of caspase-8 can result in the "execution phase" of apoptosis, described below.

Death receptor-mediated apoptosis can be inhibited by c-FLIP (Casper, I-FLICE, FLAME-1, CASH, CLARP, MRIT), which can bind to FADD and caspase-8 (FLICE, FADD-like Ice, Mach-1, Mch5). Toso can block Fas-induced apoptosis in T-cells by inhibiting caspase-8 processing.

In the perforin/granzyme pathway, cytotoxic T lymphocytes (CTLs) can kill tumor cells and virus-infected cells by secreting perforin, a transmembrane pore-forming molecule, and subsequently releasing cytoplasmic granules through the pore and into the target cell. Serine proteases granzyme A and granzyme B can be components of the granules. Granzyme B can cleave and thereby activate procaspase-10 and can cleave ICAD (Inhibitor of Caspase Activated DNAse). Granzyme B can play a role in the mitochondrial pathway by cleaving Bid and inducing cytochrome c release. Granzyme B can also directly activate caspase-3. Granzyme A can activate DNA nicking via DNAse NM23-H1, which can be inhibited by the SET complex. Granzyme A can cleave the SET complex to release the inhibition of NM23-H1.

The intrinsic apoptosis pathway can have non-receptor-mediated stimuli, and the stimuli can act in a positive or negative manner. For example, the absence of certain factors (e.g., growth factors, hormones, cytokines) can include apoptosis. Stimuli that can act in a positive fashion include, e.g., radiation, free radicals, viral infections, toxins, hypoxia, and hyperthermia. These stimuli can cause an opening of the mitochondrial permeability transition (MPT) pore, loss of mitochondrial transmembrane potential, and release of pro-apoptotic proteins from the intermembrane space into the cytosol. One group of proteins released includes cytochrome c, Smac/DIABLO, and the serine protease HtrA2/Omi, which can activate the caspase-dependent mitochondrial pathway. Cytochrome c can bind and activate Apaf-1 and procaspase-9 to form an apoptosome, and caspase-9 can be activated. Smac/DIABLO and HtrA2/Omi can promote apoptosis by inhibiting IAP (inhibitors of apoptosis proteins). A second group of pro-apoptotic proteins, AIF, endonuclease G, and CAD can be released by mitochondria during apoptosis. AIF can move to the nucleus and can cause DNA to fragment into pieces of about 50 to about 300 kb. AIF can cause condensation of the peripheral nuclear chromatin ("stage I" condensation). Endonuclease G can move to the nucleus where it can cleave nuclear chromatin to form oligonucleosomal DNA fragments. AIF and endonuclease G can function independent of caspases. CAD can be released by mitochondria and move to the nucleus where it can lead to oligonucleosomal DNA fragmentation and advanced chromatin condensation ("stage II" condensation).

The Bcl-2 family of proteins can regulate mitochondrial membrane permeability. The Bcl-2 family proteins can be pro-apoptotic or anti-apoptotic. Anti-apoptotic proteins include Bcl-2, Bcl-x, Bcl-XL, Bcl-XS, Bcl-2, and BAG. Pro-apoptotic proteins include, e.g., Bcl-10, Bax, Bak, Bid, Bad, Bim, Bik, and Blk. The Bcl-2 family of proteins can regulate cytochrome c release from the mitochondria by alteration of mitochondrial membrane permeability. The protein 14-3-3 can regulate Bad based on the phosphorylation state of Bad.

Bad can heterodimerize with Bcl-XI or Bcl-2, which can neutralize their protective effect and promote cell death. When Bcl-2 and Bcl-XI are not sequestered by Bad, Bcl-2 and Bcl-XI can prevent cytochrome c release from mitochondria. Binding of Aven to Bcl-XI and Apaf-1 can prevent activation of procaspase-9.

Other Bcl2 family members include Puma and Noxa. Puma and Noxa can play a role in p53-mediated apoptosis. Also, MYC can regulate apoptosis in p53 dependent and independent manners.

The death receptor pathway (extrinsic) and mitochondrial pathway (intrinsic) can end at the execution phase. Caspase-3, caspase-6, and caspase-7 can function as executioner caspases and can cleave substrates including PARP, cytokeratins, fodrin, NuMA, gelsolin, and others. Caspase-3 can be activated by initiator caspases such as caspase-8, caspase-9, or caspase-10. Caspase-3 can activate the endonuclease CAD by cleaving its inhibitor, ICAD. CAD can degrade chromosomal DNA in nuclei and cause chromatin condensation. Apoptosis can involve the phagocytic uptake of apoptotic cells, which can involve recognition of phospholipid asymmetry and externalization of phosphatidylserine.

An overview of apoptosis can be found, e.g., in Elmore S. (2007) Apoptosis: A Review of Programmed Cell Death. *Toxicologic pathology* 35: 495-516, which is hereby incorporated by reference in its entirety.

The methods, compositions, and kits described herein can be used to analyze DNA fragmentation during autophagy.

Checkpoints, DNA Damage, and the Cell Cycle

Determining whether loci are linked or separated (fragmented) can be used to study DNA damage repair, double strand break repair, homologous recombination, microhomology-mediated end joining, single-strand annealing (SSA), breakage-induced replication, or non-homologous end joining (NHEJ). The methods described herein can be used to diagnose and prognose diseases associated with these processes.

DNA damage can arise from environmental factors and endogenous or normal metabolic processes. Endogenous factors that can damage DNA include, e.g., reactive oxygen species and replication errors. Physiologic double-strand DNA breaks can include V(D)J recombination breaks and class switch breaks. Pathologic double-strand DNA breaks can result from ionizing radiation, oxidative free radicals, replication across a nick, inadvertent enzyme action at fragile sites, topoisomerase failure, and mechanical stress. Environmental or exogenous factors that can cause DNA damage include ultraviolet radiation, x-rays, gamma-rays, DNA intercalating agents, some plant toxins, viruses, thermal disruption, and chemotherapy. Meiotic cells can have additional sources of DSBs, including the enzyme Spo11.

Double strand DNA breaks can be repaired by, e.g., NHEJ. Factors that can be involved in NHEJ include, e.g., Ku70/86, DNA-PKcs, Artemis, pol μ and λ, XRCC4, DNA ligase IV, XRC44, and XLF-Cernunnos. After formation of a double-strand break, Ku can bind to the break to form a DNA complex. The DNA end complex can recruit nuclease, polymerase, and ligase activities. Ku at the end of DNA can form a stable complex with DNA-PKcs. DNA-PKcs can comprise 5' endonuclease activity, 3' endonuclease activity, and a hairpin opening activity. Artemis can comprise a 5' exonuclease activity. The 3' exonuclease of PALF (APLF) can play a role in NHEJ. Polymerase mu and lambda can bind Ku:DNA complexes through their BRCT domains. DNA ligase IV can ligate across gaps, ligate incompatible DNA ends, and ligate single-stranded DNA. NHEJ can involve strand resection. XRCC4 can tetramerize, and PNK (polynucleotide kinase), APTX (aprataxin, a protein that can play a role in deadenylation of aborted ligation products), and PALF can interact with XRCC4. Double-strand DNA break repair by NHEJ is review, e.g., in Lieber, M (2011) Annu. Rev. Biochem. 79: 181-211, which is hereby incorporated by reference in its entirety. NHEJ can occur at any time in the cell cycle.

NHEJ proteins can play a role in V(D)J recombination. The proteins RAG1 and RAG2 can play a role in V(D)J recombination. Class switch recombination can occur in B cells after completion of V(D)J recombination and can be used to change immunoglobulin heavy chain genes. This process can involve activation-induced deaminase (AID), RNase H, uracil glycosylase, APE1, and Exo1.

Double strand DNA breaks can be repaired by homology-directed repair (e.g., homologous recombination or single-strand annealing). Examples of factors that can be involved in these process include RAD50, MRE11, Nbs1 (collectively, the MRN complex); RAD51 (B, C, D), XRCC2, XRCC3, RAD52, RAD54B, and BRCA2. During the S and G2 phases of the cell cycle, there are two sister chromatids in close proximity, so homology-directed repair can be more common in these phases.

The ATM and ATR kinases can recognize damaged DNA. These kinases, along with DNA-PK, can phosphorylate H2AX and generate γH2AX foci. ATR can be activated by single-stranded DNA regions that result from replication fork stalling or the processing of bulky lesions. ATR can interact with ATRIP. The 9-1-1 complex (Rad9, Hus1, and Rad1) can play a role in substrate phosphorylation by ATR. RPA can bind ssDNA and can play a role in substrate phosphorylation by ATR.

ATM can recognize DNA ends through MRN. Phosphorylated H2AX can recruit MDC1, the ubiquitin ligases RNF8 and RNF168, and 53BP1. ATM can phosphorylate Chk2 and p53.

Checkpoints and cell cycle regulation can also be analyzed using the methods, compositions, and kits described herein. Cells can proceed through a cell cycle, and the cell cycle can comprise G1 phase, S phase (DNA synthesis), G2 phase, and M phase (mitosis). Cells that have stopped dividing can be in G0 phase (quiescence). Checkpoints can be used to halt the cell cycle and permit repair of DNA damage before the cell cycle is permitted to continue. A DNA damage checkpoint can occur at the boundaries of G1 and S phases and G2 and M phases. Another checkpoint is the intra-S phase checkpoint.

Other Processes

Determining whether nucleic acids are linked or separated (fragmented) can be used to study a polymerase (e.g., DNA polymerase, RNA polymerase, reverse transcriptase) in processes such as DNA replication and transcription. For example, the processivity of a polymerase can be determined (e.g., to determine the percentage of nascent strands that are full length versus partial length, one can measure how many truncated versions of a gene are present by counting the number of first half copies versus last half copies of a gene). Because synthesis occurs 5' to 3', it is expected that more of the 1st half (5' end) of a product to be synthesized would be produced than the last half (3' end).

Determining whether loci are linked or separated (fragmented) in a sample can be useful for studying one or more restriction enzymes, RNAzymes, DNAzymes, exonucleases, endonucleases, RNases, DNase, etc., to determine the efficiency of cleavage (e.g., separation to two linked targets) by these enzymes.

Determining whether genetic loci are linked or separated (fragmented) can be useful for studying RNA splicing, genetic rearrangement, localization of genes, and DNA rearrangement in cancer. The genetic rearrangement can be, e.g., a chromosomal translocation. The translocation can be a reciprocal (non-Robertsonian translocation), which can involve the exchange of material between nonhomologous chromosomes. The translocation can be a Roberstonian translocation. A Robertsonian translocation can involve a rearrangement of two acrocentric chromosomes that fuse near a centromere. Translocations associated with disease include, e.g., t(8;14)(q24; a32) (Burkitt's lymphoma; fusion of c-myc with IGH); t(11;14)(q13;q32) (Mantle cell lymphoma; fusion of cyclin D1 with IGH); t(14;18)(q32;q21) (follicular lymphoma; fusion of IGH with Bcl-2); t(10;(various))(q11;(various)) (papillary thyroid cancer; involves RET proto-oncogene on chromosome 10); t(2;3)(q13;p25) (follicular thyroid cancer; fusion of PAX8 with PPARγ1)); t(8;21)(q22;q22) (acute myeloblastic leukemia); t(9;22)(q34;q11) Philadelphia chromosome (chronic myelogenous leukemia; acute lymphoblastic leukemia; fusion of ETO with AML I); t(15; 17) (acute promyolocytic leukemia; fusion of PML with RAR-α); t(12;15)(p13;q25) (Acute myeloid leukemia, congenital fibrosarcoma, secretory breast carcinoma; fusion of TEL with TrkC receptor), t(9;12)(p24;p13) (CML, ALL; fusion of JAK with TEL); t(12;21)(p12;q22) (ALL; fusion of TEL with AML1); t(11;18)(q21;q21) (MALT lymphoma; fusion of Bcl-2 with MLT); and t(1;11)(q42.1;q14.3) (schizophrenia).

Copy number variation analysis described herein can be used to diagnose prenatal conditions, e.g., fetal aneuploidy, e.g., trisomy 13, trisomy 18, or trisomy 21.

Determining the degree of degradation (fragmentation) of forensic genetic material can help determine what analyses can be successfully performed prior to wasting precious sample. Determining whether nucleic acids are linked or separated (fragmented) can be useful for determining an expected defect from perfect integer value copy number estimates due to random shearing of the DNA.

Collocation of Species

Provided herein are methods for determining the collocation of microRNAs and other RNAs. For example, microRNA and other types of RNA can be packaged in exosomes in blood. An exosome can be a be a 30-90 nm vesicle that can comprise both protein and RNA. RNA, including, e.g., microRNA, can be packaged together in protein-complexes. In one embodiment, a method is provided for determining whether transcripts are co-localized in exosomes or protein complexes.

In one embodiment, plasma, or a derivative of plasma, is processed in a way that preserves exosomes or protein complexes of interest, e.g., by cross-linking with formaldehyde, and then the plasma is partitioned into a plurality of spatially isolated partitions. The exosomes can be broken, proteins can be digested, and PCR reactions (in conjunction with reverse transcription) can be performed within the partitions (e.g., ddPCR). The PCR reactions can amplify at least 2, 3, 4, 5, 6, 7, 8, 9, 10 or more target nucleic acid sequences. If the target nucleic acid sequences are colocalized to the same partition, the target transcription may have been in the same protein complex. In another embodiment, a control is performed in which a sample is not subjected to a process to preserve an exosome or protein complex. In one embodiment, bursting (breaking) of the exosomes can be accomplished through a temperature adjustment. In another embodiment, bursting (breaking) of an exosome can be accomplished by releasing an inner emulsion in a partition that carries an exosome or protein-complex breaking agent.

In another embodiment, a method of determining the collocation of two or more species of cell-free DNA is provided. Cell free DNA molecules can be aggregated in a blood or plasma sample. A sample with aggregated cell free DNA molecules can be partitioned into spatially isolated regions, the aggregation can be disrupted, amplification for two or more different cell free DNA molecules can be performed, and the partitions can be analyzed to determine whether or not the cell free DNA molecules are in the same or different partitions.

The methods provided herein allow one to determine if a particular RNA, DNA, or protein target travels together in plasma. Additional fluorescence channels can allow for collocation measurement of two or more (e.g., 2, 3, 4, 5, 6, 7, 8, 9, 10, 11, 12, 13, 14, 15, 16, 17, 18, 19, 20 or more) targets simultaneously. For example, using probes with three different fluorophores, collocation frequency can be determined across three target nucleic acid sequences.

Detecting Deletions of Target Sequence

A method is provided for garnering linkage information through collocation. This method can be used to determine if there is a deletion of a target nucleic acid sequence, or for haplotyping CNV copies. A marker sequence (detected with, e.g., VIC labeled probe) can be outside but near a target sequence (detected with, e.g., a FAM-labeled probe), in a copy number variation region. A sample comprising nucleic acid can be partitioned into a plurality of spatially-isolated regions, and the marker and target nucleic acid sequences can be detected (e.g., through amplification and detection with probes). The collocation of the VIC (marker) and FAM (target) can be analyzed as depicted in FIG. 49. If VIC and FAM always colocalize in a partition, then there are likely no deletions of the target sequence (FIG. 49B). If there are partitions with VIC only that do not colocalize with FAM, this result suggests a deletion of the target sequence (FIG. 49A).

Storage of Digested Nucleic Acid

The length of storage of digested nucleic acid (e.g., DNA) can impact copy number variation measurements. Extended storage can cause reduction in the copy number estimated. For example, extended storage can result in nucleic acid degradation. The length of storage of a digested nucleic acid sample can be about, or less than about, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 hrs. The length of storage of a digested nucleic acid sample can be about, or less than about, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 days. The length of storage of a digested nucleic acid sample can be about, or less than about, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 years.

Figure 20A:
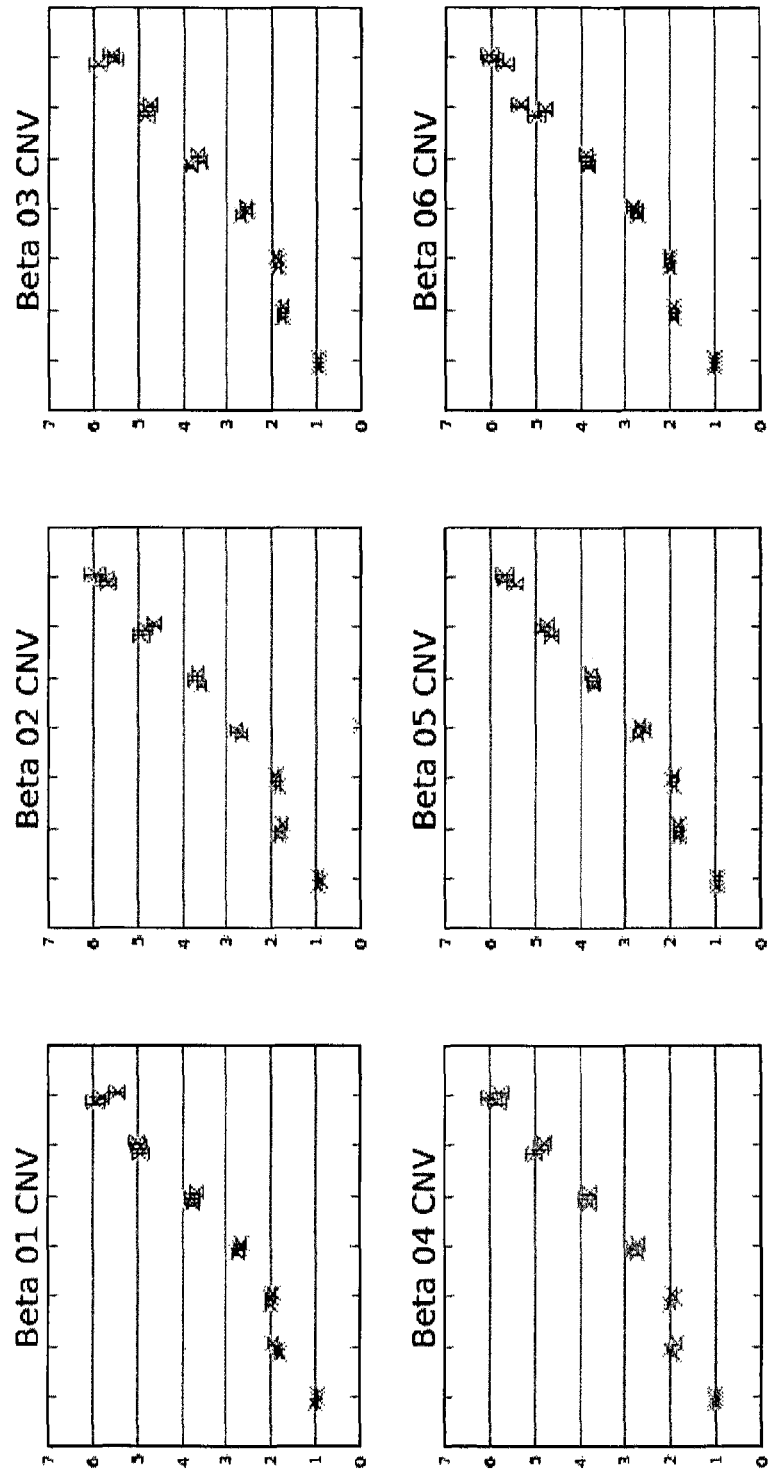
FIGS. 20A and 20B illustrate drift of CNV values of stored, digested DNA.
Figure 20B:
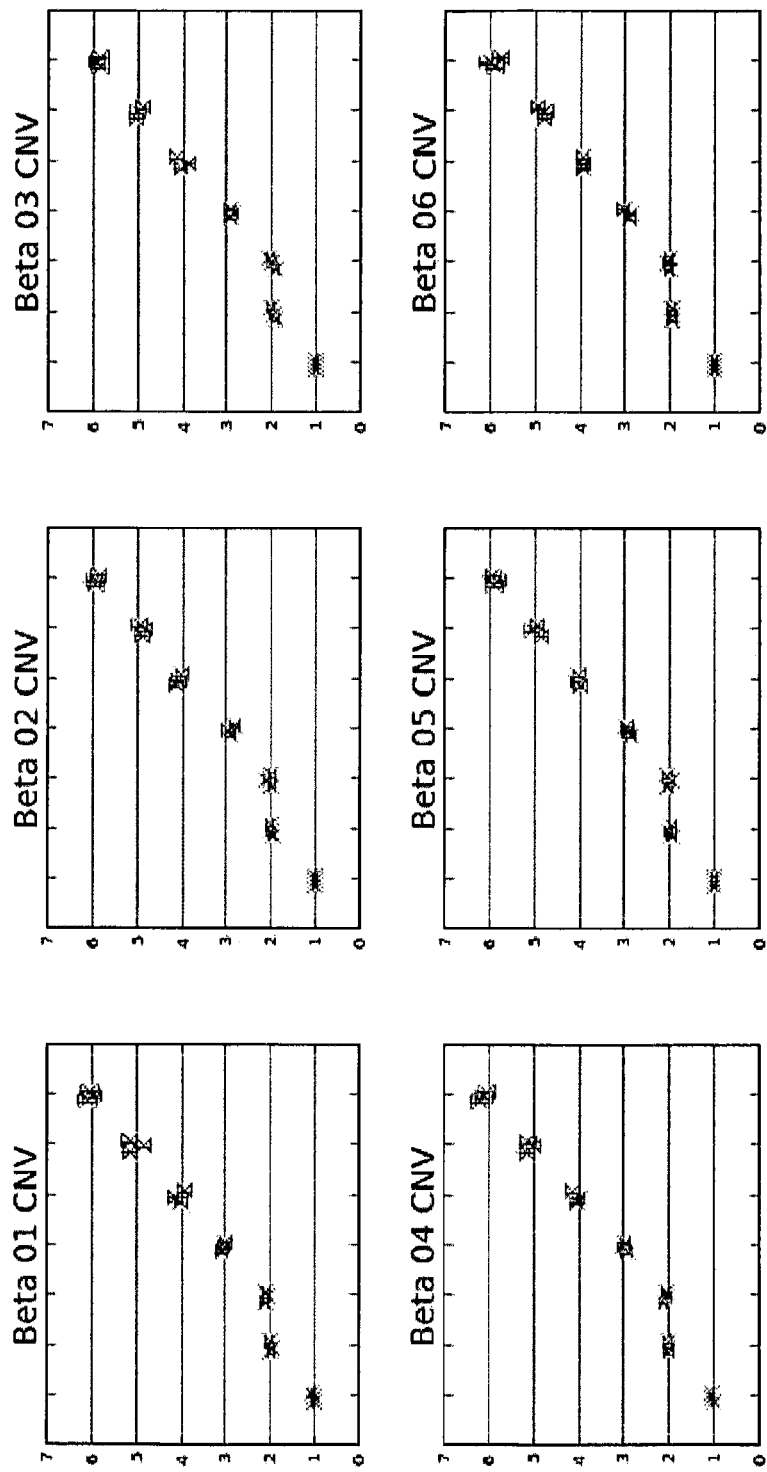

FIGS. 20A and 20B illustrate drift of MRGPRX1 CNV values of stored, digested DNA. In FIG. 20A, digested samples show CNV values consistently below integers. In FIG. 20B, CNV values, were closer to integers (see Example 20).

In one embodiment, storing digested DNA at 4° C. for extended periods of time can affect the quality of a CN estimate (e.g., the a copy number estimate can become smaller over time, e.g., a sample with a target with an estimated CNV of 6.0, if stored for 3 weeks at 4° C., might yield a CNV of 5.7).

The storage temperature of a nucleic acid sample, (e.g., a digested nucleic acid sample) can be about, or less than about 4, 0, −10, −20, −30, −40, −50, −60, −70, −80, −90, −100, −110, −120, −130, −140, −150, −160, −170, −180, −190, or −200° C.

In one embodiment, digested DNA can be stored in a buffer solution (e.g., 10 mM tris, pH 8.0).

Impact of Nucleic Acid Length on CNV Analysis

The presence of long nucleic acids in a sample can affect copy number variation values even if target nucleic acid sequences are not linked (e.g., if they are on different chromosomes). Reduction of nucleic acid size in a sample by, e.g., restriction digestion, heat treatment, shearing, sonication, filtration, etc., can improve the results of a copy number variation experiment. Reduction in nucleic acid length can also improve target accessibility for PCR.

At high nucleic acid loads, reduction in the length of nucleic acids can be used to ensure consistent droplet formation in a droplet digital PCR experiment. At high nucleic acid loads with long nucleic acids, droplet formation can be reduced or prevented, and a stream can result. Nucleic acid length can be reduced by, e.g., sonication, heat treatment, restriction enzyme digest, filtering, or shearing.

Droplet digital PCR can be used to measure restriction enzyme efficiency and specificity.

This application incorporates by reference in their entirety for all purposes the following materials: U.S. Pat. No. 7,041,481, issued May 9, 2006; U.S. Patent Application Publication No. 2010/0173394 A1, published Jul. 8, 2010; and Joseph R. Lakowicz, PRINCIPLES OF FLUORESCENCE SPECTROSCOPY (2nd Ed. 1999).

Kits

Provided herein are kits for carrying out the methods of the provided invention. The kits can comprise one or more restriction enzymes, devices, buffers, reagents, and instructions for use. A kit can comprise a restriction enzyme, a buffer, a salt, and instructions for use. A kit can comprise one or more primers and one or more probes. In one embodiment, a kit comprises at least one restriction enzyme, four primers, and two probes. In another embodiment, a kit comprises at least one restriction enzyme, at least four primers, and at least one probe. In another embodiment, a kit comprises at least one restriction enzyme at least four primers, and at least two probes.

Associated Technologies

Conventional techniques can be used in the methods described herein. Such conventional techniques can be found in standard laboratory manuals such as Genome Analysis: A Laboratory Manual Series (Vols. I-IV), Using Antibodies: A Laboratory Manual, Cells: A Laboratory Manual, PCR Primer: A Laboratory Manual, and Molecular Cloning: A Laboratory Manual (all from Cold Spring Harbor Laboratory Press); Stryer, L. (1995) Biochemistry (4th Ed.) Freeman, New York; Gait, "Oligonucleotide Synthesis: A Practical Approach" 1984, IRL Press, London, Nelson and Cox (2000), Lehninger, (2004) Principles of Biochemistry $4^{th}$ Ed., W. H. Freeman Pub., New York, N.Y. and Berg et al. (2006) Biochemistry, 6th Ed., W. H. Freeman Pub., New York, N.Y., all of which are herein incorporated in their entirety by reference for all purposes.

Copy number variations can be detected by a variety of means including, e.g., fluorescence in situ hybridization, comparative genomic hybridization, array comparative genomic hybridization, virtual karyotyping with SNP arrays, and next-generation sequencing. Methods of determining copy number variation by digital PCR are described, for example, in U.S. Patent Application Publication No. 20090239308. Copy number variations can be detected by digital PCR by diluting nucleic acids. Copy number variations can be detected by digital PCR by using a nanofluidic chip (digital array) which can partition individual DNA molecules into separate reaction chambers (e.g., Fluidigm nanofluidic chip). Copy number variation can be detected by droplet digital PCR. The methods described herein can be used to confirm the result of a copy number variation analysis performed with one or more of the aforementioned techniques.

Next generation sequencing techniques that can be used to determine copy number variations include, e.g., DNA nanoball sequencing (using rolling circle replication to amplify small fragments of genomic DNA into DNA nanoballs) (used by, e.g., Complete Genomics), nanopore sequencing (used by, e.g., Oxford Nanopore Technologies) (Soni G. V. and Meller A. (2007) *Clin. Chem.* 53: 1996-2001), ion semiconductor sequencing (Ion Torrent Systems) (U.S. Patent Application Publication No. 20090026082), SOLiD sequencing (sequencing by ligation; used by, e.g., Applied Biosystems), Illumina (Solexa) sequencing (using bridge amplification), 454 pyrosequencing (used by, e.g., Roche Diagnostics) (Margulies, M. et al. 2005 *Nature*, 437: 376-380), true single molecule sequencing (used by, e.g., Helicos) (Harris T. D. et al. (2008) *Science* 320: 106-109), or single molecule real-time sequencing (SMRT) used by Pacific Biosciences. The methods, compositions, and/or kits described herein can be used to follow-up on a CNV analysis performed by one of these methods.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. The term "about" as used herein refers to a range that is 15% plus or minus from a stated numerical value within the context of the particular usage. For example, about 10 would include a range from 8.5 to 11.5.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

EXAMPLES

Example 1

Amylase CNV Analysis

Figure 21:
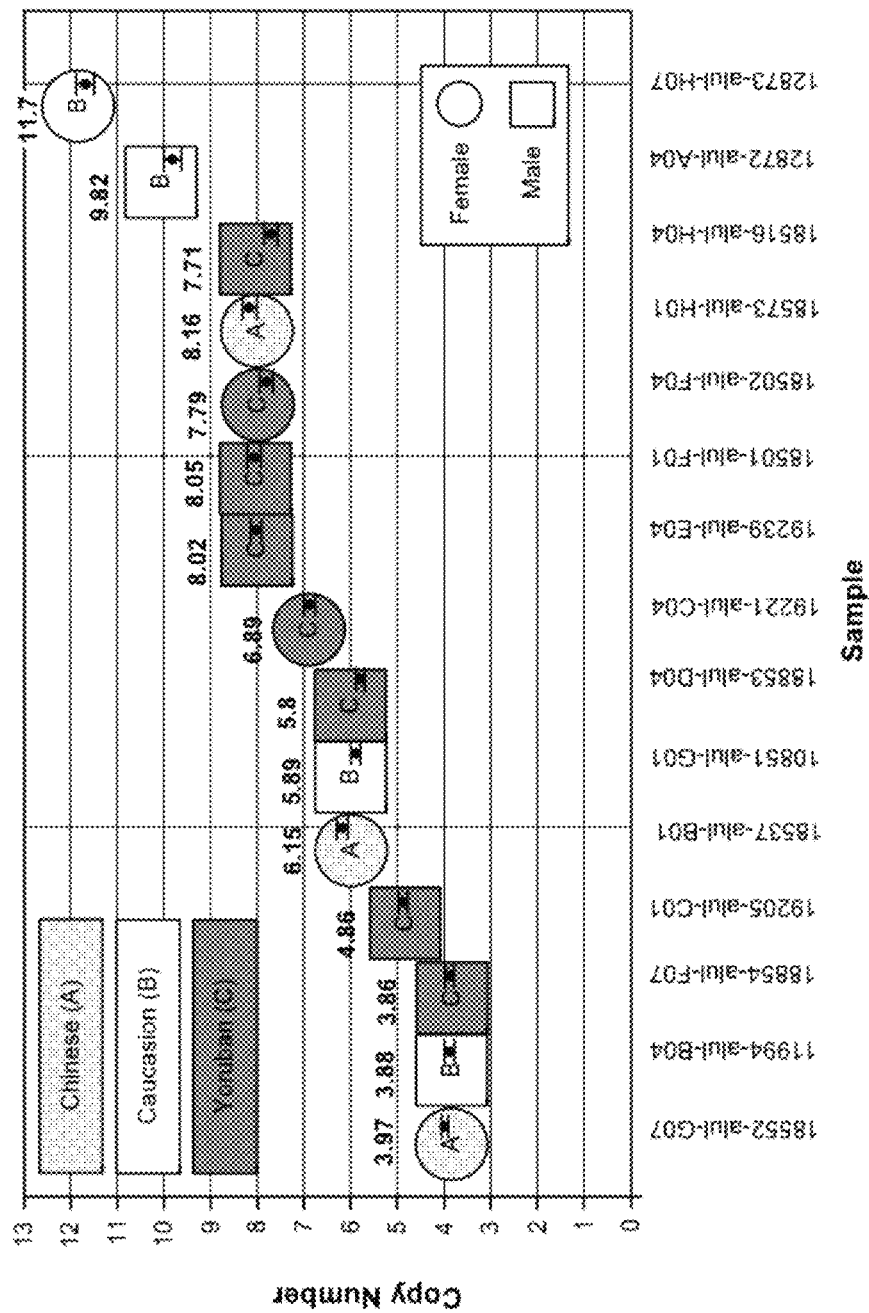
FIG. 21 illustrates high variability in the copy number of the amylase gene among individuals.

The methods described herein can be used to determine copy number variation in the amylase gene. Amylase is an enzyme that can hydrolyze bonds of polysaccharides. Copy number variation among groups suggests an evolutionary change based on diet. An amylase assay yields discrete estimates corresponding to distinct CNV states. Results with 15 Coriell reference DNA samples demonstrate high human variability in copy number for this gene. See FIG. 21.

Samples from the Coriell Institute for Medical Research are used. Sample DNA are digested with AluI at 10 U/μg DNA, at 37° C. for 1 hour. About 20-100 μg of digested DNA is loaded into each ddPCR reaction. Each sample is processed in triplicate and the data is merged to arrive at the values shown in FIG. 21. The sequence of the forward primer for the amylase assay is 5'-TTCTGAGATTTATCTAGAG-GCTGGGA-3' (SEQ ID NO: 17), the reverse primer is 5'-CCCTGACAGACCGACAAGAC-3' (SEQ ID NO: 18), and the probe is 5'-6FAM-CTGGTTCAGGAGCCCT-MGB-NFQ-3' (SEQ ID NO: 19). The assay is duplexed to RPP30: FWD primer: 5'-GATTTGGACCTGCGAGCG-3' (SEQ ID NO: 20), REV primer 5'-GCGGCTGTCTCCACAAGT-3' (SEQ ID NO: 21) and probe 5'-VIC-CTGACCTGAAG-GCTCT-MGB-NFQ-3' (SEQ ID NO: 22). The following thermal cycling conditions are used: 95° C. 10 min, (94° C. 30 sec+60° C. 1 min) for 55 cycles.

Example 2

CCL3L1 CNV Analysis

Figure 22:
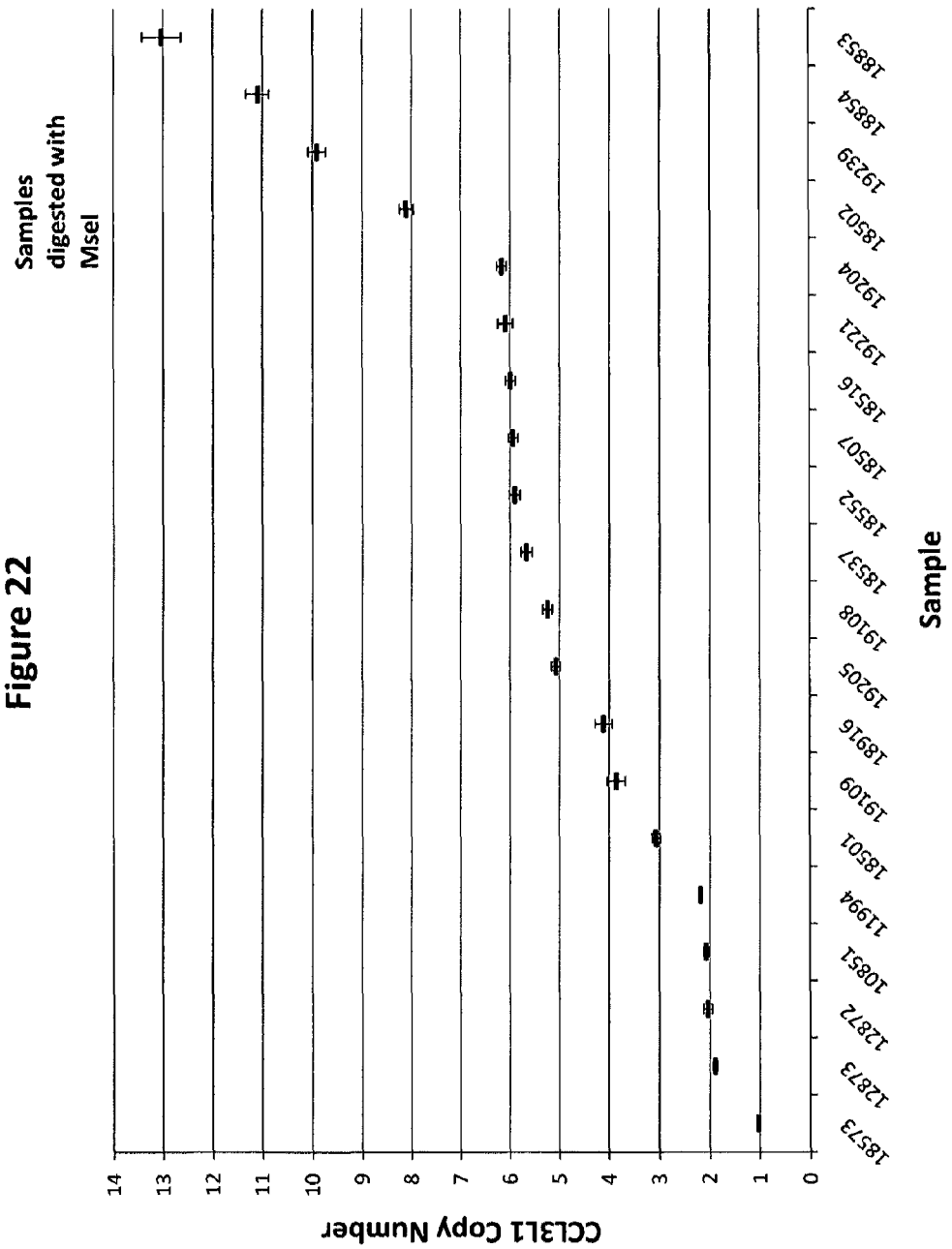
FIG. 22 illustrates copy number variation for CCL3L1.

The methods described herein can be used to determine copy number variation in the CCL3L1 gene. Copy number variations of CCL3L1 have been implicated in HIV-1 susceptibility, but these associations have been inconsistent due to inaccurate copy number assessment using standard qPCR. The CCL3L gene cluster includes five pseudogenes which can make specific amplification difficult. Integer-based CNV analysis adds confidence to correct quantitation. Alkan et al. ((2009) *Nat. Genetics.* 41: 1061-1067) found NA18507 had 5.7 copies of CCL3L1. In the analysis here, 5.94 copies with error bars crossing '6' were found. See FIG. 22. The methods described herein provide the ability to specifically design an assay to target a gene and specifically select a restriction enzyme to liberate this gene, while also cutting pseudogenes to reduce the chance of false positives inflating copy number estimates.

Using annealing temperature of 57° C. can result in some pseudogenes being amplified and CNV values being about 1 greater than expected.

For CCL3L1, 815 ng of each purified human genomic DNA sample (Coriell) is digested with 7.5 units of MseI (NEB) in 10 µL for 1 h at 37° C. The digest is diluted 3.5-fold to 35 µL with TE buffer and then 69 ng (3 µL) is assayed per 20 µL ddPCR reaction. Modified CCL3L1 assay sequences 19 are (forward primer) 5'-GGGTCCAGAAATACGT-CAGT-3' (SEQ ID NO: 23); (reverse primer) 5'-CATGTTC-CCAAGGCTCAG-3' (SEQ ID NO: 24); and (probe) 6FAM-TTCGAGGCCCAGCGACCTCA-MGBNFQ (SEQ ID NO: 25). All CNV assays are duplexed with an RPP30 reference assay (forward primer) 5'-GATTTGGACCTGCGAGCG-3' (SEQ ID NO: 20); (reverse primer) 5'-GCGGCTGTCTCCA-CAAGT-3' (SEQ ID NO: 21); and (probe) VIC-CTGACCT-GAAGGCTCT-MGBNFQ (SEQ ID NO: 22). Thermal cycling conditions are 95° C. 10 min (1 cycle), 94° C. 30 sec and 60° C. 60 sec (40 cycles), 98° C. 10 min (1 cycle), and 12° C. hold. See also Sudmant, P. H.; Kitzman, J. O.; Antonacci, F.; Alkan, C.; Malig, M.; Tsalenko, A.; Sampas, N.; Bruhn, L.; Shendure, J.; Eichler, E. E. *Science* 2010, 330, 641-646.

Example 3

MRGPRX1 CNV Analysis

The methods described herein can be used to determine copy number variation for the MRGPRX1 gene. Mas-related G-protein coupled receptor member X1 is a protein that in humans is encoded by the MRGPRX1 gene. MRGPRX1 is a sensory neuron-specific receptor involved in itching and pain sensation. MRGPRX1 proteins are thought to be involved in blocking pain, therefore deletions are associated with chronic pain. FIGS. 23A and 23B illustrate copy number variation for the MRGPRX1 gene.

For MRGPRX1, 4.4 µg of each purified human genomic DNA sample (Coriell) was digested with 10 units of RsaI (NEB) in 50 µL for 1 h at 37° C. The digest was diluted 8-fold to 400 µL with TE buffer (pH 8.0) then 33 ng (3 µL) was assayed per 20 µL ddPCR reaction. MRGPRX1 assay sequences were (forward primer) 5'-TTAAGCTTCATCAG-TATCCCCCA-3' (SEQ ID NO: 26), (reverse primer) 5'-CAAAGTAGGAAAACATCATCACAGGA-3' (SEQ ID NO: 27), and (probe) 6FAM-ACCATCTCTAAAATCCT-MGBNFQ (SEQ ID NO: 28). CNV assays were duplexed with an RPP30 reference assay (forward primer) 5'-GATTTGGACCTGCGAGCG-3' (SEQ ID NO: 20), (reverse primer) 5'-GCGGCTGTCTCCACAAGT-3' (SEQ ID NO: 21), and (probe) VIC-CTGACCTGAAGGCTCT-MGB-NFQ (SEQ ID NO: 22). Thermal cycling conditions were 95° C.×10 min (1 cycle), 94° C.×30 s and 60° C.×60 s (40 cycles), 98° C.×10 min (1 cycle), and 12° C. hold (see also Hindson B et al. (2011) *Anal. Chem.* 83: 8604-8610).

Example 4

CYP2D6 CNV Analysis

The methods described herein can be used to determine copy number variation for the CYP2D6 gene. Cytochrome P450 2D6 (CYP2D6), a member of the cytochrome P450 mixed-function oxidase system, is involved in the metabolism of xenobiotics in the body. CYP2D6 copy number is associated with metabolizing drugs. Little to no CYP2D6 function can result in poor drug metabolism. High amounts of CYP2D6 function can result in extensive drug metabolism. Multiple copies of the CYP2D6 gene can be expressed and result in greater-than-normal CYP2D6 function (ultrarapid metaboliser). FIGS. 24A and 24B illustrate copy number variation for CYP2D6.

For CYP2D6, 4.4 µg of each purified human genomic DNA sample (Coriell) was digested with 10 units of RsaI (NEB) in 50 µL for 1 h at 37° C. The digest was diluted 8-fold to 400 µL with TE buffer (pH 8.0) then 33 ng (3 µL) was assayed per 20 µL ddPCR reaction. The CYPD2D6 (Hs00010001_cn) was purchased as a 20× premix of primers and FAM-MGBNFQ probe (Applied Biosystems. CNV assays were duplexed with an RPP30 reference assay (forward primer) 5'-GATTTG-GACCTGCGAGCG-3' (SEQ ID NO: 20), (reverse primer) 5'-GCGGCTGTCTCCACAAGT-3' (SEQ ID NO: 21), and (probe) VIC-CTGACCTGAAGGCTCT-MGBNFQ (SEQ ID NO: 22). Thermal cycling conditions were 95° C.×10 min (1 cycle), 94° C.×30 s and 60° C.×60 s (40 cycles), 98° C.×10 min (1 cycle), and 12° C. hold. (see also Hindson B et al. (2011) *Anal. Chem.* 83: 8604-8610)

Example 5

Spinal Muscular Atrophy CNV Analysis

Spinal Muscular Atrophy (SMA) can be caused by motor neuron loss in the spinal cord area due to low amount of survival motor neuron protein, which is encoded by SMN1 and SMN2. SMN1 and SMN2 are subject to deletions and amplifications. These genes are identical except for one nucleotide that reduces the level of full-length transcripts transcribed from SMN2. SMA can be caused by a loss of SMN1 copies. Disease severity can be related to how well the SMN2 compensates for SMN1 loss. Assays can be designed for allele-specific gene detection and differentiation (e.g., including ddPCR).

Inheritance can be autosomal recessive. 1/6,000 births can be affected by SMA; 1/40 people are carriers of defective SMN1. Types 0 & 1 can result in death before 2 years. Types 2-4 can result in onset after 2 years (severe to mild weakness).

Figure 25:
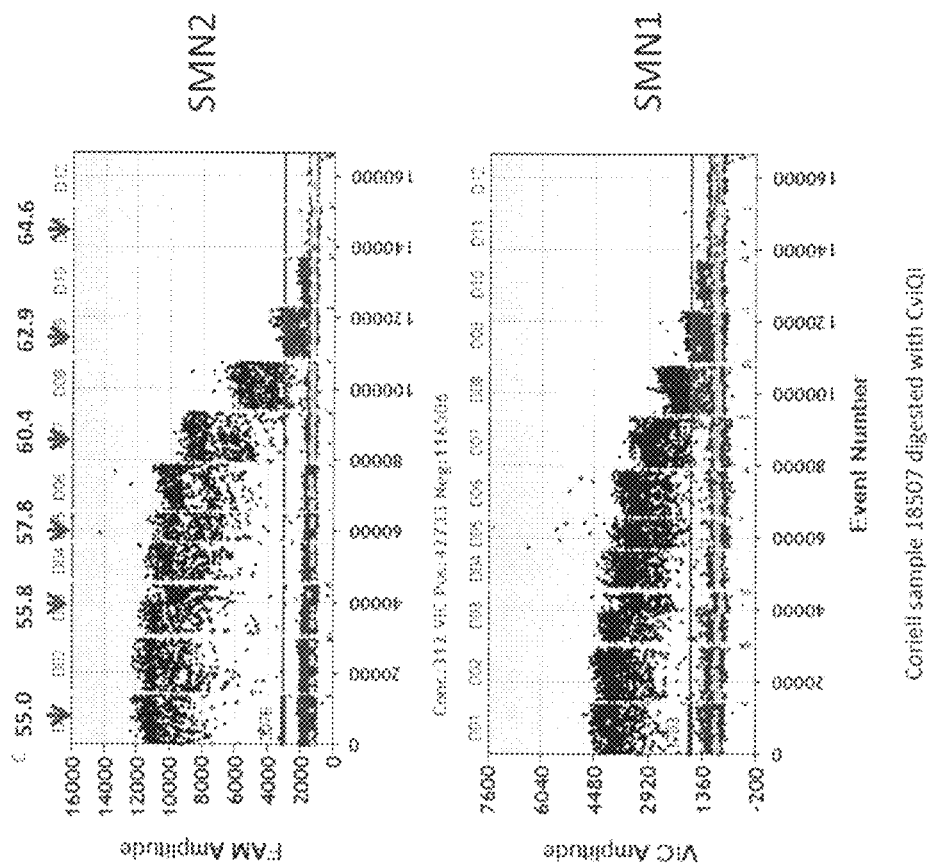
FIG. 25 illustrates an optimal common annealing temperature identified using a simple gradient plate.
Figure 26:
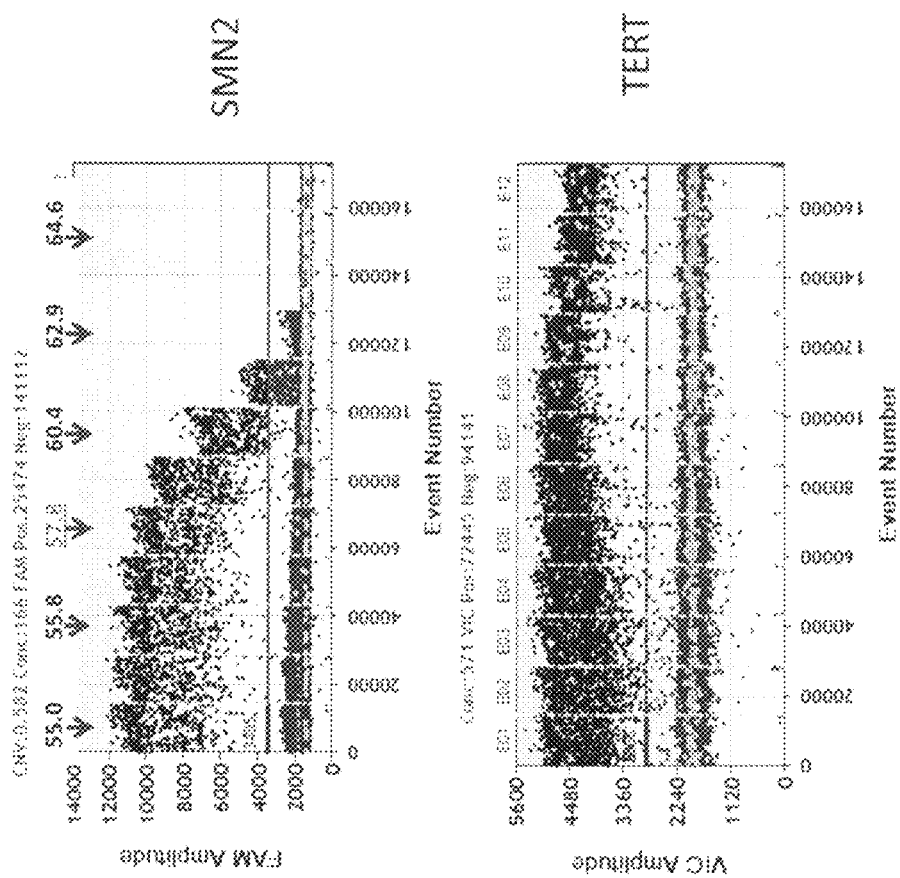
FIG. 26 illustrates an optimal common annealing temperature identified using a simple gradient plate.
Figure 27:
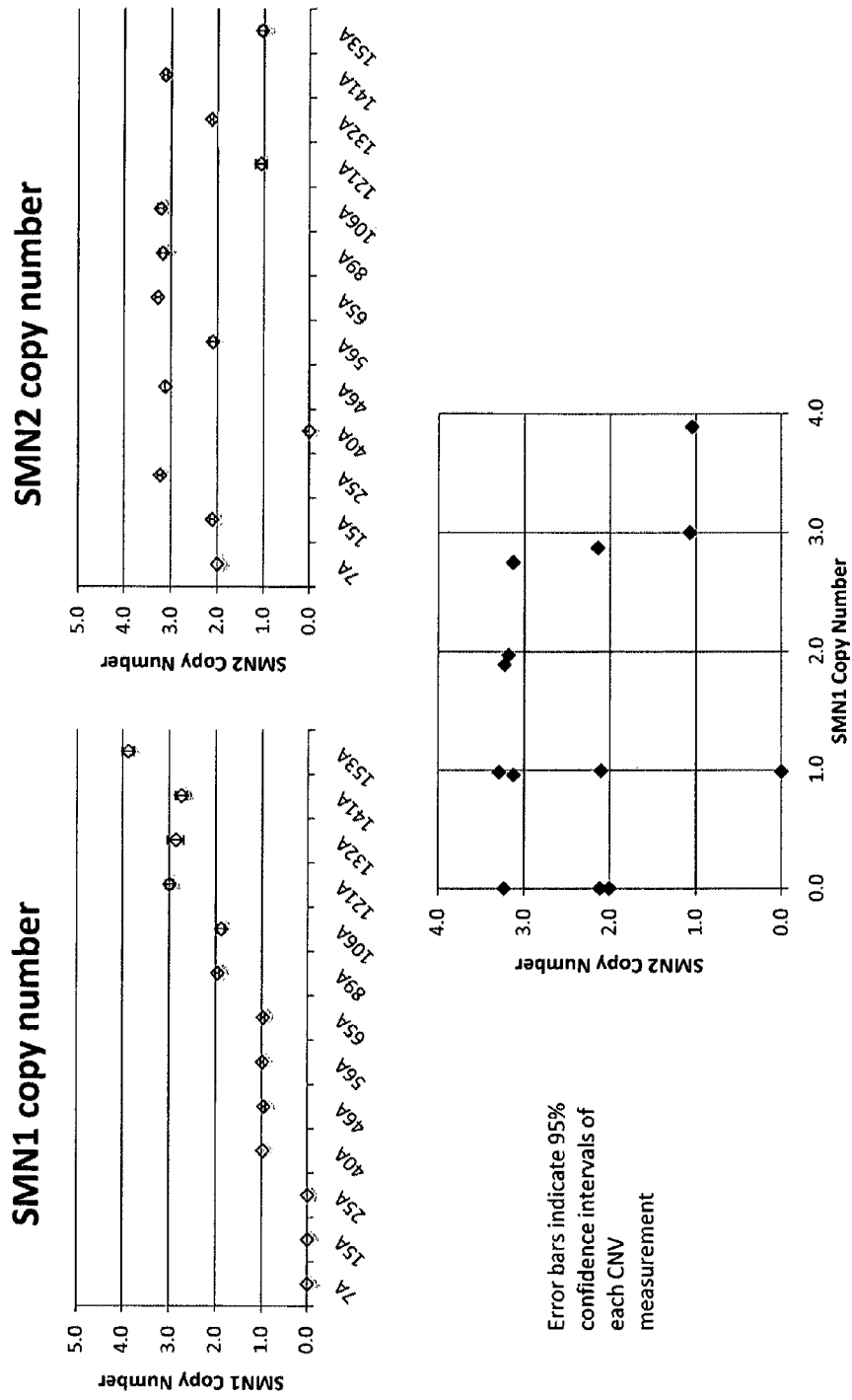
FIG. 27 illustrates SMI and SMN2 copy number.

FIGS. 25 and 26 illustrate an optimal common annealing temperature identified using a simple gradient plate. FIG. 27 illustrates SMI and SMN2 copy number.

Independent duplexes (SMN1/Her2 & SMN2/Tert) can be used to determine SMN1 and SMN2 copy number. Ratio of SMN1/SMN2 copies from duplex can be used to confirm the measured copy number values. Validation can be through triangulation (e.g., see upper schematic in FIG. 28). Triangulation can mean that the CNV of a target can be validated by assessing the CNV using two different references. For example, the ratio (CNV) of the two different references can be measured by duplexing them together, thereby avoiding the possibility of estimating a CNV using a reference that does not contain the expected two copies/diploid genome.

The copy number of three different targets can be evaluated in determining CNV, making it much less likely that an error in CNV estimate is being made.

For this experiment, SMN1 copy number was assessed using SMN1 (VIC) duplexed to a Her2 (FAM) assay. Approximately 50 ng/assay DNA was digested using CviQI. A standard PCR protocol was performed. SMN2 copy number was determined using SMN2 (FAM) duplexed to an assay to detect TERT (VIC). The ratio of SMN1/SMN2 was determined by performing a duplex of SMN1 (VIC) and SMN2 (FAM). The DNA is digested using CviQI, using roughly 50 ng/assay. Thermal cycling conditions are 95° C. 10 min (1 cycle), 94° C. 30 s and 60° C. 60 s (40 cycles), 98° C. 10 min (1 cycle), and 12° C. hold.

Figure 28:
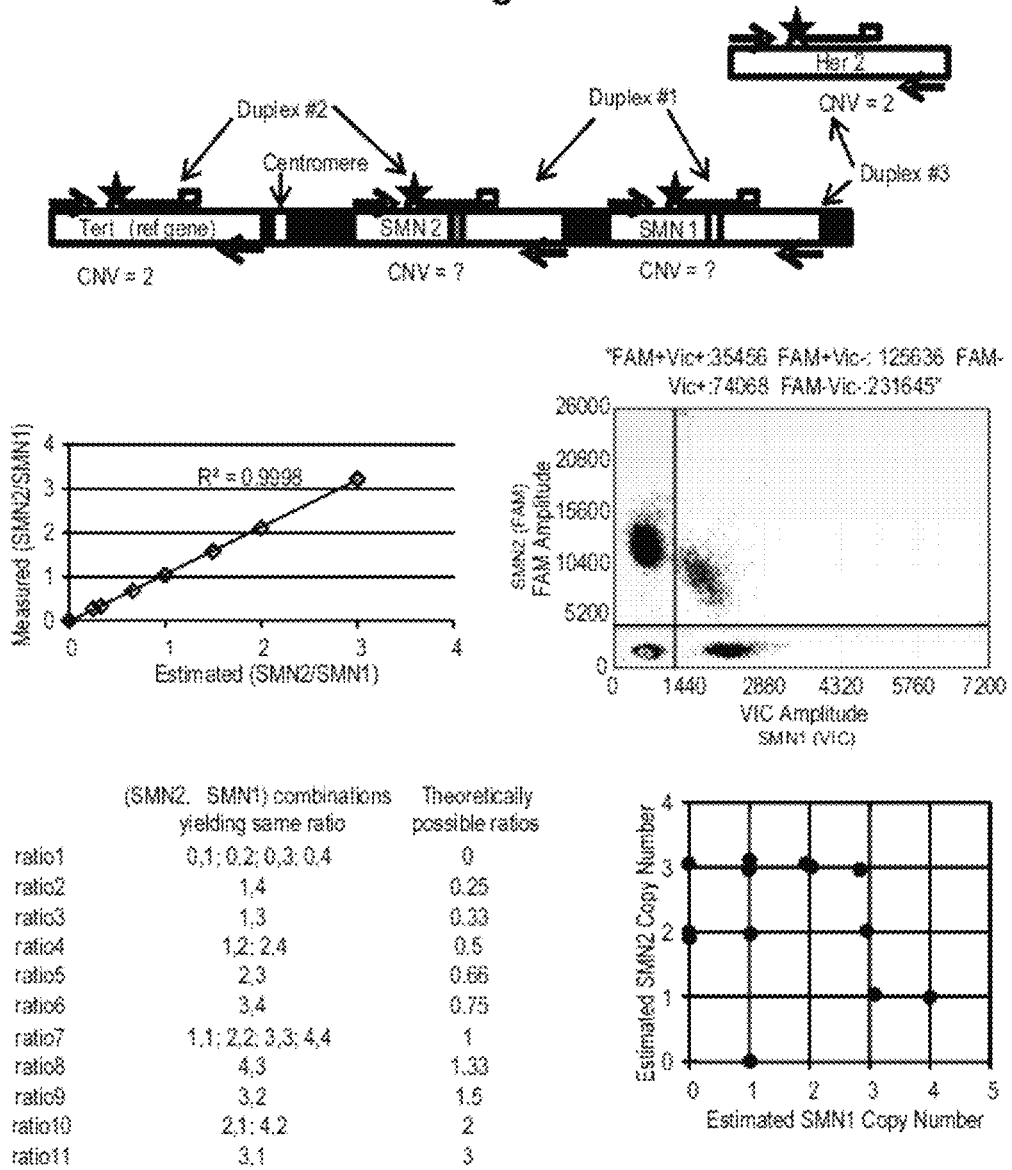
FIG. 28 illustrates copy number variation for SMN1 and SMN2.

FIG. 28 illustrates copy number variation for SMN1 and SMN2.

Detecting the SMN genes can be done by using the same primer pair and changing the probe. The common primer pair is FWD primer: 5'-ATAGCTATTTTTTTTAACTTCCTT-TATTTTCC-3' (SEQ ID NO: 29); REV primer 5'-TGAG-CACCTTCCTTCTTTTTGA-3' (SEQ ID NO: 30). The SMN1 probe sequence is: 5'-VIC-TTGTCTGAAACCCTG-MGB-NFQ-3' (SEQ ID NO: 31), whereas the SMN2 probe sequence is: 5'-6FAM-TTTTGTCTAAAACCC-3' (SEQ ID NO: 32). The Tert reference gene FWD primer is 5'-GGCA-CACGTGGCTTTTCG-3' (SEQ ID NO: 33); REV primer is 5'-GGTGAACCTCGTAAGTTTATGCAA-3' (SEQ ID NO: 34). The probe is 5'-VIC-TCAGGACGTCGAGTGGA-CACGGTG-MGB-NFQ-3' (SEQ ID NO: 35). The Her2 assay sequence is FWD primer 5'-CCCTGAGCAAAGAGT-CACAGATAAA-3' (SEQ ID NO: 36), REV primer 5'-TGC-CAGGGTCTGAGTCTCT-3' (SEQ ID NO: 37), Probe: 5'-6FAM-ACTGCGTTTGTCCTGG-MGB-NFQ-3' (SEQ ID NO: 38).

Example 6

Her2 CNV Analysis

Figure 29:
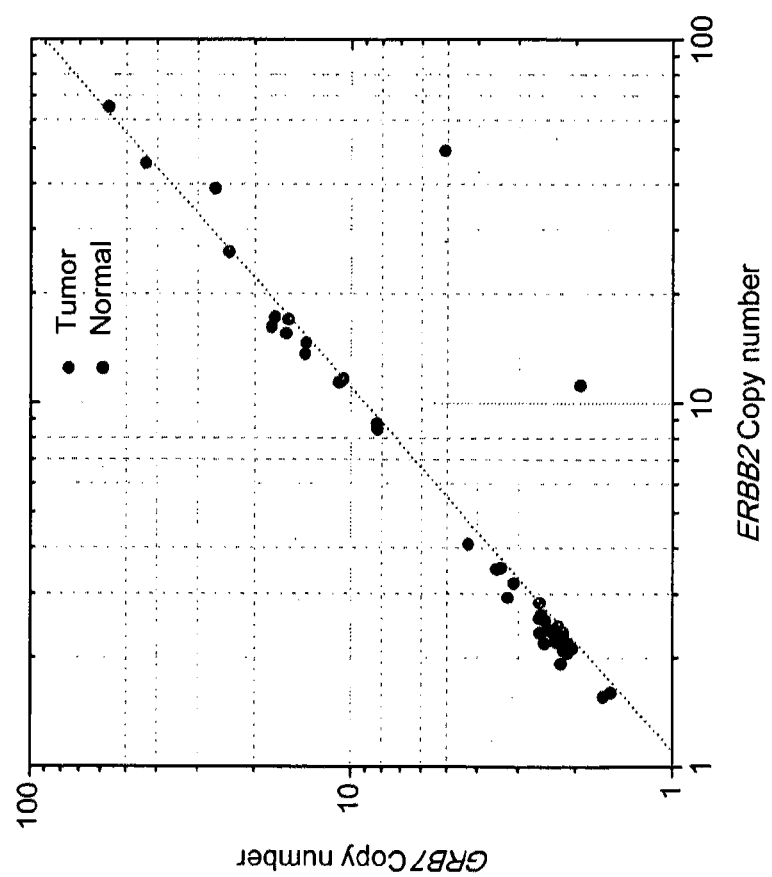
FIG. 29 illustrate analysis of HER2.

30% of breast cancers have Her2 amplification. Her2+ cancers are highly aggressive, but can respond to Herceptin. HER2 levels are widely tested, but there are many drawbacks with existing technologies. Her2, also known as ERBB2, is 20 KB away from GRB7, which is also often over-expressed in several cancers. Assays targeting two clinically relevant genes can validate each copy number determination. Not unexpected, one sample is only amplified for Her2 (ERBB2) and another displays mosaicism. See FIG. 29.

Purified DNA (20 ng) from each normal and tumorous breast tissue sample (D8235086-1, Biochain) was digested with 0.2 units of NlaIII in 10 µL for 1 h at 37° C. The restricted DNA was added directly to ddPCR Mastermix at 8.8 ng (4.4 µL) per 20 µL of ddPCR reaction. ERBB2 (Hs02803918_cn) and GRB7 (Hs02139994_cn) assays were purchased as 20× premixes of primers and FAM-MGBNFQ probe (Applied Biosystems) and duplexed with the RPP30 reference assay described above. Thermal cycling conditions were 95° C.×10 min (1 cycle), 94° C.×30 s and 60° C.×60 s (40 cycles), 98° C.×10 min (1 cycle), and 12° C. hold (see also Hindson B et al. (2011) *Anal. Chem.* 83: 8604-8610).

Example 7

Linkage Analysis

If the copy number (CN) of a target nucleic acid sequence is 2.0 for a particular assay post-digestion, it is not clear if there are (A) 2 copies of the target on one chromosome and 0 on another; or (B) 1 copy of the target nucleic acid sequence on each of two different chromosomes. An assay run with undigested DNA can be used to resolve the two possibilities. Using undigested DNA, in principle, a CN of 1 should be achieved if the arrangement is (A) (2 copies of the target nucleic acid sequence on one chromosomes) and a CN of 2 if the arrangement is (B) (one copy of each of two different chromosomes). Because DNA in a sample can be fragmented, the results may not be precise—(A) may yield a reading higher than 1.0 for the CN, but presumably significantly less than 2.0; (B) should yield exactly 2.0.

Higher fragmentation of the starting material would bring the CN reading in (A) closer to 2.0. As an example, for a given assay it is anticipated that the linked copies are separated by about 10 kb and based on our fragmentation analysis 30% of 10 kb segments are fragmented. In that case, scenario (A) should yield a reading of 1.3 and scenario (B) a reading of 2.0.

Example 8

Linkage Analysis

If a CN reading is 3.0 post-digestion, it is not clear if there are (A) 3 copies on one chromosome and 0 on another; or (B) 2 on one and 1 on another. If the same assay is run on undigested DNA, and the same parameters of a 10 kb separation and 30% fragmentation are assumed as above, scenario (A) would yield a reading of 1.6 copies (=0.7* 0.3*2+0.7*0.3*1+0.3*0.7*2+0.3*0.3*3), whereas (B) would yield a reading of 2.3 copies.

For digital PCR-realtime hybrids, (e.g., Life's Biotrove arrays), one can attempt to extract additional linkage information from undigested DNA. For example, one can estimate how many of the partitions contain two, three, etc. copies of the target by analyzing real time curves within each partition.

Endpoint fluorescence can be examined to determine if segments with two copies of a target nucleic acid sequence yield higher amplitudes than segments with one copy of a target nucleic acid sequence. Under scenario (A) there should be fewer positives, but those positives should on average have higher fluorescence.

One can tweak the number of cycles to gain the best separation (e.g., by making it so that segments carrying one copy do not reach the endpoint).

Example 9

Confirming ddPCR can be Used to Haplotype Samples that are CNV=2 (e.g., Distinguish Between Cis- and Trans-Configured Copies of a Gene)

A strategy to haplotype chromosomes is to 1) compare the CNV of digested and undigested samples (using, e.g., ddPCR); 2) examine the mean fluorescence intensity of droplets while they undergo exponential amplification (before any reagents become limiting—which can happen during later cycles of PCR), and 3) perform long-range PCR to either detect the presence of two copies of a gene (or target) on the same chromosome (cis-configuration), or, if a gene (or target, or duplicated region) is too long, then examine the other chromosome to confirm a deletion for the gene (or target) of interest (e.g., PCR across the deleted section should work, but PCR with the gene (or target) in place will not work because the distance between the primers is too great).

General Protocol Guidelines.

1) ddPCR:

A restriction enzyme digested sample is compared to an undigested sample and, the results are examined for a significant drop in estimated CNV for the undigested sample in the samples that have cis-configured copies. DNA can be included in the sweet spot for Poisson statistics (point at which there is the least amount of statistical error in the Poisson correction factor). For 20,000 droplets, the sweet spot can be ~1.6 cpd (copies per droplet).

2) Fluorescence Based Confirmation:

At an appropriate cycle or cycles (which can be empirically determined and can be different for every assay depending on assay efficiency), one can examine whether the mean intensity of the drops containing the cis-configured sample is higher than that of the trans-configured sample, which would happen if two linked copies are contained in the same droplet. For this experiment, one can use a low cpd. One can aim for 0.1 cpd to minimize the chance that two unlinked copies will be in the same droplet. With good optics, one can see banding in the fluorescence intensity (drops with two copies should be twice as bright as drops with only one copy). Fluorescence can be examined at, e.g., about cycle 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50. Fluorescence can be examined at more than one cycle. For example, fluorescence can be examined at 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 different cycles. For example, fluorescence can be measured at cycle 25, 28, 31, and 40.

3) Confirmation of Linkage by Long-Range PCR.

Generally the size of the amplified regions in a CNV can be too large to permit PCR amplification of two tandemly located genes (or targets); therefore, it is can be easier to detect the presence of a gene (or target) deletion rather than two copies of a target side by side. For this analysis, primers can be selected that face one another that are outside the region suspected of being amplified. A long-range polymerase can be used. PCR can be performed using the appropriate length extension times (note that times too long or too short may cause the reaction to fail). This long-range PCR can be performed in bulk or in droplets.

Figure 30:
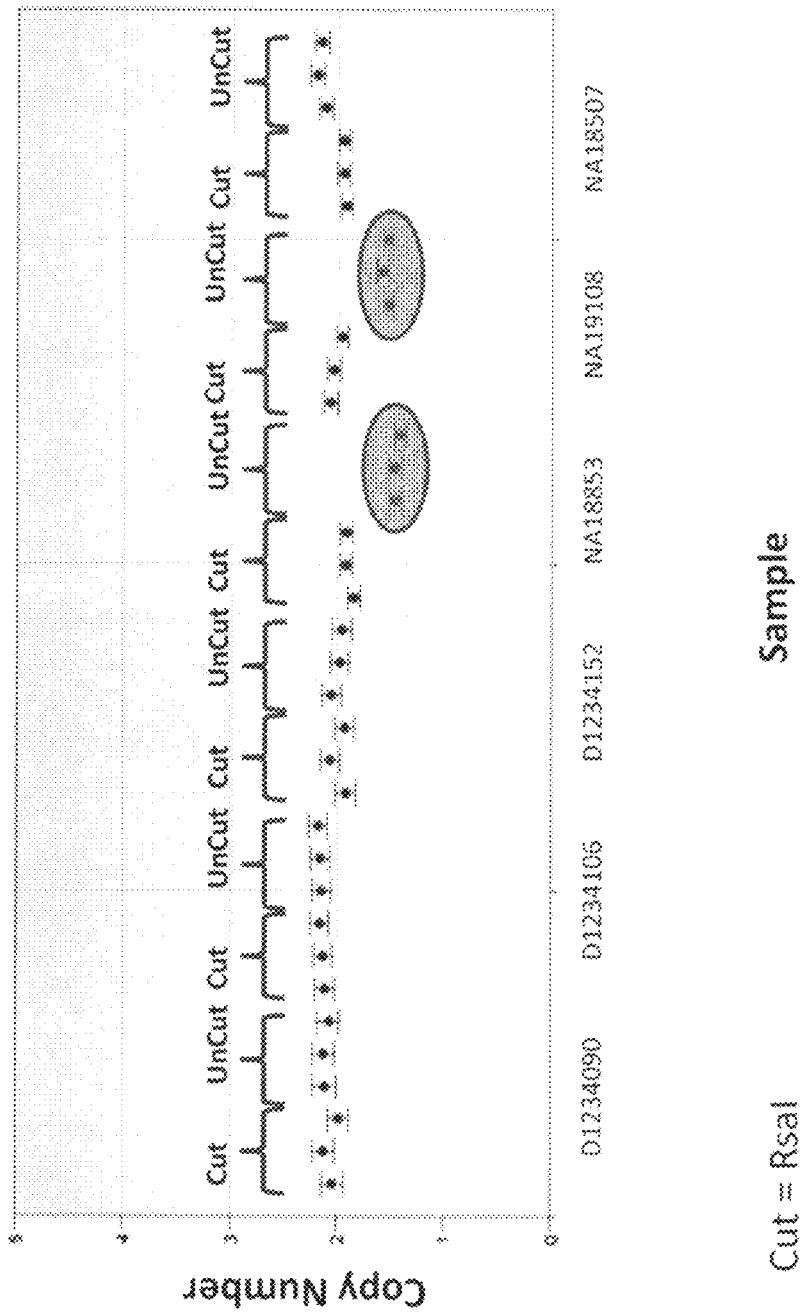
FIG. 30 illustrates results of a linkage experiment. Six samples were subjected to a restriction digest or not, and copy number of a target sequence was determined. The data suggest that samples 4 and 5 have two target sequences on the same chromosome.

FIG. 30 illustrates copy number estimation for 6 samples, each cut and uncut with a restriction enzyme. The data suggest that samples 4 and 5 have two target sequences are linked on the same chromosome, whereas the other samples contain a single target sequence on both chromosomes.

Sample D1234090 (Colon), D1234106 (Esophagus), and D1234152 (Lung) are from BioChain Institute Inc. Samples NA18853, NA19108, and NA18507 are from the Coriell Institute for Medical Research. Coriell samples comprise B-lymphocyte DNA.

About 10 U of RsaI were used per microgram of DNA, and digests lasted for 1 hr at 37° C. Fluorescence of the droplets was read after 40 cycles using a droplet reader.

MRGPRX1 assay sequences can be (forward primer) 5'-TTAAGCTTCATCAGTATCCCCCA-3' (SEQ ID NO: 26); (reverse primer) 5'-CAAAGTAGGAAAACATCATCA-CAGGA-3' (SEQ ID NO: fl; and (probe) 6FAM-AC-CATCTCTAAAATCCT-MGBNFQ (SEQ ID NO: 28). CNV assays can be duplexed with an RPP30 reference assay (forward primer) 5'-GATTTGGACCTGCGAGCG-3' (SEQ ID NO: 20), (reverse primer) 5'-GCGGCTGTCTCCACAAGT-3' (SEQ ID NO: 21), and (probe) VIC-CTGACCTGAAG-GCTCT-MGBNFQ (SEQ ID NO: 22). Thermal cycling conditions can be 95° C.×10 min (1 cycle), 94° C.×30 s and 60° C.×60 s (40 cycles), 98° C.×10 min (1 cycle), and 12° C. hold (see also Hindson B et al. (2011) Anal. Chem. 83: 8604-8610).

Figure 31:
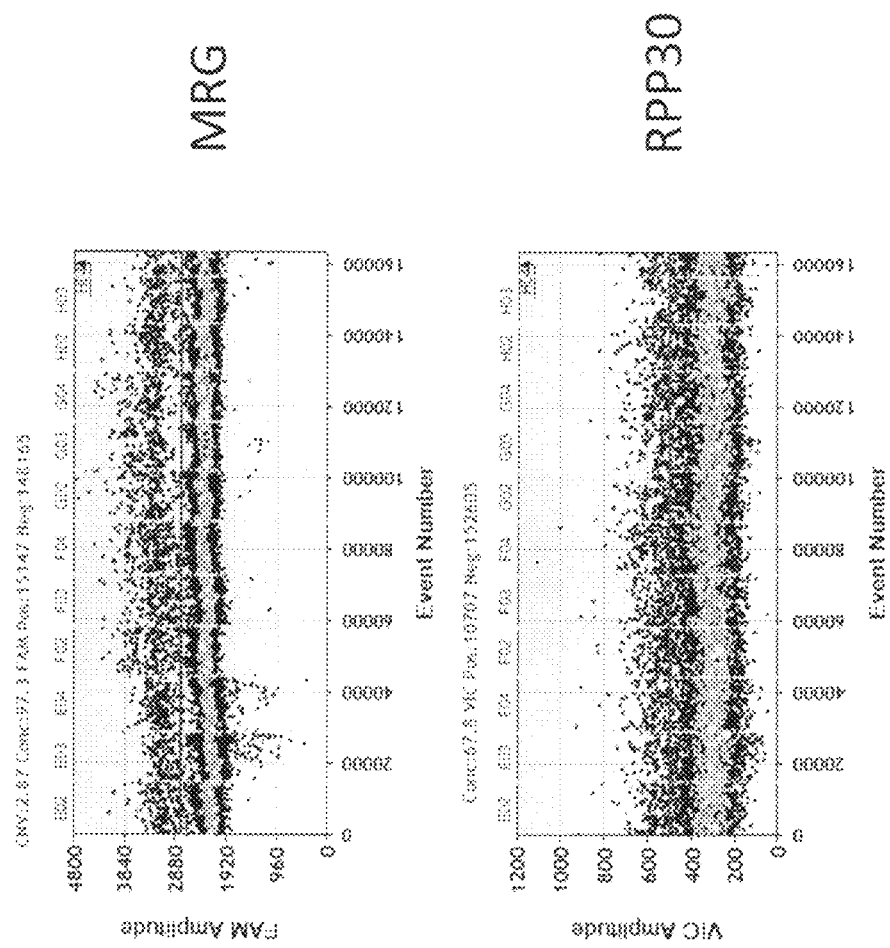
FIG. 31 illustrates an analysis of fluorescence intensity in a real-time PCR experiment after 25 cycles for MRGPRX1 and RPP30.

FIG. 31 illustrates an analysis of fluorescence intensity in a ddPCR experiment after 25 cycles for MRGPRX1 and RPP30. Event number refers to droplet count.

Figure 32:
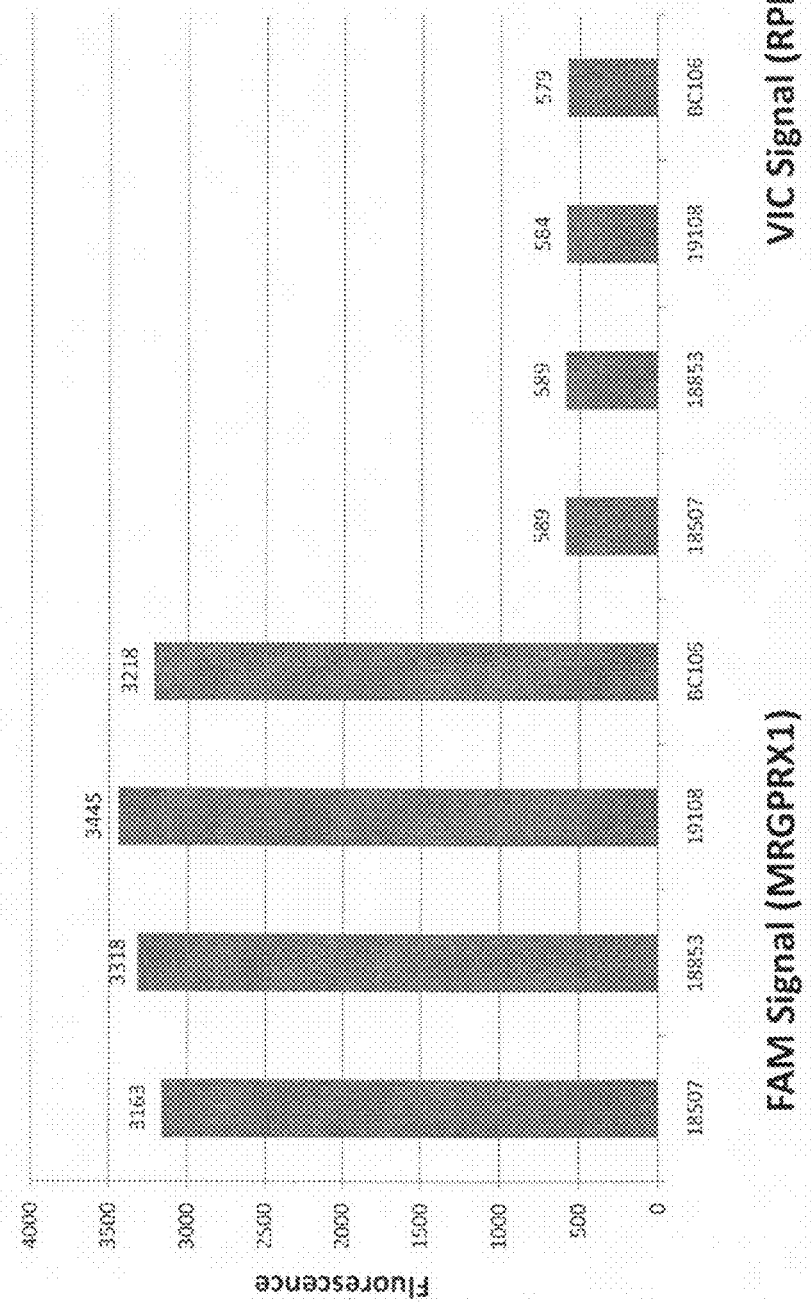
FIG. 32 illustrates average fluorescence of triplication measurements for 4 samples in a real-time PCR experiment. Samples suspected of having two targets on one chromosome and 0 on another (18853 and 19108) have higher fluorescence than samples suspected of having one copy of a target on a chromosome (trans-configuration) (18507 and BC106).

FIG. 32 illustrates average fluorescence at cycle 25 of triplication measurements for 4 samples in a ddPCR experiment. Samples suspected of having two targets on one chromosome and 0 are another (NA18853 and NA19108) have higher fluorescence than samples suspected of having one copy of a target on a chromosome (trans-configuration) (NA18507 and D1234106).

Figure 33:
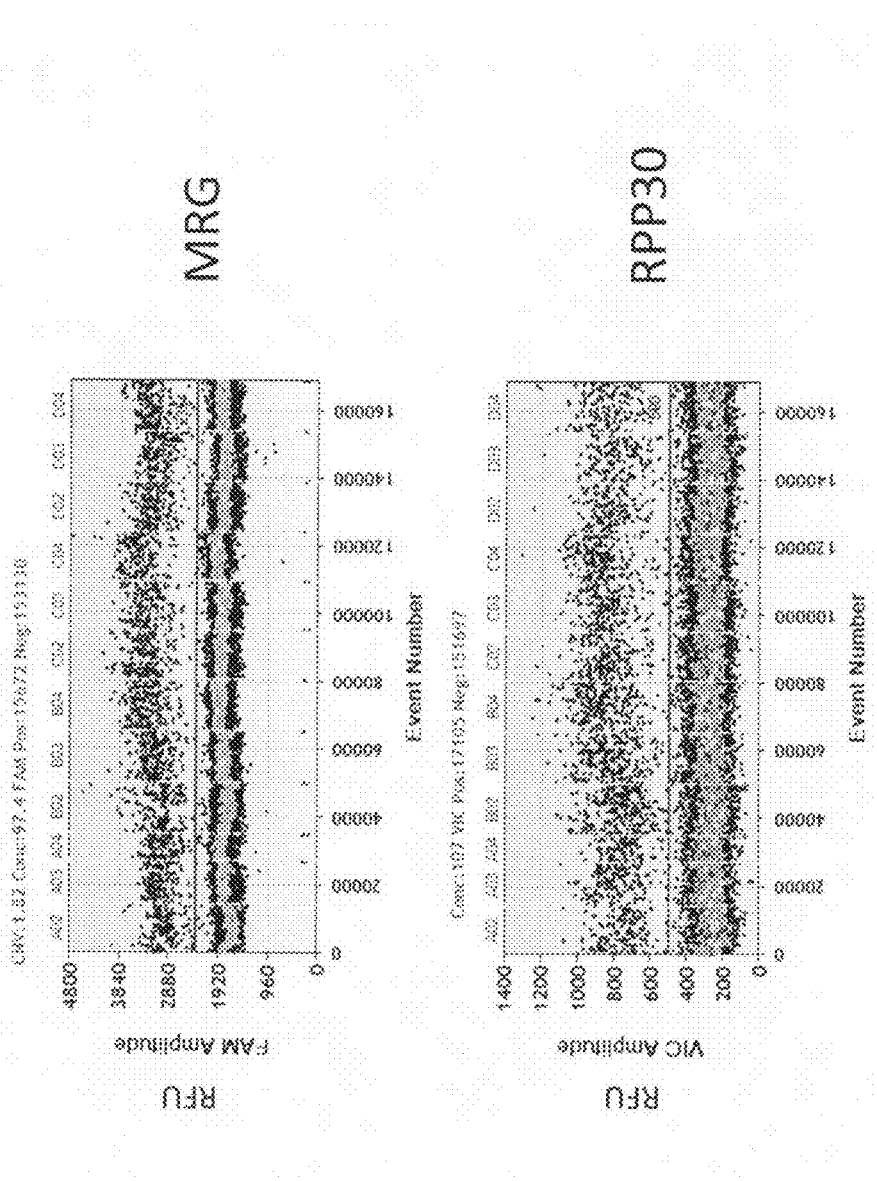
FIG. 33 illustrates an analysis of fluorescence intensity in a real-time PCR experiment after 28 cycles for MRGPRX1 and RPP30.

FIG. 33 illustrates an analysis of fluorescence intensity in a ddPCR experiment after 28 cycles for MRGPRX1 and RPP30.

Figure 34:
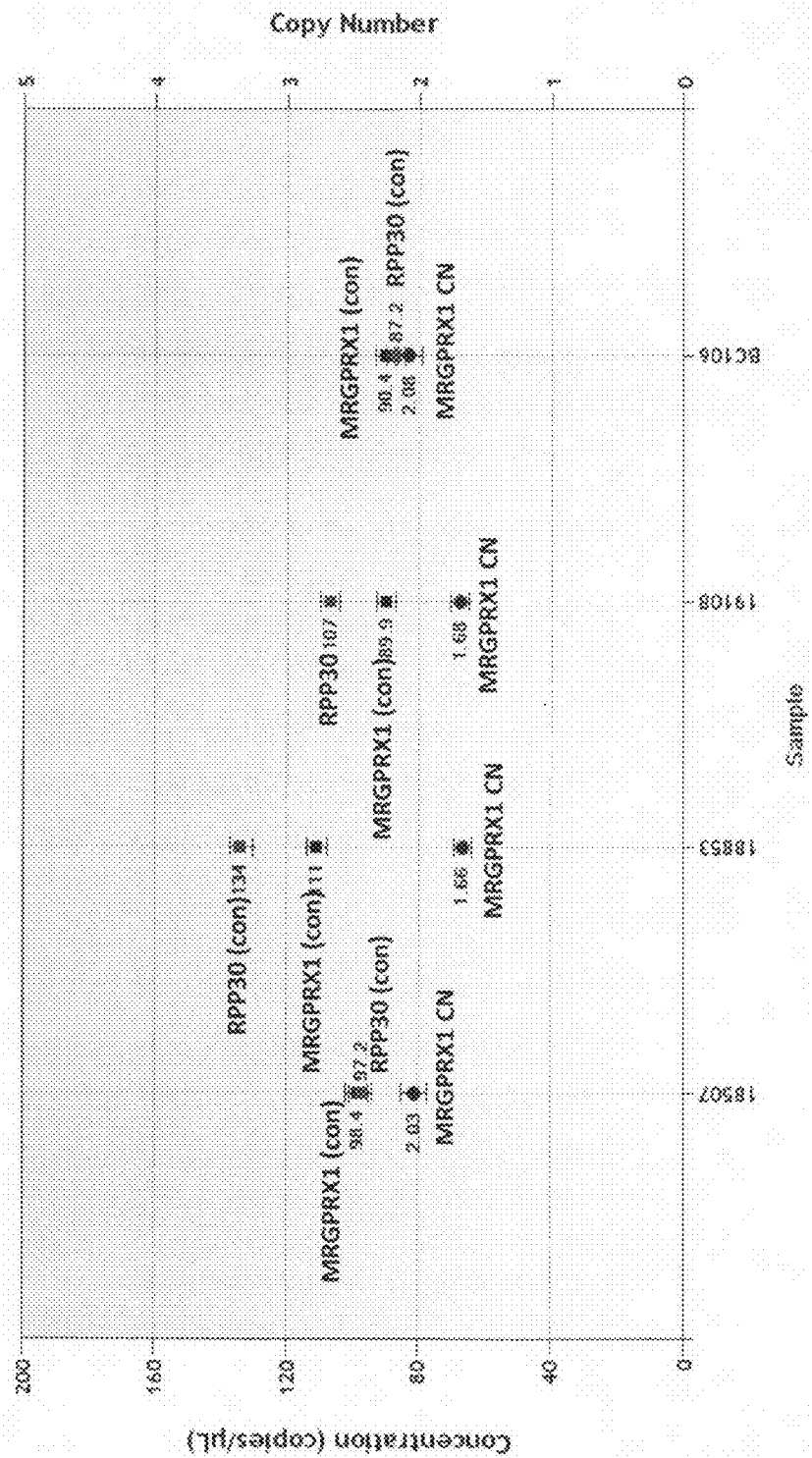
FIG. 34 illustrates a comparison of ddPCR concentration and copy number variation. In samples 18853 and 19108, depressed CNV for uncut samples is observed at 28 cycles.

FIG. 34 illustrates a comparison of ddPCR concentration and copy number variation. In samples NA18853 and NA19108, depressed CNV for uncut samples is observed at 28 cycles. Signals for VIC (RPP30) concentration, FAM (MRGPRX1) concentration, and MRGPRX1 copy number are shown.

Figure 35:
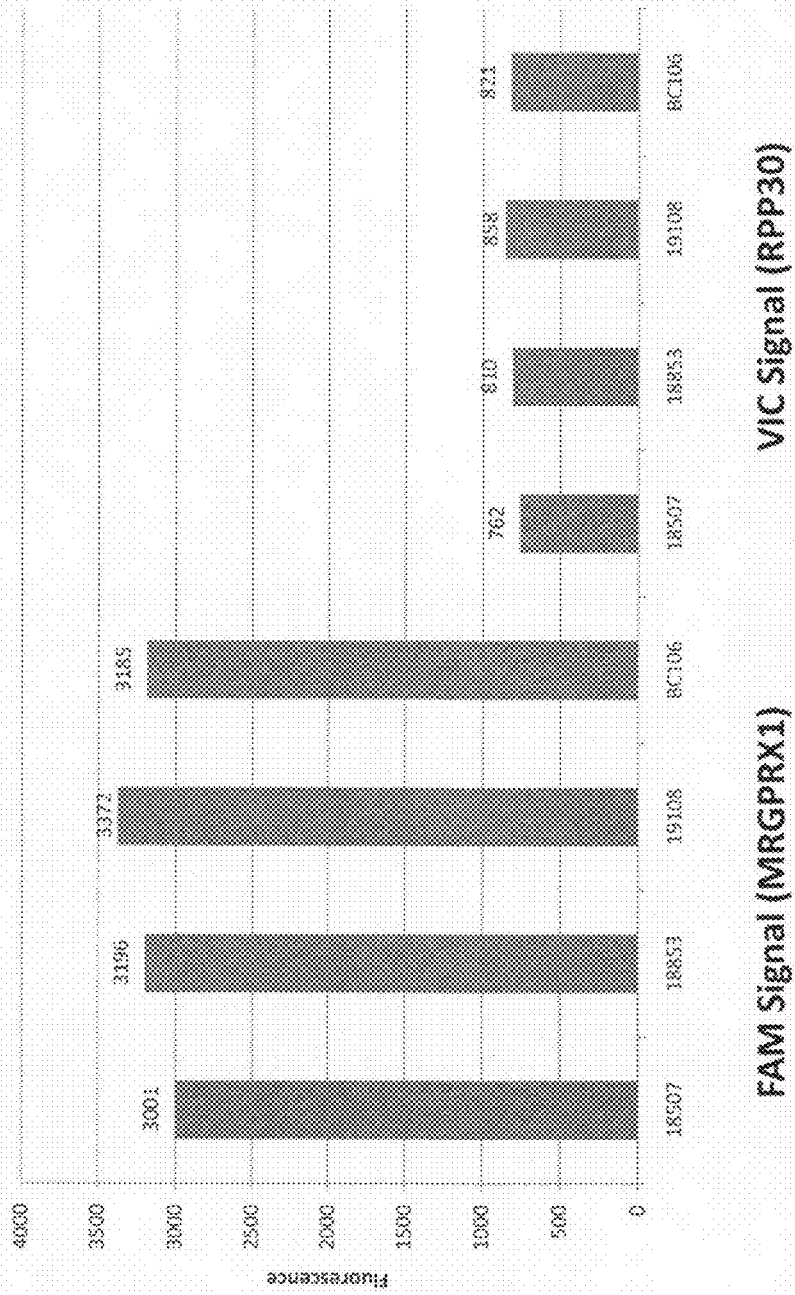
FIG. 35 illustrates average fluorescence of triplicate measurements for 4 samples in a ddPCR experiment after 28 cycles. Samples suspected of having two targets on one chromosome and 0 on another (18853 and 19108) have higher fluorescence than samples suspected of having one copy of a target on each of two chromosomes (trans-configuration) (18507 and BC106).

FIG. 35 illustrates average fluorescence of triplicate measurements for 4 samples in a ddPCR experiment after 28 cycles. Samples suspected of having two targets on one chromosome and 0 on another (18853 and 19108) have higher fluorescence than samples suspected of having one copy of a target on each of two chromosomes (trans-configuration) (18507 and BC106).

Figure 36:
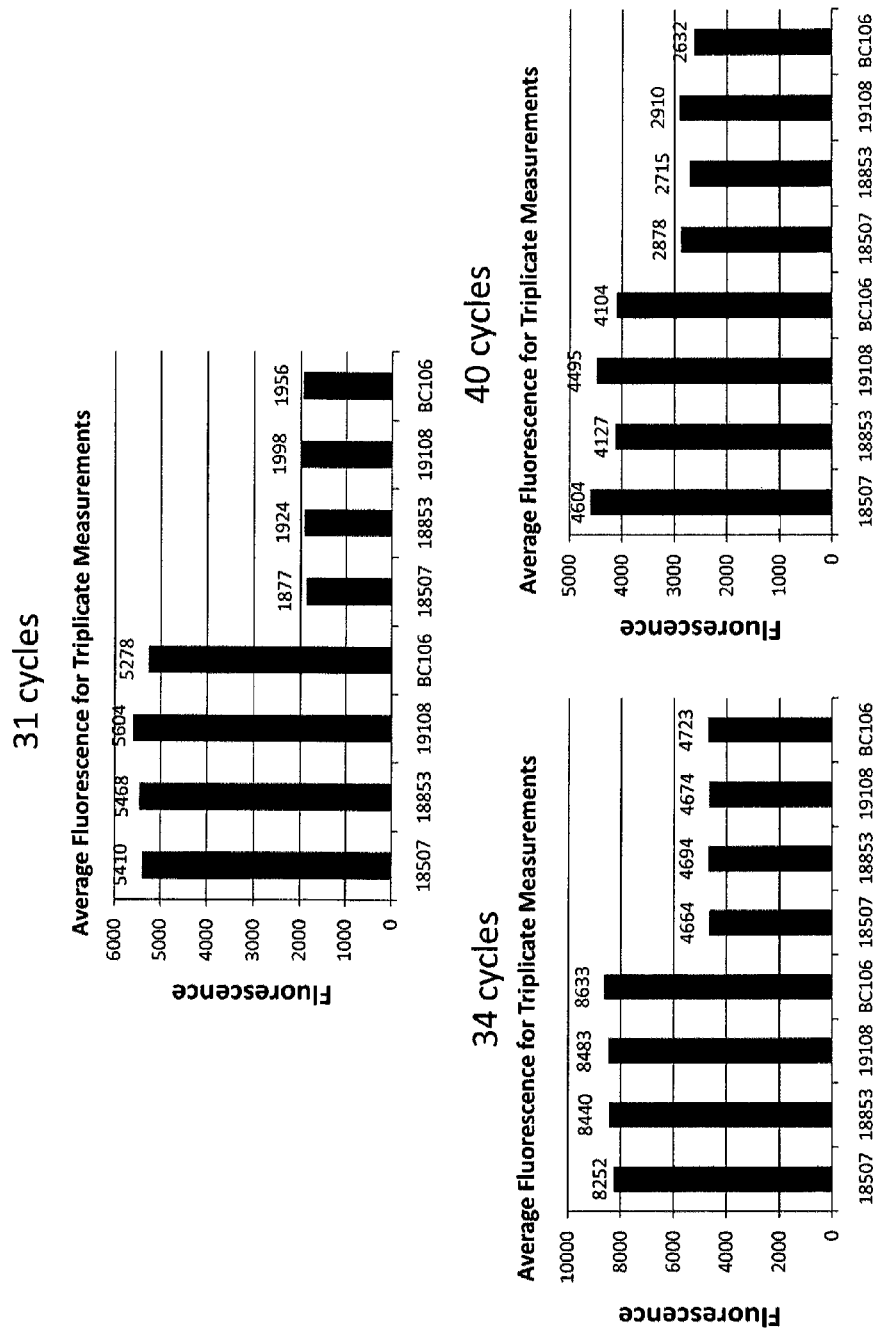
FIG. 36 illustrates average fluorescence of triplicate measurements for 4 samples in a ddPCR experiment after 31, 34, and 40 cycles. Samples suspected of having two targets on one chromosome and 0 on another (18853 and 19108) have higher fluorescence than samples suspected of having one copy of a target on each of two chromosomes (trans-configuration) (18507 and BC106) at cycle 31 but not cycle 34 or 40.

FIG. 36 illustrates average fluorescence of triplicate measurements for 4 samples in a ddPCR experiment after 31, 34, and 40 cycles. Samples suspected of having two targets on one chromosome and 0 on another (NA18853 and NA19108) have higher fluorescence than samples suspected of having one copy of a target on each of two chromosomes (trans-configuration) (NA18507 and D1234106) at cycle 31 but not cycle 34 or 40.

In sum, the ddPCR experiment supports the notion that samples 18853 and 19108 have two linked copies of MRG-PRX1 on a single chromosome.

A long-range PCR experiment is also performed to support the finding on linkage of targets from the droplet digital PCR experiment. CN=1 samples can serve as a control for amplification of a deleted region.

Figure 37:
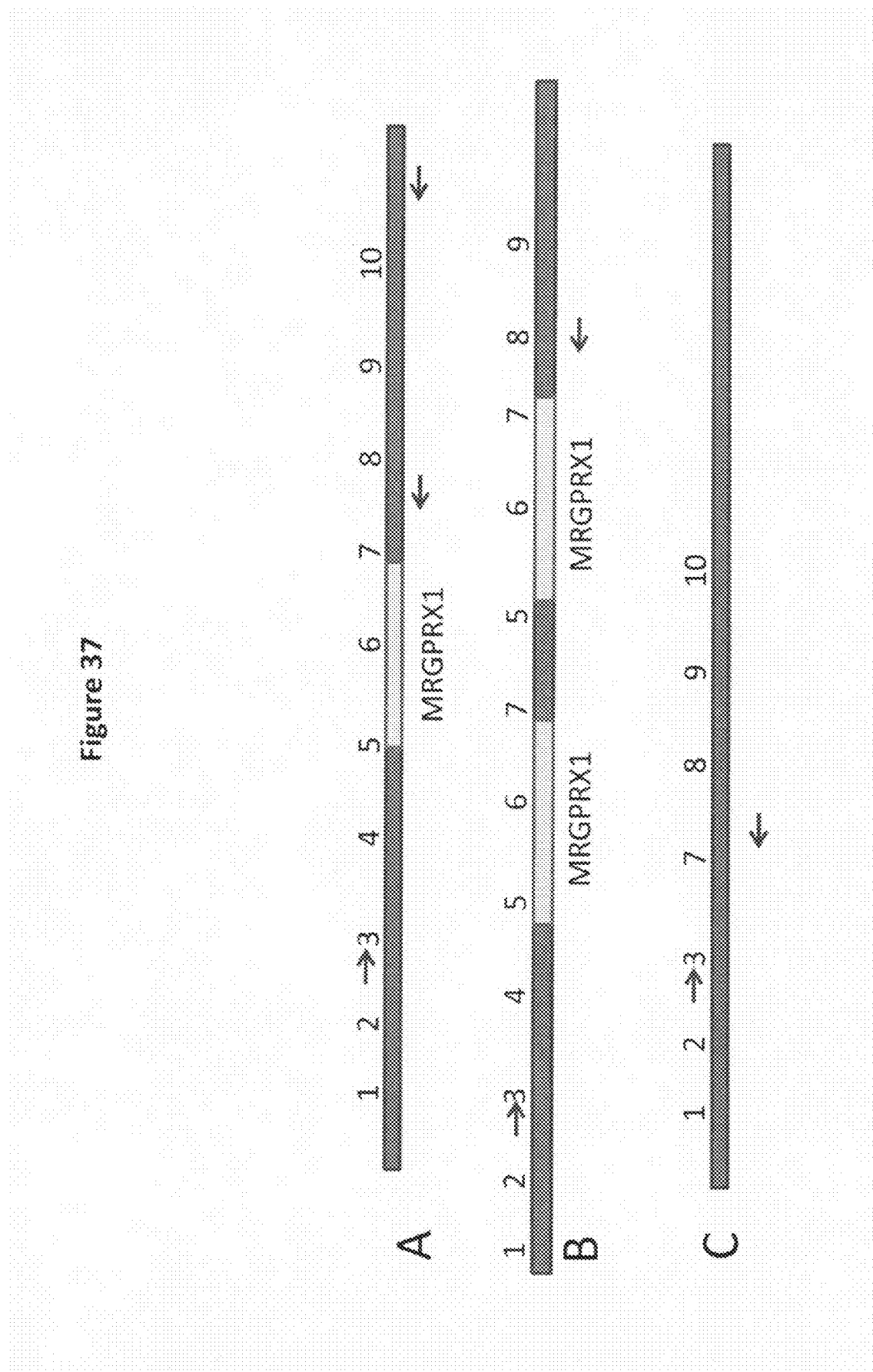
FIG. 37 illustrates an experimental setup for a long range PCR experiment. Long-range PCR for scenarios A & B are expected to fail because the distance between primers is too great. However, PCR should work for scenario C containing a chromosome that has a deletion for MRGPRX1. Arrows indicate primers.

FIG. 37 illustrates can experimental setup for a long range PCR experiment. Long-range PCR for scenarios A & B are expected to fail because the distance between primers is too great. However, PCR should work for scenario C containing a chromosome that has a deletion for MRGPRX1. Arrows indicate primers.

Figure 38:
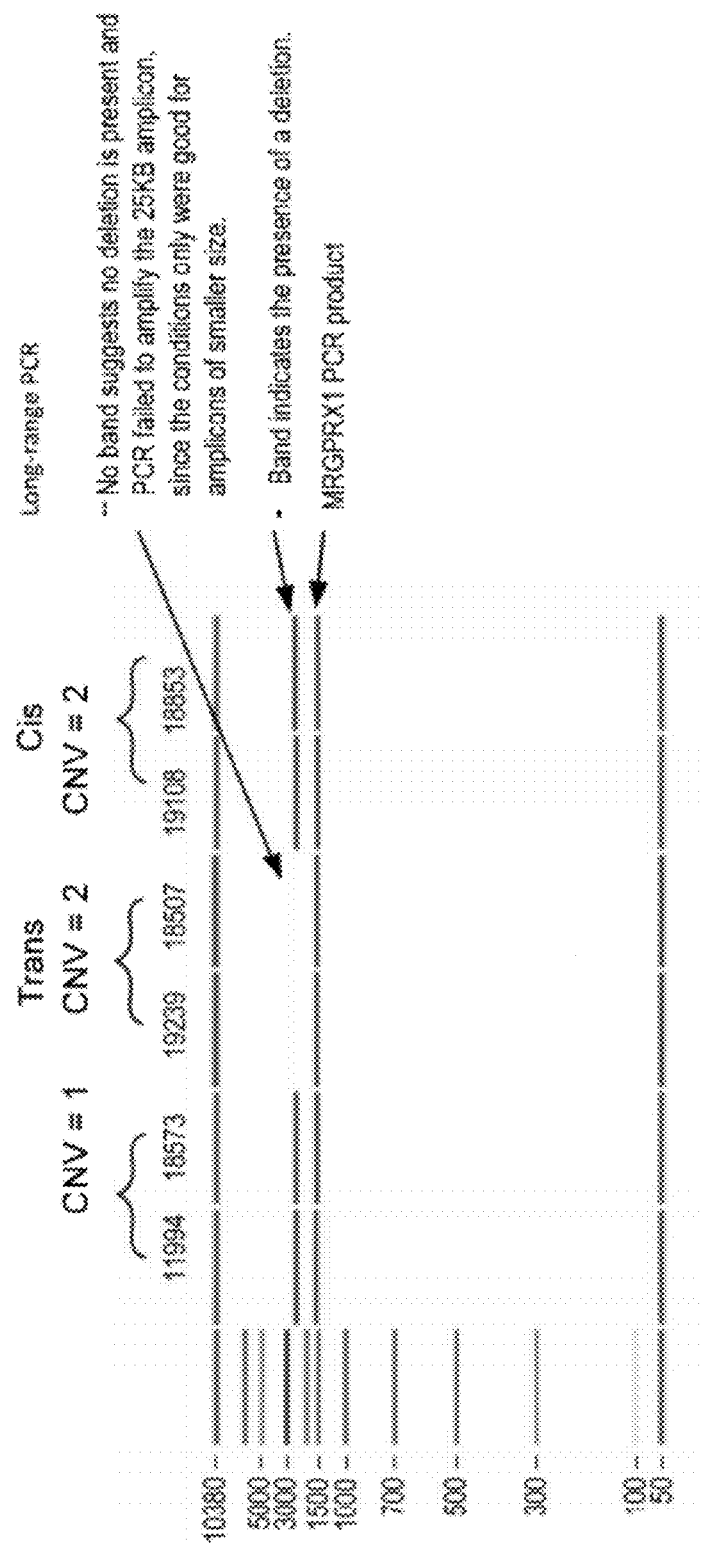
FIG. 38 illustrates a long-range PCR experiment with 6 samples. Bands migrating at 1500 indicate PCR products from MRGPRX1 internal primers, and bands migrating just below 3000 indicate PCR products from primers flanking the MRGPRX1 gene.
Figure 39:
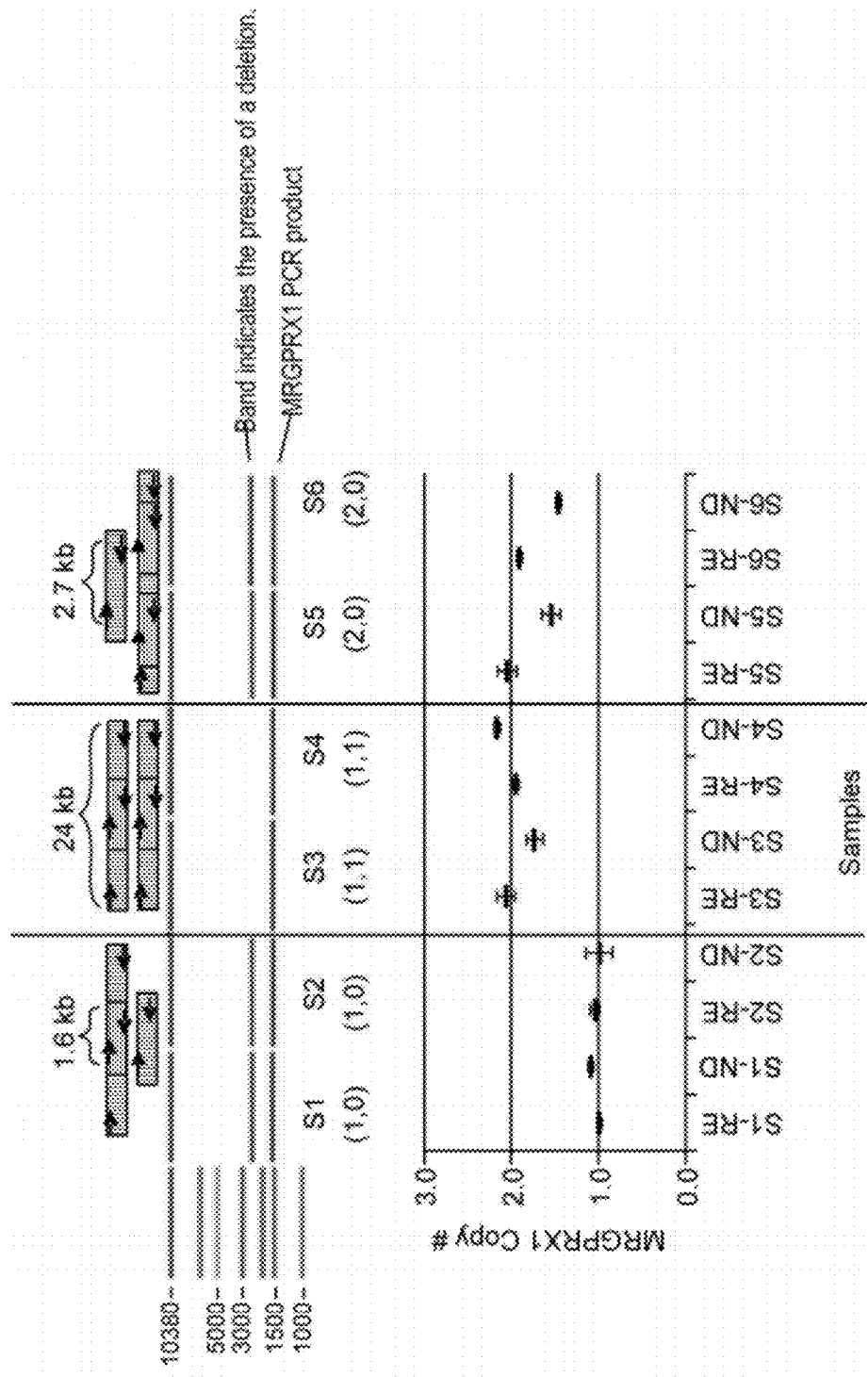
FIG. 39 illustrates long-range PCR products and MRGPRX1 CNV results from six samples, further distinguishing the samples with one or two MRGPRX1 copies on the same chromosome by restriction digest analysis.

FIG. 38 illustrates a Bioanalyzer image of a long-range PCR experiment with 6 samples to confirm linkage by ddPCR (See FIG. 39 for schematic of setup). The band in each lane at about 1500 is a MRGPRX1 PCR product (primers internal to the MRGPRX1 sequence. Primers were also designed to anneal external to the MRGPRX1 sequence. Samples 11994 and 18573 have a copy number of one: one chromosome contains a copy of MRGPRX1 and another contains a deletion. The PCR product between 3000 and 1500 is presumably from amplification from the chromosome that has the deletion. Samples 19239 and 18507 have two copies of MRG-PRX1 on different chromosomes. These samples do not have a band between 3000 and 1500 presumably because the presence of the MRGPRX1 gene makes the PCR too long to generate a product (25 KB). Samples 19108 and 18553 have two copies of MRGPRX1 on the same chromosome and a chromosome with a deletion for MRGPRX1. The PCR product between 3000 and 1500 is presumably from amplification from the chromosome that has the deletion. These data confirm the results of the droplet digital PCR experiment.

FIG. 39 illustrates long-range PCR results and MRGPRX1 copy number results for 6 samples. The schematics at the top illustrate PCR primer positions and expected lengths of PCR products. Samples S1 and S2 have one copy of MRGPRX1 on one chromosome and a deletion on another chromosome. Primers are internal to the MRGPRX1 gene and can generate a product of about 1.6 kb. Primers also anneal external to the MRGPRX1 gene. Samples S3 and S4 have two copies of MRGPRX1 in trans (on different chromosomes). A PCR product from the outermost primers is estimated to be about 24 kb. Samples S5 and S6 have two copies of MRGPRX1 on one chromosome and a deletion of MRGPRX1 on another chromosome. The length of the PCR product generated using the outermost primers on the chromosome with the deletion is about 2.7 kb. Below the schematic of the PCR setup is an illustration of long-range PCR results. All samples have a PCR product that corresponds to the product from the internal MRGPRX1 primers at 1.6 kb. Samples S1, S2, S5, and S6 have a PCR product of about 2.7 kb from the sample with the chromosome deletion. Samples S3 and S4 do not have a PCR product of about 2.7 kb. The PCR using the outermost primers on a chromosome comprising one or two copies of MRGPRX1 fails because of the distance between the primers. Below the illustration of the long range PCR is an illustration of MRGPRX1 copy number determined by ddPCR with or without a restriction enzyme digest (RE=restriction enzyme digest; ND=no digest). Samples S1 and S2 are estimated to have 1 copy of MRGPRX1 whether or not the samples are digested with a restriction enzyme. Samples S3 and S4 are estimated to have about 2 copies of MRGPRX1 whether or not the samples are digested. Samples S5 and S6 are estimated to have about 2 copies of MRGPRX1 if the samples are digested, but less than two copies if the samples are not digested. The difference in copy number estimation in S5 and S6 depending on whether the samples are digested or not suggests that the two copies of MRGPRX1 are on the same chromosome.

The Protocol for long-range PCR is the following: Agilent PfuUltraII Fusion HS DNA polymerase was used using the following thermal cycling conditions: 2 min 95° C. (1 cycle), 20 sec 95° C., 20 sec 60° C., 75 sec 72° C. (40 cycles), 3 min at 72° C. (1 cycle). Primers were included at 200 nM, 250 uM dNTPs, 100 ng DNA, 1 uL PfuUltraII fusion HS DNA polymerase, Agilent supplied master mix at 1×, in a 50 uL reaction. The sequence of the forward primer was 5'-GATCTAGCTAAGAGACAGAGATAGACACATG-3' (SEQ ID NO: 39), the reverse primer sequence was 5'-cagtattttgcactgctttcctcat-3' (SEQ ID NO: 48).

Figure 40:
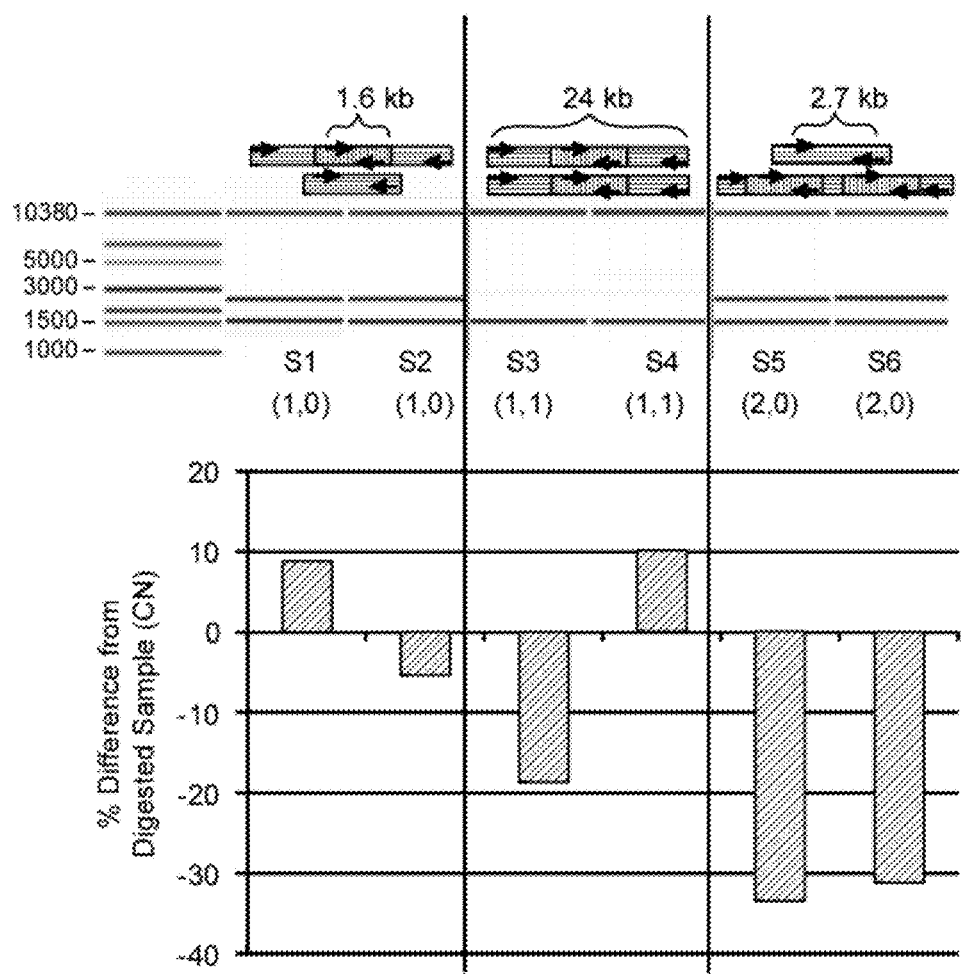
FIG. 40 illustrates the percentage difference from digested sample of the estimated copy number.

FIG. 40 illustrates the percentage difference from digested sample of the estimated copy number.

Example 10

Algorithm for Determining Fragmentation

In this example, two different types of target nucleic acid are being analyzed. One is being detected with a FAM probe and one is being detected with VIC. Assume that the two target nucleic acid sequences are on the same polynucleotide. In a sample, there can be three types of DNA fragments: 1) Fam-Vic together (not chopped), 2) Fam fragment, and 3) Vic fragment. Some probabilities are observed (counts in FAM-VIC cross plot), and the goal is to infer the concentrations. Forward is done first. Given concentrations, counts are computed. Then to do inverse, try out different values of concentrations and select one which gives actual counts.

```
N=20000;
A=10000;
B=20000;
AB=10000; % Joined together
cA=A/N;
cB=B/N;
cAB=AB/N;
fprintf(1, '%f%f%f\n', cAB, cA, cB);
pA=1-exp(-cA);
pB=1-exp(-cB);
pAB=1-exp(-cAB);
% A is X and B is Y in cross plot
p(2,1)=(1-pA)*(1-pB)*(1-pAB); % Bottom left
p(2,2)=pA*(1-pB)*(1-pAB); % Bottom right
p(1,1)=(1-pA)*pB*(1-pAB); % Top Left
p(1,2)=1-p(2,1)-p(2,2)-p(1,1); % Top Right
disp(round(p*N));
% Also compute marginals directly
cAorAB=(A+AB)/N; %=c_A+c_AB;
cBorAB=(B+AB)/N; %=c_B+c_AB;
pAorAB=1-exp(-cAorAB); % Can be computed from p too
pBorAB=1-exp(-cBorAB);
% Inverse
H=p*N; % We are given some hits
% H=[0 8000;2000 0];
% Compute prob
estN=sum(H(:));
i_p=H/estN;
i_pAorAB=i_p(1,2)+i_p(2,2);
i_pBorAB=i_p(1,1)+i_p(1,2);
i_cAorAB=-log(1-i_pAorAB);
i_cBorAB=-log(1-i_pBorAB);
maxVal=min(i_cAorAB, i_cBorAB);
delta=maxVal/1000;
errArr=[ ];
gcABArr=[ ];
for gcAB=0:delta:maxVal
  gcA=i_cAorAB-gcAB;
  gcB=i_cBorAB-gcAB;
  gpA=1-exp(-gcA);
  gpB=1-exp(-gcB);
  gpAB=1-exp(-gcAB);
  gp(2,1)=(1-gpA)*(1-gpB)*(1-gpAB); % Bottom left
  gp(2,2)=gpA*(1-gpB)*(1-gpAB); % Bottom right
  gp(1,1)=(1-gpA)*gpB*(1-gpAB); % Top Left
  gp(1,2)=1-gp(2,1)-gp(2,2)-gp(1,1); % Top Right
  gH=gp*estN;
  err=sqrt(sum((H(:)-gH(:)).^2));
  errArr=[errArr; err];
  gcABArr=[gcABArr; gcAB];
end
figure, plot(gcABArr, errArr);
minidx=find(errArr==min(errArr(:)));
minidx=minidx(1);
estAB=gcABArr(minidx);
estA=i_cAorAB-estAB;
estB=i_cBorAB-estAB;
fprintf(1, '%f%f%f\n', estAB, estA, estB);
gpA=1-exp(-estA);
gpB=1-exp(-estB);
gpAB=1-exp(-estAB);
gp(2,1)=(1-gpA)*(1-gpB)*(1-gpAB); % Bottom left
gp(2,2)=gpA*(1-gpB)*(1-gpAB); % Bottom right
```

```
gp(1,1)=(1-gpA)*gpB*(1-gpAB); % Top Left
gp(1,2)=1-gp(2,1)-gp(2,2)-gp(1,1); % Top Right
gH=gp*estN;
disp(round(gH));
% Confirm the results using simulation
numMolA=round(estA*estN);
numMolB=round(estB*estN);
numMolAB=round(estAB*estN);
A=unique(randsample(estN, numMolA, 1));
B=unique(randsample(estN, numMolB, 1));
AB=unique(randsample(estN, numMolAB, 1));
U=1:estN;
notA=setdiff(U, A);
notB=setdiff(U, B);
notAB=setdiff(U, AB);
AorBorAB=union(A, union(B, AB));
none=setdiff(U, AorBorAB);
simcount(2,1)=length(none);
simcount(2,2)=length(intersect(A, intersect(notB, notAB)));
simcount(1,1)=length(intersect(B, intersect(notA, notAB)));
simcount(1,2)=length(AorBorAB)-simcount(2,2)-simcount(1,1);
disp(simcount);
```

Example 11

Milepost Assay Analysis—Probability of Fragmentation

Problem Statement

Figure 41:
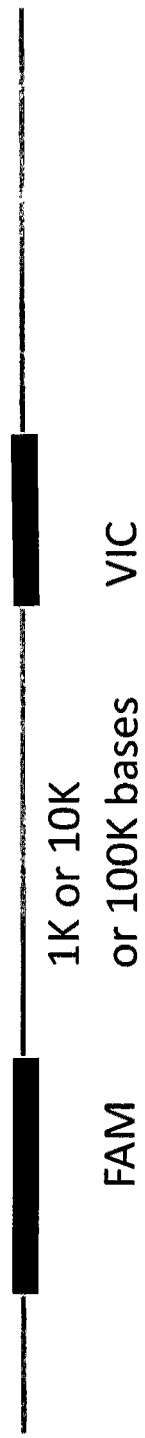
FIG. 41 is a schematic illustrating sequences recognized by FAM and VIC probes separated by 1K, 10K, or 100K bases.

If two different loci are on different molecules, there can be two species (corresponding to FAM and VIC probes). If the different loci are on the same molecule, there can be three species—fragmented FAM, fragmented VIC, and linked FAM-VIC. (See FIG. 41)

There are two dyes, so there can be ambiguity. There is a need to compute concentrations of all three species.

Algorithm: Get 2×2 table of FAM versus VIC counts. Compute concentration of fragmented FAM and linked FAM-VIC as if there is 1 species. Compute concentration of fragmented VIC and linked FAM-VIC as if there is 1 species. Try out different concentrations of linked FAM-VIC (from which concentration of fragmented FAM and VIC can be found), and find the best fit of the probability table with the observed counts:

|      | FAM−                  | FAM+              |
|------|-----------------------|-------------------|
| VIC+ | $(1-f) v (1-c)$       | $1 -$ sum of others |
| VIC− | $(1-f)(1-v)(1-c)$     | $f(1-v)(1-c)$     |

Probability of Fragmentation (in %)

| 1k Uncut    | 6    | 6    | —    |
|-------------|------|------|------|
| 10K Uncut   | 29.4 | 29.8 | 29.5 |
| 100K Uncut  | 98.7 | 97.7 | 99.9 |
| 1K Syringe  | 11.4 | 11.1 | 11   |
| 10K Syringe | 87.2 | 89.9 | 91.7 |
| 100K Syringe| 100  | 100  | 100  |
| 1K Hae III  | 100  | 100  | 100  |

Next steps can include to see if a closed formula can be easily derived and/or to integrate with QTools.

Example 12

Fragmentation Analysis

Using ddPCR, duplex reaction targeting two genomic loci can be performed, two genes on a common chromosome for example. The droplets can be categorized into four populations according to their fluorescence (FAM+/VIC+, FAM+/VIC−, FAM−/VIC+, and FAM−/VIC−). By comparing the number of droplets with these populations, it is possible to determine the frequency at which targets co-segregate to the same droplet. Using Poisson statistics, the percentage of species that are actually linked to one another can be estimated, versus instances where two separated copies are in the same droplet by chance.

An assay is designed in which a locus is 1K, 3K, 10K, 33K and 100K away from a common reference (RPP30). Studies in which two loci are separated by 1K, 10K and 100K have been performed. By processing uncut (not restriction enzyme digested) DNA with these three duplexes (or just one duplex), and counting the four different populations of droplets, statistical analysis can be used to assess the fragmentation status of the genetic material. These data can be used to help explain why 95% confidence limits for copy number variation studies do not always span the integer value.

Example 13

Algorithm for Computation of DNA Fragmentation or for Digital PCR Multiplexing

Total Fragmentation Between Targets

Figure 42:
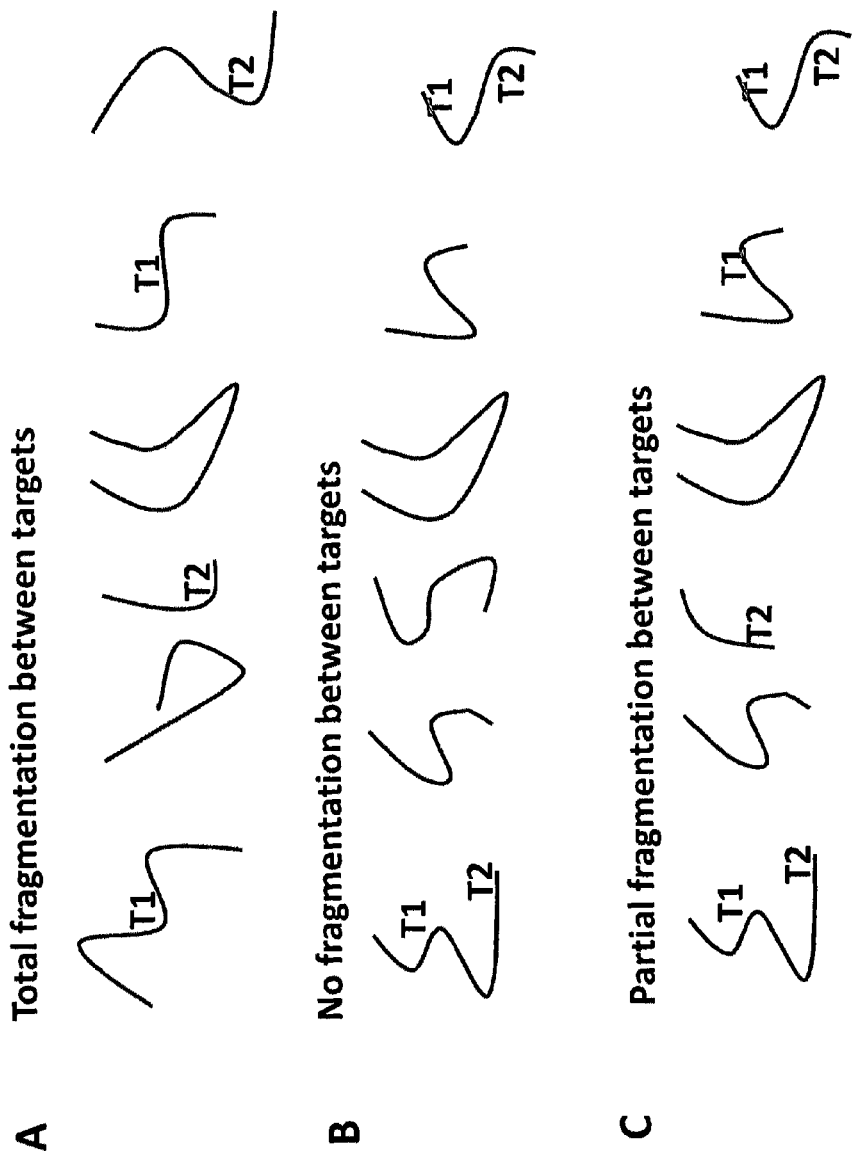
FIG. 42 illustrates fragments of nucleic acid. T1 and T2 are target sequences.

Two DNA targets T1 and T2 corresponding to two dyes, FAM and VIC, respectively. In this example, T1 and T2 are always on separate DNA fragments. The number of DNA fragments with T1 and T2 targets is M1 and M2, respectively. See FIG. 42A.

In a digital PCR experiment with multiple partitions, the counts of FAM and VIC positive partitions is N1 and N2, respectively. N1 and N2 will be smaller than M1 and M2, respectively, because there can be multiple DNA fragments in a partition. The total number of partitions is N. The counts of partitions as expected are shown in Table 2.

TABLE 2

Counts of partitions.

|              | VIC Negative            | VIC Positive      | Total   |
|--------------|-------------------------|-------------------|---------|
| FAM Positive | $N1 * (N - N2)/N$       | $N1 * N2/N$       | $N1$    |
| FAM Negative | $(N - N1) * (N - N2)/N$ | $(N - N1) * N2/N$ | $N - N1$|
| Total        | $N - N2$                | $N2$              | $N$     |

If the probability of observing a FAM positive partition is denoted as $p1=N1/N$, and the probability of observing a VIC positive partition is denoted as $p2=N2/N$, then the corresponding probability table is Table 3.

TABLE 3

Probability table.

|              | VIC Negative       | VIC Positive    | Probability |
|--------------|--------------------|-----------------|-------------|
| FAM Positive | $p1 * (1 - p2)$    | $p1 * p2$       | $p1$        |
| FAM Negative | $(1 - p1) * (1 - p2)$ | $(1 - p1) * p2$ | $1 - p1$    |
| Total        | $1 - p2$           | $P2$            | $1$         |

In this case, 100% fragmentation between T1 and T2 exists.

The number of T1 and T2 molecules, M1 and M2, respectively, can be computed as follows:

M1=N log(1−p1)
M2=−N log(1−p2)

(Given N digital partitions in which P are positive, the number of molecules is M=−N log(1−P/N))

No Fragmentation Between Targets

If both T1 and T2 are always on the same DNA fragment, they are linked (perhaps because their loci are quite close to each other on the same part of a chromosome and restriction enzyme digest did not digest between T1 and T2). See FIG. 42B. Therefore, N1=N2.

TABLE 4

Counts of partitions.

|  | VIC Negative | VIC Positive | Total |
| --- | --- | --- | --- |
| FAM Positive | 0 | N1 | N1 |
| FAM Negative | N − N1 | 0 | N − N1 |
| Total | N − N1 | N1 | N |

TABLE 5

Probability table.

|  | VIC Negative | VIC Positive | Probability |
| --- | --- | --- | --- |
| FAM Positive | 0 | p1 | p1 |
| FAM Negative | 1 − p1 | 0 | 1 − p1 |
| Total | 1 − p1 | p1 | 1 |

In this case, 0% fragmentation exist.

The number of T1 and T2 molecules can be computed as follows, where p1=N1/N:

M1=−N log(1−p1)
M2=−N log(1−p1)

Partial Fragmentation

In an intermediate situation, T1 and T2 are linked on some fragments, but also happen to be on separation fragments. See FIG. 42C.

If there are M3 molecules of linked T1 and T2 fragments, M1 molecules of separate T1 fragments, and M2 molecules of separate T2 fragments, the following table of counts of partitions can be made:

TABLE 6

Counts of partitions.

|  | VIC Negative | VIC Positive | Total |
| --- | --- | --- | --- |
| FAM Positive | N01 | N11 | N1 |
| FAM Negative | N00 | N10 | N − N1 |
| Total | N − N2 | N2 | N |

If M1=M2=M3, then there is 50% fragmentation, because 50% of linked molecules were fragmented into separate fragments and 50% remained intact.

Example 14

Assessing DNA Quality in Plasma with the Milepost Assay

Figure 43:
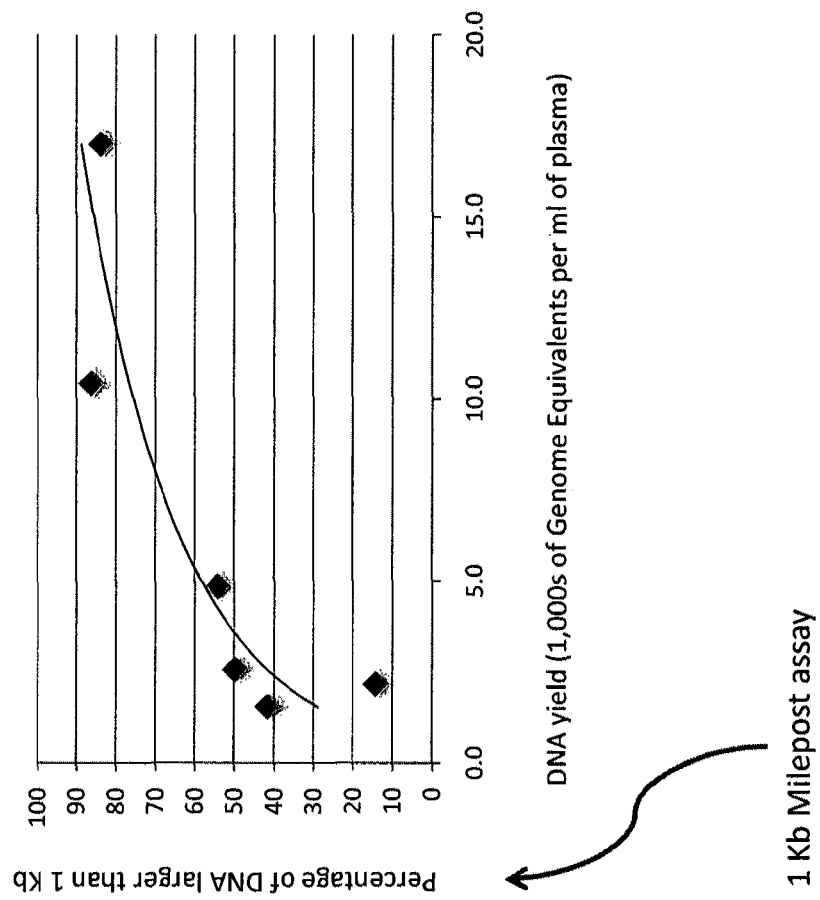
FIG. 43 illustrates a DNA quality assessment.

It appears that in samples with higher DNA yield, the extra DNA is predominantly large in size. As shown in FIG. 43 when the DNA yield is around 2 kGE (Genome equivalents)/ml, roughly half of the DNA is less than 1 Kb in size; when the yield is extremely high (10 kGE/ml or more), 90% of the DNA is larger than 1 Kb. This suggests that small DNA is relatively constant in concentration. This suggests further that higher DNA yields are due to contamination from cellular DNA.

Example 15

Contamination by Large DNA in Plasma Affects CNV Values

Large size DNA contamination can suppress a measured CNV value. The top figure (FIG. 44) shows a good correlation between measured CNV value and DNA size. This size impact is largely eliminated by pre-treatment of DNA (bottom figure, diamonds). Preliminary data have shown that with appropriate fragmentation of the DNA before CNV measurement, the measured CNV values among different species are identical (data not shown here).

Example 16

Restriction Enzyme Titration for CNV Analysis

Figure 46:
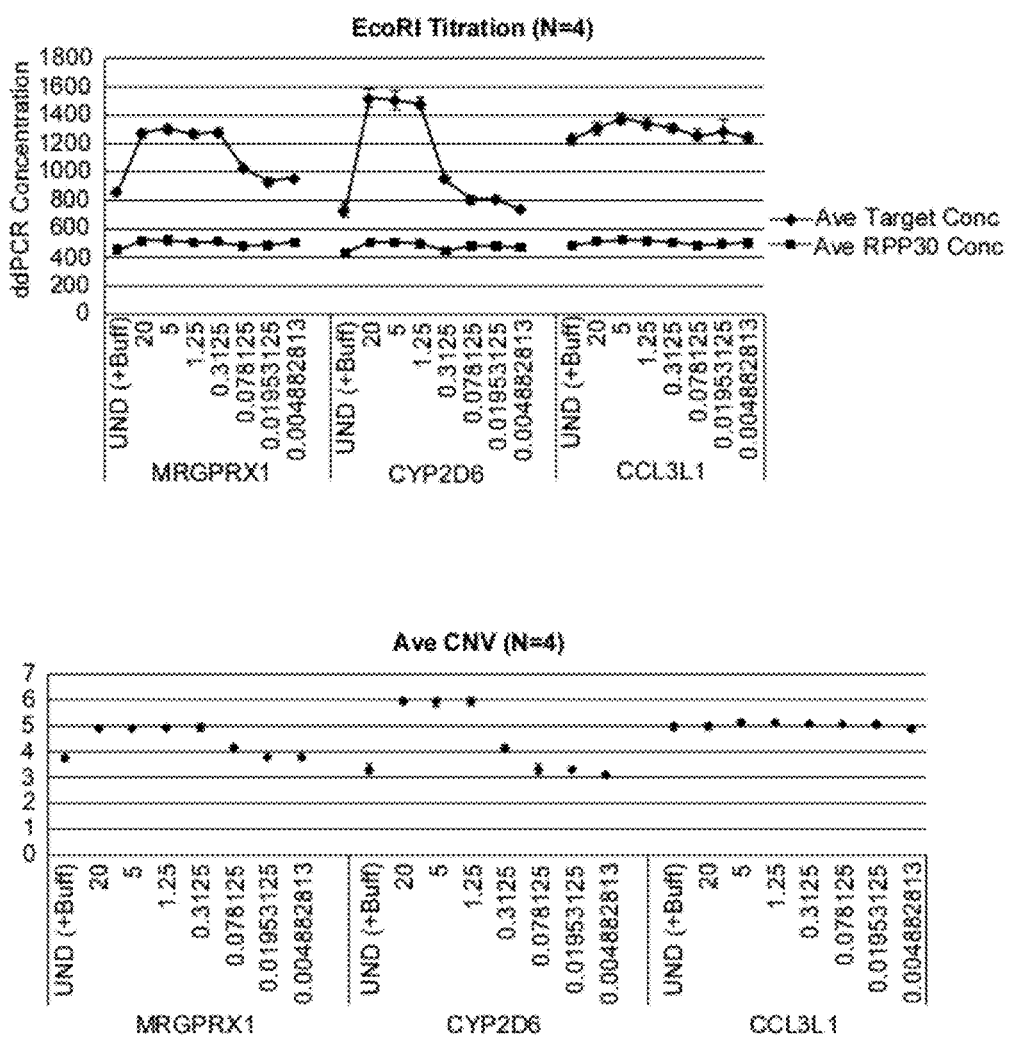
FIG. 46 illustrates restriction enzyme titration for CNV analysis.

Restriction enzymes (RE) can be titrated to determine their use for CNV analysis in test assays. Seventeen restriction enzymes (mostly 4-cutters) are analyzed. See FIG. 45. Restriction enzyme concentration involves a 4-fold dilution series: 20, 5, 1.25, 0.31, 0.08, 0.02 & 0.005 U/μg DNA; Undigested Control+Buffer; 4 replicate ddPCR per concentration; DNA Input: 0.5 cpd. Efficient/complete restriction digestion can be achieved at concentrations as low as 0.02 U/μg DNA. The effective RE concentration range may vary with target and enzyme. 5 U/μg DNA appears to give the highest ddPCR concentration for most restriction enzymes allowing for a more universal digestion protocol for CNV analysis. Non-specific RE activity at 20 U RE/μg DNA was not observed with all the 17 restriction enzymes tested. See FIG. 46.

Example 17

Development of Protocols to Optimize Challenging ddPCR CNV Assays

Figure 47:
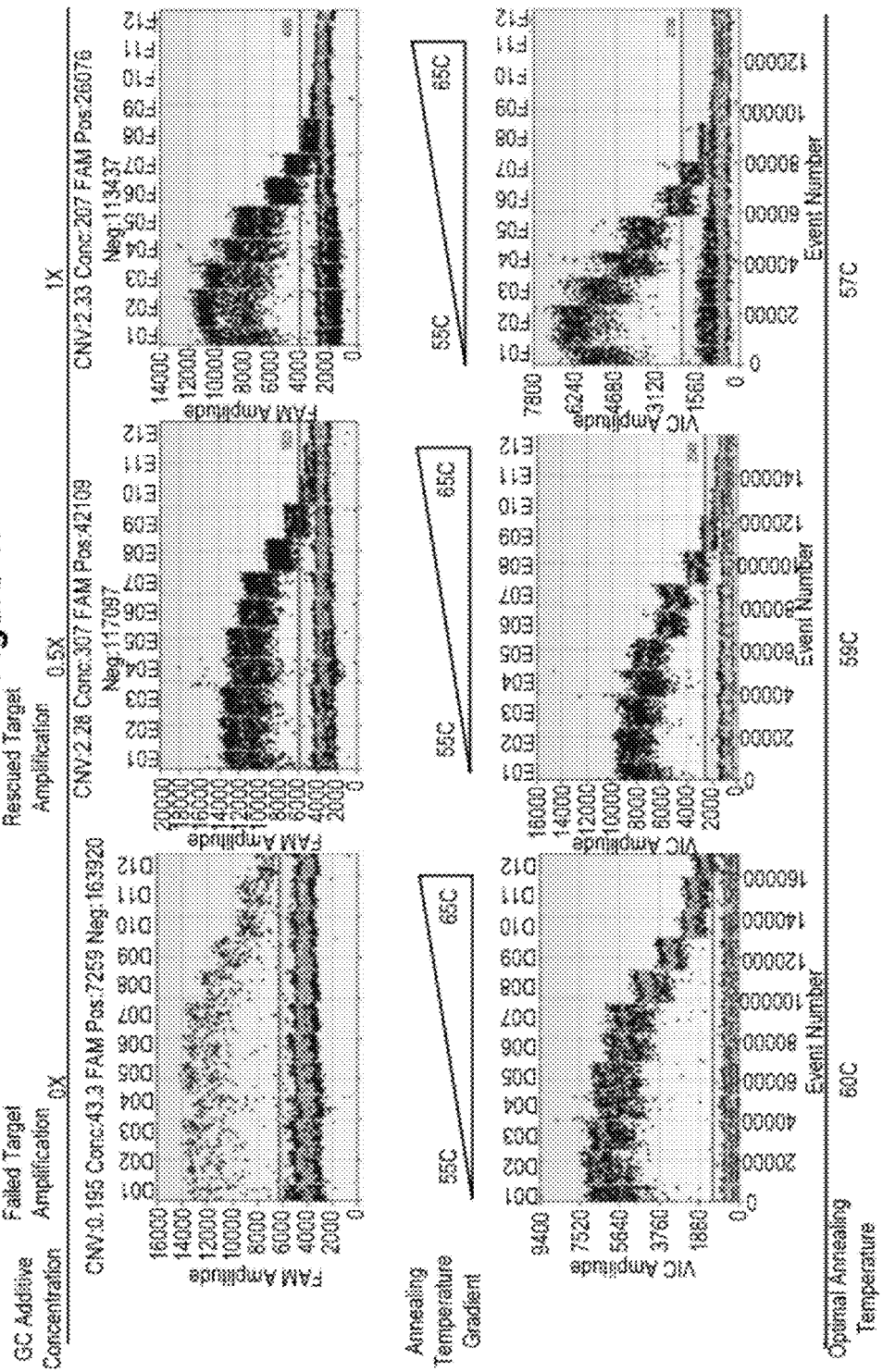
FIG. 47 illustrates development of protocols to optimize challenging ddPCR CNV assays.

Use of a temperature gradient can permit determination of an optimal anneal temperature. Use of a GC additive can reduce secondary structure that can otherwise block polymerase activity or lead to the formation of competing non-specific amplification products. An example of an additive is GC Rich Enhancer Solution (5×) (Roche). See FIG. 47.

Example 18

Measuring Restriction Enzyme Activity with ddPCR

Alu I and Mse I perform acceptably over a wide range of concentrations. Small amounts of residual target remain at enzyme concentrations where complete cutting is supposed to occur. Both NEB and Fermentas enzymes perform well, but Fermentas enzymes are somewhat more effective. Fermentas enzymes have advantages in ease of use.

Figure 48:
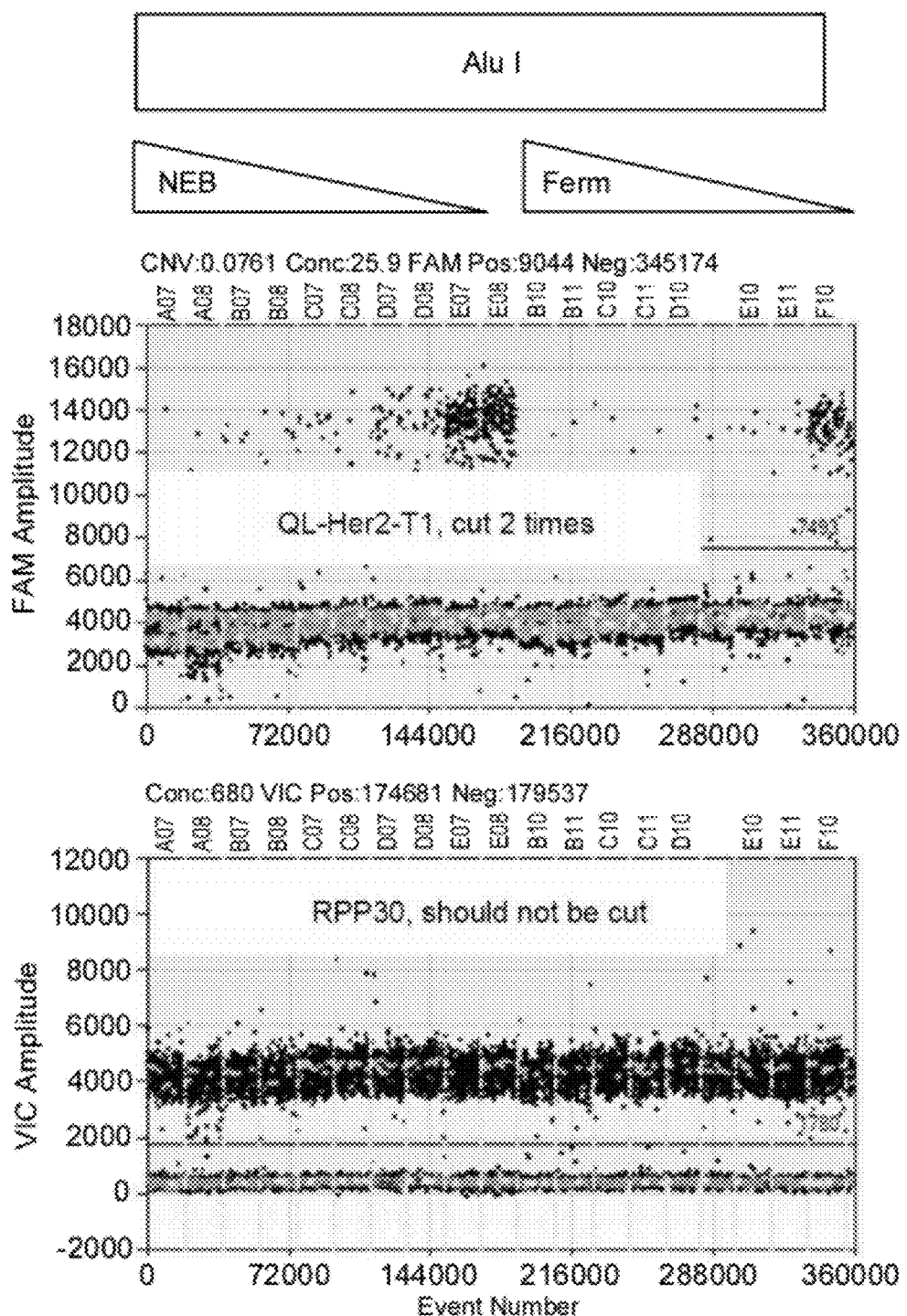
FIG. 48 illustrates measurement of restriction enzyme activity with ddPCR.
Figure 48:
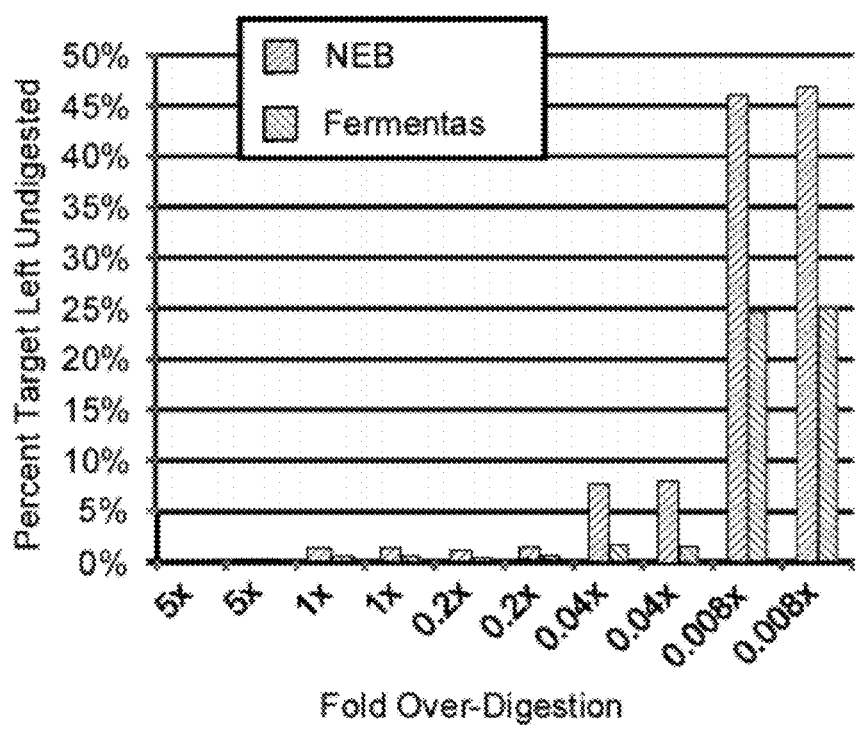
Figure 48:
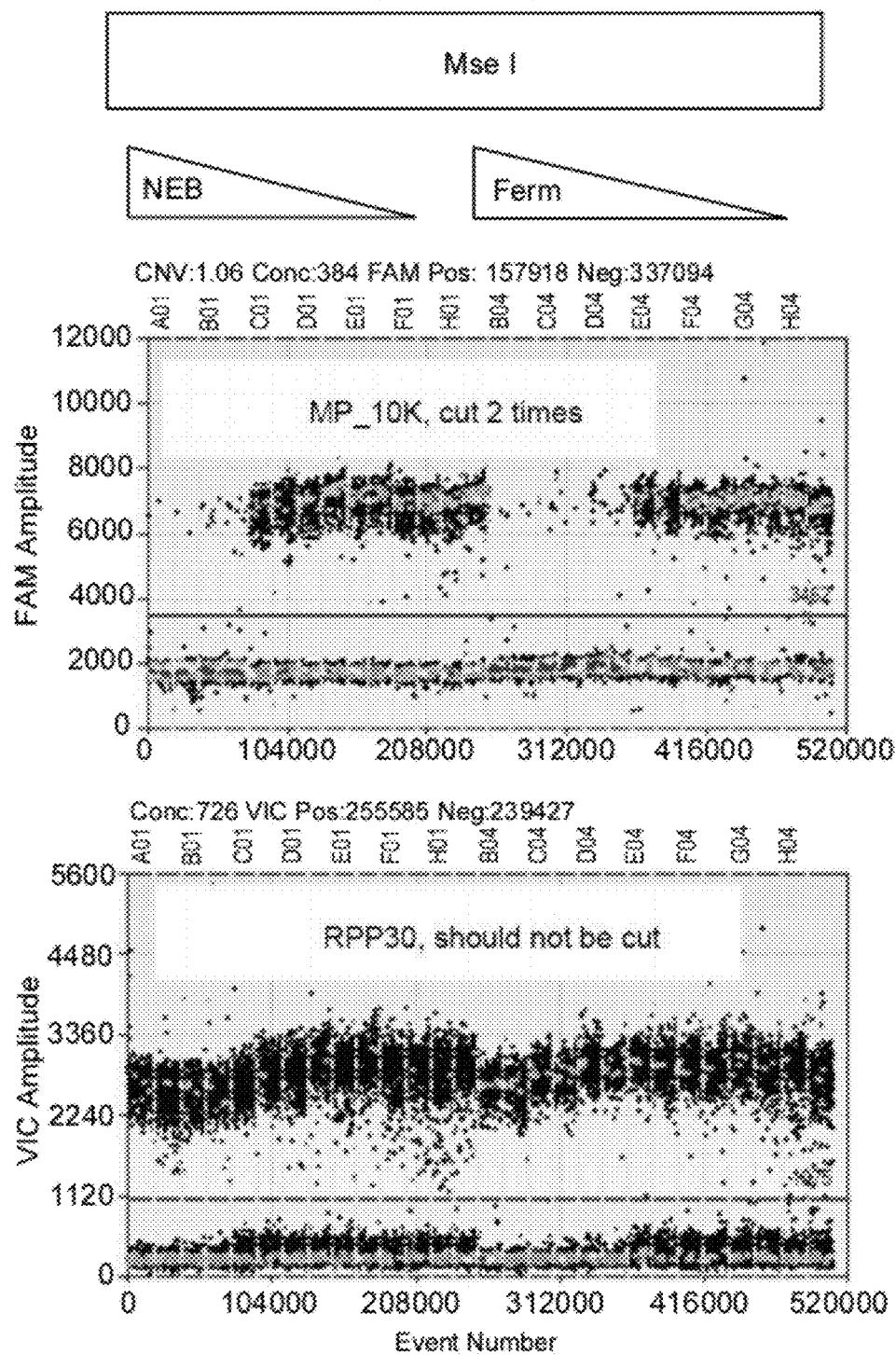
Figure 48:
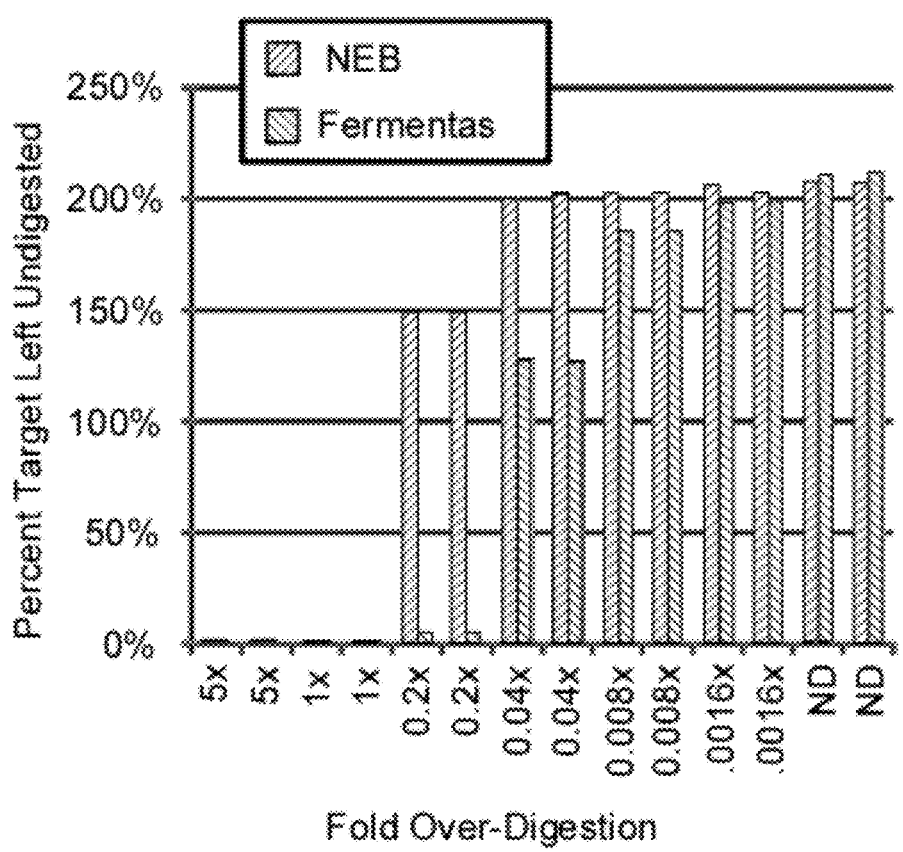

The left panel of FIG. 48 depicts an assay using Alu I purchased from NEW and Fermentas. The primers used in the assay can be: FWD primer 5'-GGCCCTCATCCACCATAA- CAC-3' (SEQ ID NO: 40), REV primer 5'-GTGTGGAGCA-GAGCTTGGT-3' (SEQ ID NO: 41). The probe can be 5'-6FAM-TCCGAAAGAGCTGGTC-MGB-NFQ-3' (SEQ ID NO: 42); Alu I cuts this amplicon sequence twice. The right panel of FIG. 48 depicts an assay using Mse I. The primers used in the assay can be: 5'-CTCCCTCTCCATAGC-TACTTAAGGA-3' (SEQ ID NO: 43), REV 5'-CAAGGAGC-CCTAACCAATGGA-3' (SEQ ID NO: 44), while the probe can be 5'-6FAM-AAGGCAGAGATTAAAG-MGB-NFQ-3' (SEQ ID NO: 45). Mse I cuts this amplicon sequence twice. As shown in FIG. 48, either Alu I or MseI cuts the reference gene. In this experiment, the amount of RE added to the sample is titered. When RE is present at a high level, it should digest the target that the assay is designed to amplify. The number of positive droplets decreases as the target is digested. If the target is digested, few to no positive droplets appear. See FIG. 48.

Example 19

Haplotyping Through Collocation

A method is provided for garnering haplotyping information through collocation. This method can be used to determine if there is a deletion of a target nucleic acid sequence. A marker sequence (detected with, e.g., VIC labeled probe) can be outside but near a target sequence (detected with, e.g., a FAM-labeled probe), in a copy number variation region. A sample comprising nucleic acid can be partitioned into a plurality of spatially-isolated regions, and the marker and target nucleic acid sequences can be detected (e.g., through amplification and detection with probes). The collocation of the VIC (marker) and FAM (target) can be analyzed as depicted in FIG. 49. If VIC and FAM always colocalize in a partition, then there are likely no deletions of the target sequence (FIG. 49B). If there are partitions with VIC only that do not colocalize with FAM, this result suggests a deletion of the target sequence (FIG. 49A).

Example 20

Storage of DNA Samples

FIGS. 20A and 20B illustrate drift of MRGPRX1 CNV values of stored, digested DNA. In FIG. 20A, digested samples show CNV values consistently below integers. In FIG. 20B, CNV values, were closer to integers. Analyzed samples included Coriell purified DNA samples: NA11994, NA18507, NA18502, NA19221, NA19205, NA18916, and NA19108. Samples depicted in FIG. 20A were analyzed on a different day than samples in FIG. 20B. Briefly, RsaI was used to digest the samples, standard ddPCR thermal cycling conditions were used: 95° C. 10 min (1 cycle), 94° C. 30 sec and 60° C. 1 min (40 cycles), 98° C. 10 min (1 cycle), 12° C. hold.

MRGPRX1 assay sequences were (forward primer) 5'-TTAAGCTTCATCAGTATCCCCCA-3' (SEQ ID NO: 26), (reverse primer) 5'-CAAAGTAGGAAAACATCATCA-CAGGA-3' (SEQ ID NO: 27), and (probe) 6FAM-AC-CATCTCTAAAATCCT-MGBNFQ (SEQ ID NO: 28). Samples were duplexed to RRP30 (VIC labeled); RPP30 reference assay (forward primer) 5'-GATTTGGACCTGC-GAGCG-3' (SEQ ID NO: 20), (reverse primer) 5'-GCGGCT-GTCTCCACAAGT-3' (SEQ ID NO: 21), and (probe) VIC-CTGACCTGAAGGCTCT-MGBNFQ (SEQ ID NO: 22). DNA was processed soon (within 24 hrs of digestion).

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of detecting variations in copy number of a target nucleic acid, the method comprising:
   a. contacting a sample comprising a plurality of polynucleotides with at least one agent, wherein each of one or more of polynucleotides comprises multiple copies of a target nucleic acid;
   b. subjecting the sample to conditions that enable the agent to cleave a specifically-selected target site between the multiple copies of the target nucleic acid, thereby separating the multiple copies from one another;
   c. separating the sample contacted with the agent into a plurality of droplets;
   d. subjecting the target nucleic acid to an amplification reaction in droplets;
   e. detecting amplification data for the target nucleic acid from individual droplets;
   f. enumerating a number of droplets comprising the target nucleic acid based on the amplification data; and
   g. determining a copy number of the target nucleic acid based on the step of enumerating.

2. The method of claim 1, wherein the target nucleic acid is are present at an average concentration of less than about five copies per droplet.

3. The method of claim 1, wherein the multiple copies have identical sequences.

4. The method of claim 1, wherein the specifically-selected target site is a site capable of digestion with a restriction enzyme.

5. The method of claim 1, wherein the agent is one or more restriction enzymes.

6. The method of claim 1, wherein the specifically-selected site and the target nucleic acid are located within the same gene.

7. The method of claim 1, wherein the target nucleic acid is correlated with a disease or disorder.

8. The method of claim 1, further comprising enumerating a number of droplets comprising a reference nucleic acid.

9. The method of claim 8, wherein the reference nucleic acid is present at a fixed number of copies in a genome from which the sample is derived.

10. The method of claim 8, wherein the reference nucleic acid is a housekeeping gene.

11. The method of claim 8, wherein the reference nucleic acid is present at two copies per diploid genome from which the sample is derived.

12. The method of claim 8, wherein determining the copy number of the target nucleic acid comprises dividing the number of droplets comprising the target nucleic acid by the number of droplets comprising the reference nucleic acid.

13. The method of claim 1, wherein the agent does not cut the sequence of the target nucleic acid.

14. The method of claim 8, wherein the agent does not cut the sequence of the reference nucleic acid.

15. The method of claim 5, wherein the one or more restriction enzymes have more than one recognition sequence between the multiple copies of the target nucleic acid.

16. The method of claim 5, wherein the one or more restriction enzymes do not exhibit significant star activity.

17. The method of claim 5, wherein the one or more restriction enzymes comprise two or more restriction enzymes.

18. The method of claim 5, wherein software is used to select the one or more restriction enzymes.

19. The method of claim 5, wherein the one or more restriction enzymes are heat-inactivated after digesting the polynucleotides.

20. The method of claim 19, wherein a temperature of the heat inactivation is below a melting point of the restricted target fragments in order to maintain the double-stranded nature of the target fragments.

21. The method of claim 5, wherein a control restriction enzyme digest is performed to measure an efficiency of digestion of nucleic acid by the one or more restriction enzymes.

22. The method of claim 1, wherein a percentage of linked target sequences that are fragmented in the sample is determined.

23. The method of claim 1, wherein less than 1 megabase separates the multiple copies of the target nucleic acid.

24. The method of claim 1, wherein less than 1 kilobase separates the multiple copies of the target nucleic acid.

25. The method of claim 1, wherein subjecting the target nucleic acid to an amplification reaction includes conducting a PCR reaction.

26. The method of claim 1, wherein the method does not comprise a sequencing reaction.

27. A method of detecting variations in copy number of a target nucleic acid comprising:
   a. obtaining a sample comprising (i) a plurality of polynucleotides, wherein at least one of the polynucleotides comprises multiple copies of a target nucleic acid; (ii) a probe with a fluorescent label to detect the target nucleic acid; and (iii) reagents to enable a PCR reaction;
   b. separating the sample into a plurality of spatially-isolated partitions, wherein the spatially-isolated partitions comprise on average less than five copies of the target nucleic acid;
   c. subjecting the sample to a PCR amplification reaction in order to detect the target nucleic acid;
   d. detecting the fluorescence intensity of the fluorescent label before any of the reagents for the PCR reaction become limiting;
   e. enumerating the number of partitions that have a fluorescence intensity above a threshold value indicative of one copy of the target nucleic acid;
   f. enumerating the number of partitions that have a fluorescence intensity above a threshold value indicative of multiple copies of the target nucleic acid; and g. calculating the copy number of the target nucleic acid based on the numbers obtained in step e and step f.

28. The method of claim 27, wherein increased copy number of the target nucleic acid is correlated with a disease or disorder.

* * * * *